US012630600B2

(12) United States Patent
Genapathy et al.

(10) Patent No.: US 12,630,600 B2
(45) Date of Patent: May 19, 2026

(54) GLP-1 AND GLUCAGON DUAL AGONIST PEPTIDES WITH IMPROVED BIOLOGICAL STABILITY

(71) Applicant: MEDIMMUNE LIMITED, Cambridge (GB)

(72) Inventors: Sivaneswary Genapathy, Cambridge (GB); Maria Aleksandra Bednarek, Cambridge (GB)

(73) Assignee: MedImmune Limited, Cambridge (GB)

( * ) Notice: Subject to any disclaimer, the term of this patent is extended or adjusted under 35 U.S.C. 154(b) by 180 days.

(21) Appl. No.: 18/164,802

(22) Filed: Feb. 6, 2023

(65) Prior Publication Data

US 2023/0357348 A1     Nov. 9, 2023

Related U.S. Application Data

(60) Provisional application No. 63/307,206, filed on Feb. 7, 2022.

(51) Int. Cl.
| | |
|---|---|
| *C07K 14/605* | (2006.01) |
| *A61K 9/00* | (2006.01) |
| *A61K 38/00* | (2006.01) |
| *A61K 47/54* | (2017.01) |

(52) U.S. Cl.
CPC .......... *C07K 14/605* (2013.01); *A61K 9/0019* (2013.01); *A61K 47/543* (2017.08); *A61K 38/00* (2013.01)

(58) Field of Classification Search
None
See application file for complete search history.

(56) References Cited

FOREIGN PATENT DOCUMENTS

| | | |
|---|---|---|
| EP | 3415526 A1 | 12/2018 |
| EP | 3865504 A1 | 8/2021 |
| WO | WO-2014091316 A2 | 6/2014 |
| WO | 2014170496 A1 | 10/2014 |
| WO | 2017211922 A2 | 12/2017 |
| WO | WO-2018046719 A1 | 3/2018 |

OTHER PUBLICATIONS

Hui H., et al., "Structure and Function Studies of Glucagon-Like Peptide-1 (GLP-1): the Designing of a Novel Pharmacological Agent for the Treatment of Diabetes", Diabetes/Metabolism Research and Reviews, Apr. 26, 2005, vol. 21, No. 4, pp. 313-331, XP002559636, ISSN: 1520-7552, DOI: 10.1002/dmrr.553, p. 320, left-hand column, paragraph 3-p. 323, left-hand column, paragraph 3 table 3.

International Search Report and Written Opinion for International Application No. PCT/EP2023/052778, mailed Jul. 10, 2023, 18 Pages.

Wadzinski T.J., et al., "Rapid Phenolic O-Glycosylation of Small Molecules and Complex Unprotected Peptides in Aqueous Solvent", Nature Chemistry, Nature Publishing Group UK, London, vol. 10, No. 6, Apr. 30, 2018 , pp. 644-652, XP036509205, ISSN: 1755-4330, DOI: 10.1038/S41557-018-0041-8 [retrieved on Apr. 30, 2018] figure 3.

Galia, E., et al., "Evaluation of Various Dissolution Media for Predicting in Vivo Performance of Class I and II Drugs," Pharmaceutical Research 15(5):698-705, Springer Nature, Germany (May 1998).

Karlin, S. and Altschul, S.F., "Applications and Statistics for Multiple High-scoring Segments in Molecular Sequences," Proceedings of the National Academy of Sciences of the United States of America 90(12):5873-5877, National Academy of Sciences, United States (Jun. 1993).

Merrifield, R.B., "Solid Phase Peptide Synthesis. I. The Synthesis of a Tetrapeptide," Journal of the American Chemical Society 85(14):2149-2154, ACS Publications, United States (Jul. 1963).

*Primary Examiner* — Sudhakar Katakam
*Assistant Examiner* — Zachary J Miknis
(74) *Attorney, Agent, or Firm* — Sterne, Kessler, Goldstein & Fox P.L.L.C.

(57) ABSTRACT

GLP-1 and glucagon dual agonists disclosed herein have improved biological stability, including proteolytic stability, and duration of action. The peptides can be administered about once a week.

18 Claims, 19 Drawing Sheets

Figure 1A:
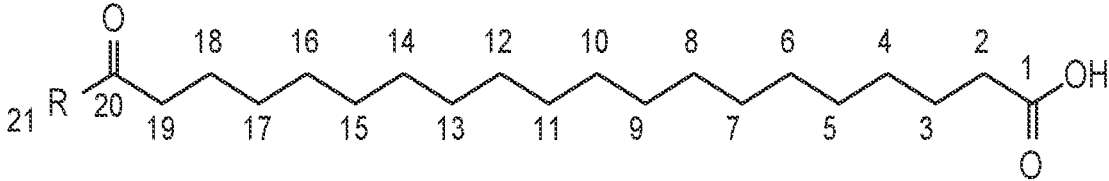
Figure 1B:
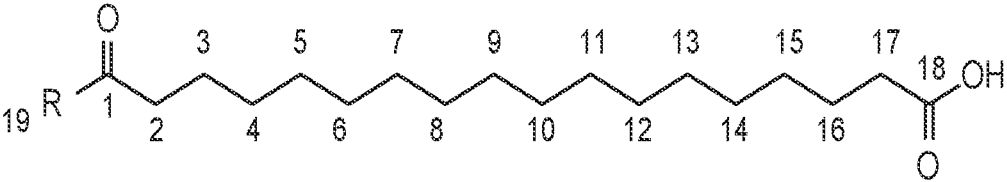
Figure 1C:
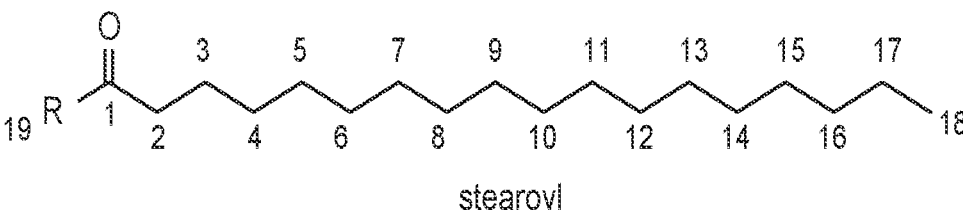
Figure 1D:
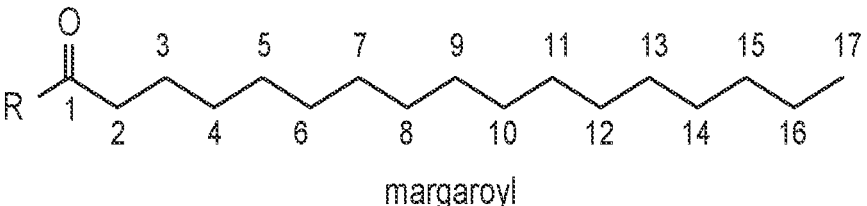

Specification includes a Sequence Listing.

Icosanedioic acid (C20 diacid)

Octadecanedioic acid (C18 diacid)

stearoyl margaroyl

FIG. 1E
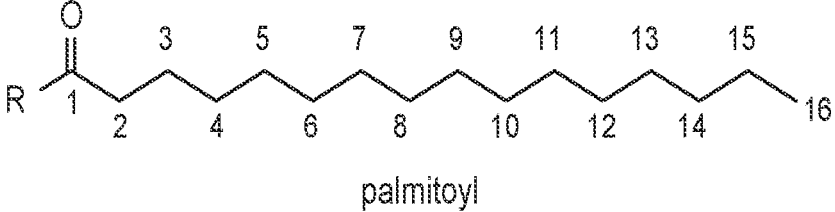
palmitoyl
FIG. 1F
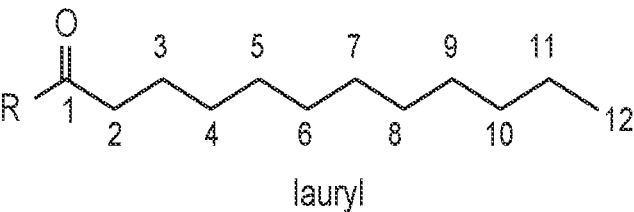
myristoyl
FIG. 1G
lauryl

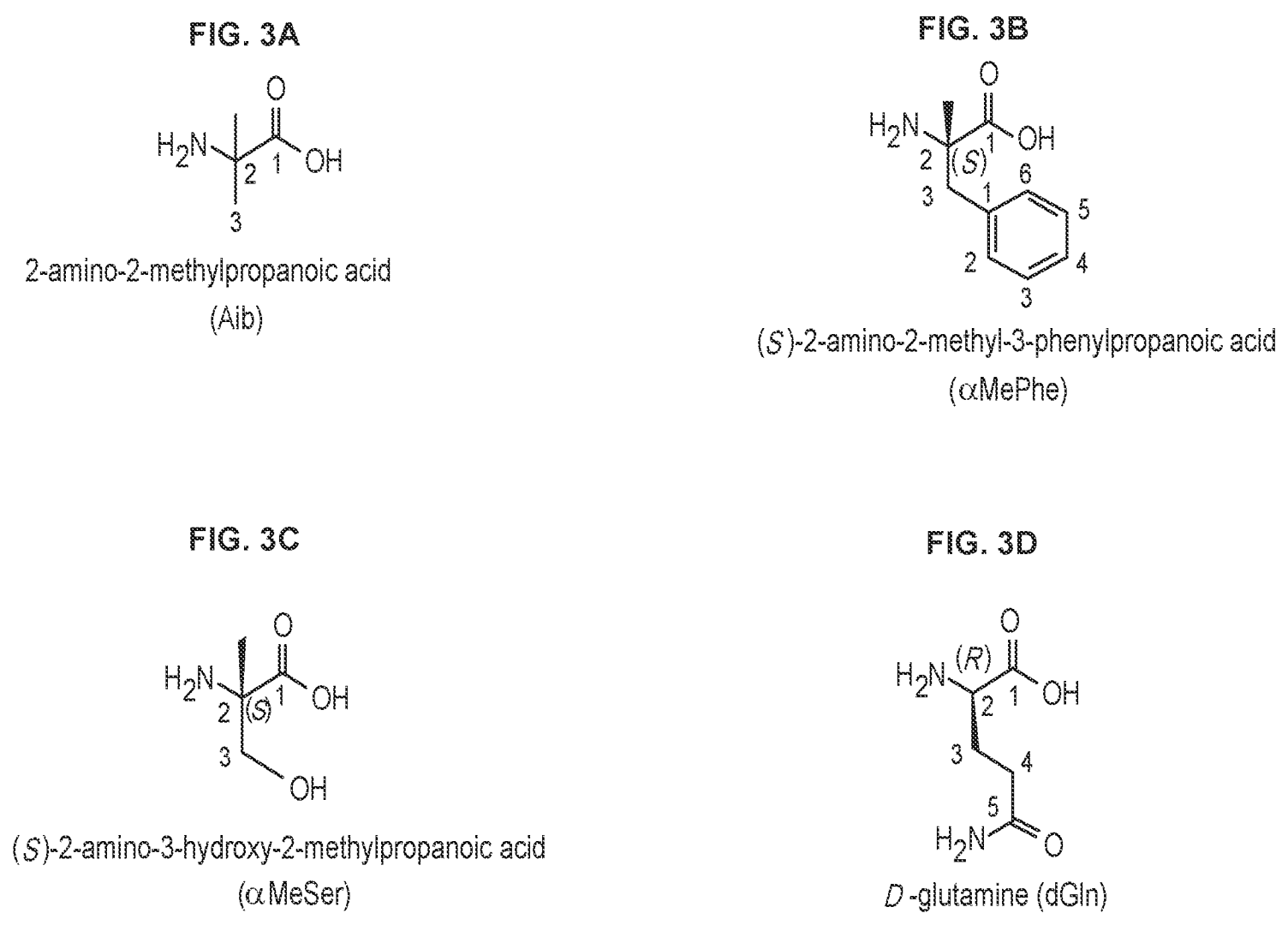

2-amino-2-methylpropanoic acid
(Aib)

FIG. 3B

(S)-2-amino-2-methyl-3-phenylpropanoic acid
(αMePhe)

FIG. 3C

(S)-2-amino-3-hydroxy-2-methylpropanoic acid
(αMeSer)

FIG. 3D

D-glutamine (dGln)

FIG. 3E

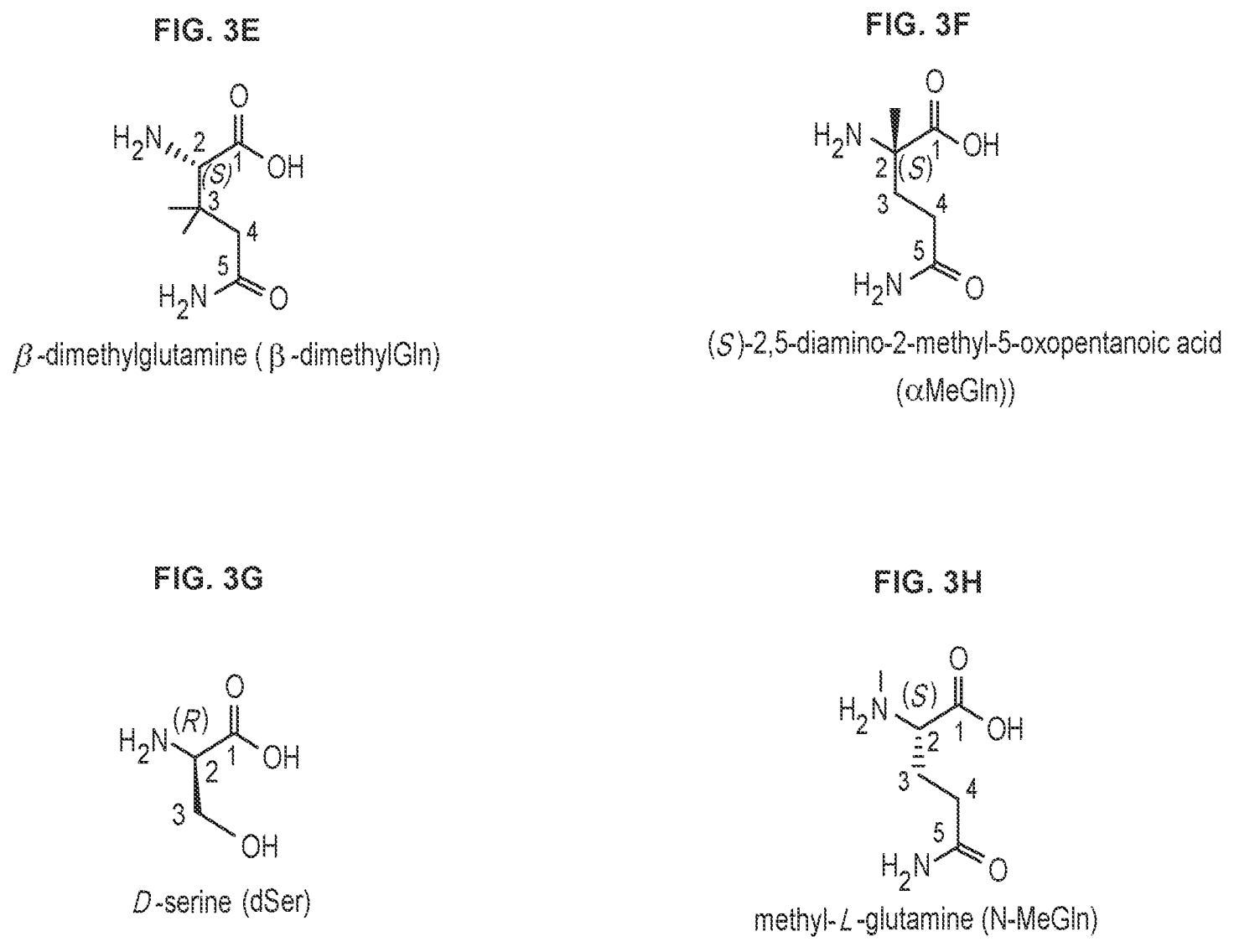

β-dimethylglutamine (β-dimethylGln)

FIG. 3F (S)-2,5-diamino-2-methyl-5-oxopentanoic acid (αMeGln))

FIG. 3G

D-serine (dSer)

FIG. 3H methyl-L-glutamine (N-MeGln)

FIG. 3I (($1H$-imidazol-4-yl)methyl)glycine (NHis)

FIG. 3J 1-aminocyclopropane-1-carboxylic acid (Acpr)

FIG. 3K 1-aminocyclobutane-1-carboxylic acid (Acbu)

FIG. 3L $N^6$-acetyl-$L$-lysine (Ac-Lys)

FIG. 3M

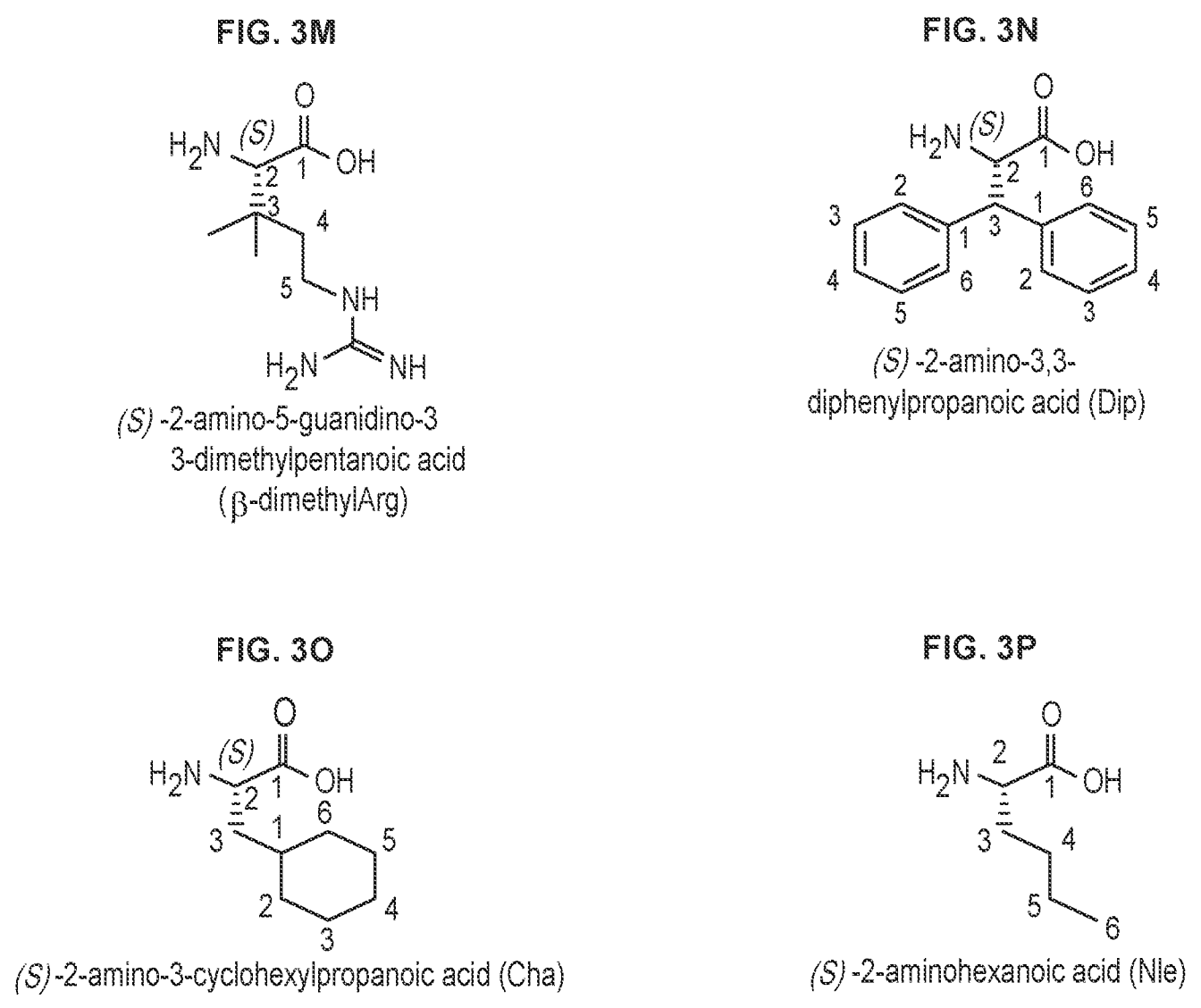

(S)-2-amino-5-guanidino-3
3-dimethylpentanoic acid
(β-dimethylArg)

FIG. 3N

(S)-2-amino-3,3-
diphenylpropanoic acid (Dip)

FIG. 3O

(S)-2-amino-3-cyclohexylpropanoic acid (Cha)

FIG. 3P

(S)-2-aminohexanoic acid (Nle)

FIG. 3Q (S)-3-([1,1'-biphenyl]-4-yl)-2-aminopropanoic acid (Bip)

FIG. 3R 1-methyl-L-tryptophan

FIG. 3S (S)-2-amino-3-(5-bromo-1H-indol-3-yl)propanoic acid (5-Br-Trp)

Peptide 224

(SEQ ID NO: 228)

Peptide 229

(SEQ ID NO: 233)

Peptide 188

(SEQ ID NO: 99)

Peptide 195

(SEQ ID NO: 106)

```
                          SEQUENCE LISTING

Sequence total quantity: 541
SEQ ID NO: 1              moltype = AA  length = 29
FEATURE                   Location/Qualifiers
source                    1..29
                          mol_type = protein
                          organism = Synthetic construct
SEQUENCE: 1
HSQGTFTSDY SKYLDSRRAQ DFVQWLMNT                                   29

SEQ ID NO: 2              moltype = AA  length = 30
FEATURE                   Location/Qualifiers
source                    1..30
                          mol_type = protein
                          organism = Synthetic construct
SEQUENCE: 2
HAEGTFTSDV SSYLEGQAAK EFIAWLVKGR                                  30

SEQ ID NO: 3              moltype = AA  length = 31
FEATURE                   Location/Qualifiers
source                    1..31
                          mol_type = protein
                          organism = Synthetic construct
SEQUENCE: 3
HAEGTFTSDV SSYLEGQAAK EFIAWLVKGR G                                31

SEQ ID NO: 4              moltype = AA  length = 32
FEATURE                   Location/Qualifiers
source                    1..32
                          mol_type = protein
                          organism = synthetic construct
VARIANT                   1
                          note = X is H or NHis
VARIANT                   2
                          note = X is S, 1-aminocyclobutane-1-carboxylic acid (Acbu),
                          1-aminocyclopropane-1-carboxylic acid (Acpr),
                          Aminoisobutyric acid (Aib), D-serine (dSer), or
                          alphaMethyl-Serine (alphaMeSer)
VARIANT                   3
```

-continued

```
                              note = X is Q, H, I, D-glutamine (dGln), methyl-L-glutamine
                               (N-MeGln), alpha-Methyl-glutamine (alphaMeGln), or
                               beta-dimethylglutamine (beta-dimethylGln)
VARIANT                       5
                              note = X is T or S
VARIANT                       6
                              note = X is F or alphaMethyl-Phenylalanine (alphaMePhe)
VARIANT                       10
                              note = X is Y, K, or V, wherein the K can comprise an acyl
                               moiety and/or can be lipidated
VARIANT                       12
                              note = K, acetylated lysine (Ac-Lys), E, or R
VARIANT                       13
                              note = X is Y, Aib, alphaMethyl-Phenylalanine (alphaMePhe),
                               Diphenylalanine (Dip), I, or K, wherein the K can comprise
                               an acyl moiety and/or can be lipidated
VARIANT                       15
                              note = X is D or E
VARIANT                       16
                              note = X is S, Aib, E, T, R, A, K, L, or V
VARIANT                       17
                              note = X is R, E, K, Q, or beta-dimethylarganine
                               (beta-dimethylArg), wherein the K can comprise an acyl
                               moiety and/or can be lipidated
VARIANT                       18
                              note = X is R, A, Aib, Q, S, or beta-dimethylArg
VARIANT                       19
                              note = X is A or V
VARIANT                       20
                              note = X is Q, Aib, E, K, L, or R, wherein the K can
                               comprise an acyl moiety and/or can be lipidated
VARIANT                       21
                              note = X is D, E, or L
VARIANT                       22
                              note = X is F, I, or alphaMePhe
VARIANT                       23
                              note = X is V or I
VARIANT                       24
                              note = Q, A, E, K, L, or R, wherein the K can comprise an
                               acyl moiety and/or can be lipidated
VARIANT                       25
                              note = W, Aib, Dip, H, I, S, biphenyl-alanine (Bip),
                               1-methyl tryptophan (1-Methyl-Trp), 5-Bromo trptophan
                               (5-BrTrp), or alphaMePhe
VARIANT                       26
                              note = L, beta-cyclohexyl-L-alanine (Cha), I, or V
VARIANT                       27
                              note = X is M, A, E, I, L, norleucine (Nle), S, K, or V
VARIANT                       28
                              note = N, (PEG)4, A, Aib, E, G, R, S, or not present
VARIANT                       29
                              note = X is T, Aib, E, G, A, R, or not present
VARIANT                       30
                              note = X is not present, E, A, Aib, K, T, or G
VARIANT                       31
                              note = X is not present, I, or G
VARIANT                       32
                              note = Z is amide or acid
SEQUENCE: 4
XXXGXXTSDX SXXLXXXXXX XXXXXXXXXX XZ                                       32

SEQ ID NO: 5                  moltype = AA  length = 32
FEATURE                       Location/Qualifiers
source                        1..32
                              mol_type = protein
                              organism = synthetic construct
VARIANT                       2
                              note = X is S, Aminoisobutyric acid (Aib), or
                               alphaMethyl-Serine (alphaMeSer)
VARIANT                       3
                              note = X is Q or H
VARIANT                       5
                              note = X is T or S
VARIANT                       6
                              note = X is F or alphaMethyl-Phenylalanine (alphaMePhe)
VARIANT                       10
                              note = X is Y or V
VARIANT                       12
                              note = X is K or acetylated lysine (Ac-Lys)
```

-continued

```
VARIANT             13
                    note = X is Y, alphaMePhe, Aib, Diphenylalanine (Dip), or I
VARIANT             15
                    note = X is D or E
VARIANT             16
                    note = X is S, T, A, E, K, L, R, or V
VARIANT             17
                    note = X is R or K, wherein the K can comprise an acyl
                     moiety and/or can be lipidated
VARIANT             18
                    note = X is R, A, Q, or beta-dimethylarganine
                     (beta-dimethylArg)
VARIANT             20
                    note = X is Q, R, Aib, L, or E
VARIANT             22
                    note = X is F, I, or alphaMePhe
VARIANT             23
                    note = X is V or I
VARIANT             24
                    note = X is Q, E, A, L, or R
VARIANT             25
                    note = X is W, Aib, S, Dip, I, H, biphenyl-alanine (Bip),
                     1-methyl tryptophan (1-Methyl-Trp), 5-Bromo trptophan
                     (5-BrTrp), or alphaMePhe
VARIANT             26
                    note = X is L, I, or beta-cyclohexyl-L-alanine (Cha) or V
VARIANT             27
                    note = X is M, A, L, E, V, I, K, norleucine (Nle), or S
VARIANT             28
                    note = X is N, Aib, E, (PEG)4, A, S, or G
VARIANT             29
                    note = X is T, not present, Aib, G, A, R, or E
VARIANT             30
                    note = X is not present, G, A, Aib, K, or E
VARIANT             31
                    note = X is not present
VARIANT             32
                    note = Z is amide or acid
SEQUENCE: 5
HXXGXXTSDX SXXLXXXXAX DXXXXXXXXX XZ                                   32

SEQ ID NO: 6        moltype = AA  length = 28
FEATURE             Location/Qualifiers
source              1..28
                    mol_type = protein
                    organism = Synthetic construct
MOD_RES             6
                    note = alpha-methyl-L-phenylalanine
MOD_RES             13
                    note = 2-Aminoisobutyric acid
MOD_RES             17
                    note = Lys, wherein the side chain of Lys is connected to
                     O2Oc-O2Oc-gamma-Glu-C18diacid
MOD_RES             22
                    note = alpha-methyl-L-phenylalanine
MOD_RES             25
                    note = 2-Aminoisobutyric acid
SEQUENCE: 6
HSQGSXTSDV SKXLDSXAAQ DXVQXIAN                                        28

SEQ ID NO: 7        moltype = AA  length = 29
FEATURE             Location/Qualifiers
source              1..29
                    mol_type = protein
                    organism = Synthetic construct
MOD_RES             6
                    note = alpha-methyl-L-phenylalanine
MOD_RES             13
                    note = 2-Aminoisobutyric acid
MOD_RES             17
                    note = Lys, wherein the side chain of Lys is connected to
                     O2Oc-O2Oc-gamma-Glu-C20diacid
MOD_RES             22
                    note = alpha-methyl-L-phenylalanine
SEQUENCE: 7
HSQGSXTSDV SKXLDSXAAQ DXVQWIANT                                       29

SEQ ID NO: 8        moltype = AA  length = 29
FEATURE             Location/Qualifiers
```

-continued

```
source                  1..29
                        mol_type = protein
                        organism = Synthetic construct
MOD_RES                 6
                        note = alpha-methyl-L-phenylalanine
MOD_RES                 13
                        note = alpha-methyl-L-phenylalanine
MOD_RES                 17
                        note = Lys, wherein the side chain of Lys is connected to
                         gamma-Glu-C18diacid
MOD_RES                 6
                        note = alpha-methyl-L-phenylalanine
MOD_RES                 13
                        note = alpha-methyl-L-phenylalanine
MOD_RES                 17
                        note = Lys, wherein the side chain of Lys is connected to
                         O2Oc-O2Oc-gamma-Glu-C18diacid
SEQUENCE: 8
HSQGSXTSDV SKXLDSXAAQ DFVQWIANT                                       29

SEQ ID NO: 9            moltype = AA   length = 29
FEATURE                 Location/Qualifiers
source                  1..29
                        mol_type = protein
                        organism = Synthetic construct
MOD_RES                 6
                        note = alpha-methyl-L-phenylalanine
MOD_RES                 13
                        note = alpha-methyl-L-phenylalanine
MOD_RES                 17
                        note = Lys, wherein the side chain of Lys is connected to
                         O2Oc-O2Oc-gamma-Glu-C18diacid
SEQUENCE: 9
HSQGSXTSDV SKXLDSXAAQ DFVQWIANT                                       29

SEQ ID NO: 10           moltype = AA   length = 28
FEATURE                 Location/Qualifiers
source                  1..28
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 17
                        note = Lys, wherein the side chain of Lys is connected to
                         O2Oc-O2Oc-gamma-Glu- gamma-Glu-C18diacid
MOD_RES                 22
                        note = alpha-methyl-L-phenylalanine
MOD_RES                 25
                        note = 2-Aminoisobutyric acid
SEQUENCE: 10
HXQGSXTSDV SKXLDSXAAQ DXVQXIAN                                        28

SEQ ID NO: 11           moltype = AA   length = 28
FEATURE                 Location/Qualifiers
source                  1..28
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 17
                        note = Lys, wherein the side chain of Lys is connected to
                         O2Oc-O2Oc-gamma-Glu-C18diacid
MOD_RES                 22
                        note = alpha-methyl-L-phenylalanine
SEQUENCE: 11
HXHGSXTSDV SKXLDSXAAQ DXVEWIAN                                        28

SEQ ID NO: 12           moltype = AA   length = 29
FEATURE                 Location/Qualifiers
source                  1..29
                        mol_type = protein
```

```
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   17
                          note = Lys, wherein the side chain of Lys is connected to
                           gamma-Glu-C18diacid
SEQUENCE: 12
HXHGSXTSDV SKXLDSXAAQ DXVEWIANT                                              29

SEQ ID NO: 13             moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   17
                          note = Lys, wherein the side chain of Lys is connected to
                           O2Oc-O2Oc-gamma-Glu-C18diacid
SEQUENCE: 13
HXHGSXTSDV SKXLDSXAAQ DFVQWIANT                                              29

SEQ ID NO: 14             moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   17
                          note = Lys, wherein the side chain of Lys is connected to
                           O2Oc-O2Oc-gamma-Glu-C18diacid
SEQUENCE: 14
HXGSMXTSDV SKXLDSXAAR DFVQWIANT                                              29

SEQ ID NO: 15             moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   17
                          note = Lys, wherein the side chain of Lys is connected to
                           O2Oc-O2Oc-gamma-Glu-C18diacid
SEQUENCE: 15
HXHGSXTSDV SKXLDSXAAR DFVEWIANT                                              29

SEQ ID NO: 16             moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   17
                          note = Lys, wherein the side chain of Lys is connected to
                           O2Oc-O2Oc-gamma-Glu-C18diacid
MOD_RES                   25
```

```
                              note = 2-Aminoisobutyric acid
SEQUENCE: 16
HXHGSXTSDV SKXLDSXAAQ DFVQXIANT                                    29

SEQ ID NO: 17        moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              6
                     note = alpha-methyl-L-phenylalanine
MOD_RES              13
                     note = alpha-methyl-L-phenylalanine
MOD_RES              17
                     note = Lys, wherein the side chain of Lys is connected to
                      O2Oc-O2Oc-gamma-Glu-C18diacid
MOD_RES              25
                     note = 2-Aminoisobutyric acid
SEQUENCE: 17
HXHGSXTSDV SKXLDSXAAR DFVQXIANT                                    29

SEQ ID NO: 18        moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              6
                     note = alpha-methyl-L-phenylalanine
MOD_RES              13
                     note = alpha-methyl-L-phenylalanine
MOD_RES              17
                     note = Lys, wherein the side chain of Lys is connected to
                      O2Oc-O2Oc-gamma-Glu-C18diacid
MOD_RES              22
                     note = alpha-methyl-L-phenylalanine
MOD_RES              25
                     note = 2-Aminoisobutyric acid
SEQUENCE: 18
HXHGSXTSDV SKXLDSXAAR DXVQXIANT                                    29

SEQ ID NO: 19        moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              6
                     note = alpha-methyl-L-phenylalanine
MOD_RES              13
                     note = alpha-methyl-L-phenylalanine
MOD_RES              17
                     note = Lys, wherein the side chain of Lys is connected to
                      O2Oc-gamma-Glu-gamma-Glu-C20diacid
MOD_RES              25
                     note = 2-Aminoisobutyric acid
MOD_RES              22
                     note = alpha-methyl-L-phenylalanine
SEQUENCE: 19
HXHGSXTSDV SKXLDSXAAR DXVQXIANT                                    29

SEQ ID NO: 20        moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              6
                     note = alpha-methyl-L-phenylalanine
MOD_RES              13
                     note = alpha-methyl-L-phenylalanine
MOD_RES              17
                     note = Lys, wherein the side chain of Lys is connected to
                      O2Oc-O2Oc-gamma-Glu-C18diacid
```

-continued

```
MOD_RES                 22
                        note = alpha-methyl-L-phenylalanine
MOD_RES                 25
                        note = 2-Aminoisobutyric acid
SEQUENCE: 20
HXHGSXTSDV SKXLDSXAAR DXVEXIANT                                        29

SEQ ID NO: 21           moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 17
                        note = Lys, wherein the side chain of Lys is connected to
                        O2Oc-O2Oc-gamma-Glu-C18diacid
MOD_RES                 22
                        note = alpha-methyl-L-phenylalanine
MOD_RES                 25
                        note = 2-Aminoisobutyric acid
SEQUENCE: 21
HXHGSXTSDV SKXLDSXAAR DXIAXIANT                                        29

SEQ ID NO: 22           moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 17
                        note = Lys, wherein the side chain of Lys is connected to
                        O2Oc-O2Oc-gamma-Glu-C18diacid
MOD_RES                 22
                        note = alpha-methyl-L-phenylalanine
SEQUENCE: 22
HXHGSXTSDV SKXLDSXAAR DXVESIANT                                        29

SEQ ID NO: 23           moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 17
                        note = Lys, wherein the side chain of Lys is connected to
                        O2Oc-O2Oc-gamma-Glu-C18diacid
MOD_RES                 22
                        note = alpha-methyl-L-phenylalanine
SEQUENCE: 23
HXHGSXTSDV SKXLDSXAAR DXVQSIANT                                        29

SEQ ID NO: 24           moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 17
                        note = Lys, wherein the side chain of Lys is connected to
```

```
                         O2Oc-gamma-Glu-gamma-Glu-C18diacid
MOD_RES                  22
                         note = alpha-methyl-L-phenylalanine
MOD_RES                  25
                         note = 2-Aminoisobutyric acid
SEQUENCE: 24
HXHGSXTSDV SKXLDSXAAR DXVQXIANT                                              29

SEQ ID NO: 25            moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  6
                         note = alpha-methyl-L-phenylalanine
MOD_RES                  13
                         note = alpha-methyl-L-phenylalanine
MOD_RES                  17
                         note = Lys, wherein the side chain of Lys is connected to
                          O2Oc-gamma-Glu-gamma-Glu-C18diacid
MOD_RES                  22
                         note = alpha-methyl-L-phenylalanine
MOD_RES                  25
                         note = 2-Aminoisobutyric acid
SEQUENCE: 25
HXHGSXTSDV SKXLDSXAAR DXVEXIANT                                              29

SEQ ID NO: 26            moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  6
                         note = alpha-methyl-L-phenylalanine
MOD_RES                  13
                         note = alpha-methyl-L-phenylalanine
MOD_RES                  17
                         note = Lys, wherein the side chain of Lys is connected to
                          gamma-Glu-C18diacid
MOD_RES                  22
                         note = alpha-methyl-L-phenylalanine
SEQUENCE: 26
HXHGSXTSDV SKXLDSXAAQ DXVESIANT                                              29

SEQ ID NO: 27            moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  6
                         note = alpha-methyl-L-phenylalanine
MOD_RES                  13
                         note = alpha-methyl-L-phenylalanine
MOD_RES                  17
                         note = Lys, wherein the side chain of Lys is connected to
                          O2Oc-O2Oc-gamma-Glu-gamma-Glu-C20diacid
MOD_RES                  22
                         note = alpha-methyl-L-phenylalanine
SEQUENCE: 27
HXHGSXTSDV SKXLDSXAAQ DXVESIANT                                              29

SEQ ID NO: 28            moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  6
                         note = alpha-methyl-L-phenylalanine
MOD_RES                  13
                         note = alpha-methyl-L-phenylalanine
MOD_RES                  17
```

```
                          note = Lys, wherein the side chain of Lys is connected to
                           O2Oc-O2Oc-gamma-Glu-C18diacid
MOD_RES                   22
                          note = alpha-methyl-L-phenylalanine
SEQUENCE: 28
HXHGSXTSDV SKXLDSXAAQ DXVESIANT                                            29

SEQ ID NO: 29             moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   17
                          note = Lys, wherein the side chain of Lys is connected to
                           O2Oc-O2Oc-gamma-Glu-C18diacid
MOD_RES                   22
                          note = alpha-methyl-L-phenylalanine
MOD_RES                   25
                          note = 2-Aminoisobutyric acid
SEQUENCE: 29
HXHGSXTSDV SKXLDSXAAQ DXVQXIANT                                            29

SEQ ID NO: 30             moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   17
                          note = Lys, wherein the side chain of Lys is connected to
                           O2Oc-O2Oc-gamma-Glu-gamma-Glu-C20diacid
MOD_RES                   22
                          note = alpha-methyl-L-phenylalanine
MOD_RES                   25
                          note = 2-Aminoisobutyric acid
SEQUENCE: 30
HXHGSXTSDV SKXLDSXAAQ DXVQXIANT                                            29

SEQ ID NO: 31             moltype = AA  length = 28
FEATURE                   Location/Qualifiers
source                    1..28
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   17
                          note = Lys, wherein the side chain of Lys is connected to
                           O2Oc-O2Oc-gamma-Glu-C18diacid
MOD_RES                   22
                          note = alpha-methyl-L-phenylalanine
SEQUENCE: 31
HXQGSXTSDV SKXLDSXAAQ DXVQWIAN                                             28

SEQ ID NO: 32             moltype = AA  length = 28
FEATURE                   Location/Qualifiers
source                    1..28
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
```

```
MOD_RES                 17
                        note = Lys, wherein the side chain of Lys is connected to
                         O2Oc-O2Oc-gamma-Glu-C18diacid
MOD_RES                 22
                        note = alpha-methyl-L-phenylalanine
SEQUENCE: 32
HXQGSXTSDV SKXLDSXAAQ DXVEWIAN                                           28

SEQ ID NO: 33           moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C18diacid
MOD_RES                 28
                        note = 2-Aminoisobutyric acid
SEQUENCE: 33
HXQGTFTSDV SKXLDSXRAQ DFVRWLLXT                                          29

SEQ ID NO: 34           moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C18diacid
MOD_RES                 20
                        note = 2-Aminoisobutyric acid
MOD_RES                 28
                        note = 2-Aminoisobutyric acid
SEQUENCE: 34
HXQGTFTSDV SKXLDSXRAX DFVQWLLXT                                          29

SEQ ID NO: 35           moltype = AA  length = 31
FEATURE                 Location/Qualifiers
source                  1..31
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C18diacid
MOD_RES                 28
                        note = 2-Aminoisobutyric acid
SEQUENCE: 35
HXQGTFTSDV SKXLDSXRAQ DFVRWLLEXT G                                       31

SEQ ID NO: 36           moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C18diacid
MOD_RES                 29
                        note = 2-Aminoisobutyric acid
SEQUENCE: 36
HXQGTFTSDV SKXLDSXRAQ DFVRWLLEXG                                         30

SEQ ID NO: 37           moltype = AA  length = 29
```

-continued

```
FEATURE                 Location/Qualifiers
source                  1..29
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = Lys, wherein the side chain of Lys is connected to
                         gamma-Glu-C18diacid
MOD_RES                 20
                        note = 2-Aminoisobutyric acid
SEQUENCE: 37
HXQGTFTSDV SKXLDSXRAX DFVQWIANT                                    29

SEQ ID NO: 38           moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C18diacid
MOD_RES                 28
                        note = 2-Aminoisobutyric acid
SEQUENCE: 38
HXQGTFTSDV SKXLDSXRAQ DFVQWLEXT                                    29

SEQ ID NO: 39           moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C18diacid
MOD_RES                 28
                        note = 2-Aminoisobutyric acid
SEQUENCE: 39
HXQGTFTSDV SKXLDSXRAQ DFVQWLLXE                                    29

SEQ ID NO: 40           moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C18diacid
MOD_RES                 28
                        note = 2-Aminoisobutyric acid
SEQUENCE: 40
HXQGTFTSDV SKXLDTXRAQ DFVQWLLXT                                    29

SEQ ID NO: 41           moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C18diacid
```

```
MOD_RES              28
                     note = 2-Aminoisobutyric acid
SEQUENCE: 41
HXQGTFTSDV SKXLDSXRAR DFVQWLLXT                                     29

SEQ ID NO: 42        moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              13
                     note = alpha-methyl-L-phenylalanine
MOD_RES              17
                     note = Lys, wherein the side chain of Lys is connected to
                     O2Oc-O2Oc-gamma-Glu-C18diacid
MOD_RES              28
                     note = 2-Aminoisobutyric acid
SEQUENCE: 42
HXQGTFTSDV SKXLDSXRAE DFVQWLLXT                                     29

SEQ ID NO: 43        moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              13
                     note = alpha-methyl-L-phenylalanine
MOD_RES              17
                     note = Lys, wherein the side chain of Lys is connected to
                     O2Oc-O2Oc-gamma-Glu-C18diacid
MOD_RES              28
                     note = 2-Aminoisobutyric acid
SEQUENCE: 43
HXQGTFTSDV SKXLDSXRAQ DFVEWLLXT                                     29

SEQ ID NO: 44        moltype = AA  length = 30
FEATURE              Location/Qualifiers
source               1..30
                     mol_type = protein
                     organism = Synthetic construct
MOD_RES              2
                     note = 2-Aminoisobutyric acid
MOD_RES              13
                     note = alpha-methyl-L-phenylalanine
MOD_RES              17
                     note = Lys, wherein the side chain of Lys is connected to
                     O2Oc-O2Oc-gamma-Glu-C18diacid
MOD_RES              28
                     note = 2-Aminoisobutyric acid
SEQUENCE: 44
HXQGTFTSDV SKXLDSXRAQ DFVRWLLXTE                                    30

SEQ ID NO: 45        moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              13
                     note = alpha-methyl-L-phenylalanine
MOD_RES              17
                     note = Lys, wherein the side chain of Lys is connected to
                     O2Oc-O2Oc-gamma-Glu-C18diacid
MOD_RES              28
                     note = 2-Aminoisobutyric acid
SEQUENCE: 45
HXQGTFTSDV SKXLDSXRAQ DFVQWLLXT                                     29

SEQ ID NO: 46        moltype = AA  length = 28
FEATURE              Location/Qualifiers
source               1..28
                     mol_type = protein
                     organism = Synthetic construct
MOD_RES              2
```

```
                        note = 2-Aminoisobutyric acid
MOD_RES                 13
                        note = alpha-methyl-L-phenylalanine
MOD_RES                 28
                        note = polyethylene glycol
MOD_RES                 17
                        note = Lys, wherein the side chain of Lys is connected to
                        O2Oc-O2Oc-gamma-Glu-C18diacid
SEQUENCE: 46
HXQGTFTSDY SKXLDSXRAQ DFVQWLVX                                              28

SEQ ID NO: 47           moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = Lys, wherein the side chain of Lys is connected to
                        O2Oc-O2Oc-gamma-Glu-C18diacid
MOD_RES                 25
                        note = 2-Aminoisobutyric acid
SEQUENCE: 47
HXQGTFTSDV SKXLDSXRAQ DFVQXLVAT                                             29

SEQ ID NO: 48           moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = Lys, wherein the side chain of Lys is connected to
                        gamma-Glu-gamma-Glu-O2Oc-O2Oc-gamma-Glu-gamma-Glu-C18diacid
MOD_RES                 29
                        note = 2-Aminoisobutyric acid
SEQUENCE: 48
HXQGTFTSDV SKXLDSXRAR DFVRWLLEXG                                            30

SEQ ID NO: 49           moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = Lys, wherein the side chain of Lys is connected to
                        gamma-Glu-gamma-Glu-O2Oc-O2Oc-gamma-Glu-gamma-Glu-C18diacid
MOD_RES                 30
                        note = 2-Aminoisobutyric acid
SEQUENCE: 49
HXQGTFTSDV SKXLDSXRAQ DFVRWLLEGX                                            30

SEQ ID NO: 50           moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = Lys, wherein the side chain of Lys is connected to
                        gamma-Glu-gamma-Glu-O2Oc-O2Oc-gamma-Glu-gamma-Glu-C18diacid
MOD_RES                 29
                        note = 2-Aminoisobutyric acid
SEQUENCE: 50
HXQGTFTSDV SKXLDSXRAQ DFVRWLLEXG                                            30
```

-continued

```
SEQ ID NO: 51            moltype = AA   length = 30
FEATURE                  Location/Qualifiers
source                   1..30
                         mol_type = protein
                         organism = Synthetic construct
MOD_RES                  2
                         note = 2-Aminoisobutyric acid
MOD_RES                  13
                         note = alpha-methyl-L-phenylalanine
MOD_RES                  17
                         note = Lys, wherein the side chain of Lys is connected to
                          gamma-Glu-gamma-Glu-O2Oc-O2Oc-gamma-Glu-gamma-Glu=C18diacid
MOD_RES                  29
                         note = 2-Aminoisobutyric acid
SEQUENCE: 51
HXQGTFTSDV SKXLDSXRAQ DFVRWLLEXG                                                30

SEQ ID NO: 52            moltype = AA   length = 30
FEATURE                  Location/Qualifiers
source                   1..30
                         mol_type = protein
                         organism = Synthetic construct
MOD_RES                  2
                         note = 2-Aminoisobutyric acid
MOD_RES                  13
                         note = alpha-methyl-L-phenylalanine
MOD_RES                  17
                         note = Lys, wherein the side chain of Lys is connected to
                          O2Oc-O2Oc-gamma-Glu-C18diacid
MOD_RES                  29
                         note = 2-Aminoisobutyric acid
SEQUENCE: 52
HXQGTFTSDV SKXLDTXRAQ DFVRWLLEXG                                                30

SEQ ID NO: 53            moltype = AA   length = 30
FEATURE                  Location/Qualifiers
source                   1..30
                         mol_type = protein
                         organism = Synthetic construct
MOD_RES                  2
                         note = 2-Aminoisobutyric acid
MOD_RES                  13
                         note = alpha-methyl-L-phenylalanine
MOD_RES                  17
                         note = Lys, wherein the side chain of Lys is connected to
                          O2Oc-O2Oc-gamma-Glu-C18diacid
MOD_RES                  29
                         note = 2-Aminoisobutyric acid
SEQUENCE: 53
HXQGTFTSDV SKXLDSXRAQ DFVAWLLEXG                                                30

SEQ ID NO: 54            moltype = AA   length = 30
FEATURE                  Location/Qualifiers
source                   1..30
                         mol_type = protein
                         organism = Synthetic construct
MOD_RES                  2
                         note = 2-Aminoisobutyric acid
MOD_RES                  13
                         note = alpha-methyl-L-phenylalanine
MOD_RES                  17
                         note = Lys, wherein the side chain of Lys is connected to
                          O2Oc-O2Oc-gamma-Glu-C18diacid
MOD_RES                  29
                         note = 2-Aminoisobutyric acid
SEQUENCE: 54
HXQGTFTSDV SKXLDSXRAR DFVAWLLEXG                                                30

SEQ ID NO: 55            moltype = AA   length = 30
FEATURE                  Location/Qualifiers
source                   1..30
                         mol_type = protein
                         organism = Synthetic construct
MOD_RES                  2
                         note = 2-Aminoisobutyric acid
MOD_RES                  13
                         note = alpha-methyl-L-phenylalanine
MOD_RES                  17
                         note = Lys, wherein the side chain of Lys is connected to
```

-continued

```
                          O2Oc-O2Oc-gamma-Glu-C18diacid
MOD_RES                   29
                          note = 2-Aminoisobutyric acid
SEQUENCE: 55
HXQGTFTSDV SKXLDSXRAR DFVQWLLEXG                                    30

SEQ ID NO: 56             moltype = AA   length = 30
FEATURE                   Location/Qualifiers
source                    1..30
                          mol_type = protein
                          organism = Synthetic construct
MOD_RES                   2
                          note = 2-Aminoisobutyric acid
MOD_RES                   13
                          note = alpha-methyl-L-phenylalanine
MOD_RES                   17
                          note = Lys, wherein the side chain of Lys is connected to
                           gamma-Glu-gamma-Glu-O2Oc-O2Oc-gamma-Glu-gamma-Glu-C18diacid
MOD_RES                   29
                          note = 2-Aminoisobutyric acid
SEQUENCE: 56
HXQGTFTSDV SKXLDSXRAR DFVRWLLEXG                                    30

SEQ ID NO: 57             moltype = AA   length = 31
FEATURE                   Location/Qualifiers
source                    1..31
                          mol_type = protein
                          organism = Synthetic construct
MOD_RES                   2
                          note = 2-Aminoisobutyric acid
MOD_RES                   17
                          note = Lys, wherein the side chain of Lys is connected to
                           O2Oc-O2Oc-gamma-Glu-C18diacid
MOD_RES                   13
                          note = alpha-methyl-L-phenylalanine
SEQUENCE: 57
HXQGTFTSDV SKXLDSXRAQ DFVRWLASRG I                                  31

SEQ ID NO: 58             moltype = AA   length = 29
FEATURE                   Location/Qualifiers
source                    1..29
                          mol_type = protein
                          organism = Synthetic construct
MOD_RES                   2
                          note = 2-Aminoisobutyric acid
MOD_RES                   13
                          note = alpha-methyl-L-phenylalanine
MOD_RES                   17
                          note = Lys, wherein the side chain of Lys is connected to
                           O2Oc-O2Oc-gamma-Glu-C18diacid
SEQUENCE: 58
HXQGTFTSDV SKXLDSXRAQ DFVRWLASR                                     29

SEQ ID NO: 59             moltype = AA   length = 30
FEATURE                   Location/Qualifiers
source                    1..30
                          mol_type = protein
                          organism = Synthetic construct
MOD_RES                   2
                          note = 2-Aminoisobutyric acid
MOD_RES                   13
                          note = alpha-methyl-L-phenylalanine
MOD_RES                   17
                          note = Lys, wherein the side chain of Lys is connected to
                           O2Oc-O2Oc-gamma-Glu-C18diacid
MOD_RES                   29
                          note = 2-Aminoisobutyric acid
SEQUENCE: 59
HXQGTFTSDV SKXLDSXRAQ DFVRWLEAXG                                    30

SEQ ID NO: 60             moltype = AA   length = 30
FEATURE                   Location/Qualifiers
source                    1..30
                          mol_type = protein
                          organism = Synthetic construct
MOD_RES                   2
                          note = 2-Aminoisobutyric acid
MOD_RES                   13
                          note = alpha-methyl-L-phenylalanine
```

-continued

```
MOD_RES                 17
                        note = Lys, wherein the side chain of Lys is connected to
                         O2Oc-O2Oc-gamma-Glu-C18diacid
MOD_RES                 29
                        note = 2-Aminoisobutyric acid
SEQUENCE: 60
HXQGTFTSDV SKXLDSXRAQ DFVRWIAEXG                                         30

SEQ ID NO: 61           moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = O2Oc-O2Oc-gamma-Glu-C18diacid
MOD_RES                 29
                        note = 2-Aminoisobutyric acid
SEQUENCE: 61
HXQGTFTSDV SKXLDSXRAQ DFVRWVVEXG                                         30

SEQ ID NO: 62           moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 14
                        note = alpha-methyl-L-phenylalanine
MOD_RES                 17
                        note = O2Oc-O2Oc-gamma-Glu-C18diacid
MOD_RES                 28
                        note = 2-Aminoisobutyric acid
SEQUENCE: 62
HXQGTFTSDV SKXLDSXRAQ DFVQWLLXTE                                         30

SEQ ID NO: 63           moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = O2Oc-O2Oc-gamma-Glu-C18diacid
MOD_RES                 28
                        note = 2-Aminoisobutyric acid
SEQUENCE: 63
HXQGTFTSDV SKXLDSXRAQ DFVRWLLXTE                                         30

SEQ ID NO: 64           moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = O2Oc-O2Oc-gamma-Glu-C18diacid
MOD_RES                 28
                        note = 2-Aminoisobutyric acid
SEQUENCE: 64
HXQGTFTSDV SKXLDSXRAQ DFVRWLLXE                                          29

SEQ ID NO: 65           moltype = AA  length = 29
FEATURE                 Location/Qualifiers
source                  1..29
                        mol_type = protein
                        organism = Synthetic construct
MOD_RES                 2
                        note = 2-Aminoisobutyric acid
```

-continued

```
MOD_RES                  13
                         note = alpha-methyl-L-phenylalanine
MOD_RES                  17
                         note = O2Oc-O2Oc-gamma-Glu-C20diacid
MOD_RES                  28
                         note = 2-Aminoisobutyric acid
SEQUENCE: 65
HXQGTFTSDV SKXLDSXRAQ DFVRWLLXE                                       29

SEQ ID NO: 66            moltype = AA   length = 29
FEATURE                  Location/Qualifiers
source                   1..29
                         mol_type = protein
                         organism = Synthetic construct
MOD_RES                  2
                         note = 2-Aminoisobutyric acid
MOD_RES                  13
                         note = alpha-methyl-L-phenylalanine
MOD_RES                  17
                         note = Lys, wherein the side chain of Lys is connected to
                          gamma-Glu-C18diacid
MOD_RES                  28
                         note = 2-Aminoisobutyric acid
SEQUENCE: 66
HXQGTFTSDV SKXLDSXRAQ DFVQWLLXT                                       29

SEQ ID NO: 67            moltype = AA   length = 30
FEATURE                  Location/Qualifiers
source                   1..30
                         mol_type = protein
                         organism = Synthetic construct
MOD_RES                  2
                         note = 2-Aminoisobutyric acid
MOD_RES                  13
                         note = alpha-methyl-L-phenylalanine
MOD_RES                  17
                         note = Lys, wherein the side chain of Lys is connected to
                          gamma-Glu-C18diacid
MOD_RES                  29
                         note = 2-Aminoisobutyric acid
SEQUENCE: 67
HXQGTFTSDV SKXLDSXRAQ DFVRWLLEXG                                      30

SEQ ID NO: 68            moltype = AA   length = 30
FEATURE                  Location/Qualifiers
source                   1..30
                         mol_type = protein
                         organism = Synthetic construct
MOD_RES                  2
                         note = 2-Aminoisobutyric acid
MOD_RES                  13
                         note = alpha-methyl-L-phenylalanine
MOD_RES                  17
                         note = Lys, wherein the side chain of Lys is connected to
                          O2Oc-O2Oc-gamma-Glu-C18diacid
MOD_RES                  30
                         note = 2-Aminoisobutyric acid
SEQUENCE: 68
HXQGTFTSDV SKXLDSXRAQ DFVRWLLEGX                                      30

SEQ ID NO: 69            moltype = AA   length = 30
FEATURE                  Location/Qualifiers
source                   1..30
                         mol_type = protein
                         organism = Synthetic construct
MOD_RES                  2
                         note = 2-Aminoisobutyric acid
MOD_RES                  13
                         note = alpha-methyl-L-phenylalanine
MOD_RES                  17
                         note = Lys, wherein the side chain of Lys is connected to
                          gamma-Glu-C18diacid
MOD_RES                  30
                         note = 2-Aminoisobutyric acid
SEQUENCE: 69
HXQGTFTSDV SKXLDSXRAQ DFVRWLLEGX                                      30

SEQ ID NO: 70            moltype = AA   length = 30
FEATURE                  Location/Qualifiers
```

-continued

```
source                1..30
                      mol_type = protein
                      organism = Synthetic construct
MOD_RES               2
                      note = 2-Aminoisobutyric acid
MOD_RES               13
                      note = alpha-methyl-L-phenylalanine
MOD_RES               17
                      note = Lys, wherein the side chain of Lys is connected to
                       O2Oc-O2Oc-gamma-Glu-C20diacid
MOD_RES               29
                      note = 2-Aminoisobutyric acid
SEQUENCE: 70
HXQGTFTSDV SKXLDSXRAQ DFVRWLLEXG                                         30

SEQ ID NO: 71         moltype = AA  length = 30
FEATURE               Location/Qualifiers
source                1..30
                      mol_type = protein
                      organism = Synthetic construct
MOD_RES               2
                      note = 2-Aminoisobutyric acid
MOD_RES               13
                      note = alpha-methyl-L-phenylalanine
MOD_RES               17
                      note = Lys, wherein the side chain of Lys is connected to
                       O2Oc-O2Oc-gamma-Glu-C20diacid
MOD_RES               29
                      note = 2-Aminoisobutyric acid
SEQUENCE: 71
HXQGTFTSDV SKXLDTXRAQ DFVRWLLEXG                                         30

SEQ ID NO: 72         moltype = AA  length = 30
FEATURE               Location/Qualifiers
source                1..30
                      mol_type = protein
                      organism = Synthetic construct
MOD_RES               2
                      note = 2-Aminoisobutyric acid
MOD_RES               13
                      note = alpha-methyl-L-phenylalanine
MOD_RES               17
                      note = Lys, wherein the side chain of Lys is connected to
                       O2Oc-O2Oc-gamma-Glu-C18diacid
MOD_RES               29
                      note = 2-Aminoisobutyric acid
SEQUENCE: 72
HXQGTFTSDV SKXLESXRAQ DFVRWLLEXG                                         30

SEQ ID NO: 73         moltype = AA  length = 30
FEATURE               Location/Qualifiers
source                1..30
                      mol_type = protein
                      organism = Synthetic construct
MOD_RES               2
                      note = 2-Aminoisobutyric acid
MOD_RES               13
                      note = alpha-methyl-L-phenylalanine
MOD_RES               17
                      note = Lys, wherein the side chain of Lys is connected to
                       O2Oc-O2Oc-gamma-Glu-C18diacid
MOD_RES               29
                      note = 2-Aminoisobutyric acid
SEQUENCE: 73
HXQGTFTSDV SKXLEAXRAR DFVAWLLEXG                                         30

SEQ ID NO: 74         moltype = AA  length = 30
FEATURE               Location/Qualifiers
source                1..30
                      mol_type = protein
                      organism = Synthetic construct
MOD_RES               2
                      note = 2-Aminoisobutyric acid
MOD_RES               13
                      note = alpha-methyl-L-phenylalanine
MOD_RES               17
                      note = Lys, wherein the side chain of Lys is connected to
                       O2Oc-O2Oc-gamma-Glu-C18diacid
MOD_RES               28
```

-continued

```
                               note = 2-Aminoisobutyric acid
SEQUENCE: 74
HXQGTFTSDV SKXLDSXRAQ DFVRWIAXTE                                      30

SEQ ID NO: 75          moltype = AA  length = 30
FEATURE                Location/Qualifiers
source                 1..30
                       mol_type = protein
                       organism = Synthetic construct
MOD_RES                2
                       note = 2-Aminoisobutyric acid
MOD_RES                13
                       note = alpha-methyl-L-phenylalanine
MOD_RES                17
                       note = Lys, wherein the side chain of Lys is connected to
                        O2Oc-O2Oc-gamma-Glu-C18diacid
MOD_RES                29
                       note = 2-Aminoisobutyric acid
SEQUENCE: 75
HXQGTFTSDV SKXLDSXRAQ DFVRWLLEXA                                      30

SEQ ID NO: 76          moltype = AA  length = 30
FEATURE                Location/Qualifiers
source                 1..30
                       mol_type = protein
                       organism = Synthetic construct
MOD_RES                2
                       note = 2-Aminoisobutyric acid
MOD_RES                13
                       note = alpha-methyl-L-phenylalanine
MOD_RES                17
                       note = Lys, wherein the side chain of Lys is connected to
                        O2Oc-O2Oc-gamma-Glu-C18diacid
MOD_RES                30
                       note = 2-Aminoisobutyric acid
SEQUENCE: 76
HXQGTFTSDV SKXLDSXRAQ DFVRWLLEAX                                      30

SEQ ID NO: 77          moltype = AA  length = 30
FEATURE                Location/Qualifiers
source                 1..30
                       mol_type = protein
                       organism = Synthetic construct
MOD_RES                2
                       note = 2-Aminoisobutyric acid
MOD_RES                23
                       note = alpha-methyl-L-phenylalanine
MOD_RES                17
                       note = Lys, wherein the side chain of Lys is connected to
                        O2Oc-O2Oc-gamma-Glu-C18diacid
MOD_RES                28
                       note = 2-Aminoisobutyric acid
SEQUENCE: 77
HXQGTFTSDV SKXLDSXRAR DFVRWLLXTE                                      30

SEQ ID NO: 78          moltype = AA  length = 30
FEATURE                Location/Qualifiers
source                 1..30
                       mol_type = protein
                       organism = Synthetic construct
MOD_RES                2
                       note = 2-Aminoisobutyric acid
MOD_RES                13
                       note = alpha-methyl-L-phenylalanine
MOD_RES                17
                       note = Lys, wherein the side chain of Lys is connected to
                        O2Oc-O2Oc-gamma-Glu-C18diacid
MOD_RES                28
                       note = 2-Aminoisobutyric acid
SEQUENCE: 78
HXQGTFTSDV SKXLDSXRAR DFVRWLLXTE                                      30

SEQ ID NO: 79          moltype = AA  length = 30
FEATURE                Location/Qualifiers
source                 1..30
                       mol_type = protein
                       organism = Synthetic construct
MOD_RES                2
                       note = 2-Aminoisobutyric acid
```

-continued

```
MOD_RES               13
                      note = alpha-methyl-L-phenylalanine
MOD_RES               17
                      note = Lys, wherein the side chain of Lys is connected to
                       O2Oc-O2Oc-gamma-Glu-C18diacid
MOD_RES               28
                      note = 2-Aminoisobutyric acid
SEQUENCE: 79
HXQGTFTSDV SKXLDSXRAR DFVAWLLXTE                                        30

SEQ ID NO: 80         moltype = AA  length = 30
FEATURE               Location/Qualifiers
source                1..30
                      mol_type = protein
                      organism = Synthetic construct
MOD_RES               2
                      note = 2-Aminoisobutyric acid
MOD_RES               13
                      note = alpha-methyl-L-phenylalanine
MOD_RES               17
                      note = Lys, wherein the side chain of Lys is connected to
                       O2Oc-O2Oc-gamma-Glu-C18diacid
MOD_RES               28
                      note = 2-Aminoisobutyric acid
SEQUENCE: 80
HXQGTFTSDV SKXLDSXRAL DFVRWLLXTE                                        30

SEQ ID NO: 81         moltype = AA  length = 30
FEATURE               Location/Qualifiers
source                1..30
                      mol_type = protein
                      organism = Synthetic construct
MOD_RES               2
                      note = 2-Aminoisobutyric acid
MOD_RES               13
                      note = alpha-methyl-L-phenylalanine
MOD_RES               17
                      note = Lys, wherein the side chain of Lys is connected to
                       O2Oc-O2Oc-gamma-Glu-C18diacid
MOD_RES               28
                      note = 2-Aminoisobutyric acid
SEQUENCE: 81
HXQGTFTSDV SKXLELXRAQ DFVRWLLXTE                                        30

SEQ ID NO: 82         moltype = AA  length = 30
FEATURE               Location/Qualifiers
source                1..30
                      mol_type = protein
                      organism = Synthetic construct
MOD_RES               2
                      note = 2-Aminoisobutyric acid
MOD_RES               13
                      note = alpha-methyl-L-phenylalanine
MOD_RES               17
                      note = Lys, wherein the side chain of Lys is connected to
                       O2Oc-O2Oc-gamma-Glu-C18diacid
MOD_RES               28
                      note = 2-Aminoisobutyric acid
SEQUENCE: 82
HXQGTFTSDV SKXLDEXRAQ DFVRWLLXTE                                        30

SEQ ID NO: 83         moltype = AA  length = 30
FEATURE               Location/Qualifiers
source                1..30
                      mol_type = protein
                      organism = Synthetic construct
MOD_RES               2
                      note = 2-Aminoisobutyric acid
MOD_RES               13
                      note = alpha-methyl-L-phenylalanine
MOD_RES               17
                      note = Lys, wherein the side chain of Lys is connected to
                       O2Oc-O2Oc-gamma-Glu-C18diacid
MOD_RES               28
                      note = 2-Aminoisobutyric acid
SEQUENCE: 83
HXQGTFTSDV SKXLDSXRAQ DFVRWLEXTE                                        30

SEQ ID NO: 84         moltype = AA  length = 30
```

-continued

```
FEATURE              Location/Qualifiers
source               1..30
                     mol_type = protein
                     organism = Synthetic construct
MOD_RES              2
                     note = 2-Aminoisobutyric acid
MOD_RES              13
                     note = alpha-methyl-L-phenylalanine
MOD_RES              17
                     note = Lys, wherein the side chain of Lys is connected to
                      O2Oc-O2Oc-gamma-Glu-C18diacid
MOD_RES              28
                     note = 2-Aminoisobutyric acid
SEQUENCE: 84
HXQGTFTSDV SKXLESXRAQ DFVRWLLXTE                                        30

SEQ ID NO: 85        moltype = AA   length = 29
FEATURE              Location/Qualifiers
source               1..29
                     mol_type = protein
                     organism = Synthetic construct
MOD_RES              2
                     note = 2-Aminoisobutyric acid
MOD_RES              13
                     note = alpha-methyl-L-phenylalanine
MOD_RES              17
                     note = Lys, wherein the side chain of Lys is connected to
                      O2Oc-O2Oc-gamma-Glu-C18diacid
MOD_RES              28
                     note = 2-Aminoisobutyric acid
SEQUENCE: 85
HXQGTFTSDV SKXLESXRAQ DFVRWLLXE                                         29

SEQ ID NO: 86        moltype = AA   length = 30
FEATURE              Location/Qualifiers
source               1..30
                     mol_type = protein
                     organism = Synthetic construct
MOD_RES              2
                     note = 2-Aminoisobutyric acid
MOD_RES              13
                     note = alpha-methyl-L-phenylalanine
MOD_RES              17
                     note = Lys, wherein the side chain of Lys is connected to
                      O2Oc-O2Oc-gamma-Glu-C18diacid
MOD_RES              28
                     note = 2-Aminoisobutyric acid
SEQUENCE: 86
HXQGTFTSDV SKXLDTXRAQ DFVRWLLXTE                                        30

SEQ ID NO: 87        moltype = AA   length = 30
FEATURE              Location/Qualifiers
source               1..30
                     mol_type = protein
                     organism = Synthetic construct
MOD_RES              2
                     note = 2-Aminoisobutyric acid
MOD_RES              13
                     note = alpha-methyl-L-phenylalanine
MOD_RES              17
                     note = Lys, wherein the side chain of Lys is connected to
                      O2Oc-O2Oc-gamma-Glu-C18diacid
MOD_RES              28
                     note = 2-Aminoisobutyric acid
SEQUENCE: 87
HXQGTFTSDV SKXLDSXRAQ DFVRWLAXTE                                        30

SEQ ID NO: 88        moltype = AA   length = 30
FEATURE              Location/Qualifiers
source               1..30
                     mol_type = protein
                     organism = Synthetic construct
MOD_RES              2
                     note = 2-Aminoisobutyric acid
MOD_RES              13
                     note = alpha-methyl-L-phenylalanine
MOD_RES              17
                     note = Lys, wherein the side chain of Lys is connected to
                      O2Oc-O2Oc-gamma-Glu-C18diacid
```

-continued

```
MOD_RES                 28
                        note = 2-Aminoisobutyric acid
SEQUENCE: 88
HXQGTFTSDV SKXLDSXRAQ DFVRWLLXTA                                    30

SEQ ID NO: 89           moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C18diacid
MOD_RES                 28
                        note = 2-Aminoisobutyric acid
SEQUENCE: 89
HXQGTFTSDV SKXLDSXRAQ DFVRWLLXTK                                    30

SEQ ID NO: 90           moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C18diacid
MOD_RES                 28
                        note = 2-Aminoisobutyric acid
SEQUENCE: 90
HXQGTFTSDV SKXLDKXRAQ DFVRWLLXTE                                    30

SEQ ID NO: 91           moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C18diacid
SEQUENCE: 91
HXQGTFTSDV SKXLDSXRAQ DFVRWLLEAG                                    30

SEQ ID NO: 92           moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C18diacid
MOD_RES                 29
                        note = 2-Aminoisobutyric acid
SEQUENCE: 92
HXQGTFTSDV SKXLDSXRAQ DFVRWLLAXG                                    30

SEQ ID NO: 93           moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 13
```

-continued

```
                         note = alpha-methyl-L-phenylalanine
MOD_RES                  17
                         note = Lys, wherein the side chain of Lys is connected to
                          O2Oc-O2Oc-C18diacid
MOD_RES                  29
                         note = 2-Aminoisobutyric acid
SEQUENCE: 93
HXQGTFTSDV SKXLDSXRAQ DFVRWLLEXG                                        30

SEQ ID NO: 94            moltype = AA  length = 30
FEATURE                  Location/Qualifiers
source                   1..30
                         mol_type = protein
                         organism = Synthetic construct
MOD_RES                  2
                         note = 2-Aminoisobutyric acid
MOD_RES                  13
                         note = alpha-methyl-L-phenylalanine
MOD_RES                  17
                         note = Lys, wherein the side chain of Lys is connected to
                          O2Oc-O2Oc-gamma-Glu-C18diacid
MOD_RES                  29
                         note = 2-Aminoisobutyric acid
SEQUENCE: 94
HXQGTFTSDV SKXLDKXRAQ DFVRWLLEXG                                        30

SEQ ID NO: 95            moltype = AA  length = 30
FEATURE                  Location/Qualifiers
source                   1..30
                         mol_type = protein
                         organism = Synthetic construct
MOD_RES                  2
                         note = 2-Aminoisobutyric acid
MOD_RES                  13
                         note = alpha-methyl-L-phenylalanine
MOD_RES                  17
                         note = Lys, wherein the side chain of Lys is connected to
                          O2Oc-O2Oc-gamma-Glu-C18diacid
MOD_RES                  29
                         note = 2-Aminoisobutyric acid
SEQUENCE: 95
HXQGTFTSDV SKXLDSXRAQ DFVRWLLEXK                                        30

SEQ ID NO: 96            moltype = AA  length = 30
FEATURE                  Location/Qualifiers
source                   1..30
                         mol_type = protein
                         organism = Synthetic construct
MOD_RES                  2
                         note = 2-Aminoisobutyric acid
MOD_RES                  13
                         note = alpha-methyl-L-phenylalanine
MOD_RES                  17
                         note = Lys, wherein the side chain of Lys is connected to
                          O2Oc-O2Oc-C18diacid
MOD_RES                  29
                         note = 2-Aminoisobutyric acid
SEQUENCE: 96
HXQGTFTSDV SKXLDKXRAQ DFVRWLLAXK                                        30

SEQ ID NO: 97            moltype = AA  length = 30
FEATURE                  Location/Qualifiers
source                   1..30
                         mol_type = protein
                         organism = Synthetic construct
MOD_RES                  2
                         note = 2-Aminoisobutyric acid
MOD_RES                  13
                         note = alpha-methyl-L-phenylalanine
MOD_RES                  17
                         note = Lys, wherein the side chain of Lys is connected to
                          O2Oc-O2Oc-gamma-Glu-C18diacid
MOD_RES                  29
                         note = 2-Aminoisobutyric acid
SEQUENCE: 97
HXQGTFTSDV SKXLDTXRAQ DFVRWLLEXG                                        30

SEQ ID NO: 98            moltype = AA  length = 30
FEATURE                  Location/Qualifiers
```

-continued

```
source                    1..30
                          mol_type = protein
                          organism = Synthetic construct
MOD_RES                   2
                          note = 2-Aminoisobutyric acid
MOD_RES                   13
                          note = alpha-methyl-L-phenylalanine
MOD_RES                   17
                          note = Lys, wherein the side chain of Lys is connected to
                           O2Oc-O2Oc-gamma-Glu-C18diacid
SEQUENCE: 98
HXQGTFTSDV SKXLDTXRAQ DFVRWLLEAG                                            30

SEQ ID NO: 99             moltype = AA  length = 30
FEATURE                   Location/Qualifiers
source                    1..30
                          mol_type = protein
                          organism = Synthetic construct
MOD_RES                   2
                          note = 2-Aminoisobutyric acid
MOD_RES                   13
                          note = alpha-methyl-L-phenylalanine
MOD_RES                   17
                          note = Lys, wherein the side chain of Lys is connected to
                           O2Oc-O2Oc-gamma-Glu-C18diacid
MOD_RES                   29
                          note = 2-Aminoisobutyric acid
SEQUENCE: 99
HXQGTFTSDV SKXLDTXRAR DFVRWLVEXG                                            30

SEQ ID NO: 100            moltype = AA  length = 30
FEATURE                   Location/Qualifiers
source                    1..30
                          mol_type = protein
                          organism = Synthetic construct
MOD_RES                   2
                          note = 2-Aminoisobutyric acid
MOD_RES                   13
                          note = alpha-methyl-L-phenylalanine
MOD_RES                   17
                          note = Lys, wherein the side chain of Lys is connected to
                           O2Oc-O2Oc-gamma-Glu-C18diacid
MOD_RES                   29
                          note = 2-Aminoisobutyric acid
SEQUENCE: 100
HXQGTFTSDV SKXLDTXRAR DFVQWLLEXG                                            30

SEQ ID NO: 101            moltype = AA  length = 30
FEATURE                   Location/Qualifiers
source                    1..30
                          mol_type = protein
                          organism = Synthetic construct
MOD_RES                   2
                          note = 2-Aminoisobutyric acid
MOD_RES                   13
                          note = alpha-methyl-L-phenylalanine
MOD_RES                   17
                          note = Lys, wherein the side chain of Lys is connected to
                           O2Oc-O2Oc-gamma-Glu-C18diacid
MOD_RES                   29
                          note = 2-Aminoisobutyric acid
SEQUENCE: 101
HXQGTFTSDV SKXLDTXRAR DFVRWLLEXG                                            30

SEQ ID NO: 102            moltype = AA  length = 30
FEATURE                   Location/Qualifiers
source                    1..30
                          mol_type = protein
                          organism = Synthetic construct
MOD_RES                   2
                          note = 2-Aminoisobutyric acid
MOD_RES                   13
                          note = alpha-methyl-L-phenylalanine
MOD_RES                   17
                          note = O2Oc-O2Oc-gamma-Glu-C20diacid
MOD_RES                   29
                          note = 2-Aminoisobutyric acid
SEQUENCE: 102
HXQGTFTSDV SKXLDTXRAQ DFVRWLVEXG                                            30
```

-continued

```
SEQ ID NO: 103          moltype = AA   length = 30
FEATURE                 Location/Qualifiers
source                  1..30
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C18diacid
MOD_RES                 29
                        note = 2-Aminoisobutyric acid
SEQUENCE: 103
HXQGTFTSDV SKXLDTXRAQ DFVRWLVEXG                                       30

SEQ ID NO: 104          moltype = AA   length = 29
FEATURE                 Location/Qualifiers
source                  1..29
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = O2Oc-O2Oc-gamma-Glu-C18diacid
MOD_RES                 29
                        note = 2-Aminoisobutyric acid
SEQUENCE: 104
HXQGTFTSDV SKXLDTXRAQ DFVRWLLXE                                        29

SEQ ID NO: 105          moltype = AA   length = 29
FEATURE                 Location/Qualifiers
source                  1..29
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = O2Oc-O2Oc-gamma-Glu-C20diacid
MOD_RES                 28
                        note = 2-Aminoisobutyric acid
SEQUENCE: 105
HXQGTFTSDV SKXLDTXRAQ DFVRWLLXE                                        29

SEQ ID NO: 106          moltype = AA   length = 29
FEATURE                 Location/Qualifiers
source                  1..29
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-gamma-Glu-C20diacid
MOD_RES                 28
                        note = 2-Aminoisobutyric acid
SEQUENCE: 106
HXQGTFTSDV SKXLDTXRAQ DFVRWLLXE                                        29

SEQ ID NO: 107          moltype = AA   length = 30
FEATURE                 Location/Qualifiers
source                  1..30
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C20diacid
```

-continued

```
MOD_RES                  29
                         note = 2-Aminoisobutyric acid
SEQUENCE: 107
HXQGTFTSDV SKXLDTXRAR DFVQWLLEXG                          30

SEQ ID NO: 108           moltype = AA  length = 29
FEATURE                  Location/Qualifiers
source                   1..29
                         mol_type = protein
                         organism = Synthetic construct
METAL                    2
                         note = 2-Aminoisobutyric acid
MOD_RES                  13
                         note = alpha-methyl-L-phenylalanine
MOD_RES                  17
                         note = Lys, wherein the side chain of Lys is connected to
                          O2Oc-O2Oc-gamma-Glu-C18diacid
MOD_RES                  28
                         note = 2-Aminoisobutyric acid
SEQUENCE: 108
HXQGTFTSDV SKXLDSXRAQ DFVRWLIXE                           29

SEQ ID NO: 109           moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  13
                         note = alpha-methyl-L-phenylalanine
MOD_RES                  17
                         note = Lys, wherein the side chain of Lys is connected to
                          O2Oc-O2Oc-gamma-Glu-C18diacid
MOD_RES                  28
                         note = 2-Aminoisobutyric acid
SEQUENCE: 109
HXQGTFTSDV SKXLDTXRAR DFVRWLLXE                           29

SEQ ID NO: 110           moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  13
                         note = alpha-methyl-L-phenylalanine
MOD_RES                  17
                         note = Lys, wherein the side chain of Lys is connected to
                          O2Oc-O2Oc-gamma-Glu-C18diacid
MOD_RES                  28
                         note = 2-Aminoisobutyric acid
SEQUENCE: 110
HXQGTFTSDV SKXLDTXRAR DFIAWLLXE                           29

SEQ ID NO: 111           moltype = AA  length = 30
FEATURE                  Location/Qualifiers
source                   1..30
                         mol_type = protein
                         organism = Synthetic construct
MOD_RES                  2
                         note = 2-Aminoisobutyric acid
MOD_RES                  13
                         note = alpha-methyl-L-phenylalanine
MOD_RES                  17
                         note = Lys, wherein the side chain of Lys is connected to
                          O2Oc-O2Oc-gamma-Glu-C18diacid
MOD_RES                  29
                         note = 2-Aminoisobutyric acid
SEQUENCE: 111
HXQGTFTSDV SKXLDTXRAR DFIAWLLEXG                          30

SEQ ID NO: 112           moltype = AA  length = 30
FEATURE                  Location/Qualifiers
source                   1..30
                         mol_type = protein
                         organism = Synthetic construct
MOD_RES                  2
```

```
                           note = 2-Aminoisobutyric acid
MOD_RES                    13
                           note = alpha-methyl-L-phenylalanine
MOD_RES                    17
                           note = Lys, wherein the side chain of Lys is connected to
                            O2Oc-O2Oc-gamma-Glu-C18diacid
MOD_RES                    29
                           note = 2-Aminoisobutyric acid
SEQUENCE: 112
HXQGTFTSDV SKXLDTXRAR DFVAWLLEXG                                      30

SEQ ID NO: 113             moltype = AA  length = 30
FEATURE                    Location/Qualifiers
source                     1..30
                           mol_type = protein
                           organism = Synthetic construct
MOD_RES                    2
                           note = 2-Aminoisobutyric acid
MOD_RES                    13
                           note = alpha-methyl-L-phenylalanine
MOD_RES                    17
                           note = Lys, wherein the side chain of Lys is connected to
                            O2Oc-O2Oc-gamma-Glu-C18diacid
MOD_RES                    29
                           note = 2-Aminoisobutyric acid
SEQUENCE: 113
HXQGTFTSDV SKXLDTXRAR DFVAWLEAXG                                      30

SEQ ID NO: 114             moltype = AA  length = 30
FEATURE                    Location/Qualifiers
source                     1..30
                           mol_type = protein
                           organism = Synthetic construct
MOD_RES                    2
                           note = 2-Aminoisobutyric acid
MOD_RES                    13
                           note = alpha-methyl-L-phenylalanine
MOD_RES                    17
                           note = Lys, wherein the side chain of Lys is connected to
                            O2Oc-O2Oc-gamma-Glu-C20diacid
MOD_RES                    29
                           note = 2-Aminoisobutyric acid
SEQUENCE: 114
HXQGTFTSDV SKXLDTXRAR DFVQWLEAXG                                      30

SEQ ID NO: 115             moltype = AA  length = 30
FEATURE                    Location/Qualifiers
source                     1..30
                           mol_type = protein
                           organism = Synthetic construct
MOD_RES                    2
                           note = 2-Aminoisobutyric acid
MOD_RES                    6
                           note = alpha-methyl-L-phenylalanine
MOD_RES                    13
                           note = diphenylpropanoic acid
MOD_RES                    17
                           note = Lys, wherein the side chain of Lys is connected to
                            polyethylene glycol 4-gamma-Glu-gamma-Glu-Palmitoyl
MOD_RES                    22
                           note = alpha-methyl-L-phenylalanine
MOD_RES                    25
                           note = 2-Aminoisobutyric acid
SEQUENCE: 115
HXQGSXTSDV SKXLDSXRAQ DXVEXLEAGG                                      30

SEQ ID NO: 116             moltype = AA  length = 30
FEATURE                    Location/Qualifiers
source                     1..30
                           mol_type = protein
                           organism = Synthetic construct
MOD_RES                    2
                           note = 2-Aminoisobutyric acid
MOD_RES                    6
                           note = alpha-methyl-L-phenylalanine
MOD_RES                    13
                           note = diphenylpropanoic acid
MOD_RES                    17
                           note = Lys, wherein the side chain of Lys is connected to
```

```
                        polyethylene glycol 2-polyethylene glycol
                        2-gamma-Glu-gamma-Glu-Stearoyl
MOD_RES                 22
                        note = alpha-methyl-L-phenylalanine
MOD_RES                 25
                        note = 2-Aminoisobutyric acid
SEQUENCE: 116
HXQGSXTSDV SKXLDSXAAQ DXVEXLEAGG                                        30

SEQ ID NO: 117          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = diphenylpropanoic acid
MOD_RES                 17
                        note = Lys, wherein the side chain of Lys is connected to
                         polyethylene glycol 2-polyethylene glycol
                         2-gamma-Glu-gamma-Glu-Stearoyl
MOD_RES                 22
                        note = alpha-methyl-L-phenylalanine
MOD_RES                 25
                        note = 2-Aminoisobutyric acid
SEQUENCE: 117
HXQGSXTSDV SKXLDSXAAQ DXVEXLANT                                         29

SEQ ID NO: 118          moltype = AA  length = 30
FEATURE                 Location/Qualifiers
source                  1..30
                        mol_type = protein
                        organism = Synthetic construct
MOD_RES                 6
                        note = alpha-methyl-L-phenylalanine
MOD_RES                 13
                        note = diphenylpropanoic acid
MOD_RES                 17
                        note = Lys, wherein the side chain of Lys is connected to
                         polyethylene glycol 2-polyethylene glycol
                         2-gamma-Glu-gamma-Glu-Stearoyl
MOD_RES                 22
                        note = alpha-methyl-L-phenylalanine
MOD_RES                 25
                        note = 2-Aminoisobutyric acid
SEQUENCE: 118
HSQGSXTSDV SKXLDSXAAQ DXVEXLEAGG                                        30

SEQ ID NO: 119          moltype = AA  length = 29
FEATURE                 Location/Qualifiers
source                  1..29
                        mol_type = protein
                        organism = Synthetic construct
MOD_RES                 6
                        note = alpha-methyl-L-phenylalanine
MOD_RES                 13
                        note = diphenylpropanoic acid
MOD_RES                 17
                        note = Lys, wherein the side chain of Lys is connected to
                         polyethylene glycol 2-polyethylene glycol
                         2-gamma-Glu-gamma-Glu-Stearoyl
MOD_RES                 22
                        note = alpha-methyl-L-phenylalanine
MOD_RES                 25
                        note = 2-Aminoisobutyric acid
SEQUENCE: 119
HSQGSXTSDV SKXLDSXAAQ DXVEXLANT                                         29

SEQ ID NO: 120          moltype = AA  length = 29
FEATURE                 Location/Qualifiers
source                  1..29
                        mol_type = protein
                        organism = Synthetic construct
MOD_RES                 6
                        note = alpha-methyl-L-phenylalanine
MOD_RES                 13
```

```
                          note = diphenylpropanoic acid
MOD_RES                   17
                          note = Lys, wherein the side chain of Lys is connected to
                           polyethylene glycol 2-polyethylene glycol
                           2-gamma-Glu-gamma-Glu-Stearoyl
MOD_RES                   22
                          note = alpha-methyl-L-phenylalanine
MOD_RES                   25
                          note = 2-Aminoisobutyric acid
SEQUENCE: 120
HSQGSXTSDV SKXLDSXAAQ DXVEXLISG                                          29

SEQ ID NO: 121            moltype = AA  length = 29
FEATURE                   Location/Qualifiers
source                    1..29
                          mol_type = protein
                          organism = Synthetic construct
MOD_RES                   6
                          note = alpha-methyl-L-phenylalanine
MOD_RES                   13
                          note = diphenylpropanoic acid
MOD_RES                   17
                          note = Lys, wherein the side chain of Lys is connected to
                           polyethylene glycol 2-polyethylene glycol
                           2-gamma-Glu-gamma-Glu-Stearoyl
MOD_RES                   22
                          note = alpha-methyl-L-phenylalanine
MOD_RES                   25
                          note = 2-Aminoisobutyric acid
SEQUENCE: 121
HSQGSXTSDV SKXLDSXAAQ DXVEXIANT                                          29

SEQ ID NO: 122            moltype = AA  length = 29
FEATURE                   Location/Qualifiers
source                    1..29
                          mol_type = protein
                          organism = Synthetic construct
MOD_RES                   6
                          note = alpha-methyl-L-phenylalanine
MOD_RES                   13
                          note = diphenylpropanoic acid
MOD_RES                   17
                          note = Lys, wherein the side chain of Lys is connected to
                           polyethylene glycol 2-polyethylene glycol
                           2-gamma-Glu-gamma-Glu-Stearoyl
MOD_RES                   22
                          note = alpha-methyl-L-phenylalanine
MOD_RES                   25
                          note = 2-Aminoisobutyric acid
SEQUENCE: 122
HSQGSXTSDV SKXLDSXAAQ DXVEXIINT                                          29

SEQ ID NO: 123            moltype = AA  length = 29
FEATURE                   Location/Qualifiers
source                    1..29
                          mol_type = protein
                          organism = Synthetic construct
MOD_RES                   6
                          note = alpha-methyl-L-phenylalanine
MOD_RES                   13
                          note = diphenylpropanoic acid
MOD_RES                   17
                          note = Lys, wherein the side chain of Lys is connected to
                           polyethylene glycol 2-polyethylene glycol
                           2-gamma-Glu-gamma-Glu-Stearoyl
MOD_RES                   22
                          note = alpha-methyl-L-phenylalanine
MOD_RES                   25
                          note = 2-Aminoisobutyric acid
SEQUENCE: 123
HSQGSXTSDV SKXLDSXAAQ DXVEXLLNT                                          29

SEQ ID NO: 124            moltype = AA  length = 29
FEATURE                   Location/Qualifiers
source                    1..29
                          mol_type = protein
                          organism = Synthetic construct
MOD_RES                   26
                          note = cyclohexylpropanoic acid
```

-continued

```
SEQUENCE: 124
HSQGSXTSDV SKXLDSXAAQ DXVEXXANT                                          29

SEQ ID NO: 125        moltype = AA  length = 30
FEATURE               Location/Qualifiers
source                1..30
                      mol_type = protein
                      organism = Synthetic construct
MOD_RES               6
                      note = alpha-methyl-L-phenylalanine
MOD_RES               13
                      note = diphenylpropanoic acid
MOD_RES               17
                      note = Lys, wherein the side chain of Lys is connected to
                       polyethylene glycol 2-polyethylene glycol
                       2-gamma-Glu-gamma-Glu-Stearoyl
MOD_RES               22
                      note = alpha-methyl-L-phenylalanine
MOD_RES               25
                      note = 2-Aminoisobutyric acid
SEQUENCE: 125
HSQGSXTSDV SKXLDSXAAQ DXVEXVVEGG                                         30

SEQ ID NO: 126        moltype = AA  length = 28
FEATURE               Location/Qualifiers
source                1..28
                      mol_type = protein
                      organism = Synthetic construct
MOD_RES               6
                      note = alpha-methyl-L-phenylalanine
MOD_RES               13
                      note = diphenylpropanoic acid
MOD_RES               17
                      note = Lys, wherein the side chain of Lys is connected to
                       polyethylene glycol 2-polyethylene glycol
                       2-gamma-Glu-gamma-Glu-Stearoyl
MOD_RES               22
                      note = alpha-methyl-L-phenylalanine
MOD_RES               25
                      note = diphenylpropanoic acid
SEQUENCE: 126
HSQGSXTSDV SKXLDSXAAQ DXVQXLEA                                           28

SEQ ID NO: 127        moltype = AA  length = 29
FEATURE               Location/Qualifiers
source                1..29
                      mol_type = protein
                      organism = Synthetic construct
MOD_RES               6
                      note = alpha-methyl-L-phenylalanine
MOD_RES               13
                      note = diphenylpropanoic acid
MOD_RES               17
                      note = Lys, wherein the side chain of Lys is connected to
                       polyethylene glycol 4-gamma-Glu-gamma-Glu-Stearoyl
MOD_RES               22
                      note = alpha-methyl-L-phenylalanine
MOD_RES               25
                      note = 2-Aminoisobutyric acid
SEQUENCE: 127
HSQGSXTSDV SKXLDSXAAQ DXVEXIINT                                          29

SEQ ID NO: 128        moltype = AA  length = 29
FEATURE               Location/Qualifiers
source                1..29
                      mol_type = protein
                      organism = Synthetic construct
MOD_RES               6
                      note = alpha-methyl-L-phenylalanine
MOD_RES               13
                      note = diphenylpropanoic acid
MOD_RES               17
                      note = Lys, wherein the side chain of Lys is connected to
                       polyethylene glycol 4-gamma-Glu-gamma-Glu-Stearoyl
MOD_RES               22
                      note = alpha-methyl-L-phenylalanine
MOD_RES               25
                      note = 2-Aminoisobutyric acid
SEQUENCE: 128
```

```
HSQGSXTSDV SKXLDSXAAQ DXVEXIINT                                          29

SEQ ID NO: 129          moltype = AA  length = 29
FEATURE                 Location/Qualifiers
source                  1..29
                        mol_type = protein
                        organism = Synthetic construct
MOD_RES                 6
                        note = alpha-methyl-L-phenylalanine
MOD_RES                 13
                        note = diphenylpropanoic acid
MOD_RES                 17
                        note = Lys, wherein the side chain of Lys is connected
                         to-polyethylene glycol 8-gamma-Glu-gamma-Glu-Stearoyl
MOD_RES                 22
                        note = alpha-methyl-L-phenylalanine
MOD_RES                 25
                        note = 2-Aminoisobutyric acid
SEQUENCE: 129
HSQGSXTSDV SKXLDSXAAQ DXVEXIINT                                          29

SEQ ID NO: 130          moltype = AA  length = 29
FEATURE                 Location/Qualifiers
source                  1..29
                        mol_type = protein
                        organism = Synthetic construct
MOD_RES                 6
                        note = alpha-methyl-L-phenylalanine
MOD_RES                 13
                        note = diphenylpropanoic acid
MOD_RES                 17
                        note = Lys, wherein the side chain of Lys is connected to
                         polyethylene glycol 12-gamma-Glu-gamma-Glu-Stearoyl
MOD_RES                 22
                        note = alpha-methyl-L-phenylalanine
MOD_RES                 25
                        note = 2-Aminoisobutyric acid
SEQUENCE: 130
HSQGSXTSDV SKXLDSXAAQ DXVEXIINT                                          29

SEQ ID NO: 131          moltype = AA  length = 29
FEATURE                 Location/Qualifiers
source                  1..29
                        mol_type = protein
                        organism = Synthetic construct
MOD_RES                 6
                        note = alpha-methyl-L-phenylalanine
MOD_RES                 13
                        note = diphenylpropanoic acid
MOD_RES                 17
                        note = Lys, wherein the side chain of Lys is connected to
                         gamma-Glu-gamma-Glu-polyethylene glycol 2-polyethylene
                         glycol 2-Stearoyl
MOD_RES                 25
                        note = 2-Aminoisobutyric acid
MOD_RES                 22
                        note = alpha-methyl-L-phenylalanine
SEQUENCE: 131
HSQGSXTSDV SKXLDSXAAQ DXVEXIINT                                          29

SEQ ID NO: 132          moltype = AA  length = 29
FEATURE                 Location/Qualifiers
source                  1..29
                        mol_type = protein
                        organism = Synthetic construct
MOD_RES                 6
                        note = alpha-methyl-L-phenylalanine
MOD_RES                 13
                        note = diphenylpropanoic acid
MOD_RES                 17
                        note = Lys, wherein the side chain of Lys is connected to
                         gamma-Glu- polyethylene glycol 2-gamma-Glu-polyethylene
                         glycol 2-Stearoyl
MOD_RES                 22
                        note = alpha-methyl-L-phenylalanine
MOD_RES                 25
                        note = 2-Aminoisobutyric acid
SEQUENCE: 132
HSQGSXTSDV SKXLDSXAAQ DXVEXIINT                                          29
```

```
SEQ ID NO: 133          moltype = AA   length = 29
FEATURE                 Location/Qualifiers
source                  1..29
                        mol_type = protein
                        organism = Synthetic construct
MOD_RES                 6
                        note = alpha-methyl-L-phenylalanine
MOD_RES                 13
                        note = diphenylpropanoic acid
MOD_RES                 17
                        note = Lys, wherein the side chain of Lys is connected to
                         polyethylene glycol 2-gamma-Glu-polyethylene glycol
                         2-gamma-Glu-Stearoyl
MOD_RES                 22
                        note = alpha-methyl-L-phenylalanine
MOD_RES                 25
                        note = 2-Aminoisobutyric acid
SEQUENCE: 133
HSQGSXTSDV SKXLDSXAAQ DXVEXIINT                                        29

SEQ ID NO: 134          moltype = AA   length = 29
FEATURE                 Location/Qualifiers
source                  1..29
                        mol_type = protein
                        organism = Synthetic construct
MOD_RES                 6
                        note = alpha-methyl-L-phenylalanine
MOD_RES                 13
                        note = diphenylpropanoic acid
MOD_RES                 17
                        note = Lys, wherein the side chain of Lys is connected to
                         polyethylene glycol 2-polyethylene glycol
                         2-gamma-Glu-gamma-Glu-Lauryl
MOD_RES                 22
                        note = alpha-methyl-L-phenylalanine
MOD_RES                 25
                        note = 2-Aminoisobutyric acid
SEQUENCE: 134
HSQGSXTSDV SKXLDSXAAQ DXVEXIINT                                        29

SEQ ID NO: 135          moltype = AA   length = 29
FEATURE                 Location/Qualifiers
source                  1..29
                        mol_type = protein
                        organism = Synthetic construct
MOD_RES                 6
                        note = alpha-methyl-L-phenylalanine
MOD_RES                 13
                        note = diphenylpropanoic acid
MOD_RES                 17
                        note = Lys, wherein the side chain of Lys is connected to
                         polyethylene glycol 2-polyethylene glycol
                         2-gamma-Glu-gamma-Glu-Myristyl
MOD_RES                 22
                        note = alpha-methyl-L-phenylalanine
MOD_RES                 25
                        note = 2-Aminoisobutyric acid
SEQUENCE: 135
HSQGSXTSDV SKXLDSXAAQ DXVEXIINT                                        29

SEQ ID NO: 136          moltype = AA   length = 29
FEATURE                 Location/Qualifiers
source                  1..29
                        mol_type = protein
                        organism = Synthetic construct
MOD_RES                 6
                        note = alpha-methyl-L-phenylalanine
MOD_RES                 13
                        note = diphenylpropanoic acid
MOD_RES                 17
                        note = Lys, wherein the side chain of Lys is connected to
                         polyethylene glycol 2-polyethylene glycol
                         2-gamma-Glu-gamma-Glu-Stearoyl
MOD_RES                 22
                        note = alpha-methyl-L-phenylalanine
MOD_RES                 25
                        note = 2-Aminoisobutyric acid
SEQUENCE: 136
```

-continued

```
HSQGSXTSDV SKXLDSXAAQ DXVEXIINT                                   29

SEQ ID NO: 137        moltype = AA   length = 29
FEATURE               Location/Qualifiers
source                1..29
                      mol_type = protein
                      organism = Synthetic construct
MOD_RES               6
                      note = alpha-methyl-L-phenylalanine
MOD_RES               13
                      note = diphenylpropanoic acid
MOD_RES               17
                      note = Lys, wherein the side chain of Lys is connected to
                       polyethylene glycol 2-polyethylene glycol
                       2-gamma-Glu-gamma-Glu-C18diacid
MOD_RES               22
                      note = alpha-methyl-L-phenylalanine
MOD_RES               25
                      note = 2-Aminoisobutyric acid
SEQUENCE: 137
HSQGSXTSDV SKXLDSXAAQ DXVEXIINT                                   29

SEQ ID NO: 138        moltype = AA   length = 28
FEATURE               Location/Qualifiers
source                1..28
                      mol_type = protein
                      organism = Synthetic construct
MOD_RES               6
                      note = alpha-methyl-L-phenylalanine
MOD_RES               13
                      note = diphenylpropanoic acid
MOD_RES               17
                      note = Lys, wherein the side chain of Lys is connected to
                       polyethylene glycol 2-polyethylene glycol
                       2-gamma-Glu-gamma-Glu-Stearyl
MOD_RES               22
                      note = alpha-methyl-L-phenylalanine
MOD_RES               25
                      note = 2-Aminoisobutyric acid
SEQUENCE: 138
HXQGSXTSDV SKXLDSXAAQ DXVQXIAN                                    28

SEQ ID NO: 139        moltype = AA   length = 28
FEATURE               Location/Qualifiers
source                1..28
                      mol_type = protein
                      organism = Synthetic construct
MOD_RES               2
                      note = 2-Aminoisobutyric acid
MOD_RES               6
                      note = alpha-methyl-L-phenylalanine
MOD_RES               13
                      note = diphenylpropanoic acid
MOD_RES               17
                      note = Lys, wherein the side chain of Lys is connected to
                       polyethylene glycol 2-polyethylene glycol
                       2-gamma-Glu-Palmitoyl
MOD_RES               22
                      note = alpha-methyl-L-phenylalanine
MOD_RES               25
                      note = 2-Aminoisobutyric acid
SEQUENCE: 139
HXQGSXTSDV SKXLDSXAAQ DXVQXIAN                                    28

SEQ ID NO: 140        moltype = AA   length = 29
FEATURE               Location/Qualifiers
source                1..29
                      mol_type = protein
                      organism = Synthetic construct
MOD_RES               2
                      note = 2-Aminoisobutyric acid
MOD_RES               13
                      note = alpha-methyl-L-phenylalanine
MOD_RES               17
                      note = Lys, wherein the side chain of Lys is connected to
                       polyethylene glycol 4-gamma-Glu-Palmitoy
MOD_RES               22
                      note = alpha-methyl-L-phenylalanine
MOD_RES               27
```

-continued

```
                              note = aminohexanoic acid
SEQUENCE: 140
HXQGTFTSDV SKXLDVXRAQ DXVEXLXET                                    29

SEQ ID NO: 141            moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   13
                          note = alpha-methyl-L-phenylalanine
MOD_RES                   17
                          note = Lys, wherein the side chain of Lys is connected to
                           polyethylene glycol 2-polyethylene glycol
                           2-gamma-Glu-gamma-Glu-Stearyl
MOD_RES                   22
                          note = alpha-methyl-L-phenylalanine
MOD_RES                   25
                          note = 2-Aminoisobutyric acid
MOD_RES                   27
                          note = aminohexanoic acid
SEQUENCE: 141
HXQGTFTSDV SKXLDSXRAQ DXVQXLXET                                    29

SEQ ID NO: 142            moltype = AA  length = 30
FEATURE                   Location/Qualifiers
source                    1..30
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   17
                          note = Lys, wherein the side chain of Lys is connected to
                           polyethylene glycol 4-gamma-Glu-gamma-Glu-Stearoyl
MOD_RES                   22
                          note = alpha-methyl-L-phenylalanine
MOD_RES                   25
                          note = 2-Aminoisobutyric acid
SEQUENCE: 142
HXQGSXTSDV SKXLDSXRAQ DXVEXLEAGG                                   30

SEQ ID NO: 143            moltype = AA  length = 30
FEATURE                   Location/Qualifiers
source                    1..30
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   17
                          note = polyethylene glycol 4-gamma-Glu-gamma-Glu-Stearoyl
MOD_RES                   22
                          note = alpha-methyl-L-phenylalanine
MOD_RES                   25
                          note = 2-Aminoisobutyric acid
SEQUENCE: 143
HXQGSXTSDV SKXLDSXAAQ DXVEXLEAGG                                   30

SEQ ID NO: 144            moltype = AA  length = 30
FEATURE                   Location/Qualifiers
source                    1..30
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   17
```

-continued

```
                              note = Lys, wherein the side chain of Lys is connected to
                               polyethylene glycol 4-gamma-Glu-gamma-Glu- Palmitoyl
MOD_RES                       22
                              note = alpha-methyl-L-phenylalanine
MOD_RES                       25
                              note = 2-Aminoisobutyric acid
SEQUENCE: 144
HXQGSXTSDV SKXLDSXAAQ DXVEXLEAGG                                    30

SEQ ID NO: 145                moltype = AA  length = 28
FEATURE                       Location/Qualifiers
source                        1..28
                              mol_type = protein
                              organism = Synthetic construct
MOD_RES                       2
                              note = 2-Aminoisobutyric acid
MOD_RES                       6
                              note = alpha-methyl-L-phenylalanine
MOD_RES                       13
                              note = alpha-methyl-L-phenylalanine
MOD_RES                       17
                              note = Lys, wherein the side chain of Lys is connected to
                               polyethylene glycol 2- polyethylene glycol
                               2-gamma-Glu-gamma-Glu- Palmitoyl
MOD_RES                       22
                              note = alpha-methyl-L-phenylalanine
MOD_RES                       25
                              note = 2-Aminoisobutyric acid
SEQUENCE: 145
HXQGSXTSDV SKXLDSXAAQ DXVQXIAN                                      28

SEQ ID NO: 146                moltype = AA  length = 30
FEATURE                       Location/Qualifiers
source                        1..30
                              mol_type = protein
                              organism = Synthetic construct
MOD_RES                       2
                              note = 2-Aminoisobutyric acid
MOD_RES                       6
                              note = alpha-methyl-L-phenylalanine
MOD_RES                       13
                              note = alpha-methyl-L-phenylalanine
MOD_RES                       17
                              note = Lys, wherein the side chain of Lys is connected to
                               polyethylene glycol 2- polyethylene glycol
                               2-gamma-Glu-gamma-Glu- Stearoyl
MOD_RES                       18
                              note = dimethylGln
MOD_RES                       22
                              note = alpha-methyl-L-phenylalanine
MOD_RES                       25
                              note = 2-Aminoisobutyric acid
SEQUENCE: 146
HXQGSXTSDV SKXLDSXAQD XXVEXLEAGG                                    30

SEQ ID NO: 147                moltype = AA  length = 28
FEATURE                       Location/Qualifiers
source                        1..28
                              mol_type = protein
                              organism = Synthetic construct
MOD_RES                       2
                              note = 2-Aminoisobutyric acid
MOD_RES                       6
                              note = alpha-methyl-L-phenylalanine
MOD_RES                       13
                              note = alpha-methyl-L-phenylalanine
MOD_RES                       17
                              note = Lys, wherein the side chain of Lys is connected to
                               polyethylene glycol 2- polyethylene glycol
                               2-gamma-Glu-gamma-Glu- Palmitoy
SEQUENCE: 147
HXQGSXTSDV SKXLDSXAAQ DIVQIIAN                                      28

SEQ ID NO: 148                moltype = AA  length = 30
FEATURE                       Location/Qualifiers
source                        1..30
                              mol_type = protein
                              organism = Synthetic construct
MOD_RES                       2
```

-continued

```
                              note = 2-Aminoisobutyric acid
MOD_RES                       6
                              note = alpha-methyl-L-phenylalanine
MOD_RES                       13
                              note = alpha-methyl-L-phenylalanine
MOD_RES                       17
                              note = Lys, wherein the side chain of Lys is connected to
                               polyethylene glycol 2- polyethylene glycol
                               2-gamma-Glu-gamma-Glu-Stearoyl
MOD_RES                       22
                              note = alpha-methyl-L-phenylalanine
MOD_RES                       25
                              note = 2-Aminoisobutyric acid
SEQUENCE: 148
HXQGSXTSDV SKXLDSXAAQ DXVQXVVEGG                                              30

SEQ ID NO: 149                moltype = AA  length = 29
FEATURE                       Location/Qualifiers
source                        1..29
                              mol_type = protein
                              organism = Synthetic construct
MOD_RES                       2
                              note = 2-Aminoisobutyric acid
MOD_RES                       6
                              note = alpha-methyl-L-phenylalanine
MOD_RES                       13
                              note = alpha-methyl-L-phenylalanine
MOD_RES                       17
                              note = Lys, wherein the side chain of Lys is connected to
                               polyethylene glycol 2- polyethylene glycol
                               2-gamma-Glu-gamma-Glu-Stearoyl
MOD_RES                       22
                              note = alpha-methyl-L-phenylalanine
MOD_RES                       25
                              note = 2-Aminoisobutyric acid
SEQUENCE: 149
HXQGSXTSDV SKXLDSXAAQ DXVQXLISG                                               29

SEQ ID NO: 150                moltype = AA  length = 30
FEATURE                       Location/Qualifiers
source                        1..30
                              mol_type = protein
                              organism = Synthetic construct
MOD_RES                       6
                              note = alpha-methyl-L-phenylalanine
MOD_RES                       13
                              note = alpha-methyl-L-phenylalanine
MOD_RES                       17
                              note = Lys, wherein the side chain of Lys is connected to
                               polyethylene glycol 2- polyethylene glycol
                               2-gamma-Glu-gamma-Glu-Stearoyl
MOD_RES                       22
                              note = alpha-methyl-L-phenylalanine
MOD_RES                       25
                              note = 2-Aminoisobutyric acid
SEQUENCE: 150
HSQGSXTSDV SKXLDSXAAQ DXVQXLEAGG                                              30

SEQ ID NO: 151                moltype = AA  length = 30
FEATURE                       Location/Qualifiers
source                        1..30
                              mol_type = protein
                              organism = Synthetic construct
MOD_RES                       6
                              note = alpha-methyl-L-phenylalanine
MOD_RES                       13
                              note = alpha-methyl-L-phenylalanine
MOD_RES                       17
                              note = Lys, wherein the side chain of Lys is connected to
                               polyethylene glycol 2- polyethylene glycol
                               2-gamma-Glu-gamma-Glu-Palmitoyl
MOD_RES                       22
                              note = alpha-methyl-L-phenylalanine
MOD_RES                       25
                              note = 2-Aminoisobutyric acid
SEQUENCE: 151
HSQGSXTSDV SKXLDSXAAQ DXVQXLEAGG                                              30

SEQ ID NO: 152                moltype = AA  length = 30
```

-continued

```
FEATURE               Location/Qualifiers
source                1..30
                      mol_type = protein
                      organism = Synthetic construct
MOD_RES               6
                      note = alpha-methyl-L-phenylalanine
MOD_RES               13
                      note = alpha-methyl-L-phenylalanine
MOD_RES               17
                      note = Lys, wherein the side chain of Lys is connected to
                       polyethylene glycol 2- polyethylene glycol
                       2-gamma-Glu-gamma-Glu- Margaroyl
MOD_RES               22
                      note = alpha-methyl-L-phenylalanine
MOD_RES               25
                      note = 2-Aminoisobutyric acid
SEQUENCE: 152
HSQGSXTSDV SKXLDSXAAQ DXVQXLEAGG                                         30

SEQ ID NO: 153        moltype = AA  length = 30
FEATURE               Location/Qualifiers
source                1..30
                      mol_type = protein
                      organism = Synthetic construct
MOD_RES               6
                      note = alpha-methyl-L-phenylalanine
MOD_RES               13
                      note = alpha-methyl-L-phenylalanine
MOD_RES               17
                      note = Lys, wherein the side chain of Lys is connected to
                       polyethylene glycol 2- polyethylene glycol
                       2-gamma-Glu-gamma-Glu- Stearoyl
MOD_RES               22
                      note = alpha-methyl-L-phenylalanine
MOD_RES               25
                      note = 2-Aminoisobutyric acid
SEQUENCE: 153
HSQGSXTSDV SKXLDSXAAQ DXVEXLEAGG                                         30

SEQ ID NO: 154        moltype = AA  length = 29
FEATURE               Location/Qualifiers
source                1..29
                      mol_type = protein
                      organism = Synthetic construct
MOD_RES               6
                      note = alpha-methyl-L-phenylalanine
MOD_RES               13
                      note = alpha-methyl-L-phenylalanine
MOD_RES               17
                      note = Lys, wherein the side chain of Lys is connected to
                       polyethylene glycol 2- polyethylene glycol
                       2-gamma-Glu-gamma-Glu- Stearoyl
MOD_RES               22
                      note = alpha-methyl-L-phenylalanine
MOD_RES               25
                      note = 2-Aminoisobutyric acid
SEQUENCE: 154
HSQGSXTSDV SKXLDSXAAQ DXVQXIANT                                          29

SEQ ID NO: 155        moltype = AA  length = 29
FEATURE               Location/Qualifiers
source                1..29
                      mol_type = protein
                      organism = Synthetic construct
MOD_RES               6
                      note = alpha-methyl-L-phenylalanine
MOD_RES               13
                      note = alpha-methyl-L-phenylalanine
MOD_RES               17
                      note = Lys, wherein the side chain of Lys is connected to
                       polyethylene glycol 2- polyethylene glycol
                       2-gamma-Glu-gamma-Glu- Stearoyl
MOD_RES               22
                      note = alpha-methyl-L-phenylalanine
MOD_RES               25
                      note = 2-Aminoisobutyric acid
SEQUENCE: 155
HSQGSXTSDV SKXLDSXAAQ DXVQXIINT                                          29
```

-continued

```
SEQ ID NO: 156            moltype = AA  length = 29
FEATURE                   Location/Qualifiers
source                    1..29
                          mol_type = protein
                          organism = Synthetic construct
MOD_RES                   6
                          note = alpha-methyl-L-phenylalanine
MOD_RES                   13
                          note = alpha-methyl-L-phenylalanine
MOD_RES                   17
                          note = Lys, wherein the side chain of Lys is connected to
                           polyethylene glycol 2- polyethylene glycol
                           2-gamma-Glu-gamma-Glu- Stearoyl
MOD_RES                   22
                          note = alpha-methyl-L-phenylalanine
MOD_RES                   25
                          note = 2-Aminoisobutyric acid
SEQUENCE: 156
HSQGSXTSDV SKXLDSXAAQ DXVQXLLNT                                         29

SEQ ID NO: 157            moltype = AA  length = 30
FEATURE                   Location/Qualifiers
source                    1..30
                          mol_type = protein
                          organism = Synthetic construct
MOD_RES                   6
                          note = alpha-methyl-L-phenylalanine
MOD_RES                   13
                          note = alpha-methyl-L-phenylalanine
MOD_RES                   17
                          note = Lys, wherein the side chain of Lys is connected to
                           polyethylene glycol 2- polyethylene glycol
                           2-gamma-Glu-gamma-Glu- Stearoyl
MOD_RES                   22
                          note = alpha-methyl-L-phenylalanine
MOD_RES                   25
                          note = 2-Aminoisobutyric acid
SEQUENCE: 157
HSQGSXTSDV SKXLDSXAAQ DXVQXVVEGG                                        30

SEQ ID NO: 158            moltype = AA  length = 28
FEATURE                   Location/Qualifiers
source                    1..28
                          mol_type = protein
                          organism = Synthetic construct
MOD_RES                   6
                          note = alpha-methyl-L-phenylalanine
MOD_RES                   13
                          note = alpha-methyl-L-phenylalanine
MOD_RES                   17
                          note = Lys, wherein the side chain of Lys is connected to
                           polyethylene glycol 2- polyethylene glycol
                           2-gamma-Glu-gamma-Glu- Stearoyl
MOD_RES                   22
                          note = alpha-methyl-L-phenylalanine
MOD_RES                   25
                          note = 2-Aminoisobutyric acid
SEQUENCE: 158
HSQGSXTSDV SKXLDSXAAQ DXVQXIAN                                          28

SEQ ID NO: 159            moltype = AA  length = 28
FEATURE                   Location/Qualifiers
source                    1..28
                          mol_type = protein
                          organism = Synthetic construct
MOD_RES                   6
                          note = alpha-methyl-L-phenylalanine
MOD_RES                   13
                          note = alpha-methyl-L-phenylalanine
MOD_RES                   17
                          note = Lys, wherein the side chain of Lys is connected to
                           polyethylene glycol 2- polyethylene glycol
                           2-gamma-Glu-gamma-Glu- Palmitoyl
MOD_RES                   22
                          note = alpha-methyl-L-phenylalanine
MOD_RES                   25
                          note = 2-Aminoisobutyric acid
SEQUENCE: 159
HSQGSXTSDV SKXLDSXAAQ DXVQXIAN                                          28
```

-continued

```
SEQ ID NO: 160          moltype = AA   length = 28
FEATURE                 Location/Qualifiers
source                  1..28
                        mol_type = protein
                        organism = Synthetic construct
MOD_RES                 6
                        note = alpha-methyl-L-phenylalanine
MOD_RES                 13
                        note = alpha-methyl-L-phenylalanine
MOD_RES                 17
                        note = Lys, wherein the side chain of Lys is connected to
                         polyethylene glycol 2- polyethylene glycol
                         2-gamma-Glu-gamma-Glu- Margaroyl
MOD_RES                 22
                        note = alpha-methyl-L-phenylalanine
MOD_RES                 25
                        note = 2-Aminoisobutyric acid
SEQUENCE: 160
HSQGSXTSDV SKXLDSXAAQ DXVQXIAN                                     28

SEQ ID NO: 161          moltype = AA   length = 28
FEATURE                 Location/Qualifiers
source                  1..28
                        mol_type = protein
                        organism = Synthetic construct
MOD_RES                 6
                        note = alpha-methyl-L-phenylalanine
MOD_RES                 13
                        note = alpha-methyl-L-phenylalanine
MOD_RES                 17
                        note = Lys, wherein the side chain of Lys is connected to
                         polyethylene glycol 2- polyethylene glycol
                         2-gamma-Glu-gamma-Glu- Palmitoyl
MOD_RES                 22
                        note = alpha-methyl-L-phenylalanine
SEQUENCE: 161
HSQGSXTSDV SKXLDSXAAQ DXVQIIAN                                     28

SEQ ID NO: 162          moltype = AA   length = 28
FEATURE                 Location/Qualifiers
source                  1..28
                        mol_type = protein
                        organism = Synthetic construct
MOD_RES                 6
                        note = alpha-methyl-L-phenylalanine
MOD_RES                 13
                        note = alpha-methyl-L-phenylalanine
MOD_RES                 17
                        note = Lys, wherein the side chain of Lys is connected to
                         polyethylene glycol 2- polyethylene glycol
                         2-gamma-Glu-gamma-Glu- Palmitoyl
MOD_RES                 22
                        note = alpha-methyl-L-phenylalanine
MOD_RES                 25
                        note = 2-Aminoisobutyric acid
SEQUENCE: 162
HSQGSXTSDV SKXLDSXAAQ DXVEXIAN                                     28

SEQ ID NO: 163          moltype = AA   length = 28
FEATURE                 Location/Qualifiers
source                  1..28
                        mol_type = protein
                        organism = Synthetic construct
MOD_RES                 6
                        note = alpha-methyl-L-phenylalanine
MOD_RES                 13
                        note = alpha-methyl-L-phenylalanine
MOD_RES                 17
                        note = Lys, wherein the side chain of Lys is connected to
                         polyethylene glycol 2- polyethylene glycol
                         2-gamma-Glu-gamma-Glu- Palmitoyl
MOD_RES                 22
                        note = alpha-methyl-L-phenylalanine
MOD_RES                 25
                        note = 2-Aminoisobutyric acid
SEQUENCE: 163
HSQGSXTSDV SKXLDSXAAQ DXVQXIAG                                     28
```

-continued

```
SEQ ID NO: 164          moltype = AA  length = 28
FEATURE                 Location/Qualifiers
source                  1..28
                        mol_type = protein
                        organism = Synthetic construct
MOD_RES                 6
                        note = alpha-methyl-L-phenylalanine
MOD_RES                 13
                        note = 2-Aminoisobutyric acid
MOD_RES                 17
                        note = Lys, wherein the side chain of Lys is connected to
                         polyethylene glycol 2- polyethylene glycol
                         2-gamma-Glu-gamma-Glu- Stearoyl
MOD_RES                 22
                        note = alpha-methyl-L-phenylalanine
MOD_RES                 25
                        note = 2-Aminoisobutyric acid
SEQUENCE: 164
HSQGSXTSDV SKXLDSXAAQ DXVQXLEA                                             28

SEQ ID NO: 165          moltype = AA  length = 28
FEATURE                 Location/Qualifiers
source                  1..28
                        mol_type = protein
                        organism = Synthetic construct
MOD_RES                 6
                        note = alpha-methyl-L-phenylalanine
MOD_RES                 13
                        note = 2-Aminoisobutyric acid
MOD_RES                 17
                        note = Lys, wherein the side chain of Lys is connected to
                         polyethylene glycol 2- polyethylene glycol
                         2-gamma-Glu-gamma-Glu- Stearoyl
MOD_RES                 22
                        note = alpha-methyl-L-phenylalanine
MOD_RES                 25
                        note = 2-Aminoisobutyric acid
SEQUENCE: 165
HSQGSXTSDV SKXLDSXAAQ DXVQXLAN                                             28

SEQ ID NO: 166          moltype = AA  length = 28
FEATURE                 Location/Qualifiers
source                  1..28
                        mol_type = protein
                        organism = Synthetic construct
MOD_RES                 6
                        note = alpha-methyl-L-phenylalanine
MOD_RES                 13
                        note = 2-Aminoisobutyric acid
MOD_RES                 17
                        note = Lys, wherein the side chain of Lys is connected to
                         polyethylene glycol 2- polyethylene glycol
                         2-gamma-Glu-gamma-Glu- Stearoyl
MOD_RES                 22
                        note = alpha-methyl-L-phenylalanine
MOD_RES                 25
                        note = 2-Aminoisobutyric acid
SEQUENCE: 166
HSQGSXTSDV SKXLDSXAAQ DXVQXLSE                                             28

SEQ ID NO: 167          moltype = AA  length = 29
FEATURE                 Location/Qualifiers
source                  1..29
                        mol_type = protein
                        organism = Synthetic construct
MOD_RES                 6
                        note = alpha-methyl-L-phenylalanine
MOD_RES                 13
                        note = 2-Aminoisobutyric acid
MOD_RES                 17
                        note = Lys, wherein the side chain of Lys is connected to
                         polyethylene glycol 2- polyethylene glycol
                         2-gamma-Glu-gamma-Glu- Stearoyl
MOD_RES                 22
                        note = alpha-methyl-L-phenylalanine
MOD_RES                 25
                        note = 2-Aminoisobutyric acid
SEQUENCE: 167
HSQGSXTSDV SKXLDSXAAQ DXVQXLANT                                            29
```

```
SEQ ID NO: 168          moltype = AA  length = 29
FEATURE                 Location/Qualifiers
source                  1..29
                        mol_type = protein
                        organism = Synthetic construct
MOD_RES                 6
                        note = alpha-methyl-L-phenylalanine
MOD_RES                 13
                        note = 2-Aminoisobutyric acid
MOD_RES                 17
                        note = Lys, wherein the side chain of Lys is connected to
                         polyethylene glycol 2- polyethylene glycol
                         2-gamma-Glu-gamma-Glu- Stearoyl
MOD_RES                 22
                        note = alpha-methyl-L-phenylalanine
MOD_RES                 25
                        note = 2-Aminoisobutyric acid
SEQUENCE: 168
HSQGSXTSDV SKXLDSXAAQ DXVQXLANT                                      29

SEQ ID NO: 169          moltype = AA  length = 28
FEATURE                 Location/Qualifiers
source                  1..28
                        mol_type = protein
                        organism = Synthetic construct
MOD_RES                 6
                        note = alpha-methyl-L-phenylalanine
MOD_RES                 13
                        note = 2-Aminoisobutyric acid
MOD_RES                 17
                        note = Lys, wherein the side chain of Lys is connected to
                         polyethylene glycol 2- polyethylene glycol
                         2-gamma-Glu-gamma-Glu- Stearoyl
MOD_RES                 22
                        note = alpha-methyl-L-phenylalanine
MOD_RES                 25
                        note = 2-Aminoisobutyric acid
SEQUENCE: 169
HSQGSXTSDV SKXLDSXAAQ DXVQXIAN                                       28

SEQ ID NO: 170          moltype = AA  length = 28
FEATURE                 Location/Qualifiers
source                  1..28
                        mol_type = protein
                        organism = Synthetic construct
MOD_RES                 6
                        note = alpha-methyl-L-phenylalanine
MOD_RES                 13
                        note = 2-Aminoisobutyric acid
MOD_RES                 17
                        note = Lys, wherein the side chain of Lys is connected to
                         polyethylene glycol 2- polyethylene glycol
                         2-gamma-Glu-gamma-Glu- Stearoyl
MOD_RES                 22
                        note = alpha-methyl-L-phenylalanine
MOD_RES                 25
                        note = 2-Aminoisobutyric acid
SEQUENCE: 170
HSQGSXTSDV SKXLDSXAAQ DXVQXIIE                                       28

SEQ ID NO: 171          moltype = AA  length = 28
FEATURE                 Location/Qualifiers
source                  1..28
                        mol_type = protein
                        organism = Synthetic construct
MOD_RES                 6
                        note = alpha-methyl-L-phenylalanine
MOD_RES                 13
                        note = 2-Aminoisobutyric acid
MOD_RES                 17
                        note = Lys, wherein the side chain of Lys is connected to
                         polyethylene glycol 2- polyethylene glycol
                         2-gamma-Glu-gamma-Glu- Palmitoyl
MOD_RES                 22
                        note = alpha-methyl-L-phenylalanine
MOD_RES                 25
                        note = 2-Aminoisobutyric acid
SEQUENCE: 171
```

```
HSQGSXTSDV SKXLDSXAAQ DXVQXIAN                                            28

SEQ ID NO: 172        moltype = AA  length = 29
FEATURE               Location/Qualifiers
source                1..29
                      mol_type = protein
                      organism = Synthetic construct
MOD_RES               2
                      note = 2-Aminoisobutyric acid
MOD_RES               6
                      note = alpha-methyl-L-phenylalanine
MOD_RES               13
                      note = 2-Aminoisobutyric acid
MOD_RES               17
                      note = Lys, wherein the side chain of Lys is connected to
                       polyethylene glycol 2- polyethylene glycol
                       2-gamma-Glu-gamma-Glu- Stearyl
MOD_RES               22
                      note = alpha-methyl-L-phenylalanine
MOD_RES               25
                      note = 2-Aminoisobutyric acid
SEQUENCE: 172
HXQGSXTSDV SKXLDSXLAA QDXVQXIAN                                           29

SEQ ID NO: 173        moltype = AA  length = 28
FEATURE               Location/Qualifiers
source                1..28
                      mol_type = protein
                      organism = Synthetic construct
MOD_RES               2
                      note = 2-Aminoisobutyric acid
MOD_RES               6
                      note = alpha-methyl-L-phenylalanine
MOD_RES               13
                      note = 2-Aminoisobutyric acid
MOD_RES               17
                      note = Lys, wherein the side chain of Lys is connected to
                       polyethylene glycol 2- polyethylene glycol
                       2-gamma-Glu-gamma-Glu- Stearyl
MOD_RES               22
                      note = alpha-methyl-L-phenylalanine
MOD_RES               25
                      note = 2-Aminoisobutyric acid
SEQUENCE: 173
HXQGSXTSDV SKXLDSXAAQ DXVQXIAN                                            28

SEQ ID NO: 174        moltype = AA  length = 28
FEATURE               Location/Qualifiers
source                1..28
                      mol_type = protein
                      organism = Synthetic construct
MOD_RES               2
                      note = 2-Aminoisobutyric acid
MOD_RES               6
                      note = alpha-methyl-L-phenylalanine
MOD_RES               13
                      note = 2-Aminoisobutyric acid
MOD_RES               17
                      note = Lys, wherein the side chain of Lys is connected to
                       polyethylene glycol 2- polyethylene glycol
                       2-gamma-Glu-gamma-Glu- Stearyl
MOD_RES               22
                      note = alpha-methyl-L-phenylalanine
MOD_RES               25
                      note = 2-Aminoisobutyric acid
SEQUENCE: 174
HXQGSXTSDV SKXLDSXRAQ DXVQXIAN                                            28

SEQ ID NO: 175        moltype = AA  length = 28
FEATURE               Location/Qualifiers
source                1..28
                      mol_type = protein
                      organism = Synthetic construct
MOD_RES               2
                      note = 2-Aminoisobutyric acid
MOD_RES               6
                      note = alpha-methyl-L-phenylalanine
MOD_RES               13
                      note = 2-Aminoisobutyric acid
```

```
MOD_RES              17
                     note = Lys, wherein the side chain of Lys is connected to
                      polyethylene glycol 2- polyethylene glycol
                      2-gamma-Glu-gamma-Glu- Stearyl
MOD_RES              22
                     note = alpha-methyl-L-phenylalanine
SEQUENCE: 175
HXQGSXTSDV SKXLDSXAAQ DXVQWIAN                                               28

SEQ ID NO: 176       moltype = AA  length = 28
FEATURE              Location/Qualifiers
source               1..28
                     mol_type = protein
                     organism = Synthetic construct
MOD_RES              6
                     note = alpha-methyl-L-phenylalanine
MOD_RES              13
                     note = 2-Aminoisobutyric acid
MOD_RES              17
                     note = Lys, wherein the side chain of Lys is connected to
                      polyethylene glycol 2- polyethylene glycol
                      2-gamma-Glu-gamma-Glu- Stearyl
MOD_RES              22
                     note = alpha-methyl-L-phenylalanine
MOD_RES              25
                     note = 2-Aminoisobutyric acid
SEQUENCE: 176
HTQGSXTSDV SKXLDSXAAQ DXVQXIAN                                               28

SEQ ID NO: 177       moltype = AA  length = 29
FEATURE              Location/Qualifiers
source               1..29
                     mol_type = protein
                     organism = Synthetic construct
MOD_RES              6
                     note = alpha-methyl-L-phenylalanine
MOD_RES              13
                     note = 2-Aminoisobutyric acid
MOD_RES              17
                     note = Lys, wherein the side chain of Lys is connected to
                      polyethylene glycol 2- polyethylene glycol
                      2-gamma-Glu-gamma-Glu- Palmitoyl
MOD_RES              22
                     note = alpha-methyl-L-phenylalanine
MOD_RES              25
                     note = 2-Aminoisobutyric acid
SEQUENCE: 177
HSQGSXTSDV SKXLDSXQAQ DXVQAXIAN                                              29

SEQ ID NO: 178       moltype = AA  length = 28
FEATURE              Location/Qualifiers
source               1..28
                     mol_type = protein
                     organism = Synthetic construct
MOD_RES              6
                     note = alpha-methyl-L-phenylalanine
MOD_RES              13
                     note = 2-Aminoisobutyric acid
MOD_RES              17
                     note = Lys, wherein the side chain of Lys is connected to
                      polyethylene glycol 2- polyethylene glycol
                      2-gamma-Glu-gamma-Glu- Palmitoyl
MOD_RES              22
                     note = alpha-methyl-L-phenylalanine
SEQUENCE: 178
HSQGSXTSDV SKXLDSXAAQ DXVQHIAN                                               28

SEQ ID NO: 179       moltype = AA  length = 28
FEATURE              Location/Qualifiers
source               1..28
                     mol_type = protein
                     organism = Synthetic construct
MOD_RES              6
                     note = alpha-methyl-L-phenylalanine
MOD_RES              13
                     note = 2-Aminoisobutyric acid
MOD_RES              17
                     note = Lys, wherein the side chain of Lys is connected to
                      polyethylene glycol 2- polyethylene glycol
```

```
                                  2-gamma-Glu-gamma-Glu- Palmitoyl
MOD_RES                           22
                                  note = alpha-methyl-L-phenylalanine
SEQUENCE: 179
HSQGSXTSDV SKXLDSXQAQ DXVQHIAN                                          28

SEQ ID NO: 180          moltype = AA  length = 28
FEATURE                 Location/Qualifiers
source                  1..28
                        mol_type = protein
                        organism = Synthetic construct
MOD_RES                 6
                        note = alpha-methyl-L-phenylalanine
MOD_RES                 13
                        note = 2-Aminoisobutyric acid
MOD_RES                 17
                        note = Lys, wherein the side chain of Lys is connected to
                         O2Oc-O2Oc- gamma-Glu -C18diacid
MOD_RES                 22
                        note = alpha-methyl-L-phenylalanine
MOD_RES                 25
                        note = 2-Aminoisobutyric acid
SEQUENCE: 180
HSQGSXTSDV SKXLDSXAAQ DXVQXIAN                                          28

SEQ ID NO: 181          moltype = AA  length = 28
FEATURE                 Location/Qualifiers
source                  1..28
                        mol_type = protein
                        organism = Synthetic construct
MOD_RES                 6
                        note = alpha-methyl-L-phenylalanine
MOD_RES                 12
                        note = Acetyllysine
MOD_RES                 13
                        note = 2-Aminoisobutyric acid
MOD_RES                 17
                        note = Lys, wherein the side chain of Lys is connected to
                         O2Oc-O2Oc- gamma-Glu -C18diacid
MOD_RES                 22
                        note = alpha-methyl-L-phenylalanine
MOD_RES                 25
                        note = 2-Aminoisobutyric acid
SEQUENCE: 181
HSQGSXTSDV SXXLDSXAAQ DXVQXIAN                                          28

SEQ ID NO: 182          moltype = AA  length = 28
FEATURE                 Location/Qualifiers
source                  1..28
                        mol_type = protein
                        organism = Synthetic construct
MOD_RES                 6
                        note = alpha-methyl-L-phenylalanine
MOD_RES                 12
                        note = Acetyllysine
MOD_RES                 13
                        note = 2-Aminoisobutyric acid
MOD_RES                 17
                        note = Lys, wherein the side chain of Lys is connected to
                         polyethylene glycol 2- polyethylene glycol
                         2-gamma-Glu-gamma-Glu- Stearyl
MOD_RES                 22
                        note = alpha-methyl-L-phenylalanine
MOD_RES                 25
                        note = 2-Aminoisobutyric acid
SEQUENCE: 182
HSQGSXTSDV SXXLDSXAAQ DXVQXIAN                                          28

SEQ ID NO: 183          moltype = AA  length = 28
FEATURE                 Location/Qualifiers
source                  1..28
                        mol_type = protein
                        organism = Synthetic construct
MOD_RES                 6
                        note = alpha-methyl-L-phenylalanine
MOD_RES                 17
                        note = Lys, wherein the side chain of Lys is connected to
                         polyethylene glycol 2- polyethylene glycol
                         2-gamma-Glu-gamma-Glu- Palmitoyl
```

-continued

```
MOD_RES              22
                     note = alpha-methyl-L-phenylalanine
MOD_RES              25
                     note = 2-Aminoisobutyric acid
SEQUENCE: 183
HSQGSXTSDV SKILDSXAAQ DXVQXIAN                                               28

SEQ ID NO: 184       moltype = AA  length = 28
FEATURE              Location/Qualifiers
source               1..28
                     mol_type = protein
                     organism = Synthetic construct
MOD_RES              6
                     note = alpha-methyl-L-phenylalanine
MOD_RES              17
                     note = Lys, wherein the side chain of Lys is connected to
                      polyethylene glycol 2- polyethylene glycol
                      2-gamma-Glu-gamma-Glu- Palmitoyl
MOD_RES              22
                     note = alpha-methyl-L-phenylalanine
SEQUENCE: 184
HSQGSXTSDV SKILDSXAAQ DXVQIIAN                                               28

SEQ ID NO: 185       moltype = AA  length = 28
FEATURE              Location/Qualifiers
source               1..28
                     mol_type = protein
                     organism = Synthetic construct
MOD_RES              6
                     note = alpha-methyl-L-phenylalanine
MOD_RES              17
                     note = Lys, wherein the side chain of Lys is connected to
                      polyethylene glycol 2- polyethylene glycol
                      2-gamma-Glu-gamma-Glu- Palmitoyl
MOD_RES              22
                     note = alpha-methyl-L-phenylalanine
SEQUENCE: 185
HSQGSXTSDV SKILDSXAAQ DXVQIIAG                                               28

SEQ ID NO: 186       moltype = AA  length = 28
FEATURE              Location/Qualifiers
source               1..28
                     mol_type = protein
                     organism = Synthetic construct
MOD_RES              6
                     note = alpha-methyl-L-phenylalanine
MOD_RES              17
                     note = Lys, wherein the side chain of Lys is connected to
                      polyethylene glycol 2- polyethylene glycol
                      2-gamma-Glu-gamma-Glu- Palmitoyl
MOD_RES              22
                     note = alpha-methyl-L-phenylalanine
SEQUENCE: 186
HSQGSXTSDV SKILDSXAAQ DXVEIIAN                                               28

SEQ ID NO: 187       moltype = AA  length = 28
FEATURE              Location/Qualifiers
source               1..28
                     mol_type = protein
                     organism = Synthetic construct
MOD_RES              6
                     note = alpha-methyl-L-phenylalanine
MOD_RES              17
                     note = Lys, wherein the side chain of Lys is connected to
                      polyethylene glycol 2- polyethylene glycol
                      2-gamma-Glu-gamma-Glu- Palmitoyl
MOD_RES              22
                     note = alpha-methyl-L-phenylalanine
MOD_RES              25
                     note = alpha-methyl-L-phenylalanine
SEQUENCE: 187
HSQGSXTSDV SKILDSXAAQ DXVQXIAN                                               28

SEQ ID NO: 188       moltype = AA  length = 29
FEATURE              Location/Qualifiers
source               1..29
                     mol_type = protein
                     organism = Synthetic construct
MOD_RES              6
```

```
                          note = alpha-methyl-L-phenylalanine
MOD_RES                   17
                          note = Lys, wherein the side chain of Lys is connected to
                           polyethylene glycol 2- polyethylene glycol
                           2-gamma-Glu-gamma-Glu- Palmitoyl
MOD_RES                   22
                          note = alpha-methyl-L-phenylalanine
SEQUENCE: 188
HSQGSXTSDV SKILDSXAAQ DXVEWIINT                                    29

SEQ ID NO: 189            moltype = AA  length = 29
FEATURE                   Location/Qualifiers
source                    1..29
                          mol_type = protein
                          organism = Synthetic construct
MOD_RES                   6
                          note = alpha-methyl-L-phenylalanine
MOD_RES                   17
                          note = Lys, wherein the side chain of Lys is connected to
                           polyethylene glycol 2- polyethylene glycol
                           2-gamma-Glu-gamma-Glu- Stearoyl
MOD_RES                   22
                          note = alpha-methyl-L-phenylalanine
MOD_RES                   25
                          note = 2-Aminoisobutyric acid
SEQUENCE: 189
HSQGSXTSDV SKILDSXAAQ DXVQXIINT                                    29

SEQ ID NO: 190            moltype = AA  length = 29
FEATURE                   Location/Qualifiers
source                    1..29
                          mol_type = protein
                          organism = Synthetic construct
MOD_RES                   6
                          note = alpha-methyl-L-phenylalanine
MOD_RES                   17
                          note = Lys, wherein the side chain of Lys is connected to
                           polyethylene glycol 2- polyethylene glycol
                           2-gamma-Glu-gamma-Glu- Palmitoyl
MOD_RES                   22
                          note = alpha-methyl-L-phenylalanine
MOD_RES                   25
                          note = 2-Aminoisobutyric acid
SEQUENCE: 190
HSQGSXTSDV SKILDSXAAQ DXVQXIINT                                    29

SEQ ID NO: 191            moltype = AA  length = 29
FEATURE                   Location/Qualifiers
source                    1..29
                          mol_type = protein
                          organism = Synthetic construct
MOD_RES                   6
                          note = alpha-methyl-L-phenylalanine
MOD_RES                   17
                          note = Lys, wherein the side chain of Lys is connected to
                           polyethylene glycol 2- polyethylene glycol
                           2-gamma-Glu-gamma-Glu- Myristoyl
MOD_RES                   22
                          note = alpha-methyl-L-phenylalanine
MOD_RES                   25
                          note = 2-Aminoisobutyric acid
SEQUENCE: 191
HSQGSXTSDV SKILDSXAAQ DXVQXIINT                                    29

SEQ ID NO: 192            moltype = AA  length = 29
FEATURE                   Location/Qualifiers
source                    1..29
                          mol_type = protein
                          organism = Synthetic construct
MOD_RES                   6
                          note = alpha-methyl-L-phenylalanine
MOD_RES                   17
                          note = Lys, wherein the side chain of Lys is connected to
                           polyethylene glycol 2- polyethylene glycol 2-gamma-Glu-
                           Stearoyl
MOD_RES                   22
                          note = alpha-methyl-L-phenylalanine
MOD_RES                   25
                          note = 2-Aminoisobutyric acid
```

```
SEQUENCE: 192
HSQGSXTSDV SKILDSXAAQ DXVQXIINT                                  29

SEQ ID NO: 193        moltype = AA  length = 29
FEATURE               Location/Qualifiers
source                1..29
                      mol_type = protein
                      organism = Synthetic construct
MOD_RES               6
                      note = alpha-methyl-L-phenylalanine
MOD_RES               17
                      note = Lys, wherein the side chain of Lys is connected to
                       polyethylene glycol 2- polyethylene glycol 2-gamma-Glu-
                       Palmitoyl
MOD_RES               22
                      note = alpha-methyl-L-phenylalanine
MOD_RES               25
                      note = 2-Aminoisobutyric acid
SEQUENCE: 193
HSQGSXTSDV SKILDSXAAQ DXVQXIINT                                  29

SEQ ID NO: 194        moltype = AA  length = 29
FEATURE               Location/Qualifiers
source                1..29
                      mol_type = protein
                      organism = Synthetic construct
MOD_RES               6
                      note = alpha-methyl-L-phenylalanine
MOD_RES               17
                      note = Lys, wherein the side chain of Lys is connected to
                       polyethylene glycol 2- polyethylene glycol 2-gamma-Glu-
                       Myristoyl
MOD_RES               22
                      note = alpha-methyl-L-phenylalanine
MOD_RES               25
                      note = 2-Aminoisobutyric acid
SEQUENCE: 194
HSQGSXTSDV SKILDSXAAQ DXVQXIINT                                  29

SEQ ID NO: 195        moltype = AA  length = 28
FEATURE               Location/Qualifiers
source                1..28
                      mol_type = protein
                      organism = Synthetic construct
MOD_RES               6
                      note = alpha-methyl-L-phenylalanine
MOD_RES               17
                      note = Lys, wherein the side chain of Lys is connected to
                       polyethylene glycol 2- polyethylene glycol 2-gamma-Glu-
                       gamma-Glu- Palmitoyl
MOD_RES               22
                      note = alpha-methyl-L-phenylalanine
SEQUENCE: 195
HXQGSXTSDV SKILDSXAAQ DXVQIIAN                                   28

SEQ ID NO: 196        moltype = AA  length = 29
FEATURE               Location/Qualifiers
source                1..29
                      mol_type = protein
                      organism = Synthetic construct
MOD_RES               6
                      note = alpha-methyl-L-phenylalanine
MOD_RES               17
                      note = Lys, wherein the side chain of Lys is connected to
                       polyethylene glycol 2- polyethylene glycol 2-gamma-Glu-
                       gamma-Glu- Stearoyl
MOD_RES               22
                      note = alpha-methyl-L-phenylalanine
MOD_RES               25
                      note = 2-Aminoisobutyric acid
SEQUENCE: 196
HXQGSXTSDV SKILDSXAAQ DXVQXIINT                                  29

SEQ ID NO: 197        moltype = AA  length = 29
FEATURE               Location/Qualifiers
source                1..29
                      mol_type = protein
                      organism = Synthetic construct
MOD_RES               2
```

```
                                  note = 2-Aminoisobutyric acid
MOD_RES                           6
                                  note = alpha-methyl-L-phenylalanine
MOD_RES                           17
                                  note = Lys, wherein the side chain of Lys is connected to
                                   polyethylene glycol 2- polyethylene glycol 2-gamma-Glu-
                                   gamma-Glu- Palmitoyl
MOD_RES                           22
                                  note = alpha-methyl-L-phenylalanine
MOD_RES                           25
                                  note = 2-Aminoisobutyric acid
SEQUENCE: 197
HXQGSXTSDV SKILDSXAAQ DXVQXIINT                                          29

SEQ ID NO: 198            moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   17
                          note = Lys, wherein the side chain of Lys is connected to
                           polyethylene glycol 2- polyethylene glycol 2-gamma-Glu-
                           gamma-Glu- Myristoyl
MOD_RES                   22
                          note = alpha-methyl-L-phenylalanine
MOD_RES                   25
                          note = 2-Aminoisobutyric acid
SEQUENCE: 198
HXQGSXTSDV SKILDSXAAQ DXVQXIINT                                          29

SEQ ID NO: 199            moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   17
                          note = Lys, wherein the side chain of Lys is connected to
                           polyethylene glycol 2- polyethylene glycol 2-gamma-Glu-
                           gamma-Glu- Stearoyl
MOD_RES                   22
                          note = alpha-methyl-L-phenylalanine
MOD_RES                   25
                          note = 2-Aminoisobutyric acid
SEQUENCE: 199
HXQGSXTSDV SKILDSXAAQ DXVQXIINT                                          29

SEQ ID NO: 200            moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   17
                          note = Lys, wherein the side chain of Lys is connected to
                           polyethylene glycol 2- polyethylene glycol 2-gamma-Glu-
                           Palmitoyl
MOD_RES                   22
                          note = alpha-methyl-L-phenylalanine
MOD_RES                   25
                          note = 2-Aminoisobutyric acid
SEQUENCE: 200
HXQGSXTSDV SKILDSXAAQ DXVQXIINT                                          29

SEQ ID NO: 201            moltype = AA  length = 29
FEATURE                   Location/Qualifiers
source                    1..29
                          mol_type = protein
                          organism = Synthetic construct
```

-continued

```
MOD_RES               2
                      note = 2-Aminoisobutyric acid
MOD_RES               6
                      note = alpha-methyl-L-phenylalanine
MOD_RES               17
                      note = Lys, wherein the side chain of Lys is connected to
                       polyethylene glycol 2- polyethylene glycol 2-gamma-Glu-
                       Myristoyl
MOD_RES               22
                      note = alpha-methyl-L-phenylalanine
MOD_RES               25
                      note = 2-Aminoisobutyric acid
SEQUENCE: 201
HXQGSXTSDV SKILDSXAAQ DXVQXIINT                                       29

SEQ ID NO: 202        moltype = AA  length = 29
FEATURE               Location/Qualifiers
source                1..29
                      mol_type = protein
                      organism = Synthetic construct
MOD_RES               2
                      note = alpha-methyl-L-serine
MOD_RES               6
                      note = alpha-methyl-L-phenylalanine
MOD_RES               17
                      note = Lys, wherein the side chain of Lys is connected to
                       polyethylene glycol 2- polyethylene glycol 2-gamma-Glu-
                       gamma-Glu- Stearoyl
MOD_RES               22
                      note = alpha-methyl-L-phenylalanine
MOD_RES               25
                      note = 2-Aminoisobutyric acid
SEQUENCE: 202
HXQGSXTSDV SKILDSXAAQ DXVQXIINT                                       29

SEQ ID NO: 203        moltype = AA  length = 29
FEATURE               Location/Qualifiers
source                1..29
                      mol_type = protein
                      organism = Synthetic construct
MOD_RES               2
                      note = alpha-methyl-L-serine
MOD_RES               6
                      note = alpha-methyl-L-phenylalanine
MOD_RES               17
                      note = Lys, wherein the side chain of Lys is connected to
                       polyethylene glycol 2- polyethylene glycol 2-gamma-Glu-
                       gamma-Glu- Palmitoyl
MOD_RES               22
                      note = alpha-methyl-L-phenylalanine
MOD_RES               25
                      note = 2-Aminoisobutyric acid
SEQUENCE: 203
HXQGSXTSDV SKILDSXAAQ DXVQXIINT                                       29

SEQ ID NO: 204        moltype = AA  length = 29
FEATURE               Location/Qualifiers
source                1..29
                      mol_type = protein
                      organism = Synthetic construct
MOD_RES               2
                      note = alpha-methyl-L-serine
MOD_RES               6
                      note = alpha-methyl-L-phenylalanine
MOD_RES               17
                      note = Lys, wherein the side chain of Lys is connected to
                       polyethylene glycol 2- polyethylene glycol 2-gamma-Glu-
                       gamma-Glu- Myristoyl
MOD_RES               22
                      note = alpha-methyl-L-phenylalanine
MOD_RES               25
                      note = 2-Aminoisobutyric acid
SEQUENCE: 204
HXQGSXTSDV SKILDSXAAQ DXVQXIINT                                       29

SEQ ID NO: 205        moltype = AA  length = 29
FEATURE               Location/Qualifiers
source                1..29
                      mol_type = protein
```

-continued

```
                         organism = Synthetic construct
MOD_RES                  2
                         note = alpha-methyl-L-serine
MOD_RES                  6
                         note = alpha-methyl-L-phenylalanine
MOD_RES                  17
                         note = Lys, wherein the side chain of Lys is connected to
                          polyethylene glycol 2- polyethylene glycol 2-gamma-Glu-
                          Stearoyl
MOD_RES                  22
                         note = alpha-methyl-L-phenylalanine
MOD_RES                  25
                         note = 2-Aminoisobutyric acid
SEQUENCE: 205
HXQGSXTSDV SKILDSXAAQ DXVQXIINT                                              29

SEQ ID NO: 206           moltype = AA  length = 29
FEATURE                  Location/Qualifiers
source                   1..29
                         mol_type = protein
                         organism = Synthetic construct
MOD_RES                  2
                         note = alpha-methyl-L-serine
MOD_RES                  6
                         note = alpha-methyl-L-phenylalanine
MOD_RES                  17
                         note = Lys, wherein the side chain of Lys is connected to
                          polyethylene glycol 2- polyethylene glycol 2-gamma-Glu-
                          Palmitoyl
MOD_RES                  22
                         note = alpha-methyl-L-phenylalanine
MOD_RES                  25
                         note = 2-Aminoisobutyric acid
SEQUENCE: 206
HXQGSXTSDV SKILDSXAAQ DXVQXIINT                                              29

SEQ ID NO: 207           moltype = AA  length = 29
FEATURE                  Location/Qualifiers
source                   1..29
                         mol_type = protein
                         organism = Synthetic construct
MOD_RES                  2
                         note = alpha-methyl-L-serine
MOD_RES                  6
                         note = alpha-methyl-L-phenylalanine
MOD_RES                  17
                         note = Lys, wherein the side chain of Lys is connected to
                          polyethylene glycol 2- polyethylene glycol 2-gamma-Glu-
                          Myristoyl
MOD_RES                  22
                         note = alpha-methyl-L-phenylalanine
MOD_RES                  25
                         note = 2-Aminoisobutyric acid
SEQUENCE: 207
HXQGSXTSDV SKILDSXAAQ DXVQXIINT                                              29

SEQ ID NO: 208           moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  6
                         note = alpha-methyl-L-phenylalanine
MOD_RES                  13
                         note = alpha-methyl-L-phenylalanine
MOD_RES                  20
                         note = Lys, wherein the side chain of Lys is connected to
                          O2Oc-O2Oc-gamma-Glu-C18diacid
SEQUENCE: 208
HXHGSXTSDV SKXLDSQAAX DFVQWIANT                                              29

SEQ ID NO: 209           moltype = AA  length = 29
FEATURE                  Location/Qualifiers
source                   1..29
                         mol_type = protein
                         organism = Synthetic construct
MOD_RES                  2
```

-continued

```
                              note = 2-Aminoisobutyric acid
MOD_RES                       6
                              note = alpha-methyl-L-phenylalanine
MOD_RES                       13
                              note = alpha-methyl-L-phenylalanine
MOD_RES                       20
                              note = Lys, wherein the side chain of Lys is connected to
                               O2Oc-O2Oc-gamma-Glu-C18diacid
SEQUENCE: 209
HXQGTXTSDV SKXLDSRAAX DFVQWIANT                                              29

SEQ ID NO: 210                moltype = AA  length = 29
FEATURE                       Location/Qualifiers
source                        1..29
                              mol_type = protein
                              organism = Synthetic construct
MOD_RES                       2
                              note = 2-Aminoisobutyric acid
MOD_RES                       13
                              note = alpha-methyl-L-phenylalanine
MOD_RES                       20
                              note = Lys, wherein the side chain of Lys is connected to
                               O2Oc-O2Oc-gamma-Glu-C18diacid
SEQUENCE: 210
HXHGSXTSDV SKXLDSRAAX DFVQWIANT                                              29

SEQ ID NO: 211                moltype = AA  length = 29
FEATURE                       Location/Qualifiers
source                        1..29
                              mol_type = protein
                              organism = Synthetic construct
MOD_RES                       2
                              note = 2-Aminoisobutyric acid
MOD_RES                       6
                              note = alpha-methyl-L-phenylalanine
MOD_RES                       13
                              note = alpha-methyl-L-phenylalanine
MOD_RES                       18
                              note = 2-Aminoisobutyric acid
MOD_RES                       20
                              note = Lys, wherein the side chain of Lys is connected to
                               O2Oc-O2Oc-gamma-Glu-C18diacid
SEQUENCE: 211
HXHGSXTSDV SKXLDSRXAX DFVQWIANT                                              29

SEQ ID NO: 212                moltype = AA  length = 29
FEATURE                       Location/Qualifiers
source                        1..29
                              mol_type = protein
                              organism = Synthetic construct
MOD_RES                       2
                              note = 2-Aminoisobutyric acid
MOD_RES                       6
                              note = alpha-methyl-L-phenylalanine
MOD_RES                       13
                              note = alpha-methyl-L-phenylalanine
MOD_RES                       20
                              note = Lys, wherein the side chain of Lys is connected to
                               O2Oc-O2Oc-gamma-Glu-C18diacid
MOD_RES                       25
                              note = 2-Aminoisobutyric acid
SEQUENCE: 212
HXHGSXTSDV SKXLDSQAAX DFVQXIANT                                              29

SEQ ID NO: 213                moltype = AA  length = 29
FEATURE                       Location/Qualifiers
source                        1..29
                              mol_type = protein
                              organism = Synthetic construct
MOD_RES                       2
                              note = 2-Aminoisobutyric acid
MOD_RES                       13
                              note = alpha-methyl-L-phenylalanine
MOD_RES                       20
                              note = Lys, wherein the side chain of Lys is connected to
                               gamma-Glu-C18diacid
SEQUENCE: 213
HXQGTFTSDV SKXLDSRAAX DFVQWIANT                                              29
```

```
SEQ ID NO: 214          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 20
                        note = Lys, wherein the side chain of Lys is connected to
                         O2Oc-O2Oc-gamma-Glu-C18diacid
MOD_RES                 13
                        note = alpha-methyl-L-phenylalanine
SEQUENCE: 214
HXHGSXTSDV SKXLDSQAAX DFVEWIANT                                              29

SEQ ID NO: 215          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         O2Oc-O2Oc-gamma-Glu-C18diacid
SEQUENCE: 215
HXHGSXTSDV SKXLDSQAAX DFVEWIANT                                              29

SEQ ID NO: 216          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         O2Oc-O2Oc-gamma-Glu- gamma-Glu -C20diacid
SEQUENCE: 216
HXHGSXTSDV SKXLDSRAAX DFVQWIANT                                              29

SEQ ID NO: 217          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         O2Oc-O2Oc-gamma-Glu- C20diacid
SEQUENCE: 217
HXHGSXTSDV SKXLDSRAAX DFVEWIANT                                              29

SEQ ID NO: 218          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
```

```
MOD_RES              20
                     note = Lys, wherein the side chain of Lys is connected to
                      O2Oc-O2Oc-gamma-Glu-gamma-Glu C20diacid
SEQUENCE: 218
HXHGSXTSDV SKXLDSRAAX DFVEWIANT                                              29

SEQ ID NO: 219       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              6
                     note = alpha-methyl-L-phenylalanine
MOD_RES              13
                     note = alpha-methyl-L-phenylalanine
MOD_RES              20
                     note = Lys, wherein the side chain of Lys is connected to
                      O2Oc-O2Oc- gamma-Glu-C20diacid
SEQUENCE: 219
HXHGSXTSDV SKXLDSRAAX DFVQWIANT                                              29

SEQ ID NO: 220       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              6
                     note = alpha-methyl-L-phenylalanine
MOD_RES              13
                     note = alpha-methyl-L-phenylalanine
MOD_RES              20
                     note = Lys, wherein the side chain of Lys is connected to
                      O2Oc-O2Oc- gamma-Glu C20diacid
MOD_RES              22
                     note = alpha-methyl-L-phenylalanine
SEQUENCE: 220
HXHGSXTSDV SKXLDSRAAX DXVQWIANT                                              29

SEQ ID NO: 221       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              6
                     note = alpha-methyl-L-phenylalanine
MOD_RES              13
                     note = alpha-methyl-L-phenylalanine
MOD_RES              20
                     note = Lys, wherein the side chain of Lys is connected to
                      O2Oc-O2Oc- gamma-Glu C20diacid
MOD_RES              22
                     note = alpha-methyl-L-phenylalanine
SEQUENCE: 221
HXHGSXTSDV SKXLDSRAAX DXVEWIANT                                              29

SEQ ID NO: 222       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              6
                     note = alpha-methyl-L-phenylalanine
MOD_RES              13
                     note = alpha-methyl-L-phenylalanine
MOD_RES              18
                     note = 2-Aminoisobutyric acid
MOD_RES              20
                     note = O2Oc-O2Oc- gamma-Glu- gamma-Glu-C20diacid
SEQUENCE: 222
HXHGSXTSDV SKXLDSRXAX DFVQWIANT                                              29
```

-continued

```
SEQ ID NO: 223          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = O2Oc-O2Oc- gamma-Glu- gamma-Glu-C20diacid
SEQUENCE: 223
HXHGSXTSDV SKXLDSRAAX DFVQWIANTG                                     30

SEQ ID NO: 224          moltype = AA  length = 31
FEATURE                 Location/Qualifiers
source                  1..31
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = O2Oc-O2Oc- gamma-Glu- gamma-Glu-C20diacid
SEQUENCE: 224
HXHGSXTSDV SKXLDSRAAX DFVQWIANTG G                                   31

SEQ ID NO: 225          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 18
                        note = 2-Aminoisobutyric acid
MOD_RES                 20
                        note = Lys, wherein the side chain of Lys is connected to
                         O2Oc-O2Oc- gamma-Glu- gamma-Glu-C20diacid
MOD_RES                 25
                        note = 2-Aminoisobutyric acid
SEQUENCE: 225
HXHGSXTSDV SKXLDSRXAX DFVQXIANT                                      29

SEQ ID NO: 226          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         O2Oc-O2Oc- gamma-Glu- gamma-Glu-C20diacid
MOD_RES                 25
                        note = 2-Aminoisobutyric acid
SEQUENCE: 226
HXHGSXTSDV SKXLDSRAAX DFVQXIANT                                      29

SEQ ID NO: 227          moltype = AA  length = 29
FEATURE                 Location/Qualifiers
source                  1..29
                        mol_type = protein
                        organism = Synthetic construct
MOD_RES                 2
                        note = 2-Aminoisobutyric acid
```

-continued

```
MOD_RES              6
                     note = alpha-methyl-L-phenylalanine
MOD_RES              13
                     note = alpha-methyl-L-phenylalanine
MOD_RES              20
                     note = O2Oc-O2Oc-gamma-Glu-C20diacid
SEQUENCE: 227
HXHGSXTSDV SKXLDSQAAX DFVQSIANT                                        29

SEQ ID NO: 228       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              6
                     note = alpha-methyl-L-phenylalanine
MOD_RES              13
                     note = alpha-methyl-L-phenylalanine
MOD_RES              20
                     note = O2Oc-O2Oc-gamma-Glu-C18diacid
MOD_RES              25
                     note = 2-Aminoisobutyric acid
MOD_RES              22
                     note = alpha-methyl-L-phenylalanine
SEQUENCE: 228
HXHGSXTSDV SKXLDSRAAX DXIAXIANT                                        29

SEQ ID NO: 229       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              6
                     note = alpha-methyl-L-phenylalanine
MOD_RES              13
                     note = alpha-methyl-L-phenylalanine
MOD_RES              20
                     note = Lys, wherein the side chain of Lys is connected to
                      O2Oc-O2Oc-gamma-Glu-C18diacid
MOD_RES              22
                     note = alpha-methyl-L-phenylalanine
MOD_RES              25
                     note = 2-Aminoisobutyric acid
SEQUENCE: 229
HXHGSXTSDV SKXLDSRAAX DXVQXIANT                                        29

SEQ ID NO: 230       moltype = AA  length = 31
FEATURE              Location/Qualifiers
source               1..31
                     mol_type = protein
                     organism = Synthetic construct
MOD_RES              2
                     note = 2-Aminoisobutyric acid
MOD_RES              6
                     note = alpha-methyl-L-phenylalanine
MOD_RES              13
                     note = alpha-methyl-L-phenylalanine
MOD_RES              20
                     note = Lys, wherein the side chain of Lys is connected to
                      O2Oc-O2Oc-gamma-Glu-C18diacid
MOD_RES              22
                     note = alpha-methyl-L-phenylalanine
MOD_RES              25
                     note = 2-Aminoisobutyric acid
SEQUENCE: 230
HXHGSXTSDV SKXLDSRAAX DXVQXIANTG G                                     31

SEQ ID NO: 231       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              6
```

-continued

```
                        note = alpha-methyl-L-phenylalanine
MOD_RES                 13
                        note = alpha-methyl-L-phenylalanine
MOD_RES                 20
                        note = Lys, wherein the side chain of Lys is connected to
                         O2Oc-O2Oc-gamma-Glu-C18diacid
MOD_RES                 22
                        note = alpha-methyl-L-phenylalanine
MOD_RES                 25
                        note = 2-Aminoisobutyric acid
SEQUENCE: 231
HXHGSXTSDV SKXLDSRAAX DXVEXIANT                                     29

SEQ ID NO: 232          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         O2Oc-O2Oc-gamma-Glu-C18diacid
MOD_RES                 22
                        note = alpha-methyl-L-phenylalanine
MOD_RES                 25
                        note = 2-Aminoisobutyric acid
SEQUENCE: 232
HXHGSXTSDV SKXLDSRAAX DXIAXIANT                                     29

SEQ ID NO: 233          moltype = AA  length = 31
FEATURE                 Location/Qualifiers
source                  1..31
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         O2Oc-O2Oc-gamma-Glu-gamma-Glu-C20diacid
MOD_RES                 22
                        note = alpha-methyl-L-phenylalanine
MOD_RES                 25
                        note = 2-Aminoisobutyric acid
SEQUENCE: 233
HXHGSXTSDV SKXLDSRAAX DXVQXIANTG G                                  31

SEQ ID NO: 234          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         O2Oc-O2Oc-gamma-Glu-gamma-Glu-C20diacid
MOD_RES                 22
                        note = alpha-methyl-L-phenylalanine
MOD_RES                 25
                        note = 2-Aminoisobutyric acid
SEQUENCE: 234
HXHGSXTSDV SKXLDSRAAX DXVQXIANT                                     29

SEQ ID NO: 235          moltype = AA  length = 29
FEATURE                 Location/Qualifiers
source                  1..29
```

-continued

```
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   20
                          note = Lys, wherein the side chain of Lys is connected to
                           O2Oc-O2Oc- gamma-Glu-C18diacid
MOD_RES                   22
                          note = alpha-methyl-L-phenylalanine
SEQUENCE: 235
HXHGSXTSDV SKXLDSRAAX DXIAWIANT                                         29

SEQ ID NO: 236            moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   20
                          note = Lys, wherein the side chain of Lys is connected to
                           O2Oc-O2Oc- gamma-Glu- gamma-Glu-C18diacid
MOD_RES                   22
                          note = alpha-methyl-L-phenylalanine
MOD_RES                   25
                          note = 2-Aminoisobutyric acid
SEQUENCE: 236
HXHGSXTSDV SKXLDSRAAX DXVQXIANT                                         29

SEQ ID NO: 237            moltype = AA  length = 31
FEATURE                   Location/Qualifiers
source                    1..31
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   20
                          note = Lys, wherein the side chain of Lys is connected to
                           O2Oc-O2Oc- gamma-Glu- gamma-Glu-C20diacid
MOD_RES                   22
                          note = alpha-methyl-L-phenylalanine
MOD_RES                   25
                          note = 2-Aminoisobutyric acid
SEQUENCE: 237
HXHGSXTSDV SKXLDSRAAX DXVQXIANTG G                                      31

SEQ ID NO: 238            moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   20
                          note = Lys, wherein the side chain of Lys is connected to
                           O2Oc-O2Oc- gamma-Glu- gamma-Glu-C20diacid
MOD_RES                   22
                          note = alpha-methyl-L-phenylalanine
MOD_RES                   25
                          note = 2-Aminoisobutyric acid
SEQUENCE: 238
HXHGSXTSDV SKXLDSRAAX DXVEXIANT                                         29
```

```
SEQ ID NO: 239          moltype = AA   length = 30
FEATURE                 Location/Qualifiers
source                  1..30
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         O2Oc-O2Oc- gamma-Glu- gamma-Glu-C20diacid
MOD_RES                 25
                        note = 2-Aminoisobutyric acid
SEQUENCE: 239
HXHGSXTSDV SKXLDSRAAX DFVQXIANTG                                      30

SEQ ID NO: 240          moltype = AA   length = 31
FEATURE                 Location/Qualifiers
source                  1..31
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         O2Oc-O2Oc- gamma-Glu- gamma-Glu-C20diacid
MOD_RES                 25
                        note = 2-Aminoisobutyric acid
SEQUENCE: 240
HXHGSXTSDV SKXLDSRAAX DFVQXIANTG G                                    31

SEQ ID NO: 241          moltype = AA   length = 30
FEATURE                 Location/Qualifiers
source                  1..30
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = O2Oc-O2Oc- gamma-Glu- gamma-Glu-C18diacid
MOD_RES                 25
                        note = 2-Aminoisobutyric acid
SEQUENCE: 241
HXHGSXTSDV SKXLDSRAAX DFVQXIANTG                                      30

SEQ ID NO: 242          moltype = AA   length = 31
FEATURE                 Location/Qualifiers
source                  1..31
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         O2Oc-O2Oc- gamma-Glu- gamma-Glu-C18diacid
MOD_RES                 25
                        note = 2-Aminoisobutyric acid
SEQUENCE: 242
HXHGSXTSDV SKXLDSRAAX DFVQXIANTG G                                    31

SEQ ID NO: 243          moltype = AA   length = 30
FEATURE                 Location/Qualifiers
source                  1..30
                        mol_type = protein
```

```
MOD_RES              2
                     note = 2-Aminoisobutyric acid
MOD_RES              6
                     note = alpha-methyl-L-phenylalanine
MOD_RES              13
                     note = alpha-methyl-L-phenylalanine
MOD_RES              20
                     note = Lys, wherein the side chain of Lys is connected to
                      O2Oc-O2Oc- gamma-Glu- gamma-Glu-C20diacid
MOD_RES              22
                     note = alpha-methyl-L-phenylalanine
SEQUENCE: 243
HXHGSXTSDV SKXLDSRAAX DXVQWIANTG                                              30

SEQ ID NO: 244       moltype = AA  length = 31
FEATURE              Location/Qualifiers
source               1..31
                     mol_type = protein
                     organism = Synthetic construct
MOD_RES              2
                     note = 2-Aminoisobutyric acid
MOD_RES              6
                     note = alpha-methyl-L-phenylalanine
MOD_RES              13
                     note = alpha-methyl-L-phenylalanine
MOD_RES              20
                     note = Lys, wherein the side chain of Lys is connected to
                      O2Oc-O2Oc- gamma-Glu- gamma-Glu-C20diacid
MOD_RES              22
                     note = alpha-methyl-L-phenylalanine
SEQUENCE: 244
HXHGSXTSDV SKXLDSRAAX DXVQWIANTG G                                            31

SEQ ID NO: 245       moltype = AA  length = 30
FEATURE              Location/Qualifiers
source               1..30
                     mol_type = protein
                     organism = Synthetic construct
MOD_RES              2
                     note = 2-Aminoisobutyric acid
MOD_RES              6
                     note = alpha-methyl-L-phenylalanine
MOD_RES              13
                     note = alpha-methyl-L-phenylalanine
MOD_RES              20
                     note = Lys, wherein the side chain of Lys is connected to
                      O2Oc-O2Oc- gamma-Glu- gamma-Glu-C18diacid
MOD_RES              22
                     note = alpha-methyl-L-phenylalanine
SEQUENCE: 245
HXHGSXTSDV SKXLDSRAAX DXVQWIANTG                                              30

SEQ ID NO: 246       moltype = AA  length = 31
FEATURE              Location/Qualifiers
source               1..31
                     mol_type = protein
                     organism = Synthetic construct
MOD_RES              2
                     note = 2-Aminoisobutyric acid
MOD_RES              6
                     note = alpha-methyl-L-phenylalanine
MOD_RES              13
                     note = alpha-methyl-L-phenylalanine
MOD_RES              20
                     note = Lys, wherein the side chain of Lys is connected to
                      O2Oc-O2Oc- gamma-Glu- gamma-Glu-C18diacid
MOD_RES              22
                     note = alpha-methyl-L-phenylalanine
SEQUENCE: 246
HXHGSXTSDV SKXLDSRAAX DXVQWIANTG G                                            31

SEQ ID NO: 247       moltype = AA  length = 28
FEATURE              Location/Qualifiers
source               1..28
                     mol_type = protein
                     organism = Synthetic construct
MOD_RES              2
                     note = 2-Aminoisobutyric acid
```

-continued

```
MOD_RES                6
                       note = alpha-methyl-L-phenylalanine
MOD_RES                13
                       note = alpha-methyl-L-phenylalanine
MOD_RES                18
                       note = 2-Aminoisobutyric acid
MOD_RES                20
                       note = Lys, wherein the side chain of Lys is connected to
                        O2Oc-O2Oc- gamma-Glu- gamma-Glu-C20diacid
SEQUENCE: 247
HXHGSXTSDV SKXLDSRXAX DFVQSIAN                                          28

SEQ ID NO: 248         moltype = AA  length = 29
FEATURE                Location/Qualifiers
source                 1..29
                       mol_type = protein
                       organism = Synthetic construct
MOD_RES                2
                       note = 2-Aminoisobutyric acid
MOD_RES                6
                       note = alpha-methyl-L-phenylalanine
MOD_RES                13
                       note = alpha-methyl-L-phenylalanine
MOD_RES                20
                       note = O2Oc-O2Oc- gamma-Glu- gamma-Glu-C18diacid
MOD_RES                22
                       note = alpha-methyl-L-phenylalanine
SEQUENCE: 248
HXHGSXTSDV SKXLDSRAAX DXVQSIANT                                         29

SEQ ID NO: 249         moltype = AA  length = 29
FEATURE                Location/Qualifiers
source                 1..29
                       mol_type = protein
                       organism = Synthetic construct
MOD_RES                2
                       note = 2-Aminoisobutyric acid
MOD_RES                6
                       note = alpha-methyl-L-phenylalanine
MOD_RES                13
                       note = alpha-methyl-L-phenylalanine
MOD_RES                20
                       note = Lys, wherein the side chain of Lys is connected to
                        O2Oc-O2Oc- gamma-Glu- gamma-Glu-C20diacid
MOD_RES                22
                       note = alpha-methyl-L-phenylalanine
SEQUENCE: 249
HXHGSXTSDV SKXLDSRAAX DXVQSIANT                                         29

SEQ ID NO: 250         moltype = AA  length = 29
FEATURE                Location/Qualifiers
source                 1..29
                       mol_type = protein
                       organism = Synthetic construct
MOD_RES                2
                       note = 2-Aminoisobutyric acid
MOD_RES                6
                       note = alpha-methyl-L-phenylalanine
MOD_RES                13
                       note = alpha-methyl-L-phenylalanine
MOD_RES                20
                       note = Lys, wherein the side chain of Lys is connected to
                        O2Oc-O2Oc- gamma-Glu-C18diacid
MOD_RES                22
                       note = alpha-methyl-L-phenylalanine
SEQUENCE: 250
HXHGSXTSDV SKXLDSRAAX DXVESIANT                                         29

SEQ ID NO: 251         moltype = AA  length = 29
FEATURE                Location/Qualifiers
source                 1..29
                       mol_type = protein
                       organism = Synthetic construct
MOD_RES                2
                       note = 2-Aminoisobutyric acid
MOD_RES                6
                       note = alpha-methyl-L-phenylalanine
MOD_RES                13
                       note = alpha-methyl-L-phenylalanine
```

```
MOD_RES                   20
                          note = Lys, wherein the side chain of Lys is connected to
                           O2Oc-O2Oc-gamma-Glu-gamma-Glu-C20diacid
MOD_RES                   22
                          note = alpha-methyl-L-phenylalanine
SEQUENCE: 251
HXHGSXTSDV SKXLDSRAAX DXVESIANT                                          29

SEQ ID NO: 252            moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   20
                          note = Lys, wherein the side chain of Lys is connected to
                           O2Oc-O2Oc-gamma-Glu-gamma-Glu-C18diacid
MOD_RES                   22
                          note = alpha-methyl-L-phenylalanine
SEQUENCE: 252
HXHGSXTSDV SKXLDSRAAX DXVQWIANT                                          29

SEQ ID NO: 253            moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   20
                          note = Lys, wherein the side chain of Lys is connected to
                           O2Oc-O2Oc-gamma-Glu-gamma-Glu-C20diacid
MOD_RES                   22
                          note = alpha-methyl-L-phenylalanine
SEQUENCE: 253
NXHGSXTSDV SKXLDSRAAX DXVQWIANT                                          29

SEQ ID NO: 254            moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   18
                          note = 2-Aminoisobutyric acid
MOD_RES                   20
                          note = Lys, wherein the side chain of Lys is connected to
                           O2Oc-O2Oc-gamma-Glu-gamma-Glu-C20diacid
MOD_RES                   22
                          note = alpha-methyl-L-phenylalanine
SEQUENCE: 254
HXHGSXTSDV SKXLDSRXAX DXVESIANT                                          29

SEQ ID NO: 255            moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   18
```

```
                        note = 2-Aminoisobutyric acid
MOD_RES                 20
                        note = Lys, wherein the side chain of Lys is connected to
                         O2Oc-O2Oc-gamma-Glu-gamma-Glu-C18diacid
MOD_RES                 22
                        note = alpha-methyl-L-phenylalanine
SEQUENCE: 255
HXHGSXTSDV SKXLDSRXAX DXVESIANT                                       29

SEQ ID NO: 256          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 18
                        note = 2-Aminoisobutyric acid
MOD_RES                 20
                        note = Lys, wherein the side chain of Lys is connected to
                         O2Oc-O2Oc-gamma-Glu-gamma-Glu-C18diacid
SEQUENCE: 256
HXHGSXTSDV SKXLDSRXAX DFVESIANT                                       29

SEQ ID NO: 257          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 18
                        note = 2-Aminoisobutyric acid
MOD_RES                 20
                        note = Lys, wherein the side chain of Lys is connected to
                         O2Oc-O2Oc-gamma-Glu-C20diacid
SEQUENCE: 257
HXHGSXTSDV SKXLDSRXAX DFVESIANT                                       29

SEQ ID NO: 258          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 18
                        note = 2-Aminoisobutyric acid
MOD_RES                 20
                        note = Lys, wherein the side chain of Lys is connected to
                         O2Oc-gamma-Glu-C18diacid
SEQUENCE: 258
HXHGSXTSDV SKXLDSRXAX DFVESIANT                                       29

SEQ ID NO: 259          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 18
                        note = 2-Aminoisobutyric acid
```

-continued

```
MOD_RES                 20
                        note = Lys, wherein the side chain of Lys is connected to
                         gamma-Glu-C18diacid
SEQUENCE: 259
HXHGSXTSDV SKXLDSRXAX DFVESIANT                                         29

SEQ ID NO: 260          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         O2Oc-O2Oc-gamma-Glu-C18diacid
MOD_RES                 22
                        note = alpha-methyl-L-phenylalanine
MOD_RES                 25
                        note = 2-Aminoisobutyric acid
SEQUENCE: 260
HXHGSXTSDV SKXLDSQAAX DXVQXIANT                                         29

SEQ ID NO: 261          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         O2Oc-O2Oc-gamma-Glu- gamma-Glu -C20diacid
MOD_RES                 22
                        note = alpha-methyl-L-phenylalanine
MOD_RES                 25
                        note = 2-Aminoisobutyric acid
SEQUENCE: 261
HXHGSXTSDV SKXLDSQAAX DXVQXIANT                                         29

SEQ ID NO: 262          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         O2Oc-O2Oc-gamma-Glu- gamma-Glu-Stearoyl
MOD_RES                 22
                        note = alpha-methyl-L-phenylalanine
MOD_RES                 25
                        note = 2-Aminoisobutyric acid
SEQUENCE: 262
HXHGSXTSDV SKXLDSRAAX DXVQXIANT                                         29

SEQ ID NO: 263          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
```

```
                         note = alpha-methyl-L-phenylalanine
MOD_RES                  20
                         note = Lys, wherein the side chain of Lys is connected to
                          polyethylene glycol 2- polyethylene glycol 2-gamma-Glu-
                          gamma-Glu- C18diacid
MOD_RES                  22
                         note = alpha-methyl-L-phenylalanine
MOD_RES                  25
                         note = 2-Aminoisobutyric acid
SEQUENCE: 263
HXHGSXTSDV SKXLDSRAAX DXVQXIANT                                                29

SEQ ID NO: 264           moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  6
                         note = alpha-methyl-L-phenylalanine
MOD_RES                  13
                         note = alpha-methyl-L-phenylalanine
MOD_RES                  20
                         note = Lys, wherein the side chain of Lys is connected to
                          O2Oc- gamma-Glu-O2Oc- C18diacid
MOD_RES                  22
                         note = alpha-methyl-L-phenylalanine
MOD_RES                  25
                         note = 2-Aminoisobutyric acid
SEQUENCE: 264
HXHGSXTSDV SKXLDSRAAX DXVQXIANT                                                29

SEQ ID NO: 265           moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  6
                         note = alpha-methyl-L-phenylalanine
MOD_RES                  13
                         note = alpha-methyl-L-phenylalanine
MOD_RES                  20
                         note = Lys, wherein the side chain of Lys is connected to
                          O2Oc- gamma-Glu-O2Oc- gamma-Glu-C18diacid
MOD_RES                  22
                         note = alpha-methyl-L-phenylalanine
MOD_RES                  25
                         note = 2-Aminoisobutyric acid
SEQUENCE: 265
HXHGSXTSDV SKXLDSRAAX DXVQXIANT                                                29

SEQ ID NO: 266           moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  6
                         note = alpha-methyl-L-phenylalanine
MOD_RES                  13
                         note = alpha-methyl-L-phenylalanine
MOD_RES                  20
                         note = Lys, wherein the side chain of Lys is connected to
                          polyethylene glycol 4- gamma-Glu- C18diacid
MOD_RES                  22
                         note = alpha-methyl-L-phenylalanine
MOD_RES                  25
                         note = 2-Aminoisobutyric acid
SEQUENCE: 266
HXHGSXTSDV SKXLDSRAAX DXVQXIANT                                                29

SEQ ID NO: 267           moltype = AA  length = 29
FEATURE                  Location/Qualifiers
source                   1..29
                         mol_type = protein
```

```
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         O2Oc- gamma-Glu-C18diacid
MOD_RES                 22
                        note = alpha-methyl-L-phenylalanine
MOD_RES                 25
                        note = 2-Aminoisobutyric acid
SEQUENCE: 267
HXHGSXTSDV SKXLDSRAAX DXVQXIANT                                         29

SEQ ID NO: 268          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         polyethylene glycol 4- gamma-Glu-gamma-Glu-C18diacid
MOD_RES                 22
                        note = alpha-methyl-L-phenylalanine
MOD_RES                 25
                        note = 2-Aminoisobutyric acid
SEQUENCE: 268
HXHGSXTSDV SKXLDSRAAX DXVQXIANT                                         29

SEQ ID NO: 269          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         polyethylene glycol 2- polyethylene glycol 2-
                         gamma-Glu-gamma-Glu-C20diacid
MOD_RES                 22
                        note = alpha-methyl-L-phenylalanine
MOD_RES                 25
                        note = 2-Aminoisobutyric acid
SEQUENCE: 269
HXHGSXTSDV SKXLDSRAAX DXVQXIANT                                         29

SEQ ID NO: 270          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         O2Oc- gamma-Glu- O2Oc-C20diacid
MOD_RES                 22
                        note = alpha-methyl-L-phenylalanine
MOD_RES                 25
                        note = 2-Aminoisobutyric acid
SEQUENCE: 270
```

-continued

```
HXHGSXTSDV SKXLDSRAAX DXVQXIANT                                          29

SEQ ID NO: 271          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         O2Oc- gamma-Glu- O2Oc-C20diacid
MOD_RES                 22
                        note = alpha-methyl-L-phenylalanine
MOD_RES                 25
                        note = 2-Aminoisobutyric acid
SEQUENCE: 271
HXHGSXTSDV SKXLDSRAAX DXVQXIANT                                          29

SEQ ID NO: 272          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         polyethylene glycol 4- gamma-Glu- C20diacid
MOD_RES                 22
                        note = alpha-methyl-L-phenylalanine
MOD_RES                 25
                        note = 2-Aminoisobutyric acid
SEQUENCE: 272
HXHGSXTSDV SKXLDSRAAX DXVQXIANT                                          29

SEQ ID NO: 273          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         O2Oc- gamma-Glu-C20diacid
MOD_RES                 22
                        note = alpha-methyl-L-phenylalanine
MOD_RES                 25
                        note = 2-Aminoisobutyric acid
SEQUENCE: 273
HXHGSXTSDV SKXLDSRAAX DXVQXIANT                                          29

SEQ ID NO: 274          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         polyethylene glycol 4- gamma-Glu- gamma-Glu -C20diacid
```

-continued

```
MOD_RES                  22
                         note = alpha-methyl-L-phenylalanine
MOD_RES                  25
                         note = 2-Aminoisobutyric acid
SEQUENCE: 274
HXHGSXTSDV SKXLDSRAAX DXVQXIANT                                            29

SEQ ID NO: 275           moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  6
                         note = alpha-methyl-L-phenylalanine
MOD_RES                  13
                         note = alpha-methyl-L-phenylalanine
MOD_RES                  20
                         note = Lys, wherein the side chain of Lys is connected to
                          gamma-Glu- gamma-Glu -C18diacid
MOD_RES                  22
                         note = alpha-methyl-L-phenylalanine
MOD_RES                  25
                         note = 2-Aminoisobutyric acid
SEQUENCE: 275
HXHGSXTSDV SKXLDSRAAX DXVQXIANT                                            29

SEQ ID NO: 276           moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  6
                         note = alpha-methyl-L-phenylalanine
MOD_RES                  13
                         note = alpha-methyl-L-phenylalanine
METAL                    20
                         note = Lys, wherein the side chain of Lys is connected to
                          gamma-Glu-C18diacid
MOD_RES                  22
                         note = alpha-methyl-L-phenylalanine
MOD_RES                  25
                         note = 2-Aminoisobutyric acid
SEQUENCE: 276
HXHGSXTSDV SKXLDSRAAX DXVQXIANT                                            29

SEQ ID NO: 277           moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  6
                         note = alpha-methyl-L-phenylalanine
MOD_RES                  13
                         note = alpha-methyl-L-phenylalanine
MOD_RES                  20
                         note = Lys, wherein the side chain of Lys is connected to
                          O2Oc- O2Oc-C18diacid
MOD_RES                  22
                         note = alpha-methyl-L-phenylalanine
MOD_RES                  25
                         note = 2-Aminoisobutyric acid
SEQUENCE: 277
HXHGSXTSDV SKXLDSRAAX DXVQXIANT                                            29

SEQ ID NO: 278           moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  6
                         note = alpha-methyl-L-phenylalanine
```

-continued

```
MOD_RES              13
                     note = alpha-methyl-L-phenylalanine
MOD_RES              20
                     note = Lys, wherein the side chain of Lys is connected to
                      O2Oc-C18diacid
MOD_RES              22
                     note = alpha-methyl-L-phenylalanine
MOD_RES              25
                     note = 2-Aminoisobutyric acid
SEQUENCE: 278
HXHGSXTSDV SKXLDSRAAX DXVQXIANT                                          29

SEQ ID NO: 279       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              6
                     note = alpha-methyl-L-phenylalanine
MOD_RES              13
                     note = alpha-methyl-L-phenylalanine
MOD_RES              20
                     note = Lys, wherein the side chain of Lys is connected to
                      O2Oc- gamma-Glu- gamma-Glu -C18diacid
MOD_RES              22
                     note = alpha-methyl-L-phenylalanine
MOD_RES              25
                     note = 2-Aminoisobutyric acid
SEQUENCE: 279
HXHGSXTSDV SKXLDSRAAX DXVQXIANT                                          29

SEQ ID NO: 280       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              6
                     note = alpha-methyl-L-phenylalanine
MOD_RES              13
                     note = alpha-methyl-L-phenylalanine
MOD_RES              20
                     note = Lys, wherein the side chain of Lys is connected to
                      gamma-Glu- gamma-Glu -C20diacid
MOD_RES              22
                     note = alpha-methyl-L-phenylalanine
MOD_RES              25
                     note = 2-Aminoisobutyric acid
SEQUENCE: 280
HXHGSXTSDV SKXLDSRAAX DXVQXIANT                                          29

SEQ ID NO: 281       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              6
                     note = alpha-methyl-L-phenylalanine
MOD_RES              13
                     note = alpha-methyl-L-phenylalanine
MOD_RES              20
                     note = Lys, wherein the side chain of Lys is connected to
                      gamma-Glu- C20diacid
MOD_RES              22
                     note = alpha-methyl-L-phenylalanine
MOD_RES              25
                     note = 2-Aminoisobutyric acid
SEQUENCE: 281
HXHGSXTSDV SKXLDSRAAX DXVQXIANT                                          29

SEQ ID NO: 282       moltype = AA  length = 29
FEATURE              Location/Qualifiers
source               1..29
                     mol_type = protein
```

```
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   20
                          note = O2Oc- O2Oc-C20diacid
MOD_RES                   22
                          note = alpha-methyl-L-phenylalanine
MOD_RES                   25
                          note = 2-Aminoisobutyric acid
SEQUENCE: 282
HXHGSXTSDV SKXLDSRAAX DXVQXIANT                                             29

SEQ ID NO: 283            moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   20
                          note = Lys, wherein the side chain of Lys is connected to
                           O2Oc-C20diacid
MOD_RES                   22
                          note = alpha-methyl-L-phenylalanine
MOD_RES                   25
                          note = 2-Aminoisobutyric acid
SEQUENCE: 283
HXHGSXTSDV SKXLDSRAAX DXVQXIANT                                             29

SEQ ID NO: 284            moltype = AA  length = 29
FEATURE                   Location/Qualifiers
source                    1..29
                          mol_type = protein
                          organism = Synthetic construct
MOD_RES                   1
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   20
                          note = Lys, wherein the side chain of Lys is connected to
                           O2Oc- gamma-Glu- gamma-Glu -C20diacid
MOD_RES                   22
                          note = alpha-methyl-L-phenylalanine
MOD_RES                   25
                          note = 2-Aminoisobutyric acid
SEQUENCE: 284
HXHGSXTSDV SKXLDSRAAX DXVQXIANT                                             29

SEQ ID NO: 285            moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   20
                          note = Lys, wherein the side chain of Lys is connected to
                           O2Oc-O2Oc-gamma-Glu-C20diacid
MOD_RES                   22
                          note = alpha-methyl-L-phenylalanine
MOD_RES                   25
                          note = 2-Aminoisobutyric acid
SEQUENCE: 285
HXHGSXTSDV SKXLDSRAAX DXVQXIANT                                             29
```

```
SEQ ID NO: 286          moltype = AA  length = 29
FEATURE                 Location/Qualifiers
source                  1..29
                        mol_type = protein
                        organism = Synthetic construct
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         O2Oc-O2Oc-gamma-Glu- gamma-Glu -C20diacid
MOD_RES                 22
                        note = alpha-methyl-L-phenylalanine
MOD_RES                 25
                        note = 2-Aminoisobutyric acid
SEQUENCE: 286
HSHGSXTSDV SKXLDSRAAX DXVQXIANT                                            29

SEQ ID NO: 287          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 20
                        note = Lys, wherein the side chain of Lys is connected to
                         O2Oc-O2Oc-gamma-Glu- gamma-Glu -C20diacid
MOD_RES                 22
                        note = alpha-methyl-L-phenylalanine
MOD_RES                 25
                        note = 2-Aminoisobutyric acid
SEQUENCE: 287
HXHGSFTSDV SKXLDSRAAX DXVQXIANT                                            29

SEQ ID NO: 288          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 20
                        note = Lys, wherein the side chain of Lys is connected to
                         O2Oc-O2O- gamma-Glu- gamma-Glu -C20diacid
MOD_RES                 22
                        note = alpha-methyl-L-phenylalanine
MOD_RES                 25
                        note = 2-Aminoisobutyric acid
SEQUENCE: 288
HXHGSXTSDV SKYLDSRAAX DXVQXIANT                                            29

SEQ ID NO: 289          moltype = AA  length = 29
FEATURE                 Location/Qualifiers
source                  1..29
                        mol_type = protein
                        organism = Synthetic construct
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         O2Oc-O2Oc-gamma-Glu-C18diacid
MOD_RES                 22
                        note = alpha-methyl-L-phenylalanine
MOD_RES                 25
                        note = 2-Aminoisobutyric acid
SEQUENCE: 289
HSHGSXTSDV SKXLDSRAAX DXVQXIANT                                            29

SEQ ID NO: 290          moltype = AA  length = 29
FEATURE                 Location/Qualifiers
source                  1..29
```

-continued

```
                         mol_type = protein
                         organism = Synthetic construct
MOD_RES                  2
                         note = 2-Aminoisobutyric acid
MOD_RES                  13
                         note = alpha-methyl-L-phenylalanine
MOD_RES                  20
                         note = Lys, wherein the side chain of Lys is connected to
                          O2Oc-O2Oc gamma-Glu-C18diacid
MOD_RES                  22
                         note = alpha-methyl-L-phenylalanine
MOD_RES                  25
                         note = 2-Aminoisobutyric acid
SEQUENCE: 290
HXHGSFTSDV SKXLDSRAAX DXVQXIANT                                         29

SEQ ID NO: 291           moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  6
                         note = alpha-methyl-L-phenylalanine
MOD_RES                  20
                         note = Lys, wherein the side chain of Lys is connected to
                          O2Oc-O2Oc- gamma-Glu -C18diacid
MOD_RES                  22
                         note = alpha-methyl-L-phenylalanine
MOD_RES                  25
                         note = 2-Aminoisobutyric acid
SEQUENCE: 291
HXHGSXTSDV SKYLDSRAAX DXVQXIANT                                         29

SEQ ID NO: 292           moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  6
                         note = alpha-methyl-L-phenylalanine
MOD_RES                  13
                         note = alpha-methyl-L-phenylalanine
MOD_RES                  20
                         note = Lys, wherein the side chain of Lys is connected to
                          O2Oc- O2Oc-gamma-Glu-C18diacid
MOD_RES                  25
                         note = 2-Aminoisobutyric acid
SEQUENCE: 292
HXHGSXTSDV SKXLDSRAAX DFVQXIANT                                         29

SEQ ID NO: 293           moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  6
                         note = alpha-methyl-L-phenylalanine
MOD_RES                  13
                         note = alpha-methyl-L-phenylalanine
MOD_RES                  20
                         note = Lys, wherein the side chain of Lys is connected to
                          O2Oc- O2Oc - gamma-Glu -C18diacid
MOD_RES                  22
                         note = alpha-methyl-L-phenylalanine
SEQUENCE: 293
HXHGSXTSDV SKXLDSRAAX DXVQWIANT                                         29

SEQ ID NO: 294           moltype = AA  length = 29
FEATURE                  Location/Qualifiers
source                   1..29
                         mol_type = protein
                         organism = Synthetic construct
MOD_RES                  2
```

```
                            note = 2-Aminoisobutyric acid
MOD_RES                     6
                            note = alpha-methyl-L-phenylalanine
MOD_RES                     20
                            note = Lys, wherein the side chain of Lys is connected to
                             O2Oc- O2Oc - gamma-Glu -gamma-Glu-C20diacid
SEQUENCE: 294
HXHGSXTSDV SKYLDSRAAX DFVQWIANT                                                  29

SEQ ID NO: 295             moltype = AA  length = 29
FEATURE                    Location/Qualifiers
source                     1..29
                           mol_type = protein
                           organism = Synthetic construct
MOD_RES                     2
                           note = 2-Aminoisobutyric acid
MOD_RES                    13
                           note = alpha-methyl-L-phenylalanine
MOD_RES                    20
                           note = Lys, wherein the side chain of Lys is connected to
                            O2Oc- O2Oc - gamma-Glu - gamma-Glu C20diacid
SEQUENCE: 295
HXHGSFTSDV SKXLDSRAAX DFVQWIANT                                                  29

SEQ ID NO: 296             moltype = AA  length = 29
FEATURE                    Location/Qualifiers
source                     1..29
                           mol_type = protein
                           organism = Synthetic construct
MOD_RES                     2
                           note = 2-Aminoisobutyric acid
MOD_RES                    20
                           note = Lys, wherein the side chain of Lys is connected to
                            O2Oc- O2Oc - gamma-Glu - gamma-Glu C20diacid
MOD_RES                    22
                           note = alpha-methyl-L-phenylalanine
SEQUENCE: 296
HXHGSFTSDV SKYLDSRAAX DXVQWIANT                                                  29

SEQ ID NO: 297             moltype = AA  length = 29
FEATURE                    Location/Qualifiers
source                     1..29
                           mol_type = protein
                           organism = Synthetic construct
MOD_RES                     2
                           note = 2-Aminoisobutyric acid
MOD_RES                    20
                           note = Lys, wherein the side chain of Lys is connected to
                            O2Oc- O2Oc-gamma-Glu-C18diacid
SEQUENCE: 297
HXHGSXTSDV SKYLDSRAAX DFVQWIANT                                                  29

SEQ ID NO: 298             moltype = AA  length = 29
FEATURE                    Location/Qualifiers
source                     1..29
                           mol_type = protein
                           organism = Synthetic construct
MOD_RES                     2
                           note = 2-Aminoisobutyric acid
MOD_RES                    13
                           note = alpha-methyl-L-phenylalanine
MOD_RES                    20
                           note = Lys, wherein the side chain of Lys is connected to
                            O2Oc- O2Oc - gamma-Glu - C18diacid
SEQUENCE: 298
HXHGSFTSDV SKXLDSRAAX DFVQWIANT                                                  29

SEQ ID NO: 299             moltype = AA  length = 29
FEATURE                    Location/Qualifiers
source                     1..29
                           mol_type = protein
                           organism = Synthetic construct
MOD_RES                     2
                           note = 2-Aminoisobutyric acid
MOD_RES                    20
                           note = Lys, wherein the side chain of Lys is connected to
                            O2Oc- O2Oc - gamma-Glu-C18diacid
MOD_RES                    22
                           note = alpha-methyl-L-phenylalanine
```

```
SEQUENCE: 299
HXHGSFTSDV SKYLDSRAAX DXVQWIANT                                    29

SEQ ID NO: 300          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = 2-Aminoisobutyric acid
MOD_RES                 20
                        note = Lys, wherein the side chain of Lys is connected to
                         O2Oc- O2Oc - gamma-Glu- gamma-Glu-C20diacid
MOD_RES                 22
                        note = alpha-methyl-L-phenylalanine
MOD_RES                 25
                        note = 2-Aminoisobutyric acid
SEQUENCE: 300
HXHGSXTSDV SKXLDSRAAX DXVQXIANT                                    29

SEQ ID NO: 301          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = 2-Aminoisobutyric acid
MOD_RES                 20
                        note = Lys, wherein the side chain of Lys is connected to
                         O2Oc- O2Oc -gamma-Glu-C18diacid
MOD_RES                 22
                        note = alpha-methyl-L-phenylalanine
MOD_RES                 25
                        note = 2-Aminoisobutyric acid
SEQUENCE: 301
HXHGSXTSDV SKXLDSRAAX DXVQXIANT                                    29

SEQ ID NO: 302          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 20
                        note = Lys, wherein the side chain of Lys is connected to
                         O2Oc- O2Oc - gamma-Glu-C18diacid
MOD_RES                 22
                        note = alpha-methyl-L-phenylalanine
MOD_RES                 25
                        note = 2-Aminoisobutyric acid
SEQUENCE: 302
HXHGSXTSDV SRXLDSRAAX DXVQXIANT                                    29

SEQ ID NO: 303          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 25
                        note = 2-Aminoisobutyric acid
MOD_RES                 6
                        note = alpha-methyl-L-phenylalanine
MOD_RES                 13
                        note = alpha-methyl-L-phenylalanine
```

-continued

```
MOD_RES              22
                     note = alpha-methyl-L-phenylalanine
MOD_RES              20
                     note = Lys, wherein the side chain of Lys is connected to
                     O2Oc- O2Oc - gamma-Glu- gamma-Glu -C20diacid
SEQUENCE: 303
HXHGSXTSDV SRXLDSRAAX DXVQXIANT                                        29

SEQ ID NO: 304       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              25
                     note = 2-Aminoisobutyric acid
MOD_RES              6
                     note = alpha-methyl-L-phenylalanine
MOD_RES              13
                     note = alpha-methyl-L-phenylalanine
MOD_RES              22
                     note = alpha-methyl-L-phenylalanine
MOD_RES              20
                     note = Lys, wherein the side chain of Lys is connected to
                     O2Oc- O2Oc - gamma-Glu- gamma-Glu -C20diacid
SEQUENCE: 304
HXHGSXTSDV SKXLDSRAAX DXVQXIAET                                        29

SEQ ID NO: 305       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              25
                     note = 2-Aminoisobutyric acid
MOD_RES              6
                     note = alpha-methyl-L-phenylalanine
MOD_RES              13
                     note = alpha-methyl-L-phenylalanine
MOD_RES              22
                     note = alpha-methyl-L-phenylalanine
MOD_RES              20
                     note = Lys, wherein the side chain of Lys is connected to
                     O2Oc- O2Oc - gamma-Glu -C18diacid
SEQUENCE: 305
HXHGSXTSDV SKXLDSRAAX DXVQXIAET                                        29

SEQ ID NO: 306       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              25
                     note = 2-Aminoisobutyric acid
METAL                6
                     note = alpha-methyl-L-phenylalanine
MOD_RES              13
                     note = alpha-methyl-L-phenylalanine
MOD_RES              22
                     note = alpha-methyl-L-phenylalanine
MOD_RES              20
                     note = O2Oc- O2Oc - gamma-Glu -C18diacid
SEQUENCE: 306
HXHGSXTSDV SKXLDSRAAX DXIAXIAET                                        29

SEQ ID NO: 307       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              25
                     note = 2-Aminoisobutyric acid
```

```
MOD_RES              6
                     note = alpha-methyl-L-phenylalanine
MOD_RES              13
                     note = alpha-methyl-L-phenylalanine
MOD_RES              22
                     note = alpha-methyl-L-phenylalanine
MOD_RES              20
                     note = Lys, wherein the side chain of Lys is connected to
                     O2Oc- O2Oc - gamma-Glu - gamma-Glu-C20diacid
SEQUENCE: 307
HXHGSXTSDV SKXLDSRAAX DXIAXIAET                                          29

SEQ ID NO: 308       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              25
                     note = 2-Aminoisobutyric acid
MOD_RES              6
                     note = alpha-methyl-L-phenylalanine
MOD_RES              13
                     note = alpha-methyl-L-phenylalanine
MOD_RES              22
                     note = alpha-methyl-L-phenylalanine
MOD_RES              20
                     note = Lys, wherein the side chain of Lys is connected to
                     O2Oc- O2Oc - gamma-Glu-C18diacid
SEQUENCE: 308
HXHGSXTSDV SKXLDSRAAX DXVQXIANT                                          29

SEQ ID NO: 309       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              25
                     note = 2-Aminoisobutyric acid
MOD_RES              6
                     note = alpha-methyl-L-phenylalanine
MOD_RES              13
                     note = alpha-methyl-L-phenylalanine
MOD_RES              22
                     note = alpha-methyl-L-phenylalanine
MOD_RES              20
                     note = Lys, wherein the side chain of Lys is connected to
                     O2Oc- O2Oc - gamma-Glu- gamma-Glu-C20diacid
SEQUENCE: 309
HXHGSXTSDV SKXLDSRAAX DXVQXIANT                                          29

SEQ ID NO: 310       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              13
                     note = alpha-methyl-L-phenylalanine
MOD_RES              20
                     note = Lys, wherein the side chain of Lys is connected to
                     O2Oc- O2Oc - gamma-Glu- gamma-Glu-C20diacid
SEQUENCE: 310
HXHGTFTSDV SKXLDSRAAX DFVQWIANT                                          29

SEQ ID NO: 311       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              13
                     note = alpha-methyl-L-phenylalanine
MOD_RES              20
```

-continued

```
                              note = Lys, wherein the side chain of Lys is connected to
                                O2Oc- O2Oc-gamma-Glu-C18diacid
SEQUENCE: 311
HXQGTFTSDV SKXLDSRAAX DFVEWIANT                                        29

SEQ ID NO: 312         moltype = AA  length = 29
FEATURE                Location/Qualifiers
source                 1..29
                       mol_type = protein
                       organism = Synthetic construct
MOD_RES                2
                       note = 2-Aminoisobutyric acid
MOD_RES                13
                       note = alpha-methyl-L-phenylalanine
MOD_RES                20
                       note = Lys, wherein the side chain of Lys is connected to
                         O2Oc- O2Oc-gamma-Glu-C18diacid
SEQUENCE: 312
HXQGTFTSDV SKXLDSRAAX DFVRWIANT                                        29

SEQ ID NO: 313         moltype = AA  length = 29
FEATURE                Location/Qualifiers
source                 1..29
                       mol_type = protein
                       organism = Synthetic construct
MOD_RES                2
                       note = 2-Aminoisobutyric acid
MOD_RES                13
                       note = alpha-methyl-L-phenylalanine
MOD_RES                20
                       note = Lys, wherein the side chain of Lys is connected to
                         O2Oc- O2Oc-gamma-Glu-C18diacid
SEQUENCE: 313
HXQGTFTSDV SKXLDTRAAX DFVQWIANT                                        29

SEQ ID NO: 314         moltype = AA  length = 29
FEATURE                Location/Qualifiers
source                 1..29
                       mol_type = protein
                       organism = Synthetic construct
MOD_RES                2
                       note = 2-Aminoisobutyric acid
MOD_RES                13
                       note = alpha-methyl-L-phenylalanine
MOD_RES                20
                       note = Lys, wherein the side chain of Lys is connected to
                         O2Oc- O2Oc-gamma-Glu-C18diacid
SEQUENCE: 314
HXQGTFTSDV SKXLDERAAX DFVQWIANT                                        29

SEQ ID NO: 315         moltype = AA  length = 30
FEATURE                Location/Qualifiers
source                 1..30
                       mol_type = protein
                       organism = Synthetic construct
MOD_RES                2
                       note = 2-Aminoisobutyric acid
MOD_RES                13
                       note = alpha-methyl-L-phenylalanine
MOD_RES                20
                       note = Lys, wherein the side chain of Lys is connected to
                         O2Oc- O2Oc-gamma-Glu-C18diacid
SEQUENCE: 315
HXQGTFTSDV SKXLDSRAAX DFVQWLEAGG                                       30

SEQ ID NO: 316         moltype = AA  length = 29
FEATURE                Location/Qualifiers
source                 1..29
                       mol_type = protein
                       organism = Synthetic construct
MOD_RES                2
                       note = 2-Aminoisobutyric acid
MOD_RES                13
                       note = alpha-methyl-L-phenylalanine
MOD_RES                20
                       note = Lys, wherein the side chain of Lys is connected to
                         O2Oc- O2Oc-gamma-Glu-C18diacid
SEQUENCE: 316
HXQGTFTSDV SKXLDSRAAX DFVQWLVET                                        29
```

```
SEQ ID NO: 317          moltype = AA  length = 28
FEATURE                 Location/Qualifiers
source                  1..28
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 20
                        note = Lys, wherein the side chain of Lys is connected to
                         O2Oc- O2Oc-gamma-Glu-C18diacid
MOD_RES                 28
                        note = polyethylene glycol
SEQUENCE: 317
HXQGTFTSDY SKXLDSRRAX DFVQWLVX                                   28

SEQ ID NO: 318          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 18
                        note = 2-Aminoisobutyric acid
MOD_RES                 13
                        note = alpha-methyl-L-phenylalanine
MOD_RES                 20
                        note = Lys, wherein the side chain of Lys is connected to
                         O2Oc- O2Oc-gamma-Glu-C18diacid
SEQUENCE: 318
HXQGTFTSDV SKXLDSRXAX DFVQWLLNT                                  29

SEQ ID NO: 319          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 25
                        note = 2-Aminoisobutyric acid
MOD_RES                 18
                        note = 2-Aminoisobutyric acid
MOD_RES                 13
                        note = alpha-methyl-L-phenylalanine
MOD_RES                 20
                        note = Lys, wherein the side chain of Lys is connected to
                         O2Oc- O2Oc-gamma-Glu-C18diacid
SEQUENCE: 319
HXQGTFTSDV SKXLDSRXAX DFVQXLVAT                                  29

SEQ ID NO: 320          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 25
                        note = 2-Aminoisobutyric acid
MOD_RES                 13
                        note = alpha-methyl-L-phenylalanine
MOD_RES                 20
                        note = Lys, wherein the side chain of Lys is connected to
                         O2Oc- O2Oc-gamma-Glu-C18diacid
SEQUENCE: 320
HXQGTFTSDV SKXLDSRAAX DFVQXLVAT                                  29

SEQ ID NO: 321          moltype = AA  length = 29
FEATURE                 Location/Qualifiers
source                  1..29
                        mol_type = protein
                        organism = Synthetic construct
MOD_RES                 20
                        note = Lys, wherein the side chain of Lys is connected to
                         O2Oc- O2Oc-gamma-Glu-stearoyl
```

```
MOD_RES                 13
                        note = alpha-methyl-L-phenylalanine
SEQUENCE: 321
HSQGTFTSDY SKXLEEEAVX LFIRWLMNT                                              29

SEQ ID NO: 322          moltype = AA   length = 29
FEATURE                 Location/Qualifiers
source                  1..29
                        mol_type = protein
                        organism = Synthetic construct
MOD_RES                 2
                        note = 2-Aminoisobutyric acid
MOD_RES                 16
                        note = 2-Aminoisobutyric acid
MOD_RES                 13
                        note = alpha-methyl-L-phenylalanine
MOD_RES                 20
                        note = Lys, wherein the side chain of Lys is connected to
                         O2Oc- O2Oc-gamma-Glu-C18diacid
SEQUENCE: 322
HXQGTFTSDV SKXLDXRAAX DFVQWIANT                                              29

SEQ ID NO: 323          moltype = AA   length = 29
FEATURE                 Location/Qualifiers
source                  1..29
                        mol_type = protein
                        organism = Synthetic construct
MOD_RES                 2
                        note = alpha-methyl-L-serine
MOD_RES                 13
                        note = alpha-methyl-L-phenylalanine
MOD_RES                 20
                        note = Lys, wherein the side chain of Lys is connected to
                         O2Oc- O2Oc-gamma-Glu-C18diacid
SEQUENCE: 323
HXQGTFTSDV SKXLDSRAAX DFVQWIANT                                              29

SEQ ID NO: 324          moltype = AA   length = 29
FEATURE                 Location/Qualifiers
source                  1..29
                        mol_type = protein
                        organism = Synthetic construct
MOD_RES                 3
                        note = alpha-Methyl-glutamine
MOD_RES                 13
                        note = alpha-methyl-L-phenylalanine
MOD_RES                 20
                        note = Lys, wherein the side chain of Lys is connected to
                         O2Oc- O2Oc-gamma-Glu-C18diacid
SEQUENCE: 324
HSXGTFTSDV SKXLDSRAAX DFVQWIANT                                              29

SEQ ID NO: 325          moltype = AA   length = 29
FEATURE                 Location/Qualifiers
source                  1..29
                        mol_type = protein
                        organism = Synthetic construct
MOD_RES                 2
                        note = D-serine
MOD_RES                 13
                        note = alpha-methyl-L-phenylalanine
MOD_RES                 20
                        note = 2-Aminoisobutyric acid Lys, wherein the side chain
                         of Lys is connected to O2Oc- O2Oc-gamma-Glu-C18diacid
SEQUENCE: 325
HXQGTFTSDV SKXLDSRAAX DFVQWIANT                                              29

SEQ ID NO: 326          moltype = AA   length = 29
FEATURE                 Location/Qualifiers
source                  1..29
                        mol_type = protein
                        organism = Synthetic construct
MOD_RES                 2
                        note = 2-Aminoisobutyric acid
MOD_RES                 25
                        note = 2-Aminoisobutyric acid
MOD_RES                 6
                        note = alpha-methyl-L-phenylalanine
MOD_RES                 13
```

```
                              note = alpha-methyl-L-phenylalanine
MOD_RES                       20
                              note = Lys, wherein the side chain of Lys is connected to
                                 O2Oc- O2Oc-gamma-Glu-C18diacid
MOD_RES                       22
                              note = alpha-methyl-L-phenylalanine
SEQUENCE: 326
HXQGSXTSDV SKXLDSRAAX DXVQXIANT                                              29

SEQ ID NO: 327                moltype = AA   length = 29
FEATURE                       Location/Qualifiers
source                        1..29
                              mol_type = protein
                              organism = Synthetic construct
MOD_RES                       2
                              note = 2-Aminoisobutyric acid
MOD_RES                       25
                              note = 2-Aminoisobutyric acid
MOD_RES                       6
                              note = alpha-methyl-L-phenylalanine
MOD_RES                       13
                              note = alpha-methyl-L-phenylalanine
MOD_RES                       22
                              note = alpha-methyl-L-phenylalanine
MOD_RES                       20
                              note = Lys, wherein the side chain of Lys is connected to
                                 O2Oc- O2Oc-gamma-Glu- gamma-Glu -C20diacid
SEQUENCE: 327
HXQGSXTSDV SKXLDSRAAX DXVQXIANT                                              29

SEQ ID NO: 328                moltype = AA   length = 29
FEATURE                       Location/Qualifiers
source                        1..29
                              mol_type = protein
                              organism = Synthetic construct
MOD_RES                       3
                              note = alpha-Methyl-glutamine
MOD_RES                       6
                              note = alpha-methyl-L-phenylalanine
MOD_RES                       13
                              note = alpha-methyl-L-phenylalanine
MOD_RES                       22
                              note = alpha-methyl-L-phenylalanine
MOD_RES                       20
                              note = Lys, wherein the side chain of Lys is connected to
                                 O2Oc- O2OcGlu- gamma-Glu -C18diacid
MOD_RES                       25
                              note = 2-Aminoisobutyric acid
SEQUENCE: 328
HSXGSXTSDV SKXLDSRAAX DXVQXIANT                                              29

SEQ ID NO: 329                moltype = AA   length = 29
FEATURE                       Location/Qualifiers
source                        1..29
                              mol_type = protein
                              organism = Synthetic construct
MOD_RES                       3
                              note = Beta-dimethylglutamine
MOD_RES                       6
                              note = alpha-methyl-L-phenylalanine
MOD_RES                       13
                              note = alpha-methyl-L-phenylalanine
MOD_RES                       22
                              note = alpha-methyl-L-phenylalanine
MOD_RES                       20
                              note = Lys, wherein the side chain of Lys is connected to
                                 O2Oc- O2Oc-gamma-Glu-C18diacid
MOD_RES                       25
                              note = 2-Aminoisobutyric acid
SEQUENCE: 329
HSXGSXTSDV SKXLDSRAAX DXVQXIANT                                              29

SEQ ID NO: 330                moltype = AA   length = 29
FEATURE                       Location/Qualifiers
source                        1..29
                              mol_type = protein
                              organism = Synthetic construct
MOD_RES                       3
                              note = N-Methyl-Glutamine
```

```
MOD_RES                   6
                          note = alpha-methyl-L-phenylalanine
MOD_RES                   13
                          note = alpha-methyl-L-phenylalanine
MOD_RES                   22
                          note = alpha-methyl-L-phenylalanine
MOD_RES                   20
                          note = Lys, wherein the side chain of Lys is connected to
                           O2Oc- O2Oc- gamma-Glu -C18diacid
MOD_RES                   25
                          note = 2-Aminoisobutyric acid
SEQUENCE: 330
HSXGSXTSDV SKXLDSRAAX DXVQXIANT                                      29

SEQ ID NO: 331            moltype = AA  length = 29
FEATURE                   Location/Qualifiers
source                    1..29
                          mol_type = protein
                          organism = Synthetic construct
MOD_RES                   3
                          note = dimethylglutamine
MOD_RES                   6
                          note = alpha-methyl-L-phenylalanine
MOD_RES                   13
                          note = alpha-methyl-L-phenylalanine
MOD_RES                   22
                          note = alpha-methyl-L-phenylalanine
MOD_RES                   20
                          note = Lys, wherein the side chain of Lys is connected to
                           O2Oc- O2Oc-gamma-Glu-C18diacid
MOD_RES                   25
                          note = 2-Aminoisobutyric acid
SEQUENCE: 331
HSXGSXTSDV SKXLDSRAAX DXVQXIANT                                      29

SEQ ID NO: 332            moltype = AA  length = 29
FEATURE                   Location/Qualifiers
source                    1..29
                          mol_type = protein
                          organism = Synthetic construct
MOD_RES                   2
                          note = aminocyclopropane-1-carboxylic acid
MOD_RES                   6
                          note = alpha-methyl-L-phenylalanine
MOD_RES                   13
                          note = alpha-methyl-L-phenylalanine
MOD_RES                   22
                          note = alpha-methyl-L-phenylalanine
MOD_RES                   20
                          note = Lys, wherein the side chain of Lys is connected to
                           O2Oc- O2Oc-Glu- gamma-C18diacid
MOD_RES                   25
                          note = 2-Aminoisobutyric acid
SEQUENCE: 332
HSXGSXTSDV SKXLDSRAAX DXVQXIANT                                      29

SEQ ID NO: 333            moltype = AA  length = 29
FEATURE                   Location/Qualifiers
source                    1..29
                          mol_type = protein
                          organism = Synthetic construct
MOD_RES                   2
                          note = 1-aminocyclobutane-1-carboxylic acid
MOD_RES                   6
                          note = alpha-methyl-L-phenylalanine
MOD_RES                   13
                          note = alpha-methyl-L-phenylalanine
MOD_RES                   22
                          note = alpha-methyl-L-phenylalanine
MOD_RES                   20
                          note = Lys, wherein the side chain of Lys is connected to
                           O2Oc- O2Oc-gamma-Glu -C18diacid
MOD_RES                   25
                          note = 2-Aminoisobutyric acid
SEQUENCE: 333
HXQGSXTSDV SKXLDSRAAX DXVQXIANT                                      29

SEQ ID NO: 334            moltype = AA  length = 29
FEATURE                   Location/Qualifiers
```

```
source                  1..29
                        mol_type = protein
                        organism = Synthetic construct
MOD_RES                 2
                        note = alpha-methyl-L-serine
MOD_RES                 6
                        note = alpha-methyl-L-phenylalanine
MOD_RES                 13
                        note = alpha-methyl-L-phenylalanine
MOD_RES                 22
                        note = alpha-methyl-L-phenylalanine
MOD_RES                 20
                        note = Lys, wherein the side chain of Lys is connected to
                         O2Oc- O2Oc-gamma-Glu -C18diacid
MOD_RES                 25
                        note = 2-Aminoisobutyric acid
SEQUENCE: 334
HXQGSXTSDV SKXLDSRAAX DXVQXIANT                                       29

SEQ ID NO: 335          moltype = AA  length = 29
FEATURE                 Location/Qualifiers
source                  1..29
                        mol_type = protein
                        organism = Synthetic construct
MOD_RES                 2
                        note = D-serine
MOD_RES                 6
                        note = alpha-methyl-L-phenylalanine
MOD_RES                 13
                        note = alpha-methyl-L-phenylalanine
MOD_RES                 22
                        note = alpha-methyl-L-phenylalanine
MOD_RES                 20
                        note = Lys, wherein the side chain of Lys is connected to
                         O2Oc-O2Oc-gamma-Glu-C18diacid
MOD_RES                 25
                        note = 2-Aminoisobutyric acid
SEQUENCE: 335
HXQGSXTSDV SKXLDSRAAX DXVQXIANT                                       29

SEQ ID NO: 336          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 29
                        note = 2-Aminoisobutyric acid
MOD_RES                 13
                        note = alpha-methyl-L-phenylalanine
MOD_RES                 20
                        note = Lys, wherein the side chain of Lys is connected to
                         O2Oc- O2Oc- gamma-Glu -C18diacid
SEQUENCE: 336
HXQGTFTSDV SKXLDSRRAX DFVRWLLEXG                                      30

SEQ ID NO: 337          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 29
                        note = 2-Aminoisobutyric acid
MOD_RES                 13
                        note = alpha-methyl-L-phenylalanine
MOD_RES                 20
                        note = Lys, wherein the side chain of Lys is connected to
                         O2Oc- O2Oc- gamma-Glu -C18diacid
SEQUENCE: 337
HXQGTFTSDV SKXLDSRRAX DFVQWLLEXG                                      30

SEQ ID NO: 338          moltype = AA  length = 30
FEATURE                 Location/Qualifiers
source                  1..30
                        mol_type = protein
                        organism = Synthetic construct
```

-continued

```
MOD_RES              2
                     note = 2-Aminoisobutyric acid
MOD_RES              28
                     note = 2-Aminoisobutyric acid
MOD_RES              13
                     note = alpha-methyl-L-phenylalanine
MOD_RES              20
                     note = Lys, wherein the side chain of Lys is connected to
                     O2Oc- O2Oc- gamma-Glu -C18diacid
SEQUENCE: 338
HXQGTFTSDV SKXLDSRRAX DFVQWLLXTE                                         30

SEQ ID NO: 339       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              28
                     note = 2-Aminoisobutyric acid
MOD_RES              13
                     note = alpha-methyl-L-phenylalanine
MOD_RES              20
                     note = Lys, wherein the side chain of Lys is connected to
                     gamma-Glu -C18diacid
SEQUENCE: 339
HXQGTFTSDY SKXLDSRRAX DFVQWLAXE                                          29

SEQ ID NO: 340       moltype = AA  length = 30
FEATURE              Location/Qualifiers
source               1..30
                     mol_type = protein
                     organism = Synthetic construct
MOD_RES              2
                     note = 2-Aminoisobutyric acid
MOD_RES              29
                     note = 2-Aminoisobutyric acid
MOD_RES              13
                     note = alpha-methyl-L-phenylalanine
MOD_RES              20
                     note = Lys, wherein the side chain of Lys is connected to
                     gamma-Glu -C18diacid
SEQUENCE: 340
HXQGTFTSDY SKXLDSRRAX DFVQWLLEXG                                         30

SEQ ID NO: 341       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              13
                     note = alpha-methyl-L-phenylalanine
MOD_RES              20
                     note = Lys, wherein the side chain of Lys is connected to  g
                     amma-Glu -C18diacid
SEQUENCE: 341
HXQGTFTSDY SKXLDSRRAX DFVQWLISE                                          29

SEQ ID NO: 342       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              28
                     note = 2-Aminoisobutyric acid
MOD_RES              13
                     note = alpha-methyl-L-phenylalanine
MOD_RES              20
                     note = Lys, wherein the side chain of Lys is connected to
                     gamma-Glu -C18diacid
SEQUENCE: 342
HXQGTFTSDY SKXLDSRRAX DFVQWLLXT                                          29

SEQ ID NO: 343       moltype = AA  length = 29
```

-continued

```
FEATURE              Location/Qualifiers
source               1..29
                     mol_type = protein
                     organism = Synthetic construct
MOD_RES              2
                     note = 2-Aminoisobutyric acid
MOD_RES              28
                     note = 2-Aminoisobutyric acid
MOD_RES              13
                     note = alpha-methyl-L-phenylalanine
MOD_RES              20
                     note = Lys, wherein the side chain of Lys is connected to
                      gamma-Glu -C18diacid
MOD_RES              16
                     note = alpha-methyl-L-phenylalanine
SEQUENCE: 343
HXQGTFTSDY SKXLDXRRAX DFVQWLLXT                                          29

SEQ ID NO: 344       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              28
                     note = 2-Aminoisobutyric acid
MOD_RES              13
                     note = alpha-methyl-L-phenylalanine
MOD_RES              20
                     note = Lys, wherein the side chain of Lys is connected to
                      gamma-Glu -C18diacid
SEQUENCE: 344
HXQGTFTSDY SKXLDSRRAX DFVQWLLXE                                          29

SEQ ID NO: 345       moltype = AA  length = 30
FEATURE              Location/Qualifiers
source               1..30
                     mol_type = protein
                     organism = Synthetic construct
MOD_RES              2
                     note = 2-Aminoisobutyric acid
MOD_RES              28
                     note = 2-Aminoisobutyric acid
MOD_RES              13
                     note = alpha-methyl-L-phenylalanine
MOD_RES              20
                     note = Lys, wherein the side chain of Lys is connected to
                      gamma-Glu -C18diacid
SEQUENCE: 345
HXQGTFTSDY SKXLDSRRAX DFVQWLLXTE                                         30

SEQ ID NO: 346       moltype = AA  length = 30
FEATURE              Location/Qualifiers
source               1..30
                     mol_type = protein
                     organism = Synthetic construct
MOD_RES              2
                     note = 2-Aminoisobutyric acid
MOD_RES              29
                     note = 2-Aminoisobutyric acid
MOD_RES              13
                     note = alpha-methyl-L-phenylalanine
MOD_RES              20
                     note = Lys, wherein the side chain of Lys is connected to
                      gamma-Glu -C18diacid
SEQUENCE: 346
HXQGTFTSDY SKXLDSRRAX DFVQWLLEXT                                         30

SEQ ID NO: 347       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              13
                     note = alpha-methyl-L-phenylalanine
MOD_RES              20
```

-continued

```
                              note = Lys, wherein the side chain of Lys is connected to
                                 gamma-Glu -C18diacid
SEQUENCE: 347
HXQGTFTSDV SKXLDSRAAX DFVQWIANT                                              29

SEQ ID NO: 348           moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  13
                         note = alpha-methyl-L-phenylalanine
MOD_RES                  20
                         note = Lys, wherein the side chain of Lys is connected to
                            gamma-Glu-gamma-Glu-O2Oc- O2Oc- gamma-Glu
                            -gamma-Glu-C18diacid
SEQUENCE: 348
HXQGTFTSDV SKXLDSRAAX DFVQWIANT                                              29

SEQ ID NO: 349           moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  13
                         note = Diphenylalanine
MOD_RES                  24
                         note = Lys, wherein the side chain of Lys is connected to  g
                            amma-Glu -C18diacid
SEQUENCE: 349
HXQGSFTSDV SKXLDSRAAQ DFVXWIANT                                              29

SEQ ID NO: 350           moltype = AA  length = 28
FEATURE                  Location/Qualifiers
source                   1..28
                         mol_type = protein
                         organism = Synthetic construct
MOD_RES                  6
                         note = alpha-methyl-L-phenylalanine
MOD_RES                  22
                         note = alpha-methyl-L-phenylalanine
MOD_RES                  13
                         note = 2-Aminoisobutyric acid
MOD_RES                  25
                         note = 2-Aminoisobutyric acid
MOD_RES                  24
                         note = Lys, wherein the side chain of Lys is connected to
                            O2Oc- O2Oc- gamma-Glu -C18diacid
SEQUENCE: 350
HSQGSXTSDV SKXLDSRAAQ DXVXXIAN                                               28

SEQ ID NO: 351           moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  13
                         note = alpha-methyl-L-phenylalanine
MOD_RES                  24
                         note = Lys, wherein the side chain of Lys is connected to
                            O2Oc- O2Oc- gamma-Glu -C18diacid
SEQUENCE: 351
HXHGTFTSDV SKXLDSQAAQ DFVXWIANT                                              29

SEQ ID NO: 352           moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  13
                         note = alpha-methyl-L-phenylalanine
```

-continued

```
MOD_RES                 24
                        note = Lys, wherein the side chain of Lys is connected to
                         gamma-Glu -C18diacid
SEQUENCE: 352
HXHGTFTSDV SKXLDSQAAQ DFVXWIANT                                      29

SEQ ID NO: 353          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 24
                        note = Lys, wherein the side chain of Lys is connected to
                         gamma-Glu -C20diacid
SEQUENCE: 353
HXHGTFTSDV SKXLDSQAAQ DFVXWIANT                                      29

SEQ ID NO: 354          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 24
                        note = Lys, wherein the side chain of Lys is connected to
                         O2Oc- O2Oc- gamma-Glu -C18diacid
SEQUENCE: 354
HXQGSXTSDV SKXLDSQAAQ DFVXWIANT                                      29

SEQ ID NO: 355          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 24
                        note = Lys, wherein the side chain of Lys is connected to
                         O2Oc- O2Oc- gamma-Glu -C18diacid
SEQUENCE: 355
HXHGSXTSDV SKXLDSQAAQ DFVXWIANT                                      29

SEQ ID NO: 356          moltype = AA  length = 31
FEATURE                 Location/Qualifiers
source                  1..31
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 24
                        note = Lys, wherein the side chain of Lys is connected to
                         O2Oc- O2Oc- gamma-Glu -C18diacid
SEQUENCE: 356
HXHGSXTSDV SKXLDSQAAQ DFVXWIANTG G                                   31

SEQ ID NO: 357          moltype = AA  length = 24
FEATURE                 Location/Qualifiers
source                  1..24
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
```

```
MOD_RES                  24
                         note = Lys, wherein the side chain of Lys is connected to
                          gamma-Glu -C18diacid
SEQUENCE: 357
HXHGSXTSDV SKXLDSQAAQ DFVX                                          24

SEQ ID NO: 358           moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  6
                         note = alpha-methyl-L-phenylalanine
MOD_RES                  13
                         note = alpha-methyl-L-phenylalanine
MOD_RES                  24
                         note = Lys, wherein the side chain of Lys is connected to
                          polyethylene glycol 2-polyethylene glycol
                          2-gamma-Glu-gamma-Glu-C20diacid
SEQUENCE: 358
HXHGSXTSDV SKXLDSQAAQ DFVXWIANT                                     29

SEQ ID NO: 359           moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  6
                         note = alpha-methyl-L-phenylalanine
MOD_RES                  13
                         note = alpha-methyl-L-phenylalanine
MOD_RES                  24
                         note = Lys, wherein the side chain of Lys is connected to
                          gamma-Glu-gamma-Glu-polyethylene glycol
                          2-gamma-Glu-gamma-Glu-C28diacid
SEQUENCE: 359
HXHGSXTSDV SKXLDSQAAQ DFVXWIANT                                     29

SEQ ID NO: 360           moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  6
                         note = alpha-methyl-L-phenylalanine
MOD_RES                  13
                         note = alpha-methyl-L-phenylalanine
MOD_RES                  24
                         note = Lys, wherein the side chain of Lys is connected to
                          gamma-Glu -C20diacid
SEQUENCE: 360
HXHGSXTSDV SKXLDSQAAQ DFVXWIANT                                     29

SEQ ID NO: 361           moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  6
                         note = alpha-methyl-L-phenylalanine
MOD_RES                  13
                         note = alpha-methyl-L-phenylalanine
MOD_RES                  24
                         note = Lys, wherein the side chain of Lys is connected to
                          polyethylene glycol 2-polyethylene glycol
                          2-gamma-Glu-gamma-Glu-C20diacid
SEQUENCE: 361
HXHGSXTSDV SKXLDSQAAQ DFVXWIANT                                     29

SEQ ID NO: 362           moltype = AA  length = 29
FEATURE                  Location/Qualifiers
```

-continued

```
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 24
                        note = Lys, wherein the side chain of Lys is connected to
                         O2Oc- O2Oc- gamma-Glu -C20diacid
SEQUENCE: 362
HXHGSXTSDV SKXLDSQAAQ DFVXWIANT                                      29

SEQ ID NO: 363          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 24
                        note = Lys, wherein the side chain of Lys is connected to
                         -gamma-Glu-gamma-Glu- polyethylene glycol
                         2-gamma-Glu-gamma-Glu-C20diacid
SEQUENCE: 363
HXHGSXTSDV SKXLDSQAAQ DFVXWIANT                                      29

SEQ ID NO: 364          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 24
                        note = Lys, wherein the side chain of Lys is connected to
                         O2Oc- O2Oc- gamma-Glu -C18diacid
SEQUENCE: 364
HXIGSXTSDV SKXLDSQAAQ DFVXWIANT                                      29

SEQ ID NO: 365          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 24
                        note = Lys, wherein the side chain of Lys is connected to
                         O2Oc- O2Oc- gamma-Glu -C18diacid
SEQUENCE: 365
HXIGSXTSDV SKXLDSRAAQ DFVXWIANT                                      29

SEQ ID NO: 366          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 24
```

-continued

```
                         note = Lys, wherein the side chain of Lys is connected to
                          O2Oc- O2Oc- gamma-Glu -C20diacid
SEQUENCE: 366
HXIGSXTSDV SKXLDSRAAQ DFVXWIANT                                                29

SEQ ID NO: 367           moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  6
                         note = alpha-methyl-L-phenylalanine
MOD_RES                  13
                         note = alpha-methyl-L-phenylalanine
MOD_RES                  24
                         note = Lys, wherein the side chain of Lys is connected to
                          O2Oc- O2Oc- gamma-Glu -C18diacid
SEQUENCE: 367
HXHGSXTSDV SKXLDSRAAQ DFVXWIANT                                                29

SEQ ID NO: 368           moltype = AA  length = 29
FEATURE                  Location/Qualifiers
source                   1..29
                         mol_type = protein
                         organism = Synthetic construct
MOD_RES                  2
                         note = 2-Aminoisobutyric acid
MOD_RES                  6
                         note = alpha-methyl-L-phenylalanine
MOD_RES                  13
                         note = alpha-methyl-L-phenylalanine
MOD_RES                  24
                         note = Lys, wherein the side chain of Lys is connected to
                          O2Oc- O2Oc- gamma-Glu-gamma-Glu-C18diacid
SEQUENCE: 368
HXHGSXTSDV SKXLDSRAAQ DFVXWIANT                                                29

SEQ ID NO: 369           moltype = AA  length = 30
FEATURE                  Location/Qualifiers
source                   1..30
                         mol_type = protein
                         organism = Synthetic construct
MOD_RES                  2
                         note = 2-Aminoisobutyric acid
MOD_RES                  6
                         note = alpha-methyl-L-phenylalanine
MOD_RES                  13
                         note = alpha-methyl-L-phenylalanine
MOD_RES                  24
                         note = Lys, wherein the side chain of Lys is connected to
                          O2Oc- O2Oc- gamma-Glu -gamma-Glu-C18diacid
SEQUENCE: 369
HXHGSXTSDV SKXLDSRAAQ DFVXWIANTG                                               30

SEQ ID NO: 370           moltype = AA  length = 31
FEATURE                  Location/Qualifiers
source                   1..31
                         mol_type = protein
                         organism = Synthetic construct
MOD_RES                  2
                         note = 2-Aminoisobutyric acid
MOD_RES                  6
                         note = alpha-methyl-L-phenylalanine
MOD_RES                  13
                         note = alpha-methyl-L-phenylalanine
MOD_RES                  24
                         note = Lys, wherein the side chain of Lys is connected to
                          O2Oc- O2Oc- gamma-Glu -gamma-Glu-C18diacid
SEQUENCE: 370
HXHGSXTSDV SKXLDSRAAQ DFVXWIANTG G                                             31

SEQ ID NO: 371           moltype = AA  length = 29
FEATURE                  Location/Qualifiers
source                   1..29
                         mol_type = protein
                         organism = Synthetic construct
MOD_RES                  2
```

```
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   18
                          note = 2-Aminoisobutyric acid
MOD_RES                   20
                          note = Lys, wherein the side chain of Lys is connected to
                           O2Oc- O2Oc- gamma-Glu -C18diacid
SEQUENCE: 371
HXHGSXTSDV SKXLDSRXAQ DFVXWIANT                                    29

SEQ ID NO: 372            moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   25
                          note = 2-Aminoisobutyric acid
MOD_RES                   6
                          note = alpha-methyl-L-phenylalanine
METAL                     13
                          note = alpha-methyl-L-phenylalanine
MOD_RES                   24
                          note = Lys, wherein the side chain of Lys is connected to
                           O2Oc- O2Oc- gamma-Glu -C18diacid
SEQUENCE: 372
HXHGSXTSDV SKXLDSRAAQ DFVXXIANT                                    29

SEQ ID NO: 373            moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   24
                          note = Lys, wherein the side chain of Lys is connected to
                           O2Oc- O2Oc- gamma-Glu -C20diacid
SEQUENCE: 373
HXHGSXTSDV SKXLDSRAAQ DFVXWIANT                                    29

SEQ ID NO: 374            moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   18
                          note = 2-Aminoisobutyric acid
MOD_RES                   6
                          note = alpha-methyl-L-phenylalanine
MOD_RES                   13
                          note = alpha-methyl-L-phenylalanine
MOD_RES                   24
                          note = Lys, wherein the side chain of Lys is connected to
                           O2Oc- O2Oc- gamma-Glu -C20diacid
SEQUENCE: 374
HXHGSXTSDV SKXLDSRXAQ DFVXWIANT                                    29

SEQ ID NO: 375            moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   25
                          note = 2-Aminoisobutyric acid
MOD_RES                   6
                          note = alpha-methyl-L-phenylalanine
```

```
MOD_RES              13
                     note = alpha-methyl-L-phenylalanine
MOD_RES              24
                     note = Lys, wherein the side chain of Lys is connected to
                       O2Oc- O2Oc- gamma-Glu -C20diacid
SEQUENCE: 375
HXHGSXTSDV SKXLDSRAAQ DFVXXIANT                                      29

SEQ ID NO: 376       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              6
                     note = alpha-methyl-L-phenylalanine
MOD_RES              13
                     note = alpha-methyl-L-phenylalanine
MOD_RES              24
                     note = Lys, wherein the side chain of Lys is connected to
                       O2Oc- O2Oc- gamma-Glu -C18diacid
SEQUENCE: 376
HXHGSXTSDV SKXLDSQAAQ DXVXWIANT                                      29

SEQ ID NO: 377       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              6
                     note = alpha-methyl-L-phenylalanine
MOD_RES              13
                     note = alpha-methyl-L-phenylalanine
MOD_RES              22
                     note = alpha-methyl-L-phenylalanine
MOD_RES              24
                     note = Lys, wherein the side chain of Lys is connected to
                       O2Oc-O2Oc-gamma-Glu- gamma-Glu -C18diacid
SEQUENCE: 377
HXHGSXTSDV SKXLDSRAAQ DXVXWIANT                                      29

SEQ ID NO: 378       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              25
                     note = 2-Aminoisobutyric acid
MOD_RES              6
                     note = alpha-methyl-L-phenylalanine
MOD_RES              13
                     note = alpha-methyl-L-phenylalanine
MOD_RES              22
                     note = alpha-methyl-L-phenylalanine
MOD_RES              24
                     note = Lys, wherein the side chain of Lys is connected to
                       O2Oc- O2Oc- gamma-Glu-gamma-GluC18diacid
SEQUENCE: 378
HXHGSXTSDV SKXLDSRAAQ DXVXXIANT                                      29

SEQ ID NO: 379       moltype = AA  length = 31
FEATURE              Location/Qualifiers
source               1..31
                     mol_type = protein
                     organism = Synthetic construct
MOD_RES              2
                     note = 2-Aminoisobutyric acid
MOD_RES              25
                     note = 2-Aminoisobutyric acid
MOD_RES              6
                     note = alpha-methyl-L-phenylalanine
MOD_RES              13
                     note = alpha-methyl-L-phenylalanine
MOD_RES              22
```

-continued

```
                             note = alpha-methyl-L-phenylalanine
MOD_RES                      24
                             note = Lys, wherein the side chain of Lys is connected to
                              O2Oc- O2Oc- gamma-Glu -gamma-Glu-C18diacid
SEQUENCE: 379
HXHGSXTSDV SKXLDSRAAQ DXVXXIANTG G                                      31

SEQ ID NO: 380               moltype = AA  length = 29
FEATURE                      Location/Qualifiers
source                       1..29
                             mol_type = protein
                             organism = Synthetic construct
MOD_RES                      2
                             note = 2-Aminoisobutyric acid
MOD_RES                      6
                             note = alpha-methyl-L-phenylalanine
MOD_RES                      13
                             note = alpha-methyl-L-phenylalanine
MOD_RES                      22
                             note = alpha-methyl-L-phenylalanine
MOD_RES                      24
                             note = Lys, wherein the side chain of Lys is connected to
                              O2Oc- O2Oc-gamma-Glu- gamma-Glu -C20diacid
SEQUENCE: 380
HXHGSXTSDV SKXLDSRAAQ DXVXWIANT                                         29

SEQ ID NO: 381               moltype = AA  length = 29
FEATURE                      Location/Qualifiers
source                       1..29
                             mol_type = protein
                             organism = Synthetic construct
MOD_RES                      2
                             note = 2-Aminoisobutyric acid
MOD_RES                      25
                             note = 2-Aminoisobutyric acid
MOD_RES                      6
                             note = alpha-methyl-L-phenylalanine
MOD_RES                      13
                             note = alpha-methyl-L-phenylalanine
MOD_RES                      22
                             note = alpha-methyl-L-phenylalanine
MOD_RES                      24
                             note = Lys, wherein the side chain of Lys is connected to
                              O2Oc- O2Oc- gamma-Glu -gamma-Glu-C20diacid
SEQUENCE: 381
HXHGSXTSDV SKXLDSRAAQ DXVXXIANT                                         29

SEQ ID NO: 382               moltype = AA  length = 31
FEATURE                      Location/Qualifiers
source                       1..31
                             mol_type = protein
                             organism = Synthetic construct
MOD_RES                      2
                             note = 2-Aminoisobutyric acid
MOD_RES                      25
                             note = 2-Aminoisobutyric acid
MOD_RES                      6
                             note = alpha-methyl-L-phenylalanine
MOD_RES                      13
                             note = alpha-methyl-L-phenylalanine
MOD_RES                      22
                             note = alpha-methyl-L-phenylalanine
MOD_RES                      24
                             note = Lys, wherein the side chain of Lys is connected to
                              O2Oc- O2Oc-gamma-Glu- gamma-Glu -C20diacid
SEQUENCE: 382
HXHGSXTSDV SKXLDSRAAQ DXVXXIANTG G                                      31

SEQ ID NO: 383               moltype = AA  length = 29
FEATURE                      Location/Qualifiers
source                       1..29
                             mol_type = protein
                             organism = Synthetic construct
MOD_RES                      2
                             note = 2-Aminoisobutyric acid
MOD_RES                      6
                             note = alpha-methyl-L-phenylalanine
MOD_RES                      13
                             note = alpha-methyl-L-phenylalanine
```

-continued

```
MOD_RES          24
                 note = Lys, wherein the side chain of Lys is connected to
                 O2Oc- O2Oc- gamma-Glu -gamma-Glu-C24diacid
SEQUENCE: 383
HXHGSXTSDV SKXLDSRAAQ DFVXWIANT                                      29

SEQ ID NO: 384        moltype = AA   length = 29
FEATURE               Location/Qualifiers
source                1..29
                      mol_type = protein
                      organism = Synthetic construct
MOD_RES          2
                 note = 2-Aminoisobutyric acid
MOD_RES          6
                 note = alpha-methyl-L-phenylalanine
MOD_RES          13
                 note = alpha-methyl-L-phenylalanine
MOD_RES          22
                 note = alpha-methyl-L-phenylalanine
MOD_RES          24
                 note = Lys, wherein the side chain of Lys is connected to
                 O2Oc- O2Oc- gamma-Glu -gamma-Glu-C18diacid
SEQUENCE: 384
HXHGSXTSDV SKXLDSRAAQ DXVXSIANT                                      29

SEQ ID NO: 385        moltype = AA   length = 29
FEATURE               Location/Qualifiers
source                1..29
                      mol_type = protein
                      organism = Synthetic construct
MOD_RES          2
                 note = 2-Aminoisobutyric acid
MOD_RES          6
                 note = alpha-methyl-L-phenylalanine
MOD_RES          13
                 note = alpha-methyl-L-phenylalanine
MOD_RES          22
                 note = alpha-methyl-L-phenylalanine
MOD_RES          24
                 note = Lys, wherein the side chain of Lys is connected to
                 O2Oc- O2Oc- gamma-Glu -C18diacid
SEQUENCE: 385
HXHGSXTSDV SKXLDSRAAQ DXVXSIANT                                      29

SEQ ID NO: 386        moltype = AA   length = 29
FEATURE               Location/Qualifiers
source                1..29
                      mol_type = protein
                      organism = Synthetic construct
MOD_RES          1
                 note = 1H-imidazol-4-yl)methyl)glycine
MOD_RES          6
                 note = alpha-methyl-L-phenylalanine
MOD_RES          13
                 note = alpha-methyl-L-phenylalanine
MOD_RES          24
                 note = Lys, wherein the side chain of Lys is connected to
                 O2Oc- O2Oc- gamma-Glu -gamma-Glu-C20diacid
SEQUENCE: 386
XSHGSXTSDV SKXLDSRAAQ DFVXWIANT                                      29

SEQ ID NO: 387        moltype = AA   length = 31
FEATURE               Location/Qualifiers
source                1..31
                      mol_type = protein
                      organism = Synthetic construct
MOD_RES          2
                 note = 2-Aminoisobutyric acid
MOD_RES          6
                 note = alpha-methyl-L-phenylalanine
MOD_RES          13
                 note = alpha-methyl-L-phenylalanine
MOD_RES          24
                 note = Lys, wherein the side chain of Lys is connected to
                 O2Oc- O2Oc- gamma-Glu -gamma-Glu-C18diacid
SEQUENCE: 387
HXHGSXTSDV SKXLDSRAAQ DFVXSIANTG G                                   31

SEQ ID NO: 388        moltype = AA   length = 31
```

-continued

```
FEATURE               Location/Qualifiers
source                1..31
                      mol_type = protein
                      organism = Synthetic construct
MOD_RES               2
                      note = 2-Aminoisobutyric acid
MOD_RES               6
                      note = alpha-methyl-L-phenylalanine
MOD_RES               13
                      note = alpha-methyl-L-phenylalanine
MOD_RES               24
                      note = Lys, wherein the side chain of Lys is connected to
                       O2Oc- O2Oc- gamma-Glu -gamma-Glu-C18diacid
SEQUENCE: 388
HXHGSXTSDV SKXLDSRXAQ DFVXSIANTG G                                31

SEQ ID NO: 389        moltype = AA  length = 29
FEATURE               Location/Qualifiers
source                1..29
                      mol_type = protein
                      organism = Synthetic construct
MOD_RES               2
                      note = 2-Aminoisobutyric acid
MOD_RES               25
                      note = 2-Aminoisobutyric acid
MOD_RES               6
                      note = alpha-methyl-L-phenylalanine
MOD_RES               13
                      note = alpha-methyl-L-phenylalanine
MOD_RES               22
                      note = alpha-methyl-L-phenylalanine
MOD_RES               24
                      note = Lys, wherein the side chain of Lys is connected to
                       O2Oc- O2Oc- gamma-Glu -C18diacid
SEQUENCE: 389
HXHGSXTSDV SKXLDSQAAQ DXVXXIANT                                   29

SEQ ID NO: 390        moltype = AA  length = 29
FEATURE               Location/Qualifiers
source                1..29
                      mol_type = protein
                      organism = Synthetic construct
MOD_RES               2
                      note = 2-Aminoisobutyric acid
MOD_RES               25
                      note = 2-Aminoisobutyric acid
MOD_RES               6
                      note = alpha-methyl-L-phenylalanine
MOD_RES               13
                      note = alpha-methyl-L-phenylalanine
MOD_RES               22
                      note = alpha-methyl-L-phenylalanine
MOD_RES               24
                      note = Lys, wherein the side chain of Lys is connected to
                       O2Oc- O2Oc- gamma-Glu -gamma-Glu-C20diacid
SEQUENCE: 390
HXHGSXTSDV SKXLDSQAAQ DXVXXIANT                                   29

SEQ ID NO: 391        moltype = AA  length = 29
FEATURE               Location/Qualifiers
source                1..29
                      mol_type = protein
                      organism = Synthetic construct
MOD_RES               13
                      note = alpha-methyl-L-phenylalanine
MOD_RES               24
                      note = Lys, wherein the side chain of Lys is connected to
                       O2Oc- O2Oc- gamma-Glu -stearoyl
SEQUENCE: 391
HSQGTFTSDY SKXLEEEAVR LFIXWLMNT                                   29

SEQ ID NO: 392        moltype = AA  length = 30
FEATURE               Location/Qualifiers
source                1..30
                      mol_type = protein
                      organism = Synthetic construct
MOD_RES               2
                      note = 2-Aminoisobutyric acid
MOD_RES               29
```

-continued

```
                             note = 2-Aminoisobutyric acid
MOD_RES                      13
                             note = alpha-methyl-L-phenylalanine
MOD_RES                      24
                             note = Lys, wherein the side chain of Lys is connected to
                              O2Oc- O2Oc- gamma-Glu -C18diacid
SEQUENCE: 392
HXQGTFTSDV SKXLDSRRAQ DFVXWLVEXG                                            30

SEQ ID NO: 393               moltype = AA  length = 30
FEATURE                      Location/Qualifiers
source                       1..30
                             mol_type = protein
                             organism = Synthetic construct
MOD_RES                      2
                             note = 2-Aminoisobutyric acid
MOD_RES                      29
                             note = 2-Aminoisobutyric acid
MOD_RES                      13
                             note = alpha-methyl-L-phenylalanine
MOD_RES                      24
                             note = Lys, wherein the side chain of Lys is connected to
                              O2Oc- O2Oc- gamma-Glu -C18diacid
SEQUENCE: 393
HXQGTFTSDV SKXLESRRAQ DFVXWLVEXG                                            30

SEQ ID NO: 394               moltype = AA  length = 30
FEATURE                      Location/Qualifiers
source                       1..30
                             mol_type = protein
                             organism = Synthetic construct
MOD_RES                      2
                             note = 2-Aminoisobutyric acid
MOD_RES                      29
                             note = 2-Aminoisobutyric acid
MOD_RES                      13
                             note = alpha-methyl-L-phenylalanine
MOD_RES                      24
                             note = Lys, wherein the side chain of Lys is connected to
                              O2Oc- O2Oc- gamma-Glu -C18diacid
SEQUENCE: 394
HXQGTFTSDV SKXLDLRRAQ DFVXWLVEXG                                            30

SEQ ID NO: 395               moltype = AA  length = 29
FEATURE                      Location/Qualifiers
source                       1..29
                             mol_type = protein
                             organism = Synthetic construct
MOD_RES                      2
                             note = 2-Aminoisobutyric acid
MOD_RES                      28
                             note = 2-Aminoisobutyric acid
MOD_RES                      13
                             note = alpha-methyl-L-phenylalanine
MOD_RES                      24
                             note = Lys, wherein the side chain of Lys is connected to
                              O2Oc- O2Oc- gamma-Glu -C18diacid
SEQUENCE: 395
HXQGTFTSDV SKXLDSRRAQ DFVXWLLXT                                             29

SEQ ID NO: 396               moltype = AA  length = 30
FEATURE                      Location/Qualifiers
source                       1..30
                             mol_type = protein
                             organism = Synthetic construct
MOD_RES                      2
                             note = 2-Aminoisobutyric acid
MOD_RES                      30
                             note = 2-Aminoisobutyric acid
MOD_RES                      13
                             note = alpha-methyl-L-phenylalanine
MOD_RES                      24
                             note = Lys, wherein the side chain of Lys is connected to
                              O2Oc- O2Oc- gamma-Glu -C18diacid
SEQUENCE: 396
HXQGTFTSDV SKXLDSRRAQ DFVXWLVEGX                                            30

SEQ ID NO: 397               moltype = AA  length = 29
FEATURE                      Location/Qualifiers
```

-continued

```
source                   1..29
                         mol_type = protein
                         organism = Synthetic construct
MOD_RES                  2
                         note = 2-Aminoisobutyric acid
MOD_RES                  25
                         note = 2-Aminoisobutyric acid
MOD_RES                  10
                         note = Lys, wherein the side chain of Lys is connected to
                          O2Oc- O2Oc- gamma-Glu -gamma-Glu-C20diacid
MOD_RES                  6
                         note = alpha-methyl-L-phenylalanine
MOD_RES                  13
                         note = alpha-methyl-L-phenylalanine
MOD_RES                  22
                         note = alpha-methyl-L-phenylalanine
SEQUENCE: 397
HXHGSXTSDX SKXLDSRAAQ DXVQXIANT                                            29

SEQ ID NO: 398           moltype = AA   length = 29
FEATURE                  Location/Qualifiers
source                   1..29
                         mol_type = protein
                         organism = Synthetic construct
MOD_RES                  2
                         note = 2-Aminoisobutyric acid
MOD_RES                  25
                         note = 2-Aminoisobutyric acid
MOD_RES                  6
                         note = alpha-methyl-L-phenylalanine
MOD_RES                  13
                         note = alpha-methyl-L-phenylalanine
MOD_RES                  22
                         note = alpha-methyl-L-phenylalanine
MOD_RES                  10
                         note = Lys, wherein the side chain of Lys is connected to
                          O2Oc- O2Oc- gamma-Glu -C18diacid
SEQUENCE: 398
HXHGSXTSDX SKXLDSRAAQ DXVQXIANT                                            29

SEQ ID NO: 399           moltype = AA   length = 29
FEATURE                  Location/Qualifiers
source                   1..29
                         mol_type = protein
                         organism = Synthetic construct
MOD_RES                  6
                         note = alpha-methyl-L-phenylalanine
MOD_RES                  22
                         note = alpha-methyl-L-phenylalanine
MOD_RES                  10
                         note = Lys, wherein the side chain of Lys is connected to
                          polyethylene glycol 2-polyethylene glycol
                          2-gamma-Glu-gamma-Glu-Stearoyl
MOD_RES                  13
                         note = diphenylpropanoic acid
MOD_RES                  17
                         note = Beta-dimethylglutamine
SEQUENCE: 399
HSQGSXTSDX SKXLDSXAAQ DXVEXLANT                                            29

SEQ ID NO: 400           moltype = AA   length = 29
FEATURE                  Location/Qualifiers
source                   1..29
                         mol_type = protein
                         organism = Synthetic construct
MOD_RES                  6
                         note = alpha-methyl-L-phenylalanine
MOD_RES                  22
                         note = alpha-methyl-L-phenylalanine
MOD_RES                  10
                         note = Lys, wherein the side chain of Lys is connected to
                          polyethylene glycol 2-polyethylene glycol
                          2-gamma-Glu-gamma-Glu-Palmitoyl
MOD_RES                  13
                         note = diphenylpropanoic acid
MOD_RES                  17
                         note = Beta-dimethylglutamine
SEQUENCE: 400
HSQGSXTSDX SKXLDSXAAQ DXVEXLANT                                            29
```

-continued

```
SEQ ID NO: 401        moltype = AA  length = 29
FEATURE               Location/Qualifiers
source                1..29
                      mol_type = protein
                      organism = Synthetic construct
MOD_RES               2
                      note = 2-Aminoisobutyric acid
MOD_RES               10
                      note = Lys, wherein the side chain of Lys is connected to
                       polyethylene glycol 2-polyethylene glycol
                       2-gamma-Glu-Palmitoyl
SEQUENCE: 401
HXQGSFTSDX SKILDSRAAQ DFVEWIANT                                         29

SEQ ID NO: 402        moltype = AA  length = 29
FEATURE               Location/Qualifiers
source                1..29
                      mol_type = protein
                      organism = Synthetic construct
MOD_RES               2
                      note = 2-Aminoisobutyric acid
MOD_RES               10
                      note = Lys, wherein the side chain of Lys is connected to
                       polyethylene glycol 2-polyethylene glycol
                       2-gamma-Glu-Palmitoyl
MOD_RES               22
                      note = alpha-methyl-L-phenylalanine
MOD_RES               6
                      note = alpha-methyl-L-phenylalanine
SEQUENCE: 402
HXQGSXTSDX SKILDSRAAQ DXVEWIANT                                         29

SEQ ID NO: 403        moltype = AA  length = 29
FEATURE               Location/Qualifiers
source                1..29
                      mol_type = protein
                      organism = Synthetic construct
MOD_RES               6
                      note = alpha-methyl-L-phenylalanine
MOD_RES               22
                      note = alpha-methyl-L-phenylalanine
MOD_RES               10
                      note = Lys, wherein the side chain of Lys is connected to
                       polyethylene glycol 2-polyethylene glycol
                       2-gamma-Glu-gamma-Glu-Stearoyl
MOD_RES               13
                      note = diphenylpropanoic acid
SEQUENCE: 403
HSQGSXTSDX SKXLDSQAAQ DXVEXLANT                                         29

SEQ ID NO: 404        moltype = AA  length = 29
FEATURE               Location/Qualifiers
source                1..29
                      mol_type = protein
                      organism = Synthetic construct
MOD_RES               6
                      note = alpha-methyl-L-phenylalanine
MOD_RES               22
                      note = alpha-methyl-L-phenylalanine
MOD_RES               10
                      note = Lys, wherein the side chain of Lys is connected to
                       polyethylene glycol 2-polyethylene glycol
                       2-gamma-Glu-gamma-Glu-Stearoyl
MOD_RES               13
                      note = diphenylpropanoic acid
MOD_RES               17
                      note = Beta-dimethylglutamine
SEQUENCE: 404
HSQGSXTSDX SKXLDSXAAQ DXVEHLANT                                         29

SEQ ID NO: 405        moltype = AA  length = 29
FEATURE               Location/Qualifiers
source                1..29
                      mol_type = protein
                      organism = Synthetic construct
MOD_RES               6
                      note = alpha-methyl-L-phenylalanine
MOD_RES               22
```

```
                          note = alpha-methyl-L-phenylalanine
MOD_RES                   13
                          note = Lys, wherein the side chain of Lys is connected to
                           polyethylene glycol 2-polyethylene glycol
                           2-gamma-Glu-gamma-Glu-Stearoyl)
MOD_RES                   17
                          note = Beta-dimethylglutamine
SEQUENCE: 405
HSQGSXTSDV SKXLDSXAAQ DXVEXLANT                                              29

SEQ ID NO: 406            moltype = AA  length = 29
FEATURE                   Location/Qualifiers
source                    1..29
                          mol_type = protein
                          organism = Synthetic construct
MOD_RES                   6
                          note = alpha-methyl-L-phenylalanine
MOD_RES                   22
                          note = alpha-methyl-L-phenylalanine
MOD_RES                   13
                          note = Lys, wherein the side chain of Lys is connected to
                           polyethylene glycol 2-polyethylene glycol
                           2-gamma-Glu-gamma-Glu-Palmitoyl
MOD_RES                   17
                          note = Beta-dimethylglutamine
SEQUENCE: 406
HSQGSXTSDV SKXLDSXAAQ DXVEXLANT                                              29

SEQ ID NO: 407            moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   6
                          note = alpha-methyl-L-phenylalanine
MOD_RES                   22
                          note = alpha-methyl-L-phenylalanine
MOD_RES                   13
                          note = Lys, wherein the side chain of Lys is connected to
                           polyethylene glycol 2-polyethylene glycol
                           2-gamma-Glu-Palmitoyl
SEQUENCE: 407
HXQGSXTSDV SKXLDSRAAQ DXVEWIANT                                              29

SEQ ID NO: 408            moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   13
                          note = Lys, wherein the side chain of Lys is connected to
                           polyethylene glycol 2-polyethylene glycol
                           2-gamma-Glu-Palmitoyl
SEQUENCE: 408
HXQGSFTSDV SKXLDSRAAQ DFVEWIANT                                              29

SEQ ID NO: 409            moltype = AA  length = 29
FEATURE                   Location/Qualifiers
source                    1..29
                          mol_type = protein
                          organism = Synthetic construct
MOD_RES                   6
                          note = alpha-methyl-L-phenylalanine
MOD_RES                   22
                          note = alpha-methyl-L-phenylalanine
MOD_RES                   13
                          note = Lys, wherein the side chain of Lys is connected to
                           polyethylene glycol 2-polyethylene glycol
                           2-gamma-Glu-gamma-Glu-Stearoyl
MOD_RES                   25
                          note = 2-Aminoisobutyric acid
SEQUENCE: 409
HSQGSXTSDV SKXLDSQAAQ DXVEXLANT                                              29

SEQ ID NO: 410            moltype = AA  length = 29
```

-continued

```
FEATURE               Location/Qualifiers
source                1..29
                      mol_type = protein
                      organism = Synthetic construct
MOD_RES               6
                      note = alpha-methyl-L-phenylalanine
MOD_RES               22
                      note = alpha-methyl-L-phenylalanine
MOD_RES               13
                      note = Lys, wherein the side chain of Lys is connected to
                       polyethylene glycol 2-polyethylene glycol
                       2-gamma-Glu-gamma-Glu-Stearoyl
MOD_RES               17
                      note = Beta-dimethylglutamine
SEQUENCE: 410
HSQGSXTSDV SKXLDSXAAQ DXVEHLANT                                          29

SEQ ID NO: 411        moltype = AA  length = 29
FEATURE               Location/Qualifiers
source                1..29
                      mol_type = protein
                      organism = Synthetic construct
MOD_RES               2
                      note = 2-Aminoisobutyric acid
MOD_RES               25
                      note = 2-Aminoisobutyric acid
MOD_RES               6
                      note = alpha-methyl-L-phenylalanine
MOD_RES               22
                      note = alpha-methyl-L-phenylalanine
MOD_RES               13
                      note = Lys, wherein the side chain of Lys is connected to
                       O2Oc- O2Oc- gamma-Glu -gamma-Glu-C20diacid
SEQUENCE: 411
HXHGSXTSDV SKXLDSRAAQ DXVQXIANT                                          29

SEQ ID NO: 412        moltype = AA  length = 29
FEATURE               Location/Qualifiers
source                1..29
                      mol_type = protein
                      organism = Synthetic construct
MOD_RES               2
                      note = 2-Aminoisobutyric acid
MOD_RES               25
                      note = 2-Aminoisobutyric acid
MOD_RES               6
                      note = alpha-methyl-L-phenylalanine
MOD_RES               22
                      note = alpha-methyl-L-phenylalanine
MOD_RES               13
                      note = Lys, wherein the side chain of Lys is connected to
                       O2Oc- O2Oc- gamma-Glu -C18diacid
SEQUENCE: 412
HXHGSXTSDV SKXLDSRAAQ DXVQXIANT                                          29

SEQ ID NO: 413        moltype = AA  length = 32
FEATURE               Location/Qualifiers
source                1..32
                      mol_type = protein
                      organism = synthetic construct
VARIANT               2
                      note = X is S, Aminoisobutyric acid (Aib),
                       alphaMethyl-Serine (alphaMeS), D-serine (dSer),
                       1-aminocyclopropane-1-carboxylic acid (Acpr), or S,
                       1-aminocyclobutane-1-carboxylic acid (Acbu)
VARIANT               3
                      note = X is Q, H, alphaMethyl-Glutamine (alphaMeGln),
                       N-Methyl-Glutamine (N-MeGln), D-glutamine (dGln) or
                       beta-dimethylglutamine (beta-dimethylGln)
VARIANT               5
                      note = X is T or S
VARIANT               6
                      note = X is F or alphaMethyl-Phenylalanine (alphaMePhe)
VARIANT               10
                      note = X is Y or V
VARIANT               12
                      note = X is K, E, or R
VARIANT               13
                      note = X is Y, alphaMePhe, or Aib
```

```
VARIANT              15
                     note = X is D or E
VARIANT              16
                     note = X is S, T, E, or Aib
VARIANT              17
                     note = X is R, Q, or E
VARIANT              18
                     note = X is R, A, Aib, or S
VARIANT              19
                     note = X is A or V
VARIANT              20
                     note = X is Q or K, wherein the K can comprise an acyl
                      moiety and/or can be lipidated
VARIANT              21
                     note = X is D or L
VARIANT              22
                     note = X is F or alphaMethyl-Phenylalanine (alphaMePhe)
VARIANT              23
                     note = X is V or I
VARIANT              24
                     note = X  is Q, E, A, or R
VARIANT              25
                     note = X is W, Aib, or S
VARIANT              26
                     note = X is L or I
VARIANT              27
                     note = X is M, A, L, E, I, or V
VARIANT              28
                     note = X is N, E, (PEG)4, Aib, S, or A
VARIANT              29
                     note = X is T, not present, E, or G
VARIANT              30
                     note = X is not present, E, T,  or G
VARIANT              31
                     note = X is not present or G
VARIANT              32
                     note = Z is amide or acid
SEQUENCE: 413
HXXGXXTSDX SXXLXXXXXX XXXXXXXXXX XZ                                          32

SEQ ID NO: 414       moltype = AA  length = 31
FEATURE              Location/Qualifiers
source               1..31
                     mol_type = protein
                     organism = synthetic construct
MOD_RES              2
                     note = Aib
VARIANT              10
                     note = X is V or Y
VARIANT              12
                     note = X is K or E
MOD_RES              13
                     note = alphaMethyl-Phenylalanine (alphaMePhe)
VARIANT              16
                     note = X is S or Aib
VARIANT              17
                     note = X is R or E
VARIANT              18
                     note = X is R or A
VARIANT              24
                     note = X is A, R, or Q
VARIANT              26
                     note = X is L or I
VARIANT              27
                     note = X is E, L, A, or I
VARIANT              28
                     note = X is A, E, Aib, S, or N
VARIANT              29
                     note = X is G, Aib, T,  or E
VARIANT              30
                     note = X is G, E, T, or not present
VARIANT              31
                     note = Z is amide or acid
SEQUENCE: 414
HXQGTFTSDX SXXLDXXXAK DFVXWXXXXX Z                                           31

SEQ ID NO: 415       moltype = AA  length = 32
FEATURE              Location/Qualifiers
source               1..32
```

-continued

```
                    mol_type = protein
                    organism = synthetic construct
VARIANT             1
                    note = X is H or ((1H-imidazol-4-yl)methyl)glycine (NHis)
VARIANT             2
                    note = X is S or Aminoisobutyric acid (Aib)
VARIANT             3
                    note = X is Q, H, or I
VARIANT             5
                    note = X is T or S
VARIANT             6
                    note = X is F or alphaMethyl-Phenylalanine (alphaMePhe)
VARIANT             10
                    note = X is Y or V
VARIANT             13
                    note = X is Y, alphaMePhe, Aib, or Diphenylalanine (Dip)
VARIANT             15
                    note = X is D or E
VARIANT             16
                    note = X is S, E, or L
VARIANT             17
                    note = X is R, Q, or E
VARIANT             18
                    note = X is R, A, or Aib
VARIANT             19
                    note = X is A or V
VARIANT             20
                    note = X is Q or R
VARIANT             21
                    note = X is D or L
VARIANT             22
                    note = X is F or alphaMePhe
VARIANT             23
                    note = X is V or I
VARIANT             24
                    note = X  is Q or K, wherein the K can comprise an acyl
                     moiety and/or can be lipidated
VARIANT             25
                    note = X is W, Aib, or S
VARIANT             27
                    note = X is M, V, L, or A
VARIANT             28
                    note = X is N, E, or Aib
VARIANT             29
                    note = X is T, Aib, G, or not present
VARIANT             30
                    note = X is not present, Aib, or G
VARIANT             31
                    note = X is not present or G
VARIANT             32
                    note = Z is amide or acid
SEQUENCE: 415
XXXGXXTSDX SKXLXXXXXX XXXXXXXXXX XZ                              32

SEQ ID NO: 416      moltype = AA  length = 31
FEATURE             Location/Qualifiers
source              1..31
                    mol_type = protein
                    organism = synthetic construct
MOD_RES             2
                    note = X is Aib
MOD_RES             13
                    note = alphaMethyl-Phenylalanine (alphaMePhe)
VARIANT             15
                    note = X is D or E
VARIANT             16
                    note = X is S or L
VARIANT             27
                    note = X is V or L
VARIANT             28
                    note = X is E or Aib
VARIANT             29
                    note = X is T, Aib or G
VARIANT             30
                    note = X is G or Aib or not present
VARIANT             31
                    note = Z is amide or acid
SEQUENCE: 416
HXQGTFTSDV SKXLXXRRAQ DFVKWLXXXX Z                               31
```

```
SEQ ID NO: 417          moltype = AA  length = 32
FEATURE                 Location/Qualifiers
source                  1..32
                        mol_type = protein
                        organism = synthetic construct
VARIANT                 2
                        note = X is S or Aminoisobutyric acid (Aib)
VARIANT                 3
                        note = X is Q or H
VARIANT                 5
                        note = X is T or S
VARIANT                 6
                        note = X is F or alpha-methylphenylalanine (alphaMePhe)
VARIANT                 10
                        note = X is Y, V, or K, wherein the K can comprise an acyl
                         moiety and/or can be lipidated
VARIANT                 13
                        note = X is Y, alphaMePhe, I, or Diphenylalanine (Dip), or
                         K wherein the K can comprise an acyl moiety and/or can be
                         lipidated
VARIANT                 17
                        note = X is R, Q, or beta-dimethylarganine (beta-diMeArg)
VARIANT                 18
                        note = X is R or A
VARIANT                 22
                        note = X is F or alphaMePhe
VARIANT                 24
                        note = X  is Q or E,
VARIANT                 25
                        note = X is W, Aib, or H
VARIANT                 26
                        note = X is L or I
VARIANT                 30..31
                        note = X is not present
VARIANT                 32
                        note = Z is amide or acid
SEQUENCE: 417
HXXGXXTSDX SKXLDSXXAQ DXVXXXXNTX XZ                                     32

SEQ ID NO: 418          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 29
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C20diacid
SEQUENCE: 418
HXQGTFTSDV SKXLDTXRAQ DFVRWLEAXG                                        30

SEQ ID NO: 419          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 29
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-gamma-Glu-C20diacid
SEQUENCE: 419
HXQGTFTSDV SKXLDTXRAQ DFVRWLEAXG                                        30

SEQ ID NO: 420          moltype = AA  length = 30
FEATURE                 Location/Qualifiers
source                  1..30
                        mol_type = protein
                        organism = Synthetic construct
```

-continued

```
MOD_RES              2
                     note = 2-Aminoisobutyric acid
MOD_RES              28
                     note = 2-Aminoisobutyric acid
MOD_RES              13
                     note = alpha-methyl-L-phenylalanine
MOD_RES              17
                     note = Lys, wherein the side chain of Lys is connected to
                     O2Oc-O2Oc-gamma-Glu-C18diacid
SEQUENCE: 420
HXQGTFTSDV SKXLDTXRAR DFVAWLLXTE                                       30

SEQ ID NO: 421       moltype = AA  length = 30
FEATURE              Location/Qualifiers
source               1..30
                     mol_type = protein
                     organism = Synthetic construct
MOD_RES              2
                     note = 2-Aminoisobutyric acid
MOD_RES              28
                     note = 2-Aminoisobutyric acid
MOD_RES              13
                     note = alpha-methyl-L-phenylalanine
MOD_RES              17
                     note = Lys, wherein the side chain of Lys is connected to
                     O2Oc-O2Oc-gamma-Glu-C20diacid
SEQUENCE: 421
HXQGTFTSDV SKXLDTXRAR DFVAWLLXTE                                       30

SEQ ID NO: 422       moltype = AA  length = 30
FEATURE              Location/Qualifiers
source               1..30
                     mol_type = protein
                     organism = Synthetic construct
MOD_RES              2
                     note = 2-Aminoisobutyric acid
MOD_RES              13
                     note = alpha-methyl-L-phenylalanine
MOD_RES              17
                     note = Lys, wherein the side chain of Lys is connected to
                     O2Oc-O2Oc-gamma-Glu-C18diacid
SEQUENCE: 422
HXQGTFTSDV SKXLDTXRAQ DFVAWLEAGG                                       30

SEQ ID NO: 423       moltype = AA  length = 30
FEATURE              Location/Qualifiers
source               1..30
                     mol_type = protein
                     organism = Synthetic construct
MOD_RES              2
                     note = 2-Aminoisobutyric acid
MOD_RES              13
                     note = alpha-methyl-L-phenylalanine
MOD_RES              17
                     note = Lys, wherein the side chain of Lys is connected to
                     O2Oc-O2Oc-gamma-Glu-C20diacid
SEQUENCE: 423
HXQGTFTSDV SKXLDTXRAQ DFVAWLEAGG                                       30

SEQ ID NO: 424       moltype = AA  length = 30
FEATURE              Location/Qualifiers
source               1..30
                     mol_type = protein
                     organism = Synthetic construct
MOD_RES              2
                     note = 2-Aminoisobutyric acid
MOD_RES              13
                     note = alpha-methyl-L-phenylalanine
MOD_RES              17
                     note = Lys, wherein the side chain of Lys is connected to
                     O2Oc-O2Oc-gamma-Glu-gamma-Glu-C20diacid
SEQUENCE: 424
HXQGTFTSDV SKXLDTXRAQ DFVAWLEAGG                                       30

SEQ ID NO: 425       moltype = AA  length = 29
FEATURE              Location/Qualifiers
source               1..29
                     mol_type = protein
                     organism = Synthetic construct
```

-continued

```
MOD_RES              2
                     note = 2-Aminoisobutyric acid
MOD_RES              28
                     note = 2-Aminoisobutyric acid
MOD_RES              13
                     note = alpha-methyl-L-phenylalanine
MOD_RES              17
                     note = Lys, wherein the side chain of Lys is connected to
                        O2Oc-O2Oc-gamma-Glu-C18diacid
SEQUENCE: 425
HXQGTFTSDV SKXLDKXRAR DFVRWLLXE                                        29

SEQ ID NO: 426       moltype = AA  length = 30
FEATURE              Location/Qualifiers
source               1..30
                     mol_type = protein
                     organism = Synthetic construct
MOD_RES              2
                     note = 2-Aminoisobutyric acid
MOD_RES              29
                     note = 2-Aminoisobutyric acid
MOD_RES              13
                     note = alpha-methyl-L-phenylalanine
MOD_RES              17
                     note = Lys, wherein the side chain of Lys is connected to
                        O2Oc-O2Oc-gamma-Glu-C20diacid
SEQUENCE: 426
HXQGTFTSDV SKXLESXRAQ DFVRWLEAXG                                       30

SEQ ID NO: 427       moltype = AA  length = 30
FEATURE              Location/Qualifiers
source               1..30
                     mol_type = protein
                     organism = Synthetic construct
MOD_RES              2
                     note = 2-Aminoisobutyric acid
MOD_RES              29
                     note = 2-Aminoisobutyric acid
MOD_RES              13
                     note = alpha-methyl-L-phenylalanine
MOD_RES              17
                     note = Lys, wherein the side chain of Lys is connected to
                        O2Oc-O2Oc-gamma-Glu-C20diacid
SEQUENCE: 427
HXQGTFTSDV SKXLESXRAQ DFVRWLEAXG                                       30

SEQ ID NO: 428       moltype = AA  length = 30
FEATURE              Location/Qualifiers
source               1..30
                     mol_type = protein
                     organism = Synthetic construct
MOD_RES              2
                     note = 2-Aminoisobutyric acid
MOD_RES              29
                     note = 2-Aminoisobutyric acid
MOD_RES              13
                     note = alpha-methyl-L-phenylalanine
MOD_RES              17
                     note = Lys, wherein the side chain of Lys is connected to
                        O2Oc-O2Oc-gamma-Glu-gamma-Glu-C18diacid
SEQUENCE: 428
HXQGTFTSDV SKXLDTXRAQ DFVAWLEAXG                                       30

SEQ ID NO: 429       moltype = AA  length = 30
FEATURE              Location/Qualifiers
source               1..30
                     mol_type = protein
                     organism = Synthetic construct
MOD_RES              2
                     note = 2-Aminoisobutyric acid
MOD_RES              29
                     note = 2-Aminoisobutyric acid
MOD_RES              13
                     note = alpha-methyl-L-phenylalanine
MOD_RES              17
                     note = Lys, wherein the side chain of Lys is connected to
                        O2Oc-O2Oc-gamma-Glu-gamma-Glu-C20diacid
SEQUENCE: 429
HXQGTFTSDV SKXLDTXRAQ DFVAWLEAXG                                       30
```

-continued

```
SEQ ID NO: 430          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 28
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C18diacid
SEQUENCE: 430
HXQGTFTSDV SKXLDTXRAQ DFVRWLEXE                                  29

SEQ ID NO: 431          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 28
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C18diacid
SEQUENCE: 431
HXQGTFTSDV SKXLDKXRAQ DFVRWLLXE                                  29

SEQ ID NO: 432          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 28
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C18diacid
SEQUENCE: 432
HXQGTFTSDV SKXLDRXRAQ DFVRWLLXTE                                 30

SEQ ID NO: 433          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 28
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C18diacid
SEQUENCE: 433
HXQGTFTSDV SKXLDRXRAQ DFVRWLLXTE                                 30

SEQ ID NO: 434          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 28
                        note = 2-Aminoisobutyric acid
MOD_RES                 13
```

```
                              note = alpha-methyl-L-phenylalanine
MOD_RES                       17
                              note = Lys, wherein the side chain of Lys is connected to
                                O2Oc-O2Oc-gamma-Glu-C18diacid
SEQUENCE: 434
HXQGTFTSDV SKXLDKXRAQ DFVRWLKXTE                                  30

SEQ ID NO: 435                moltype = AA  length = 30
FEATURE                       Location/Qualifiers
source                        1..30
                              mol_type = protein
                              organism = Synthetic construct
MOD_RES                       2
                              note = 2-Aminoisobutyric acid
MOD_RES                       28
                              note = 2-Aminoisobutyric acid
MOD_RES                       13
                              note = alpha-methyl-L-phenylalanine
MOD_RES                       17
                              note = Lys, wherein the side chain of Lys is connected to
                                O2Oc-O2Oc-gamma-Glu-C18diacid
SEQUENCE: 435
HXQGTFTSDV SKXLDKXRAQ DFVRWLLXTK                                  30

SEQ ID NO: 436                moltype = AA  length = 30
FEATURE                       Location/Qualifiers
source                        1..30
                              mol_type = protein
                              organism = Synthetic construct
MOD_RES                       2
                              note = 2-Aminoisobutyric acid
MOD_RES                       29
                              note = 2-Aminoisobutyric acid
MOD_RES                       13
                              note = alpha-methyl-L-phenylalanine
MOD_RES                       17
                              note = 2-Aminoisobutyric acid Lys, wherein the side chain
                                of Lys is connected to O2Oc-O2Oc-gamma-Glu-C18diacid
SEQUENCE: 436
HXQGTFTSDV SKXLDKXRAQ DFVRWLKAXG                                  30

SEQ ID NO: 437                moltype = AA  length = 30
FEATURE                       Location/Qualifiers
source                        1..30
                              mol_type = protein
                              organism = Synthetic construct
MOD_RES                       2
                              note = 2-Aminoisobutyric acid
MOD_RES                       29
                              note = 2-Aminoisobutyric acid
MOD_RES                       13
                              note = alpha-methyl-L-phenylalanine
MOD_RES                       17
                              note = Lys, wherein the side chain of Lys is connected to
                                O2Oc-O2Oc-gamma-Glu-C18diacid
SEQUENCE: 437
HXQGTFTSDV SKXLDKXRAQ DFVRWLLRXK                                  30

SEQ ID NO: 438                moltype = AA  length = 30
FEATURE                       Location/Qualifiers
source                        1..30
                              mol_type = protein
                              organism = Synthetic construct
MOD_RES                       2
                              note = 2-Aminoisobutyric acid
MOD_RES                       29
                              note = 2-Aminoisobutyric acid
MOD_RES                       13
                              note = alpha-methyl-L-phenylalanine
MOD_RES                       17
                              note = Lys, wherein the side chain of Lys is connected to
                                O2Oc-O2Oc-gamma-Glu-C18diacid
SEQUENCE: 438
HXQGTFTSDV SKXLDTXRAR DFVQWLLEXG                                  30

SEQ ID NO: 439                moltype = AA  length = 30
FEATURE                       Location/Qualifiers
source                        1..30
                              mol_type = protein
```

```
                          organism = Synthetic construct
MOD_RES                   2
                          note = 2-Aminoisobutyric acid
MOD_RES                   29
                          note = 2-Aminoisobutyric acid
MOD_RES                   13
                          note = alpha-methyl-L-phenylalanine
MOD_RES                   17
                          note = Lys, wherein the side chain of Lys is connected to
                            O2Oc-O2Oc-gamma-Glu-gamma-Glu-C18diacid
SEQUENCE: 439
HXQGTFTSDV SKXLDTXRAR DFVQWLLEXG                                           30

SEQ ID NO: 440            moltype = AA  length = 30
FEATURE                   Location/Qualifiers
source                    1..30
                          mol_type = protein
                          organism = Synthetic construct
MOD_RES                   2
                          note = 2-Aminoisobutyric acid
MOD_RES                   29
                          note = 2-Aminoisobutyric acid
MOD_RES                   13
                          note = alpha-methyl-L-phenylalanine
MOD_RES                   17
                          note = Lys, wherein the side chain of Lys is connected to
                            O2Oc-O2Oc-gamma-Glu-C18diacid
SEQUENCE: 440
HXQGTFTSDV SKXLDSXRAQ DFVRWLEAXG                                           30

SEQ ID NO: 441            moltype = AA  length = 30
FEATURE                   Location/Qualifiers
source                    1..30
                          mol_type = protein
                          organism = Synthetic construct
MOD_RES                   2
                          note = 2-Aminoisobutyric acid
MOD_RES                   29
                          note = 2-Aminoisobutyric acid
MOD_RES                   13
                          note = alpha-methyl-L-phenylalanine
MOD_RES                   17
                          note = Lys, wherein the side chain of Lys is connected to
                            O2Oc-O2Oc-gamma-Glu-gamma-Glu-C18diacid
SEQUENCE: 441
HXQGTFTSDV SKXLDSXRAQ DFVRWLEAXG                                           30

SEQ ID NO: 442            moltype = AA  length = 30
FEATURE                   Location/Qualifiers
source                    1..30
                          mol_type = protein
                          organism = Synthetic construct
MOD_RES                   2
                          note = 2-Aminoisobutyric acid
MOD_RES                   29
                          note = 2-Aminoisobutyric acid
MOD_RES                   13
                          note = alpha-methyl-L-phenylalanine
MOD_RES                   17
                          note = Lys, wherein the side chain of Lys is connected to
                            O2Oc-O2Oc-gamma-Glu-gamma-Glu-C18diacid
SEQUENCE: 442
HXQGTFTSDV SKXLDTXRAQ DFVAWLEAXG                                           30

SEQ ID NO: 443            moltype = AA  length = 29
FEATURE                   Location/Qualifiers
source                    1..29
                          mol_type = protein
                          organism = Synthetic construct
MOD_RES                   2
                          note = 2-Aminoisobutyric acid
MOD_RES                   28
                          note = 2-Aminoisobutyric acid
MOD_RES                   13
                          note = alpha-methyl-L-phenylalanine
MOD_RES                   17
                          note = Lys, wherein the side chain of Lys is connected to
                            O2Oc-O2Oc-gamma-Glu-C18diacid
MOD_RES                   25
```

```
                              note = biphenyl-alanine
SEQUENCE: 443
HXQGTFTSDV SKXLDSXRAQ DFVRXLLXE                                 29

SEQ ID NO: 444            moltype = AA   length = 30
FEATURE                   Location/Qualifiers
source                    1..30
                          mol_type = protein
                          organism = Synthetic construct
MOD_RES                   2
                          note = 2-Aminoisobutyric acid
MOD_RES                   28
                          note = 2-Aminoisobutyric acid
MOD_RES                   13
                          note = alpha-methyl-L-phenylalanine
MOD_RES                   17
                          note = Lys, wherein the side chain of Lys is connected to
                           O2Oc-O2Oc-gamma-Glu-C18diacid
MOD_RES                   25
                          note = 1-methyl tryptophan
SEQUENCE: 444
HXQGTFTSDV SKXLDSXRAQ DFVRXPLLXE                                30

SEQ ID NO: 445            moltype = AA   length = 29
FEATURE                   Location/Qualifiers
source                    1..29
                          mol_type = protein
                          organism = Synthetic construct
MOD_RES                   2
                          note = 2-Aminoisobutyric acid
MOD_RES                   28
                          note = 2-Aminoisobutyric acid
MOD_RES                   13
                          note = alpha-methyl-L-phenylalanine
MOD_RES                   17
                          note = Lys, wherein the side chain of Lys is connected to
                           O2Oc-O2Oc-gamma-Glu-C18diacid
MOD_RES                   25
                          note = 5-Bromo trptophan
SEQUENCE: 445
HXQGTFTSDV SKXLDSXRAQ DFVRXLLXE                                 29

SEQ ID NO: 446            moltype = AA   length = 30
FEATURE                   Location/Qualifiers
source                    1..30
                          mol_type = protein
                          organism = Synthetic construct
MOD_RES                   2
                          note = 2-Aminoisobutyric acid
MOD_RES                   29
                          note = 2-Aminoisobutyric acid
MOD_RES                   25
                          note = 2-Aminoisobutyric acid
MOD_RES                   13
                          note = alpha-methyl-L-phenylalanine
MOD_RES                   17
                          note = 2-Aminoisobutyric acid Lys, wherein the side chain
                           of Lys is connected to O2Oc-O2Oc-gamma-Glu-C18diacid
SEQUENCE: 446
HXQGTFTSDV SKXLDTXRAR DFVQXLLEXG                                30

SEQ ID NO: 447            moltype = AA   length = 29
FEATURE                   Location/Qualifiers
source                    1..29
                          mol_type = protein
                          organism = Synthetic construct
MOD_RES                   2
                          note = 2-Aminoisobutyric acid
MOD_RES                   28
                          note = 2-Aminoisobutyric acid
MOD_RES                   13
                          note = alpha-methyl-L-phenylalanine
MOD_RES                   17
                          note = Lys, wherein the side chain of Lys is connected to
                           O2Oc-O2Oc-gamma-Glu-C18diacid
SEQUENCE: 447
HXQGTFTSDV SKXLDRXRAQ DFVRWLVXE                                 29

SEQ ID NO: 448            moltype = AA   length = 29
```

-continued

```
FEATURE              Location/Qualifiers
source               1..29
                     mol_type = protein
                     organism = Synthetic construct
MOD_RES              2
                     note = 2-Aminoisobutyric acid
MOD_RES              28
                     note = 2-Aminoisobutyric acid
MOD_RES              13
                     note = alpha-methyl-L-phenylalanine
MOD_RES              17
                     note = Lys, wherein the side chain of Lys is connected to
                       O2Oc-O2Oc-gamma-Glu-C20diacid
SEQUENCE: 448
HXQGTFTSDV SKXLDRXRAQ DFVRWLVXE                                        29

SEQ ID NO: 449       moltype = AA  length = 30
FEATURE              Location/Qualifiers
source               1..30
                     mol_type = protein
                     organism = Synthetic construct
MOD_RES              2
                     note = 2-Aminoisobutyric acid
MOD_RES              29
                     note = 2-Aminoisobutyric acid
MOD_RES              13
                     note = alpha-methyl-L-phenylalanine
MOD_RES              17
                     note = Lys, wherein the side chain of Lys is connected to
                       O2Oc-O2Oc-gamma-Glu-C18diacid
SEQUENCE: 449
HXQGTFTSDV SKXLDKXRAQ DFVRWLEAXG                                       30

SEQ ID NO: 450       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              28
                     note = 2-Aminoisobutyric acid
MOD_RES              13
                     note = alpha-methyl-L-phenylalanine
MOD_RES              17
                     note = Lys, wherein the side chain of Lys is connected to
                       O2Oc-O2Oc-gamma-Glu-C18diacid
SEQUENCE: 450
HXQGTFTSDV SKXLDRXRAQ DFVRWLLXE                                        29

SEQ ID NO: 451       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              28
                     note = 2-Aminoisobutyric acid
MOD_RES              13
                     note = alpha-methyl-L-phenylalanine
MOD_RES              17
                     note = Lys, wherein the side chain of Lys is connected to
                       O2Oc-O2Oc-gamma-Glu-C20diacid
SEQUENCE: 451
HXQGTFTSDV SKXLDKXRAR DFVRWLLXE                                        29

SEQ ID NO: 452       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              28
                     note = 2-Aminoisobutyric acid
MOD_RES              13
                     note = alpha-methyl-L-phenylalanine
MOD_RES              17
```

```
                          note = Lys, wherein the side chain of Lys is connected to
                             O2Oc-O2Oc-gamma-Glu-C20diacid
SEQUENCE: 452
HXQGTFTSDV SKXLDKXRAQ DFVRWLLXE                                              29

SEQ ID NO: 453            moltype = AA   length = 30
FEATURE                   Location/Qualifiers
source                    1..30
                          mol_type = protein
                          organism = Synthetic construct
MOD_RES                   2
                          note = 2-Aminoisobutyric acid
MOD_RES                   29
                          note = 2-Aminoisobutyric acid
MOD_RES                   13
                          note = alpha-methyl-L-phenylalanine
MOD_RES                   17
                          note = Lys, wherein the side chain of Lys is connected to
                             O2Oc-O2Oc-gamma-Glu-C18diacid
SEQUENCE: 453
HXQGTFTSDV SKXLDKXRAQ DFVRWLLEXG                                             30

SEQ ID NO: 454            moltype = AA   length = 29
FEATURE                   Location/Qualifiers
source                    1..29
                          mol_type = protein
                          organism = Synthetic construct
MOD_RES                   2
                          note = 2-Aminoisobutyric acid
MOD_RES                   28
                          note = 2-Aminoisobutyric acid
MOD_RES                   13
                          note = alpha-methyl-L-phenylalanine
MOD_RES                   17
                          note = Lys, wherein the side chain of Lys is connected to
                             O2Oc-O2Oc-gamma-Glu-C18diacid
SEQUENCE: 454
HXQGTFTSDV SKXLDKXRAR DFVRWLLXE                                              29

SEQ ID NO: 455            moltype = AA   length = 30
FEATURE                   Location/Qualifiers
source                    1..30
                          mol_type = protein
                          organism = Synthetic construct
MOD_RES                   2
                          note = 2-Aminoisobutyric acid
MOD_RES                   29
                          note = 2-Aminoisobutyric acid
MOD_RES                   13
                          note = alpha-methyl-L-phenylalanine
MOD_RES                   17
                          note = Lys, wherein the side chain of Lys is connected to
                             O2Oc-O2Oc-gamma-Glu-C18diacid
SEQUENCE: 455
HXQGTFTSDV SKXLETXRAR DFVQWLLEXG                                             30

SEQ ID NO: 456            moltype = AA   length = 30
FEATURE                   Location/Qualifiers
source                    1..30
                          mol_type = protein
                          organism = Synthetic construct
MOD_RES                   2
                          note = 2-Aminoisobutyric acid
MOD_RES                   29
                          note = 2-Aminoisobutyric acid
MOD_RES                   13
                          note = alpha-methyl-L-phenylalanine
MOD_RES                   17
                          note = Lys, wherein the side chain of Lys is connected to
                             O2Oc-O2Oc-gamma-Glu-C18diacid
SEQUENCE: 456
HXQGTFTSDV SKXLETXRAR DFVQWLLEXG                                             30

SEQ ID NO: 457            moltype = AA   length = 29
FEATURE                   Location/Qualifiers
source                    1..29
                          mol_type = protein
                          organism = Synthetic construct
MOD_RES                   2
```

-continued

```
                           note = 2-Aminoisobutyric acid
MOD_RES                    28
                           note = 2-Aminoisobutyric acid
MOD_RES                    13
                           note = alpha-methyl-L-phenylalanine
MOD_RES                    17
                           note = Lys, wherein the side chain of Lys is connected to
                             O2Oc-O2Oc-gamma-Glu-gamma-Glu-C18diacid
SEQUENCE: 457
HXQGTFTSDV SKXLDRXRAQ DFVRWLVXE                                          29

SEQ ID NO: 458             moltype = AA  length = 29
FEATURE                    Location/Qualifiers
source                     1..29
                           mol_type = protein
                           organism = Synthetic construct
MOD_RES                    2
                           note = 2-Aminoisobutyric acid
MOD_RES                    28
                           note = 2-Aminoisobutyric acid
MOD_RES                    13
                           note = alpha-methyl-L-phenylalanine
MOD_RES                    17
                           note = Lys, wherein the side chain of Lys is connected to
                             O2Oc-O2Oc-gamma-Glu-gamma-Glu-C20diacid
SEQUENCE: 458
HXQGTFTSDV SKXLDRXRAQ DFVRWLVXE                                          29

SEQ ID NO: 459             moltype = AA  length = 29
FEATURE                    Location/Qualifiers
source                     1..29
                           mol_type = protein
                           organism = Synthetic construct
MOD_RES                    2
                           note = 2-Aminoisobutyric acid
MOD_RES                    28
                           note = 2-Aminoisobutyric acid
MOD_RES                    13
                           note = alpha-methyl-L-phenylalanine
MOD_RES                    17
                           note = Lys, wherein the side chain of Lys is connected to
                             O2Oc-O2Oc-gamma-Glu-gamma-Glu-C18diacid
SEQUENCE: 459
HXQGTFTSDV SKXLDKXRAR DFVRWLLXE                                          29

SEQ ID NO: 460             moltype = AA  length = 30
FEATURE                    Location/Qualifiers
source                     1..30
                           mol_type = protein
                           organism = Synthetic construct
MOD_RES                    2
                           note = 2-Aminoisobutyric acid
MOD_RES                    29
                           note = 2-Aminoisobutyric acid
MOD_RES                    13
                           note = alpha-methyl-L-phenylalanine
MOD_RES                    17
                           note = Lys, wherein the side chain of Lys is connected to
                             O2Oc-O2Oc-gamma-Glu-gamma-Glu-C20diacid
SEQUENCE: 460
HXQGTFTSDV SKXLDTXRAR DFVQWLLEXG                                         30

SEQ ID NO: 461             moltype = AA  length = 30
FEATURE                    Location/Qualifiers
source                     1..30
                           mol_type = protein
                           organism = Synthetic construct
MOD_RES                    2
                           note = 2-Aminoisobutyric acid
MOD_RES                    29
                           note = 2-Aminoisobutyric acid
MOD_RES                    13
                           note = alpha-methyl-L-phenylalanine
MOD_RES                    17
                           note = Lys, wherein the side chain of Lys is connected to
                             O2Oc-O2Oc-gamma-Glu-gamma-Glu-C18diacid
SEQUENCE: 461
HXQGTFTSDV SKXLDKXRAQ DFVRWLLEXG                                         30
```

```
SEQ ID NO: 462          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 28
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C20diacid
SEQUENCE: 462
HXQGTFTSDV SKXLDKXRAR DFVLWLLXE                                            29

SEQ ID NO: 463          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 28
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C20diacid
SEQUENCE: 463
HXQGTFTSDV SKXLDKXRAL DFVRWLLXE                                            29

SEQ ID NO: 464          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 29
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C20diacid
SEQUENCE: 464
HXQGTFTSDV SKXLDKXRAQ DFVRWLLEXG                                           30

SEQ ID NO: 465          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 29
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C20diacid
SEQUENCE: 465
HXQGTFTSDV SKXLDKXRAQ DFVRWLEAXG                                           30

SEQ ID NO: 466          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 28
                        note = 2-Aminoisobutyric acid
MOD_RES                 13
                        note = alpha-methyl-L-phenylalanine
```

-continued

```
MOD_RES              17
                     note = Lys, wherein the side chain of Lys is connected to
                       O2Oc-O2Oc-gamma-Glu-gamma-Glu-C20diacid
SEQUENCE: 466
HXQGTFTSDV SKXLDKXRAQ DFVRWLLXE                               29

SEQ ID NO: 467       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              28
                     note = 2-Aminoisobutyric acid
MOD_RES              13
                     note = alpha-methyl-L-phenylalanine
MOD_RES              17
                     note = Lys, wherein the side chain of Lys is connected to
                       O2Oc-O2Oc-gamma-Glu-C20diacid
SEQUENCE: 467
HXQGTFTSDV SKXLDRXRAQ DFVRWLLXE                               29

SEQ ID NO: 468       moltype = AA  length = 30
FEATURE              Location/Qualifiers
source               1..30
                     mol_type = protein
                     organism = Synthetic construct
MOD_RES              2
                     note = 2-Aminoisobutyric acid
MOD_RES              29
                     note = 2-Aminoisobutyric acid
MOD_RES              13
                     note = alpha-methyl-L-phenylalanine
MOD_RES              17
                     note = Lys, wherein the side chain of Lys is connected to
                       O2Oc-O2Oc-gamma-Glu-C20diacid
SEQUENCE: 468
HXQGTFTSDV SKXLDTXRAR DFVQWLLEXG                              30

SEQ ID NO: 469       moltype = AA  length = 30
FEATURE              Location/Qualifiers
source               1..30
                     mol_type = protein
                     organism = Synthetic construct
MOD_RES              2
                     note = 2-Aminoisobutyric acid
MOD_RES              29
                     note = 2-Aminoisobutyric acid
MOD_RES              13
                     note = alpha-methyl-L-phenylalanine
MOD_RES              17
                     note = Lys, wherein the side chain of Lys is connected to
                       O2Oc-O2Oc-gamma-Glu-gamma-Glu-C20diacid
SEQUENCE: 469
HXQGTFTSDV SKXLDTXRAR DFVQWLLEXG                              30

SEQ ID NO: 470       moltype = AA  length = 28
FEATURE              Location/Qualifiers
source               1..28
                     mol_type = protein
                     organism = Synthetic construct
MOD_RES              2
                     note = 2-Aminoisobutyric acid
MOD_RES              13
                     note = alpha-methyl-L-phenylalanine
MOD_RES              17
                     note = Lys, wherein the side chain of Lys is connected to
                       O2Oc-O2Oc-gamma-Glu-C18diacid
SEQUENCE: 470
HXQGTFTSDV SKXLDKXRAQ DFVRWLLA                                28

SEQ ID NO: 471       moltype = AA  length = 29
FEATURE              Location/Qualifiers
source               1..29
                     mol_type = protein
                     organism = Synthetic construct
MOD_RES              2
                     note = 2-Aminoisobutyric acid
```

-continued

```
MOD_RES                 13
                        note = alpha-methyl-L-phenylalanine
MOD_RES                 17
                        note = Lys, wherein the side chain of Lys is connected to
                        O2Oc-O2Oc-gamma-Glu-C18diacid
SEQUENCE: 471
HXQGTFTSDV SKXLDKXRAQ DFVRWLLAE                                  29

SEQ ID NO: 472          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = Lys, wherein the side chain of Lys is connected to
                        O2Oc-O2Oc-gamma-Glu-C18diacid
SEQUENCE: 472
HXQGTFTSDV SKXLDRXRAQ DFVRWLLAE                                  29

SEQ ID NO: 473          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 17
                        note = Lys, wherein the side chain of Lys is connected to
                        O2Oc-O2Oc-gamma-Glu-C18diacid
SEQUENCE: 473
HXQGTFTSDV SKXLDTXRAR DFVQWLLEAG                                 30

SEQ ID NO: 474          moltype = AA  length = 29
FEATURE                 Location/Qualifiers
source                  1..29
                        mol_type = protein
                        organism = Synthetic construct
MOD_RES                 2
                        note = 2-Aminoisobutyric acid
MOD_RES                 28
                        note = 2-Aminoisobutyric acid
MOD_RES                 13
                        note = alpha-methyl-L-phenylalanine
MOD_RES                 17
                        note = Lys, wherein the side chain of Lys is connected to
                        O2Oc-O2Oc-gamma-Glu-gamma-Glu-C18diacid
SEQUENCE: 474
HXQGTFTSDV SKXLDSXRAQ DFVQWLLXT                                  29

SEQ ID NO: 475          moltype = AA  length = 30
FEATURE                 Location/Qualifiers
source                  1..30
                        mol_type = protein
                        organism = Synthetic construct
MOD_RES                 2
                        note = 2-Aminoisobutyric acid
METAL                   29
                        note = 2-Aminoisobutyric acid
MOD_RES                 13
                        note = alpha-methyl-L-phenylalanine
MOD_RES                 17
                        note = Lys, wherein the side chain of Lys is connected to
                        O2Oc-O2Oc-gamma-Glu-C18diacid
SEQUENCE: 475
HXQGTFTSDV SKXLDTXRAQ DFVQWLLEXG                                 30

SEQ ID NO: 476          moltype = AA  length = 29
FEATURE                 Location/Qualifiers
source                  1..29
                        mol_type = protein
                        organism = Synthetic construct
MOD_RES                 2
                        note = 2-Aminoisobutyric acid
```

-continued

```
MOD_RES              28
                     note = 2-Aminoisobutyric acid
MOD_RES              13
                     note = alpha-methyl-L-phenylalanine
MOD_RES              17
                     note = Lys, wherein the side chain of Lys is connected to
                      O2Oc-O2Oc-gamma-Glu-gamma-Glu-C18diacid
SEQUENCE: 476
HXQGTFTSDV SKXLDLXRAQ DFVQWLLXT                                        29

SEQ ID NO: 477       moltype = AA  length = 30
FEATURE              Location/Qualifiers
source               1..30
                     mol_type = protein
                     organism = Synthetic construct
MOD_RES              2
                     note = 2-Aminoisobutyric acid
MOD_RES              29
                     note = 2-Aminoisobutyric acid
MOD_RES              13
                     note = alpha-methyl-L-phenylalanine
MOD_RES              17
                     note = Lys, wherein the side chain of Lys is connected to
                      O2Oc-O2Oc-gamma-Glu-C18diacid
SEQUENCE: 477
HXQGTFTSDV SKXLDTXRAQ DFVQWLLEXG                                       30

SEQ ID NO: 478       moltype = AA  length = 30
FEATURE              Location/Qualifiers
source               1..30
                     mol_type = protein
                     organism = Synthetic construct
MOD_RES              2
                     note = 2-Aminoisobutyric acid
MOD_RES              29
                     note = 2-Aminoisobutyric acid
MOD_RES              13
                     note = alpha-methyl-L-phenylalanine
MOD_RES              17
                     note = Lys, wherein the side chain of Lys is connected to
                      O2Oc-O2Oc-gamma-Glu-C20diacid
SEQUENCE: 478
HXQGTFTSDV SKXLDTXRAQ DFVQWLLEXG                                       30

SEQ ID NO: 479       moltype = AA  length = 30
FEATURE              Location/Qualifiers
source               1..30
                     mol_type = protein
                     organism = Synthetic construct
MOD_RES              2
                     note = 2-Aminoisobutyric acid
MOD_RES              29
                     note = 2-Aminoisobutyric acid
MOD_RES              13
                     note = alpha-methyl-L-phenylalanine
MOD_RES              17
                     note = Lys, wherein the side chain of Lys is connected to
                      O2Oc-O2Oc-gamma-Glu-gamma-Glu-C18diacid
SEQUENCE: 479
HXQGTFTSDV SKXLDTXRAQ DFVQWLLEXG                                       30

SEQ ID NO: 480       moltype = AA  length = 30
FEATURE              Location/Qualifiers
source               1..30
                     mol_type = protein
                     organism = Synthetic construct
MOD_RES              2
                     note = 2-Aminoisobutyric acid
MOD_RES              29
                     note = 2-Aminoisobutyric acid
MOD_RES              13
                     note = alpha-methyl-L-phenylalanine
MOD_RES              17
                     note = Lys, wherein the side chain of Lys is connected to
                      O2Oc-O2Oc-gamma-Glu-gamma-Glu-C20diacid
SEQUENCE: 480
HXQGTFTSDV SKXLDTXRAQ DFVQWLLEXG                                       30

SEQ ID NO: 481       moltype = AA  length = 29
```

-continued

```
FEATURE            Location/Qualifiers
source             1..29
                   mol_type = protein
                   organism = Synthetic construct
MOD_RES            2
                   note = 2-Aminoisobutyric acid
MOD_RES            28
                   note = 2-Aminoisobutyric acid
MOD_RES            13
                   note = alpha-methyl-L-phenylalanine
MOD_RES            17
                   note = Lys, wherein the side chain of Lys is connected to
                   O2Oc-O2Oc-gamma-Glu-C20diacid
SEQUENCE: 481
HXQGTFTSDV SKXLDKXRAR DFVQWLLXE                                             29

SEQ ID NO: 482     moltype = AA  length = 29
FEATURE            Location/Qualifiers
source             1..29
                   mol_type = protein
                   organism = Synthetic construct
MOD_RES            2
                   note = 2-Aminoisobutyric acid
MOD_RES            28
                   note = 2-Aminoisobutyric acid
MOD_RES            13
                   note = alpha-methyl-L-phenylalanine
MOD_RES            17
                   note = Lys, wherein the side chain of Lys is connected to
                   O2Oc-O2Oc-gamma-Glu-C20diacid
SEQUENCE: 482
HXQGTFTSDV SKXLDRXRAR DFVQWLLXE                                             29

SEQ ID NO: 483     moltype = AA  length = 29
FEATURE            Location/Qualifiers
source             1..29
                   mol_type = protein
                   organism = Synthetic construct
MOD_RES            2
                   note = 2-Aminoisobutyric acid
MOD_RES            28
                   note = 2-Aminoisobutyric acid
MOD_RES            13
                   note = alpha-methyl-L-phenylalanine
MOD_RES            17
                   note = Lys, wherein the side chain of Lys is connected to
                   O2Oc-O2Oc-gamma-Glu-C18diacid
SEQUENCE: 483
HXQGTFTSDV SKXLDKXRAR DFVQWLLXE                                             29

SEQ ID NO: 484     moltype = AA  length = 29
FEATURE            Location/Qualifiers
source             1..29
                   mol_type = protein
                   organism = Synthetic construct
MOD_RES            2
                   note = 2-Aminoisobutyric acid
MOD_RES            28
                   note = 2-Aminoisobutyric acid
MOD_RES            13
                   note = alpha-methyl-L-phenylalanine
MOD_RES            17
                   note = Lys, wherein the side chain of Lys is connected to
                   O2Oc-O2Oc-gamma-Glu-C18diacid
SEQUENCE: 484
HXQGTFTSDV SKXLDRXRAR DFVQWLLXE                                             29

SEQ ID NO: 485     moltype = AA  length = 30
FEATURE            Location/Qualifiers
source             1..30
                   mol_type = protein
                   organism = Synthetic construct
MOD_RES            2
                   note = 2-Aminoisobutyric acid
MOD_RES            29
                   note = 2-Aminoisobutyric acid
MOD_RES            13
                   note = alpha-methyl-L-phenylalanine
MOD_RES            17
```

-continued

```
                             note = Lys, wherein the side chain of Lys is connected to
                                O2Oc-O2Oc-gamma-Glu-C18diacid
SEQUENCE: 485
HXQGTFTSDV SKXLDTXRAR DFVQWLLAXG                                          30

SEQ ID NO: 486               moltype = AA  length = 30
FEATURE                      Location/Qualifiers
source                       1..30
                             mol_type = protein
                             organism = Synthetic construct
MOD_RES                      2
                             note = 2-Aminoisobutyric acid
MOD_RES                      29
                             note = 2-Aminoisobutyric acid
MOD_RES                      13
                             note = alpha-methyl-L-phenylalanine
MOD_RES                      17
                             note = Lys, wherein the side chain of Lys is connected to
                                O2Oc-O2Oc-gamma-Glu-C20diacid
SEQUENCE: 486
HXQGTFTSDV SKXLDTXRAR DFVQWLLAXG                                          30

SEQ ID NO: 487               moltype = AA  length = 30
FEATURE                      Location/Qualifiers
source                       1..30
                             mol_type = protein
                             organism = Synthetic construct
MOD_RES                      2
                             note = 2-Aminoisobutyric acid
MOD_RES                      29
                             note = 2-Aminoisobutyric acid
MOD_RES                      13
                             note = alpha-methyl-L-phenylalanine
MOD_RES                      17
                             note = Lys, wherein the side chain of Lys is connected to
                                O2Oc-O2Oc-gamma-Glu-C18diacid
SEQUENCE: 487
HXQGTFTSDV SKXLDTXRAQ DFVRWLLAXG                                          30

SEQ ID NO: 488               moltype = AA  length = 30
FEATURE                      Location/Qualifiers
source                       1..30
                             mol_type = protein
                             organism = Synthetic construct
MOD_RES                      2
                             note = 2-Aminoisobutyric acid
MOD_RES                      29
                             note = 2-Aminoisobutyric acid
MOD_RES                      13
                             note = alpha-methyl-L-phenylalanine
MOD_RES                      17
                             note = Lys, wherein the side chain of Lys is connected to
                                O2Oc-O2Oc-gamma-Glu-C20diacid
SEQUENCE: 488
HXQGTFTSDV SKXLDTXRAQ DFVRWLLAXG                                          30

SEQ ID NO: 489               moltype = AA  length = 30
FEATURE                      Location/Qualifiers
source                       1..30
                             mol_type = protein
                             organism = Synthetic construct
MOD_RES                      2
                             note = 2-Aminoisobutyric acid
MOD_RES                      29
                             note = 2-Aminoisobutyric acid
MOD_RES                      13
                             note = alpha-methyl-L-phenylalanine
MOD_RES                      17
                             note = Lys, wherein the side chain of Lys is connected to
                                O2Oc-O2Oc-gamma-Glu-C18diacid
SEQUENCE: 489
HXQGTFTSDV SKXLDTXRAQ DFVRWLLEXK                                          30

SEQ ID NO: 490               moltype = AA  length = 30
FEATURE                      Location/Qualifiers
source                       1..30
                             mol_type = protein
                             organism = Synthetic construct
MOD_RES                      2
```

-continued

```
                                  note = 2-Aminoisobutyric acid
MOD_RES                           29
                                  note = 2-Aminoisobutyric acid
MOD_RES                           13
                                  note = alpha-methyl-L-phenylalanine
MOD_RES                           17
                                  note = Lys, wherein the side chain of Lys is connected to
                                    O2Oc-O2Oc-gamma-Glu-C20diacid
SEQUENCE: 490
HXQGTFTSDV SKXLDTXRAQ DFVRWLLEXK                                                  30

SEQ ID NO: 491        moltype = AA  length = 30
FEATURE               Location/Qualifiers
source                1..30
                      mol_type = protein
                      organism = Synthetic construct
MOD_RES               2
                      note = 2-Aminoisobutyric acid
MOD_RES               29
                      note = 2-Aminoisobutyric acid
MOD_RES               13
                      note = alpha-methyl-L-phenylalanine
MOD_RES               17
                      note = Lys, wherein the side chain of Lys is connected to
                        O2Oc-O2Oc-gamma-Glu-C18diacid
SEQUENCE: 491
HXQGTFTSDV SKXLDTXRAR DFVQWLLEXK                                                  30

SEQ ID NO: 492        moltype = AA  length = 30
FEATURE               Location/Qualifiers
source                1..30
                      mol_type = protein
                      organism = Synthetic construct
MOD_RES               2
                      note = 2-Aminoisobutyric acid
MOD_RES               29
                      note = 2-Aminoisobutyric acid
MOD_RES               13
                      note = alpha-methyl-L-phenylalanine
MOD_RES               17
                      note = Lys, wherein the side chain of Lys is connected to
                        O2Oc-O2Oc-gamma-Glu-C20diacid
SEQUENCE: 492
HXQGTFTSDV SKXLDTXRAR DFVQWLLEXK                                                  30

SEQ ID NO: 493        moltype = AA  length = 29
FEATURE               Location/Qualifiers
source                1..29
                      mol_type = protein
                      organism = Synthetic construct
MOD_RES               2
                      note = 2-Aminoisobutyric acid
MOD_RES               28
                      note = 2-Aminoisobutyric acid
MOD_RES               13
                      note = alpha-methyl-L-phenylalanine
MOD_RES               17
                      note = Lys, wherein the side chain of Lys is connected to
                        O2Oc-O2Oc-gamma-Glu-C18diacid
SEQUENCE: 493
HXQGTFTSDV SKXLESXRAQ DFVQWLLXE                                                   29

SEQ ID NO: 494        moltype = AA  length = 29
FEATURE               Location/Qualifiers
source                1..29
                      mol_type = protein
                      organism = Synthetic construct
MOD_RES               2
                      note = 2-Aminoisobutyric acid
MOD_RES               28
                      note = 2-Aminoisobutyric acid
MOD_RES               13
                      note = alpha-methyl-L-phenylalanine
METAL                 17
                      note = Lys, wherein the side chain of Lys is connected to
                        O2Oc-O2Oc-gamma-Glu-C18diacid
SEQUENCE: 494
HXQGTFTSDV SKXLDTXRAQ DFVQWLLXE                                                   29
```

-continued

```
SEQ ID NO: 495          moltype = AA   length = 29
FEATURE                 Location/Qualifiers
source                  1..29
                        mol_type = protein
                        organism = Synthetic construct
MOD_RES                 2
                        note = 2-Aminoisobutyric acid
MOD_RES                 28
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C20diacid
SEQUENCE: 495
HXQGTFTSDV SKXLDTXRAQ DFVQWLLXE                                            29

SEQ ID NO: 496          moltype = AA   length = 29
FEATURE                 Location/Qualifiers
source                  1..29
                        mol_type = protein
                        organism = Synthetic construct
MOD_RES                 2
                        note = 2-Aminoisobutyric acid
MOD_RES                 28
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C20diacid
SEQUENCE: 496
HXQGTFTSDV SKXLDTXRAQ DFVQWLLXE                                            29

SEQ ID NO: 497          moltype = AA   length = 29
FEATURE                 Location/Qualifiers
source                  1..29
                        mol_type = protein
                        organism = Synthetic construct
MOD_RES                 2
                        note = 2-Aminoisobutyric acid
MOD_RES                 28
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C20diacid
SEQUENCE: 497
HXQGTFTSDV SKXLDLXRAQ DFVRWLLXE                                            29

SEQ ID NO: 498          moltype = AA   length = 30
FEATURE                 Location/Qualifiers
source                  1..30
                        mol_type = protein
                        organism = Synthetic construct
MOD_RES                 2
                        note = 2-Aminoisobutyric acid
MOD_RES                 28
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C18diacid
SEQUENCE: 498
HXQGTFTSDV SKXLDTXRAR DFVQWLLXTE                                           30

SEQ ID NO: 499          moltype = AA   length = 30
FEATURE                 Location/Qualifiers
source                  1..30
                        mol_type = protein
                        organism = Synthetic construct
MOD_RES                 2
                        note = 2-Aminoisobutyric acid
MOD_RES                 28
                        note = 2-Aminoisobutyric acid
MOD_RES                 13
                        note = alpha-methyl-L-phenylalanine
```

-continued

```
MOD_RES                 17
                        note = Lys, wherein the side chain of Lys is connected to
                        O2Oc-O2Oc-gamma-Glu-C20diacid
SEQUENCE: 499
HXQGTFTSDV SKXLDTXRAR DFVQWLLXTE                                         30

SEQ ID NO: 500          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 28
                        note = 2-Aminoisobutyric acid
MOD_RES                 13
                        note = alpha-methyl-L-phenylalanine
MOD_RES                 17
                        note = Lys, wherein the side chain of Lys is connected to
                        O2Oc-O2Oc-gamma-Glu-C18diacid
SEQUENCE: 500
HXQGTFTSDV SKXLDTXRAR DFVQWLLXTE                                         30

SEQ ID NO: 501          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 28
                        note = 2-Aminoisobutyric acid
MOD_RES                 13
                        note = alpha-methyl-L-phenylalanine
MOD_RES                 17
                        note = Lys, wherein the side chain of Lys is connected to
                        O2Oc-O2Oc-gamma-Glu-C20diacid
SEQUENCE: 501
HXQGTFTSDV SKXLDTXRAR DFVQWLLXTE                                         30

SEQ ID NO: 502          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 28
                        note = 2-Aminoisobutyric acid
MOD_RES                 13
                        note = alpha-methyl-L-phenylalanine
MOD_RES                 17
                        note = Lys, wherein the side chain of Lys is connected to
                        O2Oc-O2Oc-gamma-Glu-C18diacid
SEQUENCE: 502
HXQGTFTSDV SKXLDTXRAR DFVRWLLXTE                                         30

SEQ ID NO: 503          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 28
                        note = 2-Aminoisobutyric acid
MOD_RES                 13
                        note = alpha-methyl-L-phenylalanine
MOD_RES                 17
                        note = Lys, wherein the side chain of Lys is connected to
                        O2Oc-O2Oc-gamma-Glu-C20diacid
SEQUENCE: 503
HXQGTFTSDV SKXLDTXRAR DFVRWLLXTE                                         30

SEQ ID NO: 504          moltype = AA  length = 30
FEATURE                 Location/Qualifiers
source                  1..30
                        mol_type = protein
                        organism = Synthetic construct
```

```
MOD_RES            2
                   note = 2-Aminoisobutyric acid
MOD_RES            29
                   note = 2-Aminoisobutyric acid
MOD_RES            13
                   note = alpha-methyl-L-phenylalanine
MOD_RES            17
                   note = Lys, wherein the side chain of Lys is connected to
                   O2Oc-O2Oc-gamma-Glu-C18diacid
SEQUENCE: 504
HXQGTFTSDV SKXLDTXRAQ DFVRWLLRXK                                    30

SEQ ID NO: 505     moltype = AA  length = 30
FEATURE            Location/Qualifiers
source             1..30
                   mol_type = protein
                   organism = Synthetic construct
MOD_RES            2
                   note = 2-Aminoisobutyric acid
MOD_RES            29
                   note = 2-Aminoisobutyric acid
MOD_RES            13
                   note = alpha-methyl-L-phenylalanine
MOD_RES            17
                   note = Lys, wherein the side chain of Lys is connected to
                   O2Oc-O2Oc-gamma-Glu-C20diacid
SEQUENCE: 505
HXQGTFTSDV SKXLDTXRAQ DFVRWLLRXK                                    30

SEQ ID NO: 506     moltype = AA  length = 30
FEATURE            Location/Qualifiers
source             1..30
                   mol_type = protein
                   organism = Synthetic construct
MOD_RES            2
                   note = 2-Aminoisobutyric acid
MOD_RES            29
                   note = 2-Aminoisobutyric acid
MOD_RES            13
                   note = alpha-methyl-L-phenylalanine
MOD_RES            17
                   note = Lys, wherein the side chain of Lys is connected to
                   O2Oc-O2Oc-gamma-Glu-C18diacid
SEQUENCE: 506
HXQGTFTSDV SKXLDTXRAQ DFVRWLLRXK                                    30

SEQ ID NO: 507     moltype = AA  length = 30
FEATURE            Location/Qualifiers
source             1..30
                   mol_type = protein
                   organism = Synthetic construct
MOD_RES            2
                   note = 2-Aminoisobutyric acid
MOD_RES            29
                   note = 2-Aminoisobutyric acid
MOD_RES            13
                   note = alpha-methyl-L-phenylalanine
MOD_RES            17
                   note = Lys, wherein the side chain of Lys is connected to
                   O2Oc-O2Oc-gamma-Glu-C20diacid
SEQUENCE: 507
HXQGTFTSDV SKXLDTXRAQ DFVRWLLRXK                                    30

SEQ ID NO: 508     moltype = AA  length = 30
FEATURE            Location/Qualifiers
source             1..30
                   mol_type = protein
                   organism = Synthetic construct
MOD_RES            2
                   note = 2-Aminoisobutyric acid
MOD_RES            29
                   note = 2-Aminoisobutyric acid
MOD_RES            13
                   note = alpha-methyl-L-phenylalanine
MOD_RES            17
                   note = Lys, wherein the side chain of Lys is connected to
                   O2Oc-O2Oc-gamma-Glu-C18diacid
SEQUENCE: 508
HXQGTFTSDV SKXLDTXRAQ DFVRWLLRXA                                    30
```

```
SEQ ID NO: 509          moltype = AA   length = 30
FEATURE                 Location/Qualifiers
source                  1..30
                        mol_type = protein
                        organism = Synthetic construct
MOD_RES                 2
                        note = 2-Aminoisobutyric acid
MOD_RES                 29
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C20diacid
SEQUENCE: 509
HXQGTFTSDV SKXLDTXRAQ DFVRWLLRXA                                      30

SEQ ID NO: 510          moltype = AA   length = 30
FEATURE                 Location/Qualifiers
source                  1..30
                        mol_type = protein
                        organism = Synthetic construct
MOD_RES                 2
                        note = 2-Aminoisobutyric acid
MOD_RES                 29
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C18diacid
SEQUENCE: 510
HXQGTFTSDV SKXLDTXRAQ DFVQWLLRXA                                      30

SEQ ID NO: 511          moltype = AA   length = 30
FEATURE                 Location/Qualifiers
source                  1..30
                        mol_type = protein
                        organism = Synthetic construct
MOD_RES                 2
                        note = 2-Aminoisobutyric acid
MOD_RES                 29
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C20diacid
SEQUENCE: 511
HXQGTFTSDV SKXLDTXRAQ DFVQWLLRXA                                      30

SEQ ID NO: 512          moltype = AA   length = 30
FEATURE                 Location/Qualifiers
source                  1..30
                        mol_type = protein
                        organism = Synthetic construct
MOD_RES                 2
                        note = 2-Aminoisobutyric acid
MOD_RES                 29
                        note = 2-Aminoisobutyric acid
MOD_RES                 13
                        note = alpha-methyl-L-phenylalanine
MOD_RES                 17
                        note = Lys, wherein the side chain of Lys is connected to
                         O2Oc-O2Oc-gamma-Glu-C18diacid
SEQUENCE: 512
HXQGTFTSDV SKXLDTXRAR DFVQWLLRXA                                      30

SEQ ID NO: 513          moltype = AA   length = 30
FEATURE                 Location/Qualifiers
source                  1..30
                        mol_type = protein
                        organism = Synthetic construct
MOD_RES                 2
                        note = 2-Aminoisobutyric acid
MOD_RES                 29
                        note = 2-Aminoisobutyric acid
MOD_RES                 13
```

-continued

```
                       note = alpha-methyl-L-phenylalanine
MOD_RES                17
                       note = Lys, wherein the side chain of Lys is connected to
                         O2Oc-O2Oc-gamma-Glu-C20diacid
SEQUENCE: 513
HXQGTFTSDV SKXLDTXRAR DFVQWLLRXA                                             30

SEQ ID NO: 514         moltype = AA  length = 30
FEATURE                Location/Qualifiers
source                 1..30
                       mol_type = protein
                       organism = Synthetic construct
MOD_RES                2
                       note = 2-Aminoisobutyric acid
MOD_RES                29
                       note = 2-Aminoisobutyric acid
MOD_RES                13
                       note = alpha-methyl-L-phenylalanine
MOD_RES                17
                       note = Lys, wherein the side chain of Lys is connected to
                         O2Oc-O2Oc-gamma-Glu-C20diacid
SEQUENCE: 514
HXQGTFTSDV SKXLDTXRAQ DFVRWLLEXK                                             30

SEQ ID NO: 515         moltype = AA  length = 30
FEATURE                Location/Qualifiers
source                 1..30
                       mol_type = protein
                       organism = Synthetic construct
MOD_RES                2
                       note = 2-Aminoisobutyric acid
MOD_RES                29
                       note = 2-Aminoisobutyric acid
MOD_RES                13
                       note = alpha-methyl-L-phenylalanine
MOD_RES                17
                       note = Lys, wherein the side chain of Lys is connected to
                         O2Oc-O2Oc-gamma-Glu-C20diacid
SEQUENCE: 515
HXQGTFTSDV SKXLESXRAQ DFVRWLLEXK                                             30

SEQ ID NO: 516         moltype = AA  length = 30
FEATURE                Location/Qualifiers
source                 1..30
                       mol_type = protein
                       organism = Synthetic construct
MOD_RES                2
                       note = 2-Aminoisobutyric acid
MOD_RES                29
                       note = 2-Aminoisobutyric acid
MOD_RES                13
                       note = alpha-methyl-L-phenylalanine
MOD_RES                17
                       note = Lys, wherein the side chain of Lys is connected to
                         O2Oc-O2Oc-gamma-Glu-C20diacid
SEQUENCE: 516
HXQGTFTSDV SKXLDTXRAQ DFVQWLLEXK                                             30

SEQ ID NO: 517         moltype = AA  length = 30
FEATURE                Location/Qualifiers
source                 1..30
                       mol_type = protein
                       organism = Synthetic construct
MOD_RES                2
                       note = 2-Aminoisobutyric acid
MOD_RES                29
                       note = 2-Aminoisobutyric acid
MOD_RES                13
                       note = alpha-methyl-L-phenylalanine
MOD_RES                17
                       note = Lys, wherein the side chain of Lys is connected to
                         O2Oc-O2Oc-gamma-Glu-C20diacid
SEQUENCE: 517
HXQGTFTSDV SKXLDTXRAR DFVAWLLEXG                                             30

SEQ ID NO: 518         moltype = AA  length = 30
FEATURE                Location/Qualifiers
source                 1..30
                       mol_type = protein
```

```
                            organism = Synthetic construct
MOD_RES                     2
                            note = 2-Aminoisobutyric acid
MOD_RES                     29
                            note = 2-Aminoisobutyric acid
MOD_RES                     13
                            note = alpha-methyl-L-phenylalanine
MOD_RES                     17
                            note = Lys, wherein the side chain of Lys is connected to
                              O2Oc-O2Oc-gamma-Glu-C20diacid
SEQUENCE: 518
HXQGTFTSDV SKXLDTXRAR DFVAWLLEXG                                     30

SEQ ID NO: 519              moltype = AA  length = 30
FEATURE                     Location/Qualifiers
source                      1..30
                            mol_type = protein
                            organism = Synthetic construct
MOD_RES                     2
                            note = 2-Aminoisobutyric acid
MOD_RES                     29
                            note = 2-Aminoisobutyric acid
MOD_RES                     13
                            note = alpha-methyl-L-phenylalanine
MOD_RES                     17
                            note = Lys, wherein the side chain of Lys is connected to
                              O2Oc-O2Oc-gamma-Glu-C20diacid
SEQUENCE: 519
HXQGTFTSDV SKXLESXRAQ DFVRWLVEXG                                     30

SEQ ID NO: 520              moltype = AA  length = 30
FEATURE                     Location/Qualifiers
source                      1..30
                            mol_type = protein
                            organism = Synthetic construct
MOD_RES                     2
                            note = 2-Aminoisobutyric acid
MOD_RES                     28
                            note = 2-Aminoisobutyric acid
MOD_RES                     13
                            note = alpha-methyl-L-phenylalanine
MOD_RES                     17
                            note = Lys, wherein the side chain of Lys is connected to
                              O2Oc-O2Oc-gamma-Glu-C20diacid
SEQUENCE: 520
HXQGTFTSDV SKXLESXRAQ DFVRWLLXTE                                     30

SEQ ID NO: 521              moltype = AA  length = 29
FEATURE                     Location/Qualifiers
source                      1..29
                            mol_type = protein
                            organism = Synthetic construct
MOD_RES                     2
                            note = 2-Aminoisobutyric acid
MOD_RES                     28
                            note = 2-Aminoisobutyric acid
MOD_RES                     13
                            note = alpha-methyl-L-phenylalanine
MOD_RES                     17
                            note = Lys, wherein the side chain of Lys is connected to
                              O2Oc-O2Oc-gamma-Glu-C20diacid
SEQUENCE: 521
HXQGTFTSDV SKXLDTXRAR DFVRWLLXE                                      29

SEQ ID NO: 522              moltype = AA  length = 29
FEATURE                     Location/Qualifiers
source                      1..29
                            mol_type = protein
                            organism = Synthetic construct
MOD_RES                     2
                            note = 2-Aminoisobutyric acid
MOD_RES                     28
                            note = 2-Aminoisobutyric acid
MOD_RES                     13
                            note = alpha-methyl-L-phenylalanine
MOD_RES                     17
                            note = Lys, wherein the side chain of Lys is connected to
                              O2Oc-O2Oc-gamma-Glu-C20diacid
SEQUENCE: 522
```

```
HXQGTFTSDV SKXLDTXRAR DFVRWLLXE                                29

SEQ ID NO: 523          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 29
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 22
                        note = alpha-methyl-L-phenylalanine
MOD_RES                 17
                        note = Lys, wherein the side chain of Lys is connected to
                          O2Oc-O2Oc-gamma-Glu-C18diacid
SEQUENCE: 523
HXQGTXTSDV SKXLDTXRAQ DXVRWLLAXG                               30

SEQ ID NO: 524          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 29
                        note = 2-Aminoisobutyric acid
MOD_RES                 6
                        note = alpha-methyl-L-phenylalanine
MOD_RES                 13
                        note = alpha-methyl-L-phenylalanine
MOD_RES                 22
                        note = alpha-methyl-L-phenylalanine
MOD_RES                 17
                        note = Lys, wherein the side chain of Lys is connected to
                          O2Oc-O2Oc-gamma-Glu-C18diacid
SEQUENCE: 524
HXQGTXTSDV SKXLDTXRAR DXVQWLLAXG                               30

SEQ ID NO: 525          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 29
                        note = 2-Aminoisobutyric acid
MOD_RES                 13
                        note = alpha-methyl-L-phenylalanine
MOD_RES                 17
                        note = Lys, wherein the side chain of Lys is connected to
                          O2Oc-O2Oc-gamma-Glu-C18diacid
SEQUENCE: 525
HXQGTFTSDV SKXLDTXAAR DFVQWLLEXG                               30

SEQ ID NO: 526          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 29
                        note = 2-Aminoisobutyric acid
MOD_RES                 13
                        note = alpha-methyl-L-phenylalanine
MOD_RES                 17
                        note = Lys, wherein the side chain of Lys is connected to
                          O2Oc-O2Oc-gamma-Glu-C20diacid
SEQUENCE: 526
HXQGTFTSDV SKXLDTXAAR DFVQWLLEXG                               30

SEQ ID NO: 527          moltype = AA  length = 29
```

-continued

```
FEATURE              Location/Qualifiers
source               1..29
                     mol_type = protein
                     organism = Synthetic construct
MOD_RES              2
                     note = 2-Aminoisobutyric acid
MOD_RES              29
                     note = 2-Aminoisobutyric acid
MOD_RES              13
                     note = alpha-methyl-L-phenylalanine
MOD_RES              17
                     note = Lys, wherein the side chain of Lys is connected to
                        O2Oc-O2Oc-gamma-Glu-C20diacid
SEQUENCE: 527
HXQGTFTSDV SKXLESXRAQ DFVRWLLXG                                   29

SEQ ID NO: 528       moltype = AA  length = 29
FEATURE              Location/Qualifiers
source               1..29
                     mol_type = protein
                     organism = Synthetic construct
MOD_RES              2
                     note = 2-Aminoisobutyric acid
MOD_RES              13
                     note = alpha-methyl-L-phenylalanine
MOD_RES              17
                     note = Lys, wherein the side chain of Lys is connected to
                        O2Oc-O2Oc-gamma-Glu-gamma-Glu-C18diacid
SEQUENCE: 528
HXQGTFTSDV SKXLEAXAAR EFIAWLLET                                   29

SEQ ID NO: 529       moltype = AA  length = 30
FEATURE              Location/Qualifiers
source               1..30
                     mol_type = protein
                     organism = Synthetic construct
MOD_RES              2
                     note = 2-Aminoisobutyric acid
MOD_RES              29
                     note = 2-Aminoisobutyric acid
MOD_RES              13
                     note = alpha-methyl-L-phenylalanine
MOD_RES              17
                     note = Lys, wherein the side chain of Lys is connected to
                        O2Oc-O2Oc-gamma-Glu-gamma-Glu-C18diacid
SEQUENCE: 529
HXQGTFTSDV SKXLDTXRAR DFVQWLLEXG                                  30

SEQ ID NO: 530       moltype = AA  length = 30
FEATURE              Location/Qualifiers
source               1..30
                     mol_type = protein
                     organism = Synthetic construct
MOD_RES              2
                     note = 2-Aminoisobutyric acid
MOD_RES              29
                     note = 2-Aminoisobutyric acid
MOD_RES              13
                     note = alpha-methyl-L-phenylalanine
MOD_RES              17
                     note = Lys, wherein the side chain of Lys is connected to
                        gamma-Glu-gamma-Glu-O2Oc-O2Oc-gamma-Glu-gamma-Glu-C18diacid
SEQUENCE: 530
HXQGTFTSDV SKXLDTXRAR DFVQWLLEXG                                  30

SEQ ID NO: 531       moltype = AA  length = 30
FEATURE              Location/Qualifiers
source               1..30
                     mol_type = protein
                     organism = Synthetic construct
MOD_RES              2
                     note = 2-Aminoisobutyric acid
MOD_RES              29
                     note = 2-Aminoisobutyric acid
MOD_RES              13
                     note = alpha-methyl-L-phenylalanine
MOD_RES              17
                     note = Lys, wherein the side chain of Lys is connected to
                        gamma-Glu-gamma-Glu- O2Oc-O2Oc-gamma-Glu-C20diacid
```

-continued

```
SEQUENCE: 531
HXQGTFTSDV SKXLDTXRAR DFVQWLLEXG                              30

SEQ ID NO: 532          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 13
                        note = 2-Aminoisobutyric acid
MOD_RES                 20
                        note = Lys, wherein the side chain of Lys is connected to
                         O2Oc- O2Oc- gamma-Glu -C18diacid
SEQUENCE: 532
HXQGTFTSDV SKXLDSERAX DFVQWLEAGG                              30

SEQ ID NO: 533          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 20
                        note = Lys, wherein the side chain of Lys is connected to
                         O2Oc- O2Oc- gamma-Glu -C18diacid
SEQUENCE: 533
HXQGTFTSDV SKXLDSERAX DFVAWLEAGG                              30

SEQ ID NO: 534          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 20
                        note = Lys, wherein the side chain of Lys is connected to
                         O2Oc- O2Oc- gamma-Glu -C20diacid
SEQUENCE: 534
HXQGTFTSDV SKXLDSERAX DFVAWLEAGG                              30

SEQ ID NO: 535          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 13
                        note = alpha-methyl-L-phenylalanine
MOD_RES                 20
                        note = Lys, wherein the side chain of Lys is connected to
                         O2Oc- O2Oc- gamma-Glu -C18diacid
SEQUENCE: 535
HXQGTFTSDV SEXLDSERAX DFVRWLEAGG                              30

SEQ ID NO: 536          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 29
                        note = 2-Aminoisobutyric acid
MOD_RES                 13
                        note = alpha-methyl-L-phenylalanine
MOD_RES                 20
                        note = Lys, wherein the side chain of Lys is connected to
                         O2Oc- O2Oc- gamma-Glu -C18diacid
SEQUENCE: 536
HXQGTFTSDV SKXLDSERAX DFVQWLEAXG                              30
```

```
SEQ ID NO: 537          moltype = AA  length = 30
FEATURE                 Location/Qualifiers
source                  1..30
                        mol_type = protein
                        organism = Synthetic construct
MOD_RES                 2
                        note = 2-Aminoisobutyric acid
MOD_RES                 29
                        note = 2-Aminoisobutyric acid
MOD_RES                 13
                        note = alpha-methyl-L-phenylalanine
MOD_RES                 20
                        note = Lys, wherein the side chain of Lys is connected to
                        O2Oc- O2Oc- gamma-Glu -C18diacid
SEQUENCE: 537
HXQGTFTSDV SKXLDSERAX DFVAWLEAXG                                   30

SEQ ID NO: 538          moltype = AA  length = 30
FEATURE                 Location/Qualifiers
source                  1..30
                        mol_type = protein
                        organism = synthetic construct
MOD_RES                 10
                        note = Lys[epsilon- gammaE-Palmitoyl]
SEQUENCE: 538
HSQGTFTSDX SEYLDSERAR DFVAWLEAGG                                   30

SEQ ID NO: 539          moltype = AA  length = 31
FEATURE                 Location/Qualifiers
source                  1..31
                        mol_type = protein
                        organism = synthetic construct
MOD_RES                 2
                        note = Aib
MOD_RES                 20
                        note = X is Lys[O2Oc-O2Oc-gammaE-C18diacid]
SEQUENCE: 539
HXEGTFTSDV SSYLEGQAAX EFIAWLVRGR G                                 31

SEQ ID NO: 540          moltype = AA  length = 32
FEATURE                 Location/Qualifiers
source                  1..32
                        mol_type = protein
                        organism = synthetic construct
MOD_RES                 13
                        note = alphaMethyl-Phenylalanine (alphaMePhe)
VARIANT                 2
                        note = X is Aminoisobutyric acid (Aib), S, or A
VARIANT                 3
                        note = X is Q, H, or E
VARIANT                 5
                        note = X is T or S
VARIANT                 6
                        note = X is F or alphaMePhe
VARIANT                 10
                        note = X is V, K or Y
VARIANT                 12
                        note = X is K, E, or S
VARIANT                 15
                        note = X is D or E
VARIANT                 16
                        note = X is T, S, or G
VARIANT                 17
                        note = X is K, R, E, or Q
VARIANT                 18
                        note = X is R or A
VARIANT                 20
                        note = X is R, K, or Q
VARIANT                 21
                        note = X is D or E
VARIANT                 22
                        note = X is alphaMePhe or F
VARIANT                 23
                        note = X is V or I
VARIANT                 24
                        note = X is Q or A
VARIANT                 25
                        note = X is Aib or W
```

-continued

```
VARIANT                 26
                        note = X is L or I
VARIANT                 27
                        note = X is L, A, E, V, or M
VARIANT                 28
                        note = X is E, N, A, R, or K
VARIANT                 29
                        note = X is Aib, T, or G
VARIANT                 30
                        note = X is G, R, or not present
VARIANT                 31
                        note = X is G or not present
VARIANT                 32
                        note = Z is amide or acid
SEQUENCE: 540
HXXGXXTSDX SXXLXXXXAX XXXXXXXXXX XZ                              32

SEQ ID NO: 541          moltype = AA  length = 30
FEATURE                 Location/Qualifiers
source                  1..30
                        mol_type = protein
                        organism = synthetic construct
MOD_RES                 2
                        note = Aib
MOD_RES                 13
                        note = alphaMePhe
MOD_RES                 29
                        note = Aib
SEQUENCE: 541
HXQGTFTSDV SKXLDTKRAR DFVQWLLEXG                                 30
```

GLP-1 AND GLUCAGON DUAL AGONIST PEPTIDES WITH IMPROVED BIOLOGICAL STABILITY

CROSS REFERENCE TO RELATED APPLICATION

This application claims the benefit of U.S. Provisional Application 63/307,206 filed on Feb. 7, 2022, the content of which is hereby incorporated by reference in its entirety.

REFERENCE TO SEQUENCE LISTING SUBMITTED ELECTRONICALLY

The content of the electronically submitted sequence listing (Name: 2943_3070001_Sequencelisting_ST26.xml; Size: 1,486,485 bytes; and Date of Creation: Sep. 5, 2024) filed with the application is incorporated herein by reference in its entirety.

BACKGROUND OF THE INVENTION

The incidence of obesity and diabetes have been rising in epidemic proportions. Diabetes is characterized by high levels of blood glucose resulting from defects in insulin production, insulin action, or both. Type 2 diabetes mellitus (T2DM) accounts for some 90 to 95 percent of all diagnosed cases of diabetes, and the risk of type 2 diabetes rises with increasing body weight. The prevalence of type 2 diabetes is three to seven times higher in those who are affected by obesity than in normal weight adults, and is 20 times more likely in those with a body mass index (BMI) greater than 35 kg/m$^2$. However, weight-loss can improve control or cure type 2 diabetes.

Glucagon and glucagon-like peptide-1 (GLP-1) derive from pre-proglucagon, a 158 amino acid precursor polypeptide that is processed in different tissues to form a number of different proglucagon-derived peptides, including glucagon, glucagon-like peptide-1 (GLP-1), glucagon-like peptide-2 (GLP-2) and oxyntomodulin (OXM), that are involved in a wide variety of physiological functions, including glucose homeostasis, insulin secretion, gastric emptying, and intestinal growth, as well as the regulation of food intake. Glucagon is a 29-amino acid peptide that corresponds to amino acids 33 through 61 of proglucagon (53 to 81 of preproglucagon), while GLP-1 is produced as a 37-amino acid peptide that corresponds to amino acids 72 through 108 of proglucagon (92 to 128 of preproglucagon). GLP-1(7-36) amide or GLP-1(7-37) acid are biologically active forms of GLP-1, that demonstrate essentially equivalent activity at the GLP-1 receptor.

Glucagon is produced by the pancreas and interacts with the glucagon receptor ("glucR"). Glucagon acts in the liver to raise blood glucose via gluconeogenesis and glycogenolysis. When blood glucose begins to fall, glucagon signals the liver to break down glycogen and release glucose, causing blood glucose levels to rise toward a normal level.

GLP-1 has different biological activities compared to glucagon. It is secreted from gut L cells and binds to the GLP-1 receptor. Its activities include stimulation of insulin synthesis and secretion, inhibition of glucagon secretion, and inhibition of food intake.

Both glucagon and GLP-1, acting as agonists at their respective receptors, have been shown to be effective in weight loss. Certain GLP-1 analogs are being sold or are in development for treatment of obesity including, e.g., Liraglutide (Saxenda® from Novo Nordisk) and Semaglutide (Wegovy® from Novo Nordisk). Glucagon/GLP-1 dual agonist peptides such as cotadutide are also known and are in clinical development for treatment of diabetes, obesity, and nonalcoholic steatohepatitis (NASH). However, all of these proposed therapies involve chronic self-medication necessitating patient compliance over an extended period of time. Other peptides, e.g., amylin analogues are also being considered for the treatment of obesity, excess food intake, and diabetes (WO 2018/046719).

Accordingly, there remains a need for therapeutics that can agonize both GLP-1 and glucagon functions to e.g., improve glycemic control, reduce weight, treat type 2 diabetes mellitus, (T2DM) and/or treat NASH, while minimizing burdens associated with administration to improve patient compliance and quality of life.

BRIEF SUMMARY OF THE INVENTION

Provided herein are GLP-1 and glucagon dual agonists with improved biological stability (e.g., proteolytic stability) and duration of action. The GLP-1 and glucagon dual agonist peptides provided herein can have improved properties, e.g., as compared to semaglutide H(Aib) EGTFTSDVSSYLEGQAAX20EFIAWLVRGRG-acid, wherein X20=Lys[O2Oc-O2Oc-γE-C18diacid] (SEQ ID NO: 539)) and/or cotadutide (HSQGTFTSDX10SEYLDSERARDFVAWLEAGG-acid, wherein X10=Lys[ε-γE-Palmitoyl] (SEQ ID NO: 538)). Accordingly, the GLP-1 and glucagon dual agonist peptides provided herein can be administered once weekly.

Certain aspects of the disclosure are directed to a peptide comprising the sequence: H-X2-X3-G-X5-X6-T-S-D-X10-S-X12-αMethyl-Phenylalanine (αMePhe)-L-X15-X16-X17-X18-A-X20-X21-X22-X23-X24-X25-X26-X27-X28-X29-X30-X31-Z, wherein X2 is Aminoisobutyric acid (Aib), S, or A, X3 is Q, H, or E, X5 is T or S, X6 is F or αMePhe, X10 is V, K or Y, X12 is K, E, or S, X15 is D or E, X16 is T, S, or G, X17 is K, R, E, or Q, X18 is R or A, X20 is R, K, or Q, X21 is D or E, X22 is αMePhe or F, X23 is V or I, X24 is Q or A, X25 is Aib or W, X26 is L or I, X27 is L, A, E, V, or M, X28 is E, N, A, R, or K, X29 is Aib, T, or G, X30 is G, R, or not present, X31 is G or not present, and Z is amide or acid (SEQ ID NO: 540).

In some aspects, X2 is Aib. In some aspects, X3 is Q. In some aspects, X3 is H. In some aspects, X5 is T. In some aspects, X5 is S. In some aspects, X6 is F. In some aspects, X6 is αMePhe. In some aspects, X10 is V. In some aspects, X12 is K. In some aspects, X15 is D. In some aspects, X16 is T. In some aspects, X16 is S. In some aspects, X17 is K. In some aspects, X17 is R. In some aspects, X18 is R. In some aspects, X18 is A. In some aspects, X20 is R. In some aspects, X20 is K. In some aspects, X21 is D. In some aspects, X22 is F. In some aspects, X22 is αMePhe. In some aspects, X23 is V. In some aspects, X24 is Q. In some aspects, X25 is W. In some aspects, X25 is Aib. In some aspects, X26 is L. In some aspects, X26 is I. In some aspects, X27 is L. In some aspects, X27 is A. In some aspects, X28 is E. In some aspects, X28 is N. In some aspects, X29 is Aib. In some aspects, X29 is T. In some aspects, X30 is G. In some aspects, X30 is not present. In some aspects, X31 is not present. In some aspects, Z is amide. In some aspects, Z is acid.

In some aspects, X2 is Aib, X12 is K, and X24 is Q. In some aspects, X16 is T, X17 is K, X27 is L, X28, is E, and X29 is Aib. In some aspects, X3 is Q, X5 is T, X6 is F, X10 is V, X12 is K, X15 is D, X16 is T, X17 is K, X18 is R, X20 is R, X21 is D, X22 is F, X23 is V, X24 is Q, X25 is W, X26 is L, X27 is L, X28 is E, X29 is Aib, X30 is G, X31 is not present, and Z is acid. In some aspects, X3 is H, X5 is S, X6 is αMePhe, X10 is V, X12 is K, X15 is D, X16 is S, X17 is R, X18 is A, X20 is K, X21 is D, X22 is αMePhe, X23 is V, X24 is Q, X25 is Aib, X26 is I, X27 is A, X28 is N, X29 is T, X30 is not present, X31 is not present, and Z is amide.

In some aspects, one or more lysine residues are acylated. In some aspects, the lysine at position 17 is acylated. In some aspects, the lysine at position 20 is acylated.

In some aspects, one or more lysine resides are lipidated. In some aspects, the lysine at position 17 is lipidated. In some aspects, the lysine at position 20 is lipidated.

In some aspects, the lipid is selected from the group consisting of octadecanedioic acid (C18diacid) and icosanedioic acid (C20diacid). In some aspects, the lipid is octadecanedioic acid (C18diacid). In some aspects, the lipid is icosanedioic acid (C20diacid). In some aspects, the lipid is linked to the epsilon amino group of lysine at position 17 or 20 via a linker.

In some aspects, the linker is ((O2Oc)-(O2Oc)-γE) or ((O2Oc)-(O2Oc)-γE-γE) in the C- to N-terminal orientation. In some aspects, the linker is ((O2Oc)-(O2Oc)-γE) in the C- to N-terminal orientation. In some aspects, the linker is ((O2Oc)-(O2Oc)-γE-γE) in the C- to N-terminal orientation. In some aspects, the linker is linked to the epsilon amino group of the residue at position 17 or 20.

Certain aspects of the disclosure are directed to a peptide comprising the sequence of H-Aib-Q-G-T-F-T-S-D-V-S-K-αMePhe-L-D-T-K-R-A-R-D-F-V-Q-W-L-L-E-Aib-G-acid (SEQ ID NO: 541).

In some aspects, the lysine at position 17 is acylated and lipidated, the lipid is linked to the acylated lysine via its epsilon amino group to ((O2Oc)-(O2Oc)-γE) linker in the C to N terminal orientation, and the lipid is octadecanedioic acid (C18diacid). In some aspects, the lysine at position 17 is acylated and lipidated, the lipid is linked to the acylated lysine via its epsilon amino group to ((O2Oc)-(O2Oc)-γE) linker in the C to N terminal orientation, and the lipid is icosanedioic acid (C20diacid).

Certain aspects of the disclosure are directed to a peptide comprising the sequence H-Aib-H-G-S-αMePhe-T-S-D-V-S-K-αMePhe-L-D-S-R-A-A-K(ε-(O2Oc)-(O2Oc)-γE-C18diacid)20-D-αMePhe-V-Q-Aib-1-A-N-T-amide (SEQ ID NO: 228).

Certain aspects of the disclosure are directed to a peptide comprising the sequence H-Aib-H-G-S-αMePhe-T-S-D-V-S-K-αMePhe-L-D-S-R-A-A-K(ε-(O2Oc)-(O2Oc)-γE-γE-C20diacid)20-D-αMePhe-V-Q-Aib-I-A-N-T-amide (SEQ ID NO: 233).

In some aspects, the peptide binds to the GLP-1 receptor (GLP-1R), binds to the glucagon receptor (GCGR), or binds to both a GLP-1 receptor and a glucagon receptor. In some aspects, the GLP-1R is a human GLP-1R. In some aspects, the GCGR is a human GCGR.

In some aspects, the peptide is an agonist of GLP-1 activity, an agonist of glucagon activity, or an agonist of both GLP-1 and glucagon activity. In some aspects, the peptide has increased proteolytic-resistance relative to the natural ligand of the GLP-1R and/or GCGR.

In some aspects, the peptide is isolated.

In some aspects, the peptide has at least 50%, at least 60%, at least 70%, at least 75%, at least 80%, at least 85%, at least 90%, at least 95, or 100% of intact peptide remaining after incubation with a protease at 37° C. for 5 min, 10 min, 15 min, 30 min, 2 hr, 4 hr, or 24 hr. In some aspects, the protease is selected from the group consisting of neprilysin, pepsin, pancreatin, simulated gastric fluid with pepsin, and simulated intestinal fluid with pancreatin.

In some aspects, the peptide has a half-life in cynomolgus monkeys after intravenous administration of at least 45 hours, at least 50 hours, at least 60 hours, at least 70 hours, at least 80 hours, at least 90 hours, at least 100 hours, at least 110 hours, at least 120 hours, or about 130 hours. In some aspects, the peptide has an s.c. bioavailability in cynomolgus monkeys of at least 75%, at least 80%, at least 90%, or about 95%.

In some aspects, a pharmaceutical composition comprising the peptide is provided herein. In some aspects, the composition is a solid composition. In some aspects, the composition is a liquid composition.

In some aspects, provided herein is a method of treating or preventing a disease or condition caused or characterized by excess body weight, wherein the method comprises administering to a subject in need of treatment an effective amount of any peptide or composition provide herein. In some aspects, the disease or condition is obesity. In some aspects, the disease or condition is type 2 diabetes.

In some aspects, provided herein is a method of treating or preventing non-alcoholic steatohepatitis (NASH), wherein the method comprises administering to a subject in need of treatment an effective amount of any peptide or composition provide herein.

In some aspects of a method provided herein, the administration is by injection. In some aspects of a method provided herein, the administration is oral. In some aspects of a method provided herein, the administration decreases body weight of the subject, increases insulin secretion in the subject, delays gastric emptying in the subject, decreases food intake in the subject, increases mitochondria function in the subject, inhibits de novo lipogenesis in the subject, decreases HbA1c in the subject, enhances fatty oxidation in the subject, decreases hepatic mitochondrial oxidative stress in the subject, decreases steatosis in the subject, decreases fibrosis in the subject, decreases glycogen synthesis in the subject, increases gluconeogenesis in the subject, halts disease progression in the subject, reverses fibrosis in the subject, and/or reduces risk of death due to cirrhosis, hepatocellular carcinoma, and/or cardiorenal disease in the subject. In some aspects of a method provided herein, the subject is a human. In some aspects of a method provided herein, the peptide is administered about once a week.

BRIEF DESCRIPTION OF THE DRAWINGS/FIGURES

FIGS. 1A-1G are drawings depicting the exemplary lipids icosanedioic acid (C20diacid) (FIG. 1A), octadecanedioic acid (C18diacid) (FIG. 1B), stearoyl (FIG. 1C), margaroyl (FIG. 1D), palmitoyl (FIG. 1E), myristoyl (FIG. 1F), and lauryl (FIG. 1G).

Figures 2A, 2B, 2C:
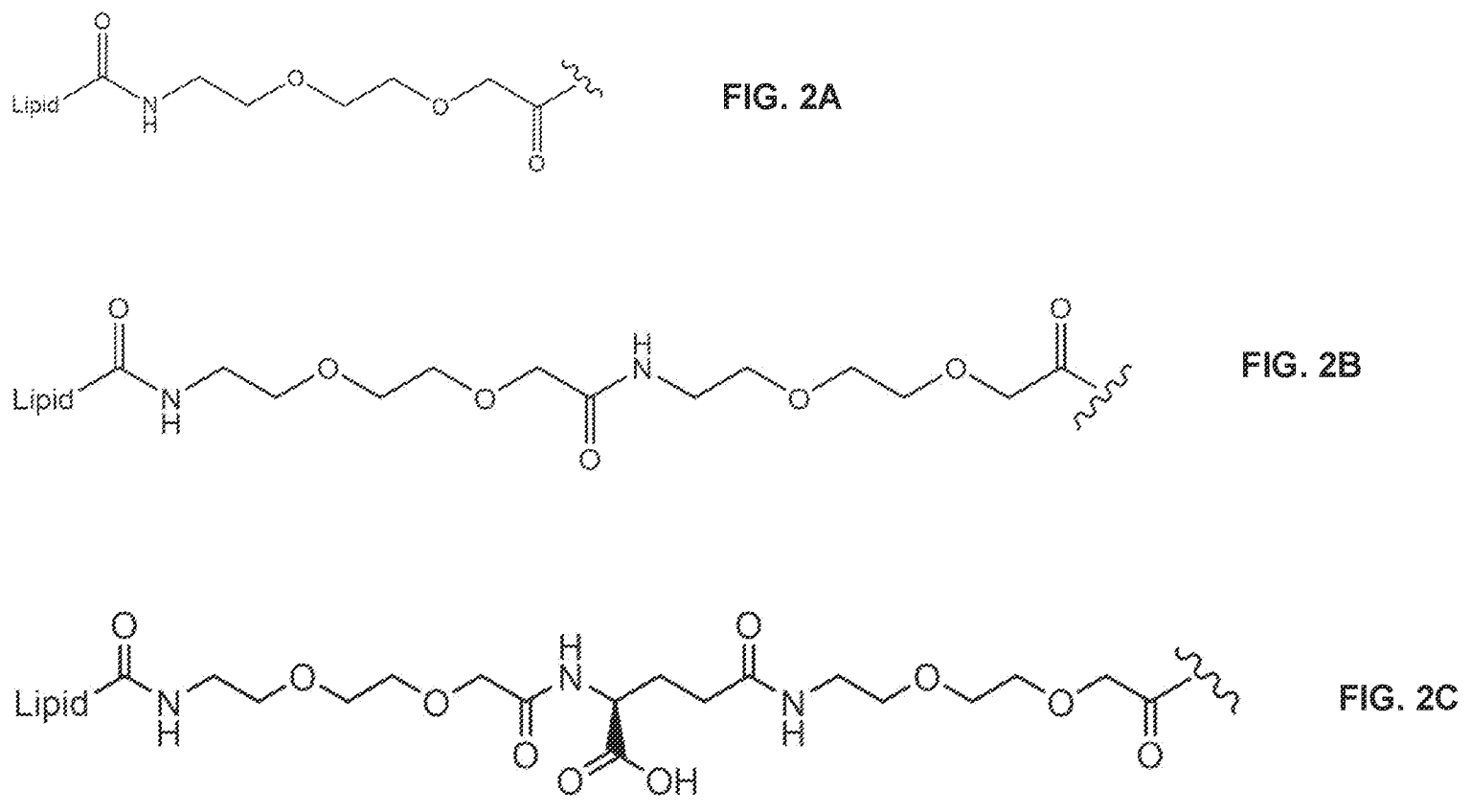
Figures 2D, 2E, 2F:
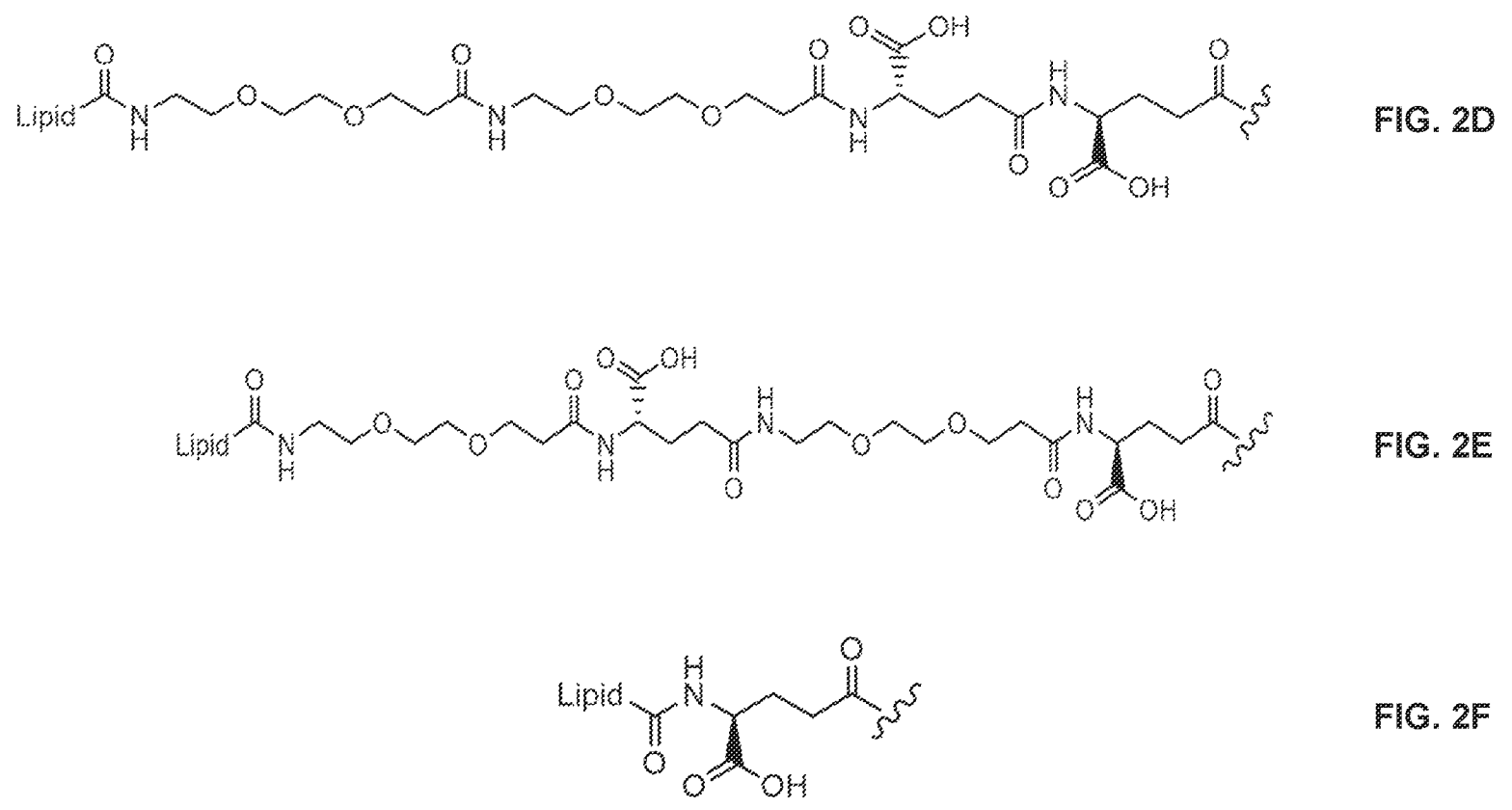
Figures 2G, 2H, 2I:
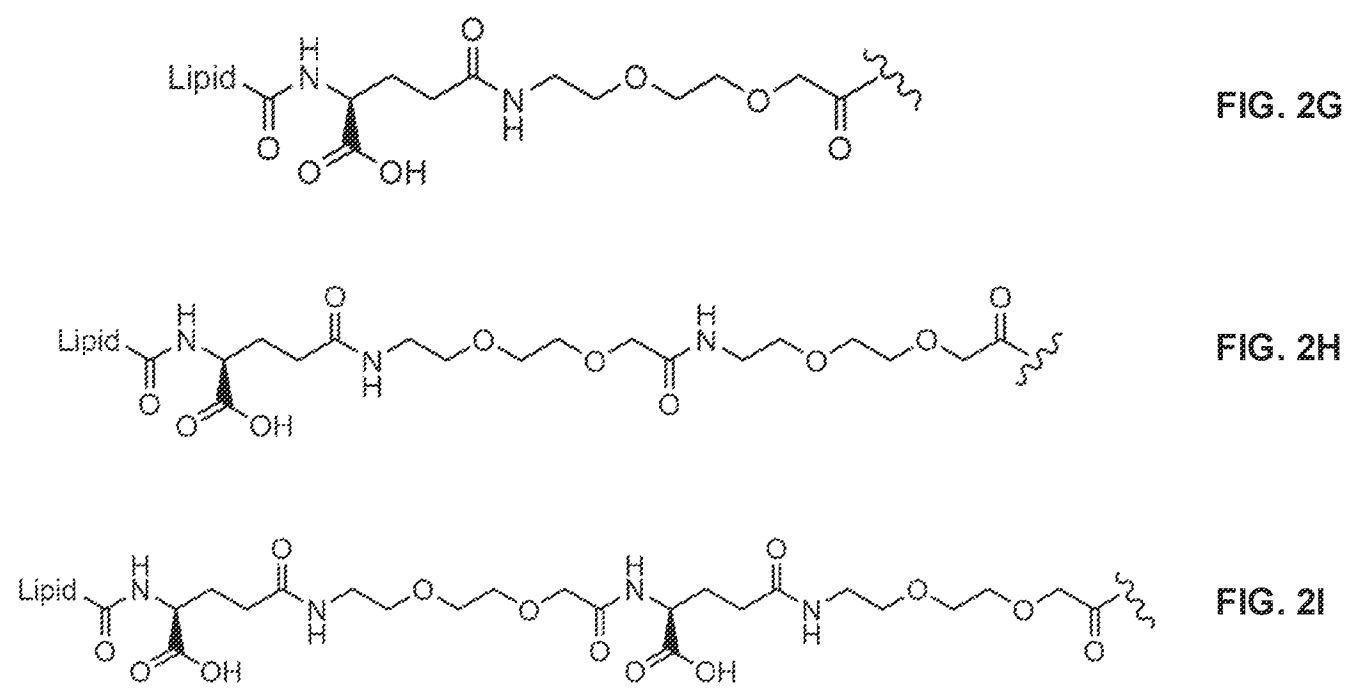
Figures 2J, 2K, 2L:
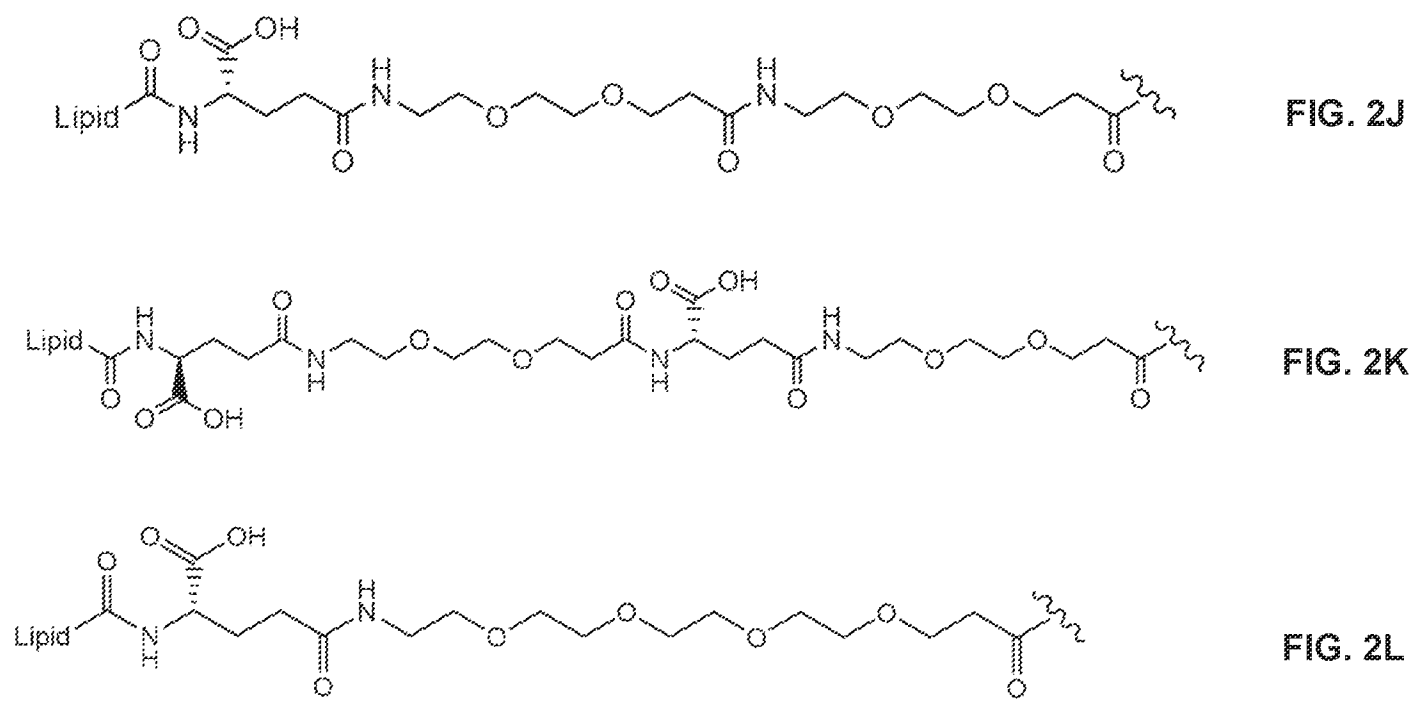
Figures 2M, 2N, 2O:
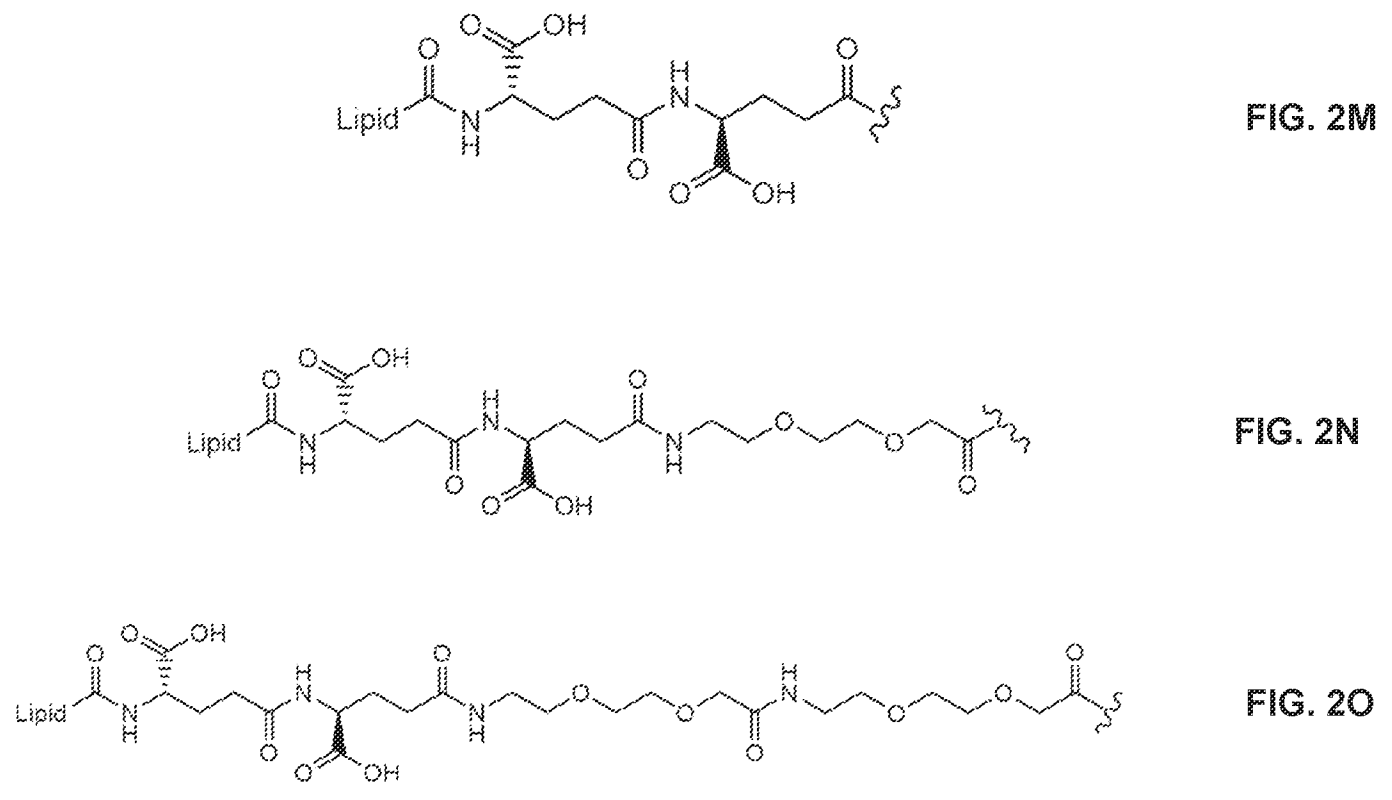
Figures 2P, 2Q, 2R:
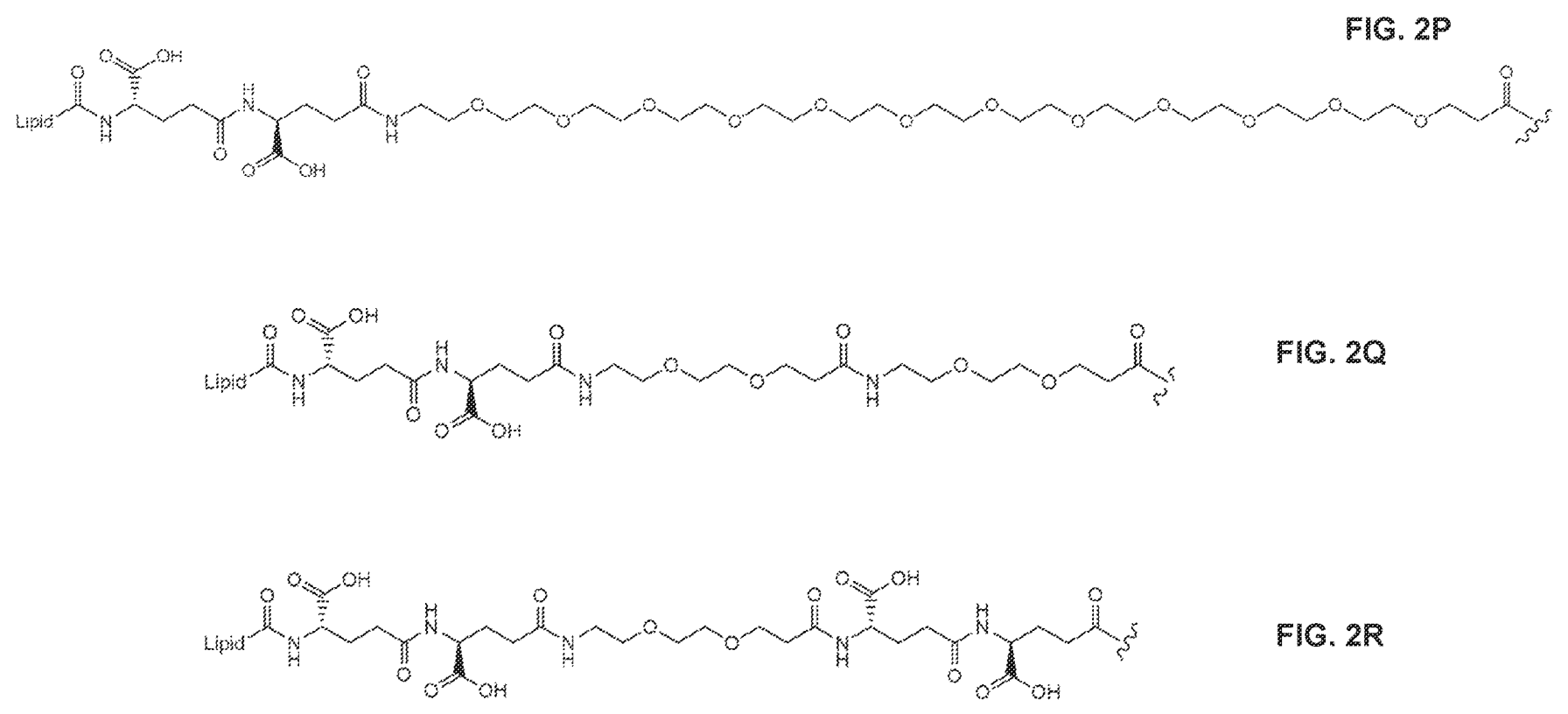
Figures 2S, 2T, 2U:
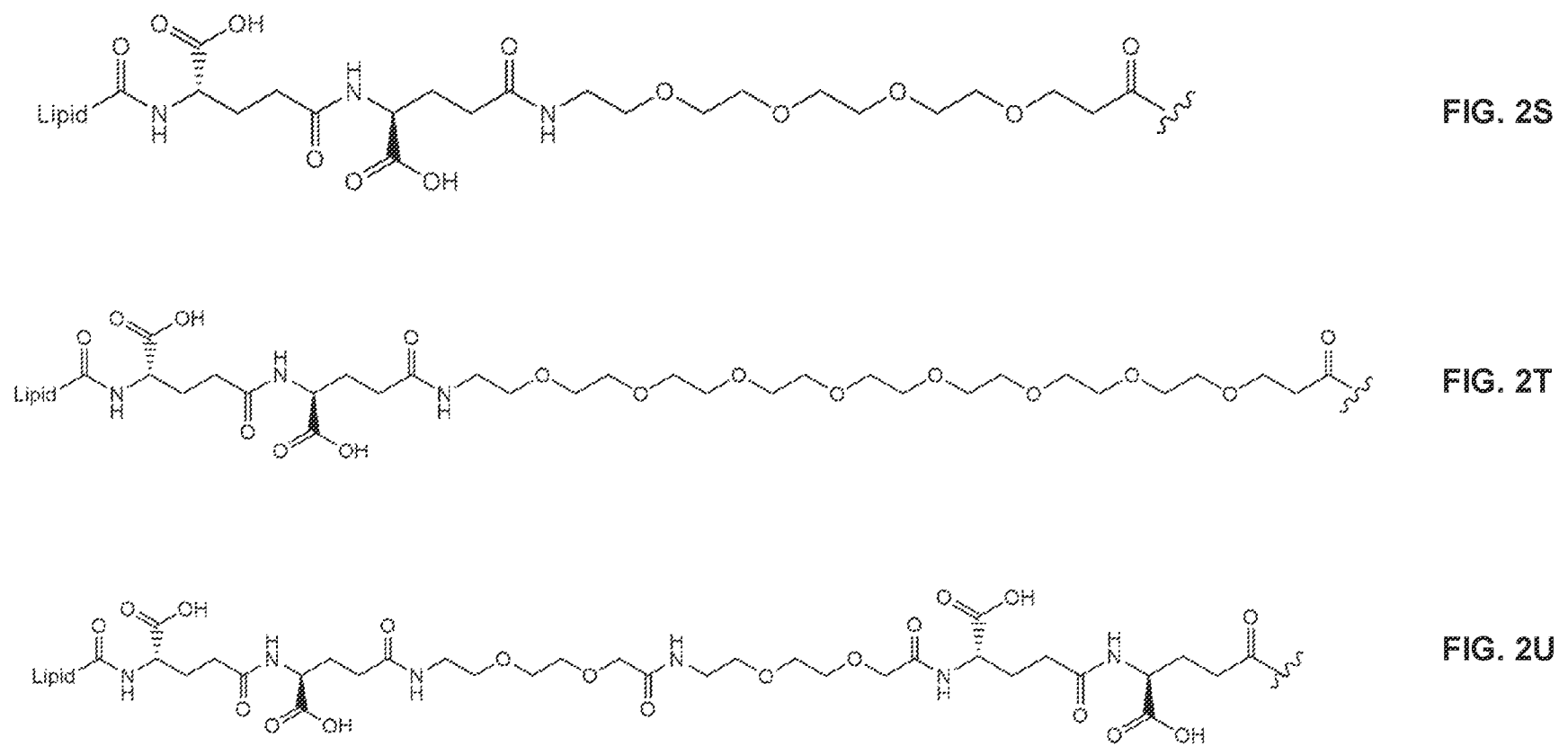
Figure 2V:
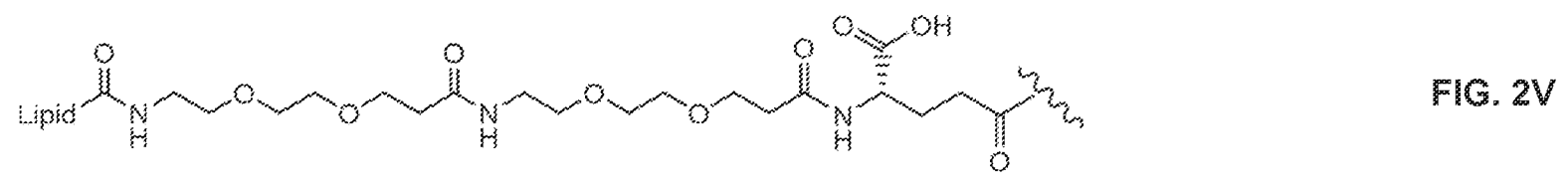

FIGS. 2A-2F are drawings depicting exemplary linkers attached to lipids depicted in FIGS. 1A-1G 2-(2-(2-amino-ethoxy)ethoxy)acetic acid (O2Oc) (FIG. 2A), (O2Oc)-(O2Oc) (FIG. 2B), (O2Oc)-γE-(O2Oc) (FIG. 2C), (PEG)2-(PEG)2-γE-γE (FIG. 2D), (PEG)2-γE-(PEG)2-γE (FIG. 2E), gammaglutamic acid (γE) (FIG. 2F), γE-(O2Oc) (FIG. 2G), γE-(O2Oc)-(O2Oc) (FIG. 2H), γE-(O2Oc)-γE-(O2Oc) (FIG. 2I), γE-(PEG)2-(PEG)2 (FIG. 2J), γE-(PEG)2-γE-(PEG)2 (FIG. 2K), γE-(PEG)4 (FIG. 2L), γE-γE (FIG. 2M), γE-γE-(O2Oc) (FIG. 2N), γE-γE-(O2Oc)-(O2Oc) (FIG. 2O), γE-γE-(PEG)12 (FIG. 2P), γE-γE-(PEG)2-(PEG)2 (FIG. 2Q), γE-γE-(PEG)2-γE-γE (FIG. 2R), γE-γE-(PEG)4 (FIG. 2S), γE-γE-(PEG)8 (FIG. 2T), γE-γE-(O2Oc)-(O2Oc)-γE-γE (FIG. 2U), and (PEG)2-(PEG)2-γE (FIG. 2V). All linkers shown with the N-terminal on the left and C-terminal on right.

Figures 3I, 3J, 3K, 3L:
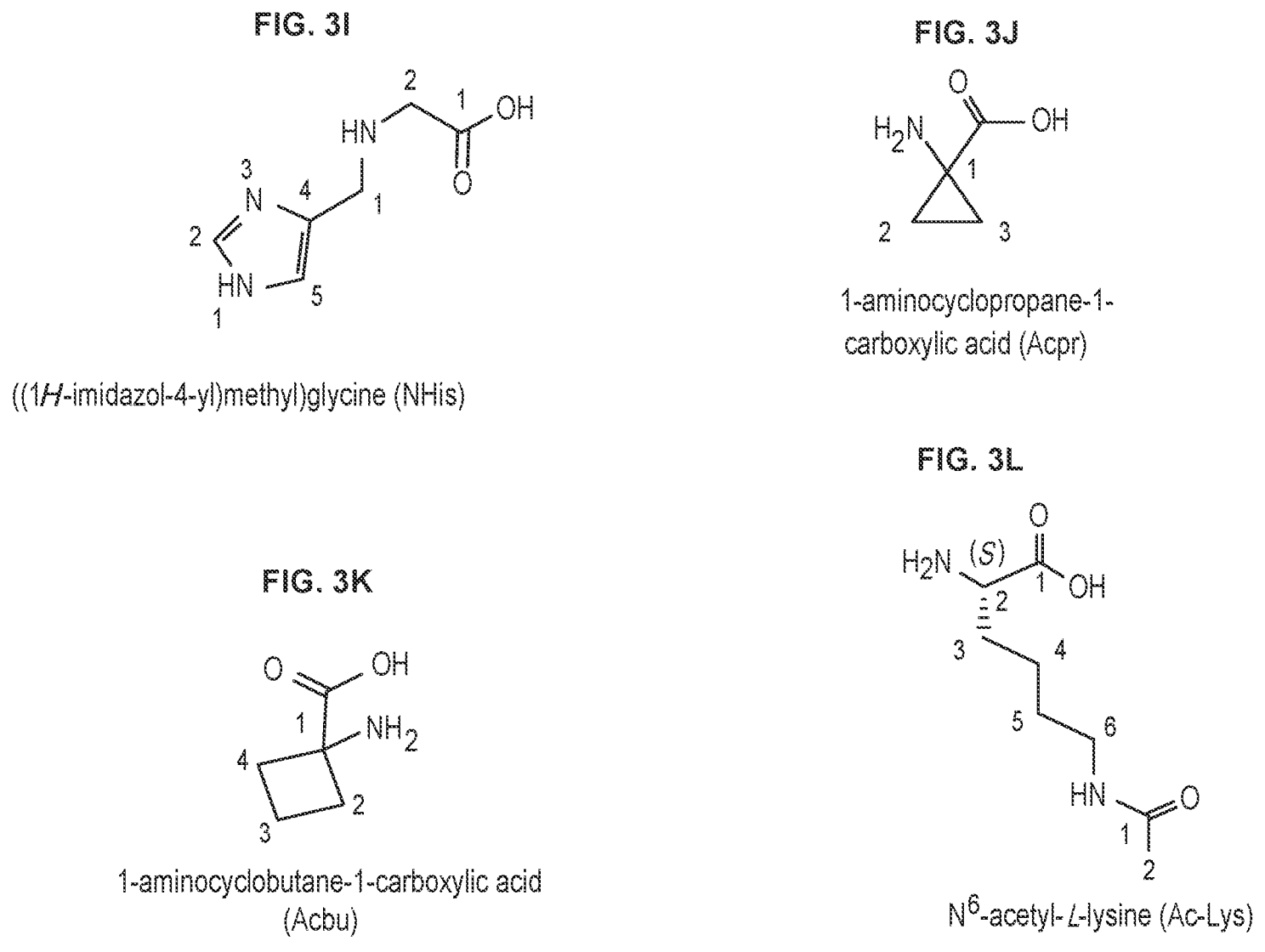
Figures 3Q, 3R, 3S:
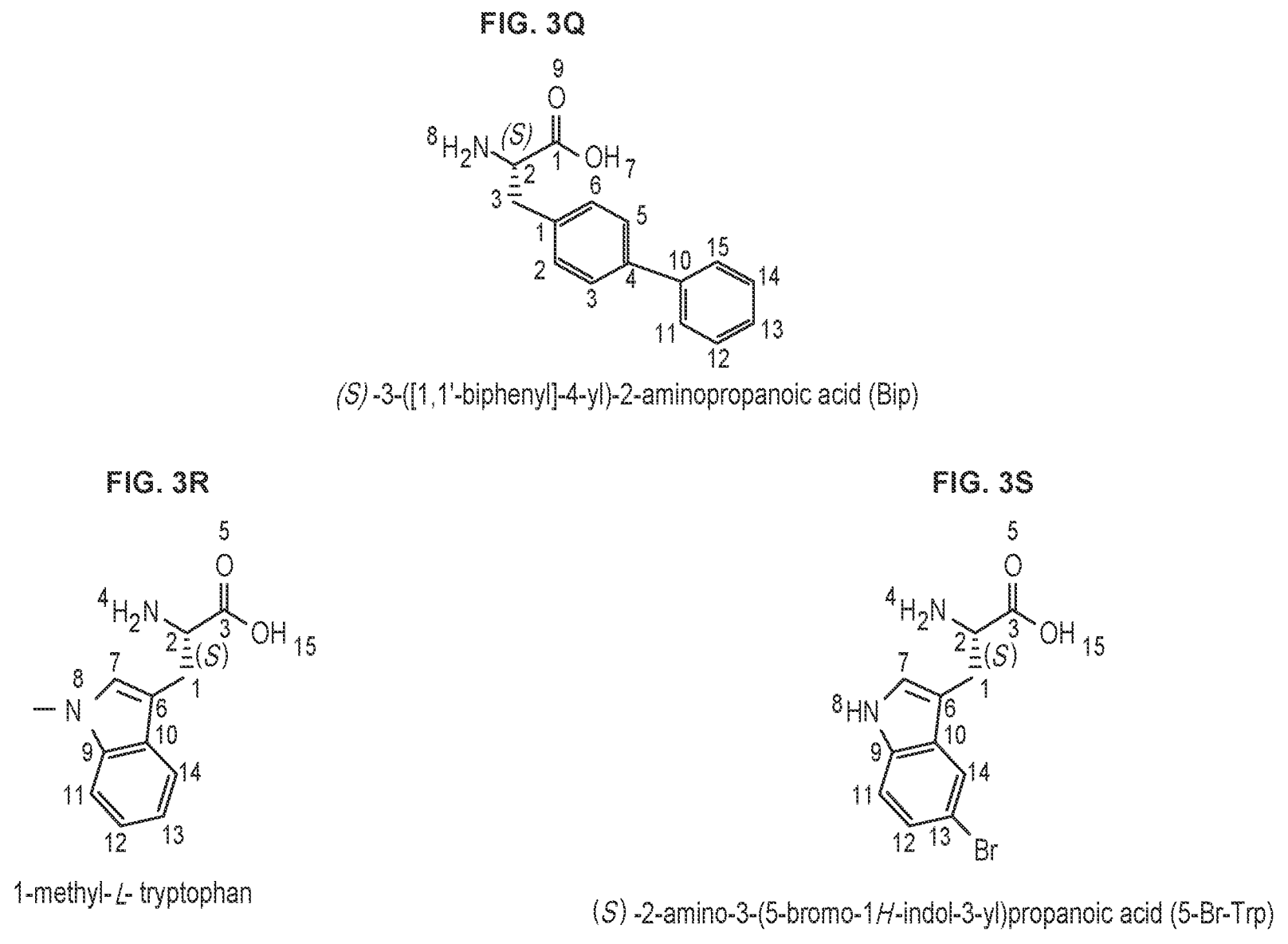

FIGS. 3A-3P are drawings depicting the exemplary non-natural amino acids 2-amino-2-methylpropanoic acid (Aib) (FIG. 3A), (S)-2-amino-2-methyl-3-phenylpropanoic acid (αMePhe) (FIG. 3B), (S)-2-amino-3-hydroxy-2-methylpro-panoic acid (αMeSer) (FIG. 3C), D-glutamine (dGln) (FIG. 3D), β-dimethylglutamine (β-dimethylGln) (FIG. 3E), (S)-2,5-diamino-2-methyl-5-oxopentanoic acid (αMeGln) (FIG. 3F), D-serine (dSer) (FIG. 3G), methyl-L-glutamine (N-MeGln) (FIG. 3H), ((1H-imidazol-4-yl)methyl)glycine (NHis) (FIG. 3I), 1-aminocyclopropane-1-carboxylic acid (Acpr) (FIG. 3J), 1-aminocyclobutane-1-carboxylic acid (Acbu) (FIG. 3K), $N^6$-acetyl-L-lysine (Ac-Lys) (FIG. 3L), (S)-2-amino-5-guanidino-3,3-dimethylpentanoic acid (β-di-methylArg) (FIG. 3M), (S)-2-amino-3,3-diphenylpropanoic acid (Dip) (FIG. 3N), (S)-2-amino-3-cyclohexylpropanoic acid (Cha) (FIG. 3O), (S)-2-aminohexanoic acid (Nle) (FIG. 3P), (S)-3-([1,1'-biphenyl]-4-yl)-2-aminopropanoic acid (Bip) (FIG. 3Q), 1-methyl-L-tryptophan (1-Methyl-Trp) (FIG. 3R), and (S)-2-amino-3-(5-bromo-1H-indol-3-yl)pro-panoic acid (5-Br-Trp) (FIG. 3S).

Figure 4A:
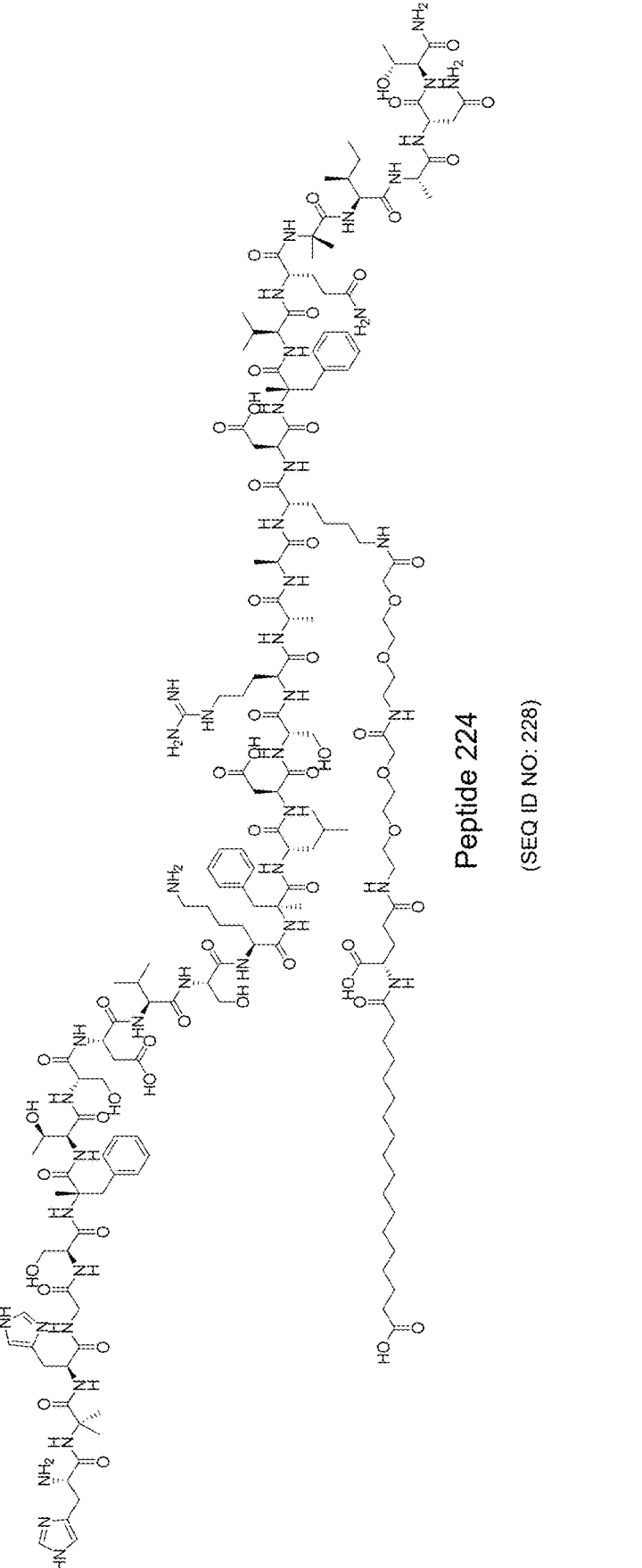
Figure 4B:
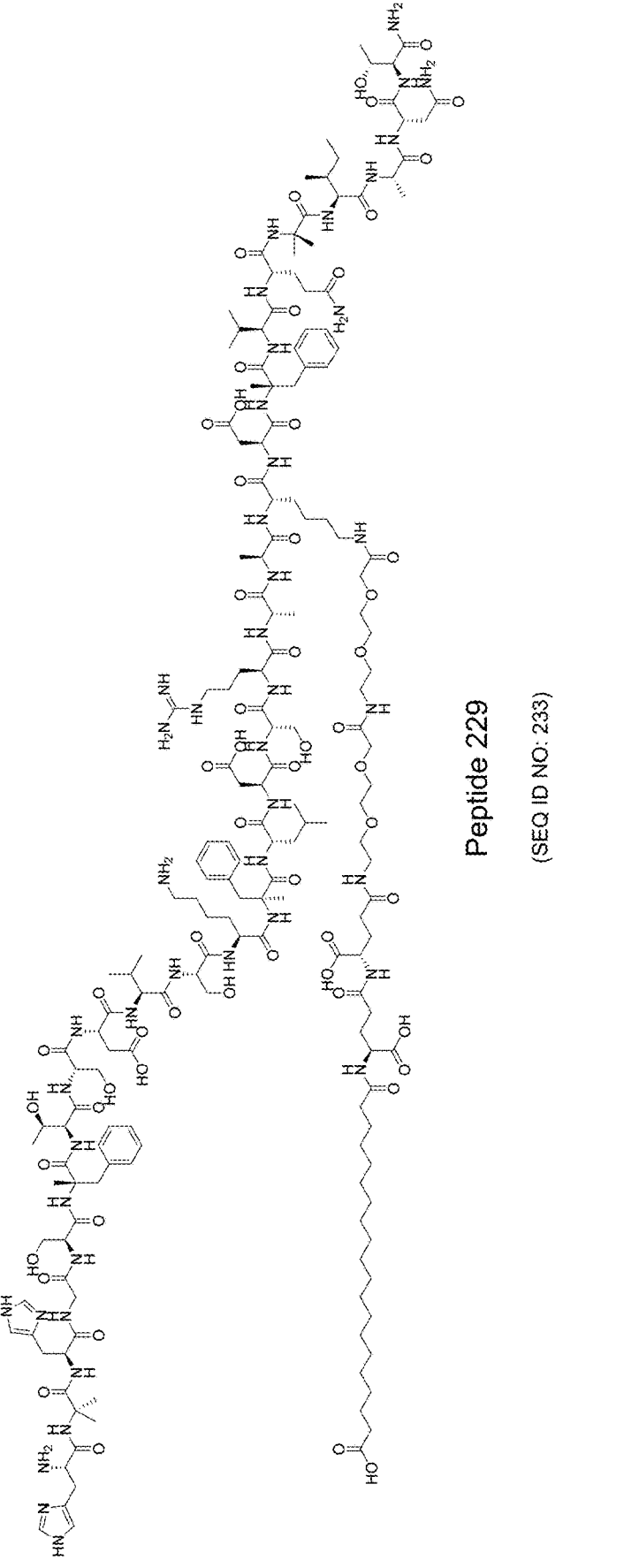
Figure 4C:
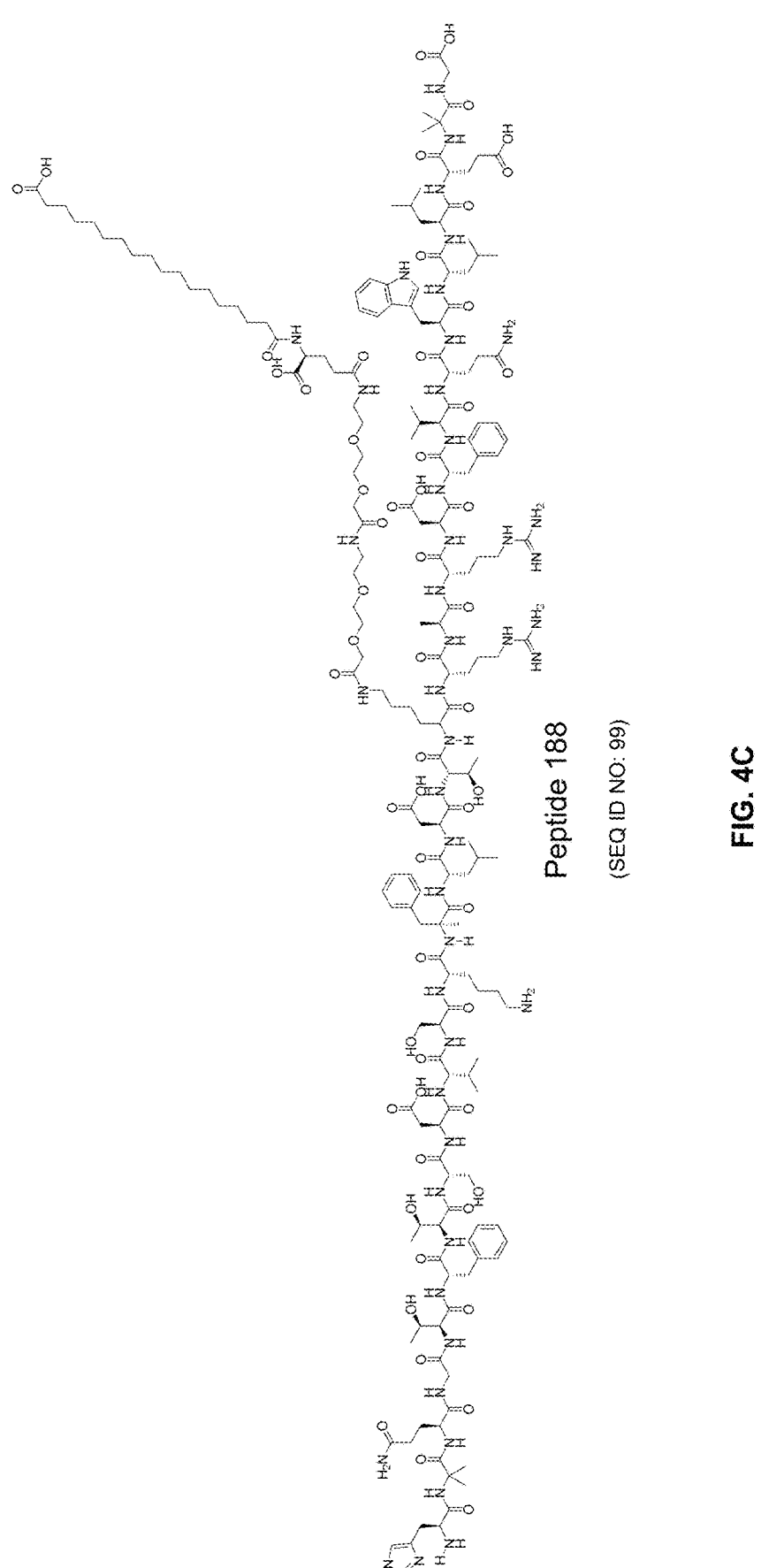
Figure 4D:
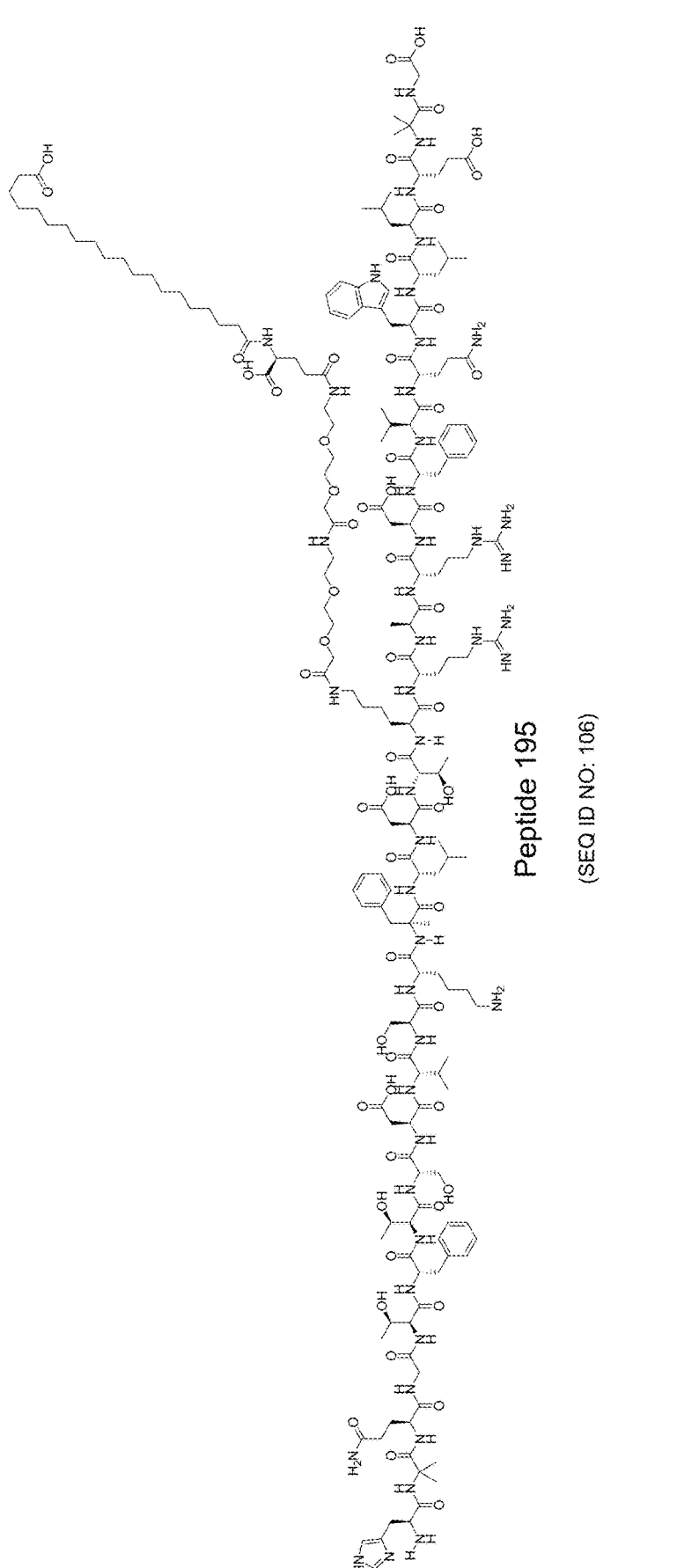

FIGS. 4A-4D are drawings depicting the structure of exemplary peptides: peptide 224 (FIG. 4A), peptide 229 (FIG. 4B), peptide 188 (FIG. 4C), and peptide 195 (FIG. 4D).

DETAILED DESCRIPTION OF THE INVENTION

I. Definitions

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

Throughout this disclosure, the term "a" or "an" entity refers to one or more of that entity; for example, "a poly-nucleotide," is understood to represent one or more poly-nucleotides. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

As used herein, the terms "about" and "approximately," when used to modify a numeric value or numeric range, indicate that deviations of up to 10% above and down to 10% below the value or range remain within the intended meaning of the recited value or range. It is understood that wherever aspects are described herein with the language "about" or "approximately" a numeric value or range, oth-erwise analogous aspects referring to the specific numeric value or range are also provided.

It is understood that wherever aspects are described herein with the language "comprising," otherwise analogous aspects described in terms of "consisting of" and/or "con-sisting essentially of" are also provided. A peptide "com-prising" a particular amino acid sequence refers to a peptide containing the amino acid sequence, wherein the peptide may or may not contain additional amino acids or other modifications to the amino acid sequence. A peptide "con-sisting of" a particular amino acid sequence refers to a peptide containing only the amino acid sequence and no additional amino acids or other modifications to the amino acid sequence. A peptide "comprising" an amino acid sequence "consisting of" a particular amino acid sequence refers to a peptide containing the amino acid sequence and no additional amino acids; however, the peptide may com-prise other modifications to the amino acid sequence (e.g., an acyl moiety or a palmitoyl moiety).

As used herein, the term "amino acid" refers to naturally occurring and non-natural amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leu-cine, lysine, methionine, phenylalanine, proline, serine, threonine, tryptophan, tyrosine, and valine) and pyrrolysine and selenocysteine. Amino acid analogs refers to com-pounds that have the same basic chemical structure as a naturally occurring amino acid, i.e., an a carbon that is bound to a hydrogen, a carboxyl group, an amino group, and an R group, such as, homoserine, norleucine, methionine sulfoxide, and methionine methyl sulfonium. Such analogs have modified R groups (such as, norleucine) or modified peptide backbones, but retain the same basic chemical structure as a naturally occurring amino acid.

A "non-natural amino acid" refers to an amino acid that is not one of the 20 common amino acids or pyrrolysine or selenocysteine; other terms that may be used synonymously with the term "non-natural amino acid" are "non-naturally encoded amino acid," "unnatural amino acid," "non-natu-rally-occurring amino acid," and variously hyphenated and non-hyphenated versions thereof. The term "non-natural amino acid" includes, but is not limited to, amino acids that occur naturally by modification of a naturally encoded amino acid (including but not limited to, the 20 common amino acids or pyrrolysine and selenocysteine) but are not themselves incorporated into a growing polypeptide chain by the translation complex.

Examples of naturally-occurring amino acids that are not naturally-encoded include, but are not limited to, ((1H-imidazol-4-yl)methyl)glycine (NHis), S, 1-aminocyclobu-tane-1-carboxylic acid (1-aminocyclobutane-1-carboxylic acid; Acbu), 1-aminocyclopropane-1-carboxylic acid (1-aminocyclopropane-1-carboxylic acid; Acpr), Ami-noisobutyric acid (2-amino-2-methylpropanoic acid; Aib), D-serine (dSer), αMethyl-Serine ((S)-2-amino-3-hydroxy-2-methylpropanoic acid (MeSer); (αMeSer), methyl-L-glutamine (N-MeGln), αMethyl-Glutamine ((S)-2,5-diamino-2-methyl-5-oxopentanoic acid; αMeGln), β-dimethylGln, αMethyl-Phenylalanine (S)-2-amino-2-methyl-3-phenyl-propanoic acid; αMePhe), acetylated lysine $N^6$-acetyl-L-lysine (Ac-Lys), Diphenylalanine ((S)-2-amino-3,3-diphenylpropanoic acid; Dip), β-dimethylarganine ((S)-2-amino-5-guanidino-3,3-dimethylpentaonic acid; β-dimethylArg), beta-cyclohexyl-L-alanine ((S)-2-amino-3-cyclohexylpropanoic acid; Cha), norleucine ((S)-2-aminohexanoic acid; Nle), D-glutamine (dGln) (S)-3-([1,1'-biphenyl]-4-yl)-2-aminopropanoic acid (Bip), 1-methyl-L-tryptophan (1-Methyl-Trp), and (S)-2-amino-3-(5-bromo-1H-indol-3-yl)propanoic acid (5-Br-Trp).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As used herein, the term "polypeptide" is intended to encompass a singular "polypeptide" as well as plural "polypeptides," and comprises any chain or chains of two or more amino acids. Thus, as used herein, a "peptide," a "peptide subunit," a "protein," an "amino acid chain," an "amino acid sequence," or any other term used to refer to a chain or chains of two or more amino acids, are included in the definition of a "polypeptide," even though each of these terms can have a more specific meaning. The term "polypeptide" can be used instead of, or interchangeably with any of these terms. The term further includes polypeptides which have undergone post-translational or post-synthesis modifications, for example, conjugation of a palmitoyl group, glycosylation, acetylation, phosphorylation, amidation, derivatization by known protecting/blocking groups, proteolytic cleavage, or modification by non-naturally occurring amino acids.

More specifically, the term "peptide" as used herein encompasses full length peptides and fragments, variants or derivatives thereof, e.g., a GLP-1/glucagon agonist peptide (e.g., 29, 30, or 31 amino acids in length). A "peptide" as disclosed herein, e.g., a GLP-1/glucagon agonist peptide, can be part of a fusion polypeptide comprising additional components such as, e.g., an Fc domain or an albumin domain, to increase half-life. A peptide as described herein can also be derivatized in a number of different ways. A peptide described herein can comprise modifications including e.g., conjugation of a lipid including a palmitoyl group, stearoyl group, lauryl group, myristoyl group, margaroyl group, octadecanedioic acid (C18diacid), or icosanedioic acid (C20diacid). Exemplary lipids are provided in FIGS. 1A-1G.

A peptide described herein can comprise modifications including e.g., conjugation of a linker comprising 2-(2-(2-aminoethoxy)ethosy)acetic acid (O2Oc), PEG, and/or gammaglutamic acid (γE). In some aspects, a linker comprises 2-(2-(2-aminoethoxy)ethosy)acetic acid (O2Oc), (O2Oc)-(O2Oc), (O2Oc)-γE-(O2Oc), 3-(2-(2-aminoethoxy)ethoxy)propanoic acid) ((PEG)2), 1-amino-3,6,9,12-tetraoxapentadecan-15-oic acid ((PEG)4), 1-amino-3,6,9,12,15,18,21,14-octaoxaheptacosan-27-oic acid ((PEG)8), 1-amino-3,6,9,12,15,18,21,24,27,30,33,36-dodecaoxanonatriacontan-39-oic acid ((PEG)12), gammaglutamic acid (γE), (PEG)2-(PEG)2-γE-γE, (PEG)2-γE-(PEG)2-γE, γE-(O2Oc), γE-(O2Oc)-(O2Oc), γE-(O2Oc)-γE-(O2Oc), γE-(PEG)2-(PEG)2, γE-(PEG)2-γE-(PEG)2, γE-(PEG)4, γE-γE, (E-γE-(O2Oc), γE-γE-(O2Oc)-(O2Oc), γE-γE-(PEG)12, γE-γE-(PEG)2-

(PEG)2, γE-γE-(PEG)2-γE-γE, γE-γE-(PEG)4, γE-γE-(PEG)8, γE-γE-(O2Oc)-(O2Oc)-γE-γE, and (PEG)2-(PEG)2-γE. Exemplary linkers are provided in FIGS. 2A-2V.

The term "isolated" refers to the state in which peptides or nucleic acids, will generally be in accordance with the present disclosure. Isolated peptides and isolated nucleic acids will be free or substantially free of material with which they are naturally associated such as other peptides or nucleic acids with which they are found in their natural environment, or the environment in which they are prepared (e.g. cell culture) when such preparation is by recombinant DNA technology practiced in vitro or in vivo. Peptides and nucleic acid can be formulated with diluents or adjuvants and still for practical purposes be isolated—for example the peptides will normally be mixed with gelatin or other carriers if used to coat microtiter plates for use in immunoassays, or will be mixed with pharmaceutically acceptable carriers or diluents when used in diagnosis or therapy.

A "recombinant" peptide refers to a peptide produced via recombinant DNA technology. Recombinantly produced peptides expressed in host cells are considered isolated for the purpose of the present disclosure, as are native or recombinant polypeptides which have been separated, fractionated, or partially or substantially purified by any suitable technique.

The terms "fragment," "analog," "derivative," or "variant" when referring to a GLP-1/glucagon agonist peptide include any peptide which retains at least some desirable activity, e.g., binding to glucagon receptors and/or GLP-1 receptors. Fragments of GLP-1/glucagon agonist peptides provided herein include proteolytic fragments, deletion fragments which exhibit desirable properties during expression, purification, and or administration to a subject.

The term "variant," as used herein, refers to a peptide that differs from the recited peptide due to amino acid substitutions, deletions, insertions, and/or modifications. Variants can be produced using art-known mutagenesis techniques. Variants can also, or alternatively, contain other modifications. For example, a peptide can be conjugated or coupled, e.g., fused to a heterologous amino acid sequence or other moiety, e.g., for increasing half-life, solubility, or stability. Examples of moieties to be conjugated or coupled to a peptide provided herein include, but are not limited to, albumin, an immunoglobulin Fc region, polyethylene glycol (PEG), and the like. The peptide can also be conjugated or produced coupled to a linker or other sequence for ease of synthesis, purification or identification of the peptide (e.g., 6-His), or to enhance binding of the polypeptide to a solid support.

The terms "composition" or "pharmaceutical composition" refer to compositions containing a GLP-1/glucagon agonist peptide provided herein, along with e.g., pharmaceutically acceptable carriers, excipients, or diluents for administration to a subject in need of treatment, e.g., a human subject in need of improved glycemic control, weight loss, treatment of Type 2 Diabetes Mellitus, and/or treatment of NASH.

The term "pharmaceutically acceptable" refers to compositions that are, within the scope of sound medical judgment, suitable for contact with the tissues of human beings and animals without excessive toxicity or other complications commensurate with a reasonable benefit/risk ratio.

An "effective amount" is that amount of an agent provided herein (e.g., a GLP-1/glucagon agonist peptide), the administration of which to a subject, either in a single dose or as part of a series, is effective for treatment, e.g., for improved glycemic control, weight loss, treatment of Type 2 Diabetes Mellitus, and/or treatment of NASH.

As used herein, the terms "subject" and "patient" are used interchangeably. The subject can be an animal. In some aspects of the present disclosure, the subject is a mammal such as a non-human animal (e.g., cow, pig, horse, cat, dog, rat, mouse, monkey or other primate, etc.). In some aspects of the present disclosure, the subject is a cynomolgus monkey. In some aspects of the present disclosure, the subject is a human.

As used herein, a "subject in need thereof" or a "patient in need thereof" refers to an individual for whom it is desirable to treat, e.g., a subject in need of improved glycemic control, weight loss, treatment of Type 2 Diabetes Mellitus, and/or treatment of NASH.

Terms such as "treating" or "treatment" or "to treat" refer to therapeutic measures that cure and/or halt progression of a diagnosed pathologic condition or disorder. Terms such as "preventing" refer to prophylactic or preventative measures that prevent and/or slow the development of a targeted pathologic condition or disorder. Thus, those in need of treatment include those already with the disease or condition. Those in need of prevention include those prone to have the disease or condition and those in whom the disease or condition is to be prevented.

Terms such as "decreasing the severity" refer to therapeutic measures that slow down or lessen the symptoms of a diagnosed pathologic condition or disorder.

As used herein, a "GLP-1 agonist peptide" is a peptide that is not native GLP-1 but exhibits activity at the GLP-1 receptor of about at least 1% or more relative to native GLP-1, under the conditions of the cAMP assay (see Example 2). In some aspects, a GLP-1 agonist peptide exhibits activity at the GLP-1 receptor of at least 5%, 10%, 20%, 30%, 40%, 50%, 60%, 70%, 80%, 90%, 95%, or more relative to native GLP-1, under the conditions of the cAMP assay (see Example 2).

As used herein, a "glucagon agonist peptide" is a peptide that is not native glucagon but exhibits activity at the glucagon receptor of at least 1%, or more relative to native glucagon, under the conditions of the cAMP assay (see Example 2). In some aspects, a glucagon agonist peptide exhibits activity at the glucagon receptor of at least 5%, 10%, 20%, 30%, 40%, 50%, 60%, 70%, 80%, 90%, 95%, or more relative to native GLP-1, under the conditions of the cAMP assay (see Example 2).

As used herein a "GLP-1/glucagon agonist peptide," "GLP-1/glucagon coagonist peptide," "GLP-1 and glucagon dual agonist peptide" or "GLP-1 and glucagon dual coagonist peptide" is a peptide that it not native GLP-1 and is not native glucagon that exhibits activity at the glucagon receptor of at least 1% or more relative to native glucagon and also exhibits activity at the GLP-1 receptor of about at least 1% or more relative to native GLP-1, under the conditions of the cAMP assay (see Example 2). In some aspects, a "GLP-1/glucagon agonist peptide" or a "GLP-1 and glucagon dual agonist peptide" exhibits activity at the glucagon receptor of at least 5%, 10%, 20%, 30%, 40%, 50%, 60%, 70%, 80%, 90%, 95%, or more relative to native glucagon and also exhibits activity at the GLP-1 receptor of about at least 5%, 10%, 20%, 30%, 40%, 50%, 60%, 70%, 80%, 90%, 95%, or more relative to native GLP-1, under the conditions of the cAMP assay (see Example 2).

As used herein, term "relative potency ratio" refers to the % GLP-1R activity relative to GLP-1/% GlucR activity relative to glucagon.

As used herein the term "native glucagon" refers to naturally-occurring glucagon, e.g., human glucagon, comprising the sequence of SEQ ID NO: 1. The term "native GLP-1" refers to naturally-occurring GLP-1, e.g., human GLP-1, and is a generic term that encompasses, e.g., GLP-1(7-36) amide (SEQ ID NO: 2), GLP-1(7-37) acid (SEQ ID NO: 3), or a mixture of those two compounds. As used herein, a general reference to "glucagon" or "GLP-1" in the absence of any further designation is intended to mean native human glucagon or native human GLP-1, respectively. Unless otherwise indicated, "glucagon" refers to human glucagon, and "GLP-1" refers to human GLP-1.

The term "sequence identity" as used herein refers to a relationship between two or more polynucleotide sequences or between two or more polypeptide sequences. When a position in one sequence is occupied by the same nucleic acid base or amino acid in the corresponding position of the comparator sequence, the sequences are said to be "identical" at that position. The percentage "sequence identity" is calculated by determining the number of positions at which the identical nucleic acid base or amino acid occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window. In order to optimally align sequences for comparison, the portion of a polynucleotide or polypeptide sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which was available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (*Proc. Natl. Acad. Sci. USA* 90(12):5873-5877, 1993). When utilizing "BLAST 2 Sequences," parameters that were default parameters as of Sep. 1, 2004, can be used for word size (3), open gap penalty (11), extension gap penalty (1), gap drop-off (50), expect value (10), and any other required parameter including but not limited to matrix option.

```
Glucagon
                              (SEQ ID NO: 1)
HSQGTFTSDYSKYLDSRRAQDFVQWLMNT-acid GLP-1(7-36) amide
                              (SEQ ID NO: 2)
HAEGTFTSDVSSYLEGQAAKEFIAWLVKGR-amide GLP-1(7-37) acid
                              (SEQ ID NO: 3)
HAEGTFTSDVSSYLEGQAAKEFIAWLVKGRG-acid
```

II. GLP-1/Glucagon Agonist Peptides

Provided herein are peptides that bind both to a glucagon receptor and to a GLP-1 receptor. In some aspects, the peptides provided herein are co-agonists (dual agonists) of glucagon and GLP-1 activity. Such peptides are referred to herein as GLP-1/glucagon agonist peptides. In some aspects, GLP-1/glucagon agonist peptides as provided herein are active at the human GLP1 and human glucagon receptors.

In certain aspects, GLP-1/glucagon agonist peptides provided herein exhibit in vitro potencies at the GLP-1 receptor as shown by an EC50 in the cAMP assay (see Example 2) of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM.

In certain aspects, GLP-1/glucagon agonist peptides provided herein exhibit in vitro potencies at the glucagon receptor as shown by an EC50 in the cAMP assay (see Example 2) of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM.

In certain aspects, GLP-1/glucagon agonist peptides provided herein have a hGLP-1R/hGCGR relative potency ratio of about 1 to about 25. In certain aspects, GLP-1/glucagon agonist peptides provided herein have a hGLP-1R/hGCGR relative potency ratio of about 1 to about 20. In certain aspects, GLP-1/glucagon agonist peptides provided herein have a hGLP-1R/hGCGR relative potency ratio of about 1 to about 15. In certain aspects, GLP-1/glucagon agonist peptides provided herein have a hGLP-1R/hGCGR relative potency ratio of about 1 to about 10.

In certain aspects, GLP-1/glucagon agonist peptides provided herein have a hGLP-1R/hGCGR relative potency ratio of about 2 to about 25. In certain aspects, GLP-1/glucagon agonist peptides provided herein have a hGLP-1R/hGCGR relative potency ratio of about 2 to about 20. In certain aspects, GLP-1/glucagon agonist peptides provided herein have a hGLP-1R/hGCGR relative potency ratio of about 2 to about 15. In certain aspects, GLP-1/glucagon agonist peptides provided herein have a hGLP-1R/hGCGR relative potency ratio of about 2 to about 10.

In certain aspects, GLP-1/glucagon agonist peptides provided herein, when administered to mice at 10 nmol/kg (as performed in Example 3) reduce 24-hour food intake by at least 10% relative to mice treated with a vehicle control. In certain aspects, GLP-1/glucagon agonist peptides provided herein, when administered to mice at 10 nmol/kg (as performed in Example 3) reduce 24-hour food intake by at least 20% relative to mice treated with a vehicle control. In certain aspects, GLP-1/glucagon agonist peptides provided herein, when administered to mice at 10 nmol/kg (as performed in Example 3) reduce 24-hour food intake by at least 30% relative to mice treated with a vehicle control.

In certain aspects, GLP-1/glucagon agonist peptides provided herein, when administered to mice at 10 nmol/kg (as performed in Example 3) reduce 24-hour food intake by at 10-70% relative to mice treated with a vehicle control. In certain aspects, GLP-1/glucagon agonist peptides provided herein, when administered to mice at 10 nmol/kg (as performed in Example 3) reduce 24-hour food intake by at least 20% or by 20-70% relative to mice treated with a vehicle control. In certain aspects, GLP-1/glucagon agonist peptides provided herein, when administered to mice at 10 nmol/kg (as performed in Example 3) reduce 24-hour food intake by at least 30% or by 30-70% relative to mice treated with a vehicle control.

In certain aspects, GLP-1/glucagon agonist peptides provided herein are stable. For example, in certain aspects, GLP-1/glucagon agonist peptides provided herein stable in the presence of FasSSGF (fasted state simulated gastric fluid) such that at least 25% of the GLP-1/glucagon agonist peptide remains intact after incubation with FasSSGF for 30 minutes (as performed in Example 4.) In certain aspects, GLP-1/glucagon agonist peptides provided herein stable in the presence of FasSSGF such that at least 40% of the GLP-1/glucagon agonist peptide remains intact after incubation with FasSSGF for 30 minutes (as performed in Example 4.) In certain aspects, GLP-1/glucagon agonist peptides provided herein stable in the presence of FasSSGF such that at least 50% of the GLP-1/glucagon agonist peptide remains intact after incubation with FasSSGF for 30 minutes (as performed in Example 4.) In certain aspects, GLP-1/glucagon agonist peptides provided herein stable in the presence of FasSSGF such that at least 60% of the GLP-1/glucagon agonist peptide remains intact after incubation with FasSSGF for 30 minutes (as performed in Example 4.) In certain aspects, GLP-1/glucagon agonist peptides provided herein stable in the presence of FasSSGF such that at least 70% of the GLP-1/glucagon agonist peptide remains intact after incubation with FasSSGF for 30 minutes (as performed in Example 4.)

In certain aspects, GLP-1/glucagon agonist peptides provided herein stable in the presence of neprilysin such that at least 55% of the GLP-1/glucagon agonist peptide remains intact after incubation with neprilysin for 24 hours (as performed in Example 5.) In certain aspects, GLP-1/glucagon agonist peptides provided herein stable in the presence of neprilysin such that at least 60% of the GLP-1/glucagon agonist peptide remains intact after incubation with neprilysin for 24 hours (as performed in Example 5.) In certain aspects, GLP-1/glucagon agonist peptides provided herein stable in the presence of neprilysin such that at least 65% of the GLP-1/glucagon agonist peptide remains intact after incubation with neprilysin for 24 hours (as performed in Example 5.) In certain aspects, GLP-1/glucagon agonist peptides provided herein stable in the presence of neprilysin such that at least 70% of the GLP-1/glucagon agonist peptide remains intact after incubation with neprilysin for 24 hours (as performed in Example 5.) In certain aspects, GLP-1/glucagon agonist peptides provided herein stable in the presence of neprilysin such that at least 75% of the GLP-1/glucagon agonist peptide remains intact after incubation with neprilysin for 24 hours (as performed in Example 5.) In certain aspects, GLP-1/glucagon agonist peptides provided herein stable in the presence of neprilysin such that at least 80% of the GLP-1/glucagon agonist peptide remains intact after incubation with neprilysin for 24 hours (as performed in Example 5.) In certain aspects, GLP-1/glucagon agonist peptides provided herein stable in the presence of neprilysin such that at least 85% of the GLP-1/glucagon agonist peptide remains intact after incubation with neprilysin for 24 hours (as performed in Example 5.) In certain aspects, GLP-1/glucagon agonist peptides provided herein stable in the presence of neprilysin such that at least 90% of the GLP-1/glucagon agonist peptide remains intact after incubation with neprilysin for 24 hours (as performed in Example 5.) In certain aspects, GLP-1/glucagon agonist peptides provided herein stable in the presence of neprilysin such that at least 95% of the GLP-1/glucagon agonist peptide remains intact after incubation with neprilysin for 24 hours (as performed in Example 5.)

In certain aspects, GLP-1/glucagon agonist peptides provided herein are stable. For example, in certain aspects, GLP-1/glucagon agonist peptides provided herein stable in the presence of FasSSIF (fasted state simulated intestinal fluid)/Pancreatin such that at least 10% of the GLP-1/glucagon agonist peptide remains intact after incubation with FasSSIF/Pancreatin for 30 minutes (as performed in Example 6.) In certain aspects, GLP-1/glucagon agonist peptides provided herein are stable. For example, in certain aspects, GLP-1/glucagon agonist peptides provided herein stable in the presence of FasSSIF/Pancreatin such that at least 20% of the GLP-1/glucagon agonist peptide remains intact after incubation with FasSSIF/Pancreatin for 30 minutes (as performed in Example 6.) In certain aspects, GLP-1/glucagon agonist peptides provided herein are stable. For example, in certain aspects, GLP-1/glucagon agonist peptides provided herein stable in the presence of FasSSIF/Pancreatin such that at least 25% of the GLP-1/glucagon agonist peptide remains intact after incubation with FasSSIF/Pancreatin for 30 minutes (as performed in Example 6.) In certain aspects, GLP-1/glucagon agonist peptides provided herein are stable. For example, in certain aspects, GLP-1/glucagon agonist peptides provided herein stable in the presence of FasSSIF/Pancreatin such that at least 50% of the GLP-1/glucagon agonist peptide remains intact after incubation with FasSSIF/Pancreatin for 30 minutes (as performed in Example 6.) In certain aspects, GLP-1/glucagon agonist peptides provided herein are stable. For example, in certain aspects, GLP-1/glucagon agonist peptides provided herein stable in the presence of FasSSIF/Pancreatin such that at least 75% of the GLP-1/glucagon agonist peptide remains intact after incubation with FasSSIF/Pancreatin for 30 minutes (as performed in Example 6.) In certain aspects, GLP-1/glucagon agonist peptides provided herein are stable. For example, in certain aspects, GLP-1/glucagon agonist peptides provided herein stable in the presence of FasSSIF/Pancreatin such that at least 80% of the GLP-1/glucagon agonist peptide remains intact after incubation with FasSSIF/Pancreatin for 30 minutes (as performed in Example 6.) In certain aspects, GLP-1/glucagon agonist peptides provided herein are stable. For example, in certain aspects, GLP-1/glucagon agonist peptides provided herein stable in the presence of FasSSIF/Pancreatin such that at least 90% of the GLP-1/glucagon agonist peptide remains intact after incubation with FasSSIF/Pancreatin for 30 minutes (as performed in Example 6.)

A GLP-1/glucagon agonist peptide as disclosed herein can comprise a heterologous moiety, e.g., to extend half-life. The heterologous moiety can be a protein, a peptide, a protein domain, a linker, an organic polymer, an inorganic polymer, a polyethylene glycol (PEG), biotin, an albumin, a human serum albumin (HSA), a HSA FcRn binding portion, an antibody, a domain of an antibody, an antibody fragment, a single chain antibody, a domain antibody, an albumin binding domain, an enzyme, a ligand, a receptor, a binding peptide, a non-FnIII scaffold, an epitope tag, a recombinant polypeptide polymer, a cytokine, and a combination of two or more of such moieties.

In some aspects, a GLP-1/glucagon agonist peptide as disclosed herein binds to a GLP-1 receptor (GLP-1R), binds to a glucagon receptor (GCGR), or binds to both a GLP-1R and a GCGR. In some aspects, the GLP-1R is human GLP-1R. In some aspects, the GCGR is human GCGR. In some aspects, the peptide is an agonist of GLP-1 activity, an agonist of glucagon activity, or an agonist of both GLP-1 and glucagon activity.

In some aspects, a GLP-1/glucagon agonist peptide as disclosed herein has increased proteolytic-resistance relative to the natural ligand of the GLP-1R and/or GCGR. In some aspects, a GLP-1/glucagon agonist peptide as disclosed herein has increased proteolytic-resistance relative to cotadutide (SEQ ID NO: 358). In some aspects, a GLP-1/glucagon agonist peptide as disclosed herein has increased proteolytic-resistance relative to semaglutide (SEQ ID NO. 359). In some aspects, a GLP-1/glucagon agonist peptide as disclosed herein has increased proteolytic-resistance relative to cotadutide (SEQ ID NO: 358) and semaglutide (SEQ ID NO: 359).

In some aspects, a GLP-1/glucagon agonist peptide provided herein comprises the sequence: X1-X2-X3-G-X5-X6-T-S-D-X10-S-X12-X13-L-X15-X16-X17-X18-X19-X20-X21-X22-X23-X24-X25-X26-X27-X28-X29-X30-X31-Z, wherein X1 is H or NHis, X2 is S, 1-aminocyclobutane-1-carboxylic acid (Acbu), 1-aminocyclopropane-1-carboxylic acid (Acpr), Aminoisobutyric acid (Aib), D-serine (dSer), or αMethyl-Serine (αMeSer), X3 is Q, H, I, D-glutamine (dGln), methyl-L-glutamine (N-MeGln), α-Methyl-glutamine (αMeGln), or β-dimethylglutamine (β-dimethylGln), X5 is T or S, X6 is F or αMethyl-Phenylalanine (αMePhe), X10 is Y, K, or V, wherein the K can comprise an acyl moiety and/or can be lipidated, X12 is K, acetylated lysine (Ac-Lys), E, or R, X13 is Y, Aib, αMethyl-Phenylalanine (αMePhe), Diphenylalanine (Dip), I, or K, wherein the K can comprise an acyl moiety and/or can be lipidated, X15 is D or E, X16 is S, Aib, E, T, R, A, K, L, or V, X17 is R, E, K, Q, or β-dimethylarganine (β-dimethylArg), wherein the K can comprise an acyl moiety and/or can be lipidated, X18 is R, A, Aib, Q, S, or β-dimethylArg, X19 is A or V, X20 is Q, Aib, E, K, L, or R, wherein the K can comprise an acyl moiety and/or can be lipidated, X21 is D, E, or L, X22 is F, I, or αMePhe, X23 is V or I, X24 is Q, A, E, K, L, or R, wherein the K can comprise an acyl moiety and/or can be lipidated, X25 is W, Aib, Dip, H, I, S, biphenyl-alanine (Bip), 1-methyl tryptophan (1-Methyl-Trp), 5-Bromo tryptophan (5-BrTrp), or αMePhe, X26 is L, beta-cyclohexyl-L-alanine (Cha), I, or V, X27 is M, A, E, I, L, norleucine (Nle), S, K, or V, X28 is N, (PEG)4, A, Aib, E, G, R, S, or not present, X29 is T, Aib, E, G, A, R, or not present, X30 is not present, E, A, Aib, K, T, or G, X31 is not present, I, or G, and Z is amide or acid (SEQ ID NO: 4), wherein the peptide does not comprise SEQ ID NO: 1 and does not comprise HSQGTFTSDX10SEYLDSERARDFVAWLEAGG-acid, wherein X10=Lys[ε-γE-Palmitoyl](SEQ ID NO: 538). In some aspects, X2 is Aib and/or X10 is V. In some aspects, X3 is Q, X15 is D, X18 is R, X20 is R, X21 is D, X23 is V, and/or X30 is G. In some aspects, X13 is αMePhe, X16 is T, X17 is K, X27 is L, X28 is E, and/or X29 is Aib.

In some aspects, the residue at position 10, 13, 17, 20, or 24 is acylated. In some aspects, the residue at position 10, 13, 17, 20, or 24 is lipidated. In some aspects, the lipid is selected from the group consisting of a palmitoyl group, stearoyl group, lauryl group, myristoyl group, margaroyl group, arachidoyl group, octadecanedioic acid (C18diacid), and icosanedioic acid (C20diacid).

In some aspects, the lipid attached to the residue at position 10, 13, 17, 20, or 24 is attached via a linker. In some aspects, the linker is selected from the group consisting of (O2Oc), (O2Oc)-(O2Oc), (O2Oc)-γE-(O2Oc), (PEG)2-(PEG)2-γE-γE, (PEG)2-γE-(PEG)2-γE, γE, γE-(O2Oc), γE-

(O2Oc)-(O2Oc), γE-(O2Oc)-γE-(O2Oc), γE-(PEG)2-(PEG)2, γE-(PEG)2-γE-(PEG)2, γE-(PEG)4, γE-γE, γE-γE-(O2Oc), γE-γE-(O2Oc)-(O2Oc), γE-γE-(PEG)12, γE-γE-(PEG)2-(PEG)2, γE-γE-(PEG)2-γE-γE, γE-γE-(PEG)4, (PEG)2-(PEG)2-γE, γE-γE-(O2Oc)-(O2Oc)-γE-γE, and γE-γE-(PEG)8.

In some aspects, the linker is linked to the epsilon amino group of the residue at position 10, 13, 17, 20, and/or 24.

In some aspects, the peptide comprises any one of SEQ ID NOs: 6-411 and 418-537. In some aspects, the peptide comprises SEQ ID NO: 99. In some aspects, the peptide comprises SEQ ID NO: 106. In some aspects, the peptide comprises SEQ ID NO: 228. In some aspects, the peptide comprises SEQ ID NO: 233.

In some aspects, the peptide comprises the sequence: H-X2-X3-G-X5-X6-T-S-D-X10-S-X12-X13-L-X15-X16-X17-X18-A-X20-D-X22-X23-X24-X25-X26-X27-X28-X29-X30-X31-Z, wherein X2 is S, Aminoisobutyric acid (Aib), or αMethyl-Serine (αMeSer), X3 is Q or H, X5 is T or S, X6 is F or αMethyl-Phenylalanine (αMePhe), X10 is Y or V, X12 is K or acetylated lysine (Ac-Lys), X13 is Y, αMePhe, Aib, Diphenylalanine (Dip), or I, X15 is D or E, X16 is S, T, A, E, K, L, R, or V, X17 is R or K, wherein the K can comprise an acyl moiety and/or can be lipidated, X18 is R, A, Q, or β-dimethylarganine (β-dimethylArg), X20 is Q, R, Aib, L, or E, X22 is F, I, or αMePhe, X23 is V or I, X24 is Q, E, A, L, or R, X25 is W, Aib, S, Dip, I, H, biphenyl-alanine (Bip), 1-methyl tryptophan (1-Methyl-Trp), 5-Bromo tryptophan (5-BrTrp), or αMePhe, X26 is L, I, or beta-cyclohexyl-L-alanine (Cha) or V, X27 is M, A, L, E, V, I, K, norleucine (Nle), or S, X28 is N, Aib, E, (PEG)4, A, S, or G, X29 is T, not present, Aib, G, A, R, or E, X30 is not present. G, A, Aib, K, or E, X31 is not present, and Z is amide or acid (SEQ ID NO: 5), wherein the peptide does not comprise SEQ ID NO: 1.

In some aspects, the residue at position 17 is acylated. In some aspects, the residue at position 17 is lipidated. In some aspects, the lipid is selected from the group consisting of a palmitoyl group, stearoyl group, lauryl group, myristoyl group, margaroyl group, arachidoyl group, octadecanedioic acid (C18diacid), and icosanedioic acid (C20diacid).

In some aspects, the lipid attached to the residue at position 17 is attached via a linker. In some aspects, the linker is selected from the group consisting of (O2Oc), (O2Oc)-(O2Oc), (O2Oc)-γE-(O2Oc), (PEG)2-(PEG)2-γE-γE, (PEG)2-γE-(PEG)2-γE, γE, γE-(O2Oc), γE-(O2Oc)-(O2Oc), γE-(O2Oc)-γE-(O2Oc), γE-(PEG)2-(PEG)2, γE-(PEG)2-γE-(PEG)2, γE-(PEG)4, γE-γE, γE-γE-(O2Oc), γE-γE-(O2Oc)-(O2Oc), γE-γE-(PEG)12, γE-γE-(PEG)2-(PEG)2, γE-γE-(PEG)2-γE-γE, γE-γE-(PEG)4, and γE-γE-(PEG)8. In some aspects, the linker is selected from the group consisting of γE-γE-(O2Oc)-(O2Oc)-γE-γE, (O2Oc)-(O2Oc), γE, γE-(O2Oc)-(O2Oc), γE-γE-(O2Oc)-(O2Oc), γE-γE-(PEG)4, γE-γE-(PEG)2-(PEG)2, γE-γE-(PEG)8, γE-γE-(PEG)12, (PEG)2-(PEG)2-γE-γE, (PEG)2-γE-(PEG)2-γE, γE-(PEG)2-γE-(PEG)2, γE-(PEG)2-(PEG)2, (PEG)2-(PEG)2-γE, and γE-(PEG)4.

In some aspects, the linker is linked to the epsilon amino group of the residue at position 17.

In some aspects, the peptide comprises the sequence: H-Aminoisobutyric acid (Aib)-Q-G-T-X6-T-S-D-V-S-K-αMethyl-Phenylalanine (αMePhe)-L-X15-X16-K-X18-A-X20-X21-X22-X23-X24-W-X26-X27-X28-X29-X30-X31-Z, wherein X6 is F or αMethyl-Phenylalanine (αMePhe), X15 is E or D, X16 is T, S, K, E, A, L, or R, X18 is R or A, X20 is R, Q, or L, X21 is D or E, X22 is F or αMePhe, X23 is V or I, X24 is R, A, Q, or L, X25 is W, αMePhe biphenyl-alanine (Bip), 1-methyl tryptophan (1-Methyl-Trp), 5-Bromo tryptophan (5-BrTrp), or Aib, X26 is L, I, or V, X27 is L, A, E, V, I, or K, X28 is E, S, A, Aib, not present, or R, X29 is G, Aib, R, T, E, A, or not present, X30 is G, Aib, E, A, K, or not present, X31 is I or not present, and or G, and Z is amide or acid (SEQ ID NO: 412).

In some aspects, the lysine at position 17 is acylated. In some aspects, the lysine at position 17 is lipidated. In some aspects, the lipid is selected from the group consisting of a palmitoyl group, stearoyl group, lauryl group, myristoyl group, margaroyl group, arachidoyl group, octadecanedioic acid (C18diacid), and icosanedioic acid (C20diacid). In some aspects, the lipid is selected from the group consisting of octadecanedioic acid (C18diacid) and icosanedioic acid (C20diacid). In some aspects, the lipid is a octadecanedioic acid (C18diacid). In some aspects, the lipid is an icosanedioic acid (C20diacid).

In some aspects, the lipid is linked to the lysine at position 17 via a linker. In some aspects, the linker is selected from the group consisting of (O2Oc), (O2Oc)-(O2Oc), (O2Oc)-γE-(O2Oc), (PEG)2-(PEG)2-γE-γE, (PEG)2-γE-(PEG)2-γE, γE, γE-(O2Oc), γE-(O2Oc)-(O2Oc), γE-(O2Oc)-γE-(O2Oc), γE-(PEG)2-(PEG)2, γE-(PEG)2-γE-(PEG)2, γE-(PEG)4, γE-γE, γE-γE-(O2Oc), γE-γE-(O2Oc)-(O2Oc), γE-γE-(PEG)12, γE-γE-(PEG)2-(PEG)2, γE-γE-(PEG)2-γE-γE, γE-γE-(PEG)4, (PEG)2-(PEG)2-γE, γE-γE-(O2Oc)-(O2Oc), and γE-γE-(PEG)8. In some aspects, the peptide of claim X, wherein the linker is selected from the group consisting of (PEG)2-(PEG)2-γE, (O2Oc)-(O2Oc), γE, γE-(O2Oc)-(O2Oc), γE-γE-(O2Oc)-(O2Oc), and γE-γE(O2Oc)-(O2Oc)-γE-γE. In some aspects, the linker is γE-(O2Oc)-(O2Oc).

In some aspects, the linker is linked to the epsilon amino group of the residue at position 17.

In certain aspects, GLP-1/glucagon agonist peptides as disclosed have desirable potencies at the glucagon and GLP-1 receptors, and have desirable relative potencies for promoting weight loss.

In some aspects, the peptide has the sequence of any one of SEQ ID NOs: 6-206 and 418-531. In some aspects, the peptide comprises SEQ ID NO: 99. In some aspects, the peptide comprises SEQ ISA NO: 106.

In some aspects, the peptide has the structure of any one of the structures depicted in FIGS. 4C-4D. In some aspects, the peptide has the structure of FIG. 4C. In some aspects, the peptide has the structure of FIG. 4D.

In some aspects, the peptide is any one of the peptides in Table 1.

TABLE 1

| | | | | Linker | | Sequence |
| Peptide | Sequence | SEQ ID NO | Albumin binding moiety | (described N→C term.) | Acylation site | modification with respect C-term.to glucagon. |
| --- | --- | --- | --- | --- | --- | --- |
| Peptide 1 | HSQGS(αMePhe)TSDVS K(Aib)LDSK(O2Oc-O2Oc-γE- | 6 | C18diacid | γE-(O2Oc)-(O2Oc) | 17 | Amide5S, 6αMePhe, 10V, 13Aib, |

TABLE 1-continued

Peptides Modified at Position 17

| Peptide | Sequence | SEQ ID NO | Albumin binding moiety | Linker (described N→C term.) | Acylation site | C-term. | Sequence modification with respect to glucagon. |
|---|---|---|---|---|---|---|---|
| | C18diacid)17AAQD (αMePhe)VQ(Aib)IAN-amide | | | | | | 17K, 18A, 22αMePhe, 25Aib, 26I, 27A, des29T |
| Peptide 2 | HSQGS(αMePhe)TSDVS K(αMePhe)LDSK(O2Oc-O2Oc-γE-C20diacid)17AAQD (αMePhe)VQWIANT-amide | 7 | C20diacid | γE-(O2Oc)-(O2Oc) | 17 | Amide | 5S 6αMePhe, 10V, 13αMePhe, 17K, 18A, 22QMePhe, 26I, 27A |
| Peptide 3 | HSQGS(αMePhe)TSDVS K(αMePhe)LDSK(γE-C18diacid)17AAQDFVQ WIANT-amide | 8 | C18diacid | γE | 17 | Amide | 5S, 6αMePhe, 10V, 13αMePhe, 17K, 18A, 26I, 27A |
| Peptide 4 | HSQGS(αMePhe)TSDVS K(αMePhe)LDSK(O2OC-O2Oc-γE-C18diacid)17AAQDFVQ WIANT-amide | 9 | C18diacid | γE-(O2Oc)-(O2Oc) | 17 | Amide | 5S, 6αMePhe, 10V, 13αMePhe, 17K, 18A, 26I, 27A |
| Peptide 5 | H(Aib)QGS(αMePhe)TS DVSK(αMePhe)LDSK (O2Oc-O2Oc-γE-γE-C18diacid)17AAQD (αMePhe)VQ(Aib)IAN-amide | 10 | C18diacid | γE-γE-(O2Oc)-(O2Oc) | 17 | Amide | 2Aib, 5S, 6αMePhe, 10V, 13αMePhe, 17K, 18A, 22αMePhe, 25Aib, 26I, 27A, des29T |
| Peptide 6 | H(Aib)HGS(αMePhe)TS DVSK(αMePhe)LDSK (O2Oc-O2Oc-γE-C18diacid)17AAQD (αMePhe)VEWIAN-amide | 11 | C18diacid | γE-(O2Oc)-(O2Oc) | 17 | Amide | 2Aib, 3H, 5S, 6QMePhe, 10V, 13αMePhe, 17K, 18A, 22αMePhe, 24E, 26I, 27A, des29T |
| Peptide 7 | H(Aib)HGS(αMePhe)TS DVSK(αMePhe)LDSK(γE-C18diacid)17AAQD (αMePhe)VEWIANT-amide | 12 | C18diacid | γE | 17 | Amide | 2Aib, 3H, 5S, 6αMePhe, 10V, 13αMePhe, 17K, 18A, 22αMePhe, 24E, 26I, 27A |
| Peptide 8 | H(Aib)HGS(αMePhe)TS DVSK(αMePhe)LDSK (O2Oc-O2Oc-γE-C18diacid)17AAQDFVQ WIANT-amide | 13 | C18diacid | γE-(O2Oc)-(O2Oc) | 17 | Amide | 2Aib, 3H, 5S, 6αMePhe, 10V, 13αMePhe, 17K, 18A 26I, 27A |
| Peptide 9 | H(Aib)HGS(αMePhe)TS DVSK(αMePhe)LDSK (O2Oc-O2Oc-γE-C18diacid)17AARDFVQ WIANT-amide | 14 | C18diacid | γE-(O2Oc)-(O2Oc) | 17 | Amide | 2Aib, 3H, 5S, 6αMePhe, 10V, 13αMePhe, 17K, 18A, 20R, 26I, 27A |

TABLE 1-continued

| | | | | Linker (described | | | Sequence modification |
|---|---|---|---|---|---|---|---|
| Peptide | Sequence | SEQ ID NO | Albumin binding moiety | N→C term.) | Acylation site | C-term. | with respect to glucagon. |

Peptides Modified at Position 17

| Peptide | Sequence | SEQ ID NO | Albumin binding moiety | Linker (described N→C term.) | Acylation site | C-term. | Sequence modification with respect to glucagon. |
|---|---|---|---|---|---|---|---|
| Peptide 10 | H(Aib)HGS(αMePhe)TS DVSK(αMePhe)LDSK (O2Oc-O2Oc-γE- C18diacid)17AARDFVE WIANT-amide | 15 | C18diacid | γE- (O2Oc)- (O2Oc) | 17 | Amide | 2Aib, 3H, 5S, 6αMePhe, 10V, 13αMePhe, 17K, 18A, 20R, 24E, 26I, 27A |
| Peptide 11 | H(Aib)HGS(αMePhe)TS DVSK(αMePhe)LDSK (O2Oc-O2Oc-γE- C18diacid)17AAQDFVQ (Aib)IANT-amide | 16 | C18diacid | γE- (O2Oc)- (O2Oc) | 17 | Amide | 2Aib, 3H, 5S, 6αMePhe, 10V, 13αMePhe, 17K, 18A, 25Aib, 26I, 27A |
| Peptide 12 | H(Aib)HGS(αMePhe)TS DVSK(αMePhe)LDSK (O2Oc-O2Oc-γE- C18diacid)17AARDFVQ (Aib)IANT-amide | 17 | C18diacid | γE- (O2Oc)- (O2Oc) | 17 | Amide | 2Aib, 3H, 5S, 6αMePhe, 10V, 13αMePhe, 17K, 18A, 20R, 25Aib, 26I, 27A |
| Peptide 13 | H(Aib)HGS(αMePhe)TS DVSK(αMePhe)LDSK (O2Oc-O2Oc-γE- C18diacid)17AARD (αMePhe)VQ(Aib)IANT- amide | 18 | C18diacid | γE- (O2Oc)- (O2Oc) | 17 | Amide | 2Aib, 3H, 5S, 6αMePhe, 10V, 13αMePhe, 17K, 18A, 20R, 22αMePhe, 25Aib, 26I, 27A |
| Peptide 14 | H(Aib)HGS(αMePhe)TS DVSK(αMePhe)LDSK (O2Oc2-VE2- C20diacid)17AARD (αMePhe)VQ(Aib)IANT- amide | 19 | C20diacid | γE-γE- (O2Oc)- (O2Oc) | 17 | Amide | 2Aib, 3H, 5S, 6αMePhe, 10V, 13αMePhe, 17K, 18A, 20R, 22αMePhe, 25Aib, 26I, 27A |
| Peptide 15 | H(Aib)HGS(αMePhe)TS DVSK(αMePhe)LDSK (O2Oc-O2Oc-γE- C18diacid)17AARD (αMePhe)VE(Aib)IANT- amide | 20 | C18diacid | γE- (O2Oc)- (O2Oc) | 17 | Amide | 2Aib, 3H, 5S, 6αMePhe, 10V, 13αMePhe, 17K, 18A, 20R, 22αMePhe, 24E, 25Aib, 26I, 27A |
| Peptide 16 | H(Aib)HGS(αMePhe)TS DVSK(αMePhe)LDSK (O2Oc-O2Oc-γE- C18diacid)17AARD (αMePhe)IA(Aib)IANT- amide | 21 | C18diacid | γE- (O2Oc)- (O2Oc) | 17 | Amide | 2Aib, 3H, 5S, 6αMePhe, 10V, 13αMePhe, 17K, 18A, 20R, 22αMePhe, 23I, 24A, 25Aib, 26I, 27A |

TABLE 1-continued

| | | | | Linker (described | | Sequence modification |
| Peptide | Sequence | SEQ ID NO | Albumin binding moiety | N→C term.) | Acylation site | C-term. with respect to glucagon. |
| --- | --- | --- | --- | --- | --- | --- |
| | | | Peptides Modified at Position 17 | | | |
| Peptide 17 | H(Aib)HGS(αMePhe)TS DVSK(αMePhe)LDSK (O2Oc-O2Oc-γE-C18diacid)17AARD (αMePhe)VESIANT-amide | 22 | C18diacid | γE-(O2Oc)-(O2Oc) | 17 | Amide2Aib, 3H, 5S, 6αMePhe, 10V, 13αMePhe, 17K, 18A, 20R, 22αMePhe, 24E, 25S, 26I, 27A |
| Peptide 18 | H(Aib)HGS(αMePhe)TS DVSK(αMePhe)LDSK (O2Oc-O2Oc-γE-C18diacid)17AARD (αMePhe)VQSIANT-amide | 23 | C18diacid | γE-(O2Oc)-(O2Oc) | 17 | Amide2Aib, 3H, 5S, 6αMePhe, 10V, 13αMePhe, 17K, 18A, 20R, 22αMePhe, 25S, 26I, 27A |
| Peptide 19 | H(Aib)HGS(αMePhe)TS DVSK(αMePhe)LDSK (O2Oc2-VE2-C18diacid)17AARD (αMePhe)VQ(Aib)IANT-amide | 24 | C18diacid | γE-γE-(O2Oc)-(O2Oc) | 17 | Amide2Aib, 3H, 5S, 6αMePhe, 10V, 13αMePhe, 17K, 18A, 20R, 22αMePhe, 25Aib, 26I, 27A |
| Peptide 20 | H(Aib)HGS(αMePhe)TS DVSK(αMePhe)LDSK (O2Oc2-VE2-C18diacid)17AARD (αMePhe)VE(Aib)IANT-amide | 25 | C18diacid | γE-γE-(O2Oc)-(O2Oc) | 17 | Amide2Aib, 3H, 5S, 6αMePhe, 10V, 13αMePhe, 17K, 18A, 20R, 22αMePhe, 24E, 25Aib, 26I, 27A |
| Peptide 21 | H(Aib)HGS(αMePhe)TS DVSK(αMePhe)LDSK(VE C18diacid)17AAQD (αMePhe)VESIANT-amide | 26 | C18diacid | VE | 17 | Amide2Aib, 3H, 5S, 6αMePhe, 10V, 13αMePhe, 17K, 18A, 22αMePhe, 24E, 25S, 26I, 27A |
| Peptide 22 | H(Aib)HGS(αMePhe)TS DVSK(αMePhe)LDSK (O2Oc-O2Oc-γE-γE-C20diacid)17AAQD (αMePhe)VESIANT-amide | 27 | C20diacid | γE-γE-(O2Oc)-(O2Oc) | 17 | Amide2Aib, 3H, 5S, 6αMePhe, 10V, 13αMePhe, 17K, 18A, 22αMePhe, 24E, 25S, 26I, 27A |
| Peptide 23 | H(Aib)HGS(αMePhe)TS DVSK(αMePhe)LDSK (O2Oc-O2Oc-γE-C18diacid)17AAQD (αMePhe)VESIANT-amide | 28 | C18diacid | γE-(O2Oc)-(O2Oc) | 17 | Amide2Aib, 3H, 5S, 6αMePhe, 10V, 13αMePhe, 17K, 18A, 22αMePhe, 24E, 25S, 26I, 27A |

TABLE 1-continued

| | | | | | | Sequence |
| | | | Albumin | Linker (described | Acylation | C- | modification |
| Peptide | Sequence | SEQ ID NO | binding moiety | N→C term.) | site | term. | with respect to glucagon. |
| --- | --- | --- | --- | --- | --- | --- | --- |
| Peptide 24 | H(Aib)HGS(αMePhe)TS DVSK(αMePhe)LDSK (O2Oc-O2Oc-γE- C18diacid)17AAQD (αMePhe)VQ(Aib)IANT- amide | 29 | C18diacid | γE- (O2Oc)- (O2Oc) | 17 | Amide | 2Aib, 3H, 5S, 6αMePhe, 10V 13αMePhe, 17K, 18A, 22αMePhe, 25Aib, 26I, 27A |
| Peptide 25 | H(Aib)HGS(αMePhe)TS DVSK(αMePhe)LDSK (O2Oc-O2Oc-γE-γE- C20diacid)17AAQD (αMePhe)VQ(Aib)IANT- amide | 30 | C20diacid | γE-γE- (O2Oc)- (O2Oc) | 17 | Amide | 2Aib, 3H, 5S, 6αMePhe, 10V, 13αMePhe, 17K, 18A, 22αMePhe, 25Aib, 26I, 27A |
| Peptide 26 | H(Aib)QGS(αMePhe)TS DVSK(αMePhe)LDSK (O2Oc-O2Oc-γE- C18diacid)17AAQD (αMePhe)VQWIAN-amide | 31 | C18diacid | γE- (O2Oc)- (O2Oc) | 17 | Amide | 2Aib, 5S, 6αMePhe, 10V, 13αMePhe, 17K, 18A, 22αMePhe, 26I, 27A, des29T |
| Peptide 27 | H(Aib)QGS(αMePhe)TS DVSK(αMePhe)LDSK (O2Oc-O2Oc-γE- C18diacid)17AAQD (αMePhe)VEWIAN-amide | 32 | C18diacid | γE- (O2Oc)- (O2Oc) | 17 | Amide | 2Aib, 5S, 6αMePhe, 10V, 13αMePhe, 17K, 18A, 22αMePhe, 24E, 26I, 27A, des29T |
| Peptide 28 | H(AIb)QGTFTSDVSK (αMePhe)LDSK(O2Oc- O2Oc-γE- C18diacid)17RAQDFVR WLL(Aib)T-acid | 33 | C18diacid | γE- (O2Oc)- (O2Oc) | 17 | Acid | 2Aib, 10V, 13αMePhe, 17K, 24R, 27L, 28Aib |
| Peptide 29 | H(Aib)QGTFTSDVSK (αMePhe)LDSK(O2Oc- O2Oc-γE- C18diacid)17RA(Aib)DF VQWLL(Aib)T-acid | 34 | C18diacid | γE- (O2Oc)- (O2Oc) | 17 | Acid | 2Aib, 10V, 13αMePhe, 17K, 20Aib, 27L, 28Aib |
| Peptide 30 | H(Aib)QGTFTSDVSK (αMePhe)LDSK(O2Oc- O2Oc-γE- C18diacid)17RAQDFVR WLL(Aib)TG-acid | 35 | C18diacid | γE- (O2Oc)- (O2Oc) | 17 | Acid | 2Aib, 10V, 13αMePhe, 17K, 24R, 27L, 28Aib, 30G |
| Peptide 31 | H(Aib)QGTFTSDVSK (αMePhe)LDSK(O2Oc- O2Oc-γE- C18diacid)17RAQDFVR WLLE(Aib)G-acid | 36 | C18diacid | γE- (O2Oc)- (O2Oc) | 17 | Acid | 2Aib, 10V, 13αMePhe, 17K, 24R, 27L, 28E, 29Aib, 30G |
| Peptide 32 | H(Aib)QGTFTSDVSK (αMePhe)LDSK(γE- C18diacid)17RA(Aib)DF VQWIANT-amide | 37 | C18diacid | VE | 17 | Amide | 2Aib, 10V, 13αMePhe, 17K, 20Aib, 26I, 27A |
| Peptide 33 | H(Aib)QGTFTSDVSK (αMePhe)LDSK(O2Oc- O2Oc-γE- C18diacid)17RAQDFVQ WLE(Aib)T-acid | 38 | C18diacid | γE- (O2Oc)- (O2Oc) | 17 | Acid | 2Aib, 10V, 13αMePhe, 17K, 27E, 28Aib |

TABLE 1-continued

| | | | | | | |
|---|---|---|---|---|---|---|
| | | | | | | Sequence |
| | | | Linker | | | modification |
| | | | (described | | | with respect |
| | | SEQ ID | Albumin binding | N→C | Acylation | C- | to glucagon. |
| Peptide | Sequence | NO | moiety | term.) | site | term. |

Peptides Modified at Position 17

| Peptide | Sequence | SEQ ID NO | Albumin binding moiety | Linker (described N→C term.) | Acylation site | C-term. | Sequence modification with respect to glucagon. |
|---|---|---|---|---|---|---|---|
| Peptide 34 | H(Aib)QGTFTSDVSK (αMePhe)LDSK(O2Oc-O2Oc-γE-C18diacid)17RAQDFVQ WLL(Aib)E-acid | 39 | C18diacid | γE-(O2Oc)-(O2Oc) | 17 | Acid | 2Aib, 10V, 13αMePhe, 17K, 27L, 28Aib, 29E |
| Peptide 35 | H(Aib)QGTFTSDVSK (αMePhe)LDTK(O2Oc-O2Oc-γE-C18diacid)17RAQDFVQ WLL(Aib)T-acid | 40 | C18diacid | γE-(O2Oc)-(O2Oc) | 17 | Acid | 2Aib, 10V, 13αMePhe, 16T, 17K, 27L, 28Aib |
| Peptide 36 | H(Aib)QGTFTSDVSK (αMePhe)LDSK(O2Oc-O2Oc-γE-C18diacid)17RARDFVQ WLL(Aib)T-acid | 41 | C18diacid | γE-(O2Oc)-(O2Oc) | 17 | Acid | 2Aib, 10V, 13αMePhe, 17K, 20R, 27L, 28Aib |
| Peptide 37 | H(Aib)QGTFTSDVSK (αMePhe)LDSK(O2Oc-O2Oc-γE-C18diacid)17RAEDFVQ WLL(Aib)T-acid | 42 | C18diacid | γE-(O2Oc)-(O2Oc) | 17 | Acid | 2Aib, 10V, 13αMePhe, 17K, 20E, 27L, 28Aib |
| Peptide 38 | H(Aib)QGTFTSDVSK (αMePhe)LDSK(O2Oc-O2Oc-yE-C18diacid)17RAQDFVE WLL(Aib)T-acid | 43 | C18diacid | γE-(O2Oc)-(O2Oc) | 17 | Acid | 2Aib, 10V, 13αMePhe, 17K, 24E, 27L, 28Aib |
| Peptide 39 | H(Aib)QGTFTSDVSK (αMePhe)LDSK(O2Oc-O2Oc-γE-C18diacid)17RAQDFVR WLL(Aib)TE-acid | 44 | C18diacid | γE-(O2Oc)-(O2Oc) | 17 | Acid | 2Aib, 10V, 13αMePhe, 17K, 24R, 27L, 28Amb, 30E |
| Peptide 40 | H(Aib)QGTFTSDVSK (αMePhe)LDSK(O2Oc-O2Oc-γE-C18diacid)17RAQDFVQ WLL(Aib)T-acid | 45 | C18diacid | γE-(O2Oc)-(O2Oc) | 17 | Acid | 2Aib, 10V, 13αMePhe, 17K, 27L, 28Aib, |
| Peptide 41 | H(Aib)QGTFTSDYSK (αMePhe)LDSK(O2Oc-O2Oc-γE-C18diacid)17RAQDFVQ WLV(PEG)4-amide | 46 | C18diacid | γE-(O2Oc)-(O2Oc) | 17 | Amide | 2Aib, 13αMePhe, 17K, 27V, 28(PEG)4, des29 |
| Peptide 42 | H(Ab)QGTFTSDVSK (αMePhe)LDSK(O2Oc-O2Oc-γE-C18diacid)17RAQDFVQ (Aib)LVAT-acid | 47 | C18diacid | γE-(O2Oc)-(O2Oc) | 17 | Acid | 2Aib, 10V, 13αMePhe, 17K, 25Aib, 27V, 28A |
| Peptide 43 | H(Aib)QGS(αMePhe)TS DVSK(Dip)LDSK((PEG)4-γE-γE-Palmitoyl)17RAQD (αMePhe)VE(Aib)LEAGG-amide | 114 | Palmitoyl | γE-γE-(PEG)4 | 17 | Amide | 2Aib, 5S, 6αMePhe, 10V, 13Dip, 17K, 22αMePhe, 24E, 25Aib, 27E, 28A, 29G, 30G |
| Peptide 44 | H(Aib)QGS(αMePhe)TS DVSK(Dip)LDSK((PEG)2-(PEG)2-γE-γE-Stearoyl)17AAQD (αMePhe)VE(Aib)LEAGG-amide | 115 | Stearoyl | γE-γE-(PEG)2-(PEG)2 | 17 | Amide | 2Aib, 5S, 6αMePhe, 10V, 13Dip, 17K, 22αMePhe, 24E, 25Aib, 27E, 28A, 29G, 30G |

TABLE 1-continued

| | | | | Linker (described | | Sequence modification |
|---|---|---|---|---|---|---|
| Peptide | Sequence | SEQ ID NO | Albumin binding moiety | N→C term.) | Acylation site | C-term. | with respect to glucagon. |

| Peptide | Sequence | SEQ ID NO | Albumin binding moiety | Linker (described N→C term.) | Acylation site | C-term. | Sequence modification with respect to glucagon. |
|---|---|---|---|---|---|---|---|
| Peptide 45 | H(Aib)QGS(αMePhe)TS DVSK(Dip)LDSK((PEG)2- (PEG)2-γE-γE- Stearoyl)17AAQD (αMePhe)VE(Aib)LANT- amide | 116 | Stearoyl | γE-γE- (PEG)2- (PEG)2 | 17 | Amide | 2Aib, 5S, 6αMePhe, 10V, 13Dip, 17K, 22αMePhe, 24E, 25Aib, 27A |
| Peptide 46 | HSQGS(αMePhe)TSDVS K(Dip)LDSK((PEG)2- (PEG)2-γE-γE- Stearoyl)17AAQD (αMePhe)VE(Aib)LEAGG- amide | 117 | Stearoyl | γE-γE- (PEG)2- (PEG)2 | 17 | Amide | 5S, 6αMePhe, 10V, 13Dip, 17K, 18A, 22αMePhe, 24E, 25Aib, 27E, 28A, 29G, 30G |
| Peptide 47 | HSQGS(αMePhe)TSDVS K(Dip)LDSK((PEG)2- (PEG)2-γE-γE- Stearoyl)17AAQD (αMePhe)VE(Aib)LANT- amide | 118 | Stearoyl | γE-γE- (PEG)2- (PEG)2 | 17 | Amide | 5S, 6QMePhe, 10V, 13Dip, 17K, 18A, 22αMePhe, 24E, 25Aib, 27A |
| Peptide 48 | HSQGS(αMePhe)TSDVS K(Dip)LDSK((PEG)2- (PEG)2-γE-γE- Stearoyl)17AAQD (αMePhe)VE(Aib)LISG- amide | 119 | Stearoyl | γE-yE- (PEG)2- (PEG)2 | 17 | Amide | 5S, 6αMePhe, 10V, 13Dip, 17K, 18A, 22αMePhe, 24E, 25Aib, 27I, 28S, 29G |
| Peptide 49 | HSQGS(αMePhe)TSDVS K(Dip)LDSK((PEG)2- (PEG)2-γE-γE- Stearoyl)17AAQD (αMePhe)VE(Aib)IANT- amide | 120 | Stearoyl | γE-yE- PEG)2- (PEG)2 | 17 | Amide | 5S, 6αMePhe, 10V, 13Dip, 17K, 18A, 22αMePhe, 24E, 25Aib, 26I, 27A |
| Peptide 50 | HSQGS(αMePhe)TSDVS K(Dip)LDSK((PEG)2- (PEG)2-γE-γE- Stearoyl)17AAQD (αMePhe)VE(Aib)IINT- amide | 121 | Stearoyl | γE-γE- (PEG)2- (PEG)2 | 17 | Amide | 5S, 6αMePhe, 10V, 13Dip, 17K, 18A, 22αMePhe, 24E, 25Aib, 26I, 27I |
| Peptide 51 | HSQGS(αMePhe)TSDVS K(Dip)LDSK((PEG)2- (PEG)2-γE-γE- Stearoyl)17AAQD (αMePhe)VE(Aib)LLNT- amide | 122 | Stearoyl | γE-γE- (PEG)2- (PEG)2 | 17 | Amide | 5S, 6αMePhe, 10V, 13Dip, 17K, 18A, 22αMePhe, 24E, 25Aib, 27L |
| Peptide 52 | HSQGS(αMePhe)TSDVS K(DIp)LDSK((PEG)2- (PEG)2-γE-γE- Stearoyl)17AAQD (αMePhe)VE(Aib)ChaANT- amide | 123 | Stearoyl | γE-γE- (PEG)2- (PEG)2 | 17 | Amide | 5S, 6αMePhe, 10V, 13Dip, 17K, 18A, 22αMePhe, 24E, 25Aib, 26Cha, 27A |
| Peptide 53 | HSQGS(αMePhe)TSDVS K(Dip)LDSK((PEG)2- (PEG)2-γE-γE- Stearoyl)17AAQD (αMePhe)VE(Aib)VVEGG- | 124 | Stearoyl | γE-γE- (PEG)2- (PEG)2 | 17 | Amide | 5S, 6αMePhe, 10V, 13Dip, 17K, 18A, 22αMePhe, |

TABLE 1-continued

Peptides Modified at Position 17

| Peptide | Sequence | SEQ ID NO | Albumin binding moiety | Linker (described N→C term.) | Acylation site | C-term. | Sequence modification with respect to glucagon. |
|---|---|---|---|---|---|---|---|
| | amide | | | | | | 24E, 25Aib, 26V, 27V, 28E, 29G, 30G |
| Peptide 54 | HSQGS(αMePhe)TSDVS K(Dip)LDSK((PEG)2- (PEG)2-γE-γE- Stearoyl)17AAQD (αMePhe)VQ(Aib)IAN- amide | 125 | Stearoyl | γE-γE- (PEG)2- (PEG)2 | 17 | Amide | 5S, 6αMePhe, 10V, 13Dip, 17K, 18A, 22αMePhe, 25Aib, 26I, 27A, des29T |
| Peptide 55 | HSQGS(αMePhe)TSDVS K(Dip)LDSK((PEG)2- (PEG)2-γE-γE- Stearoyl)17AAQD(αMePhe) VQ(Dip)LEA-amide | 126 | Stearoyl | γE-γE- (PEG)2- (PEG)2 | 17 | Amide | 5S, 6αMePhe, 10V, 13Dip, 17K, 18A, 22αMePhe, 25Dip, 27E, 28A, des29T |
| Peptide 56 | HSQGS(αMePhe)TSDVS K(Dip)LDSK(PEG)4-γE- γE- Stearoyl)17AAQD(αMePhe) VE(Aib)IINT-amide | 127 | Stearoyl | γE-γE- (PEG)4 | 17 | Amide | 5S, 6αMePhe, 10V, 13Dip, 17K, 18A, 22αMePhe, 24E, 25Aib, 26I, 27I |
| Peptide 57 | HSQGS(αMePhe)TSDVS K(Dip)LDSK((PEG)8-γE- γE- Stearoyl)17AAQD(αMePhe) VE(Aib)IINT-amide | 128 | Stearoyl | γE-γE- (PEG)8 | 17 | Amide | 5S, 6αMePhe, 10V, 13Dip, 17K, 18A, 22αMePhe, 24E, 25Aib, 26I, 27I |
| Peptide 58 | HSQGS(αMePhe)TSDVS K(Dip)LDSK((PEG)12- γE-γE- Stearoyl)17AAQD(αMePhe) VE(Aib)IINT-amide | 129 | Stearoyl | γE-γE- (PEG)12 | 17 | Amide | 5S, 6αMePhe, 10V, 13Dip, 17K, 18A, 22αMePhe, 24E, 25Aib, 26I, 27I |
| Peptide 59 | HSQGS(αMePhe)TSDVS K(Dip)LDSK(γE-γE- (PEG)2-(PEG)2- Stearoyl)17AAQD(αMePhe) VE(Aib)IINT-amide | 130 | Stearoyl | (PEG)2- (PEG)2- γE-γE | 17 | Amide | 5S, 6αMePhe, 10V, 13Dip, 17K, 18A, 22αMePhe, 24E, 25Aib, 26I, 27I |
| Peptide 60 | HSQGS(αMePhe)TSDVS K(Dip)LDSK(γE-(PEG)2- γE-(PEG)2- Stearoyl)17AAQD(αMePhe) VE(Aib)IINT-amide | 131 | Stearoyl | (PEG)2- γE- (PEG)2- γE | 17 | Amide | 5S, 6αMePhe, 10V, 13Dip, 17K, 18A, 22αMePhe, 24E, 25Aib, 26I, 27I |
| Peptide 61 | HSQGS(αMePhe)TSDVS K(Dip)LDSK((PEG)2-γE- (PEG)2-γE- Stearoyl)17AAQD(αMePhe) VE(Aib)IINT-amide | 132 | Stearoyl | γE- (PEG)2- γE- (PEG)2 | 17 | Amide | 5S, 6αMePhe, 10V, 13Dip, 17K, 18A, 22αMePhe, 24E, 25Aib, 26I, 27I |
| Peptide 62 | HSQGS(αMePhe)TSDVS K(Dip)LDSK((PEG)2- (PEG)2-γE-γE- Lauryl)17AAQD(αMePhe) | 133 | Lauryl | γE-γE- (PEG)2- (PEG)2 | 17 | Amide | 5S, 6αMePhe, 10V, 13Dip, 17K, 18A, |

TABLE 1-continued

| | | | | | Sequence |
|---|---|---|---|---|---|
| | | | Linker | | modification |
| | | | (described | | with respect |
| | | SEQ ID | Albumin binding | N→C | Acylation C- | to glucagon. |
| Peptide | Sequence | NO | moiety | term.) | site term. |

Peptides Modified at Position 17

| Peptide | Sequence | SEQ ID NO | Albumin binding moiety | Linker (described N→C term.) | Acylation site | C-term. | Sequence modification with respect to glucagon. |
|---|---|---|---|---|---|---|---|
| | VE(Aib)IINT-amide | | | | | | 22αMePhe, 24E, 25Aib, 26I, 27I |
| Peptide 63 | HSQGS(αMePhe)TSDVS K(Dip)LDSK((PEG)2-(PEG)2-γE-γE-Myristyl)17AAQD(αMePhe) VE(Aib)IINT-amide | 134 | Myristoyl | γE-γE-(PEG)2-(PEG)2 | 17 | Amide | 5S, 6αMePhe, 10V, 13Dip, 17K, 18A, 22αMePhe, 24E, 25Aib, 26I, 27I |
| Peptide 64 | HSQGS(αMePhe)TSDVS K(Dip)LDSK((PEG)2-(PEG)2-γE-γE-Palmitoyl)17AAQD (αMePhe)VE(Aib)IINT-amide | 135 | Palmitoyl | γE-γE-(PEG)2-(PEG)2 | 17 | Amide | 5S, 6αMePhe, 10V, 13Dip, 17K, 18A, 22αMePhe, 24E, 25Aib, 26I, 27I |
| Peptide 65 | HSQGS(αMePhe)TSDVS K(Dip)LDSK((PEG)2-(PEG)2-γE-γE-C18diacid)17AAQD (αMePhe)VE(Aib)IINT-amide | 136 | Stearoyl | γE-γE-(PEG)2-(PEG)2 | 17 | Amide | 5S, 6αMePhe, 10V, 13Dip, 17K, 18A, 22αMePhe, 24E, 25Aib, 26I, 27I |
| Peptide 66 | H(Aib)QGS(αMePhe)TS DVSK(Dip)LDSK(ϵ-((PEG)2-(PEG)2-γE-γE-Stearyl)17AAQD(αMeP he)VQ(Aib)IAN-amide | 137 | Stearoyl | γE-γE-(PEG)2-(PEG)2 | 17 | Amide | 2Aib, 5S, 6αMePhe, 10V, 13Dip, 17K, 18A, 22αMePhe, 25Aib, 26I, 27A, des29T |
| Peptide 67 | H(Aib)QGS(αMePhe)TS DVSK(Dip)LDSK(ϵ-((PEG)2-(PEG)2-γE-Palmitoyl)17AAQD(αMePhe) VQ(Aib)IAN-amide | 138 | Palmitoyl | γE-(PEG)2-(PEG)2 | 17 | Amide | 2Aib, 5S, 6αMePhe, 10V, 13Dip, 17K, 18A, 22αMePhe, 25Aib, 26I, 27A, des29T |
| Peptide 68 | H(Aib)QGTFTSDVSK (αMePhe)LDVK((PEG)4-γE-Palmitoyl)17RAQD (αMePhe)VE(Aib)LNleET-amide | 139 | Palmitoyl | γE-(PEG)4 | 17 | Amide | 2Aib, 10V, 13αMePhe, 16V, 17K, 22αMePhe, 24E, 25Aib, 27Nle, 28E |
| Peptide 69 | H(Aib)QGTFTSDVSK (αMePhe)LDSK((PEG)2-(PEG)2-γE-γE-Stearyl)17RAQD(αMePhe) VQ(Aib)LNleET-amide | 140 | Stearoyl | γE-γE-(PEG)2-(PEG)2 | 17 | Amide | 2Aib, 10V, 13αMePhe, 16V, 17K, 22αMePhe, 24E, 25Aib, 27Nle, 28E |
| Peptide 70 | H(Aib)QGS(αMePhe)TS DVSK(αMePhe)LDSK ((PEG)4-γE-γE-Stearoyl)17RAQD(αMePhe) VE(Aib)LEAGG-amide | 141 | Stearoyl | γE-γE-(PEG)4 | 17 | Amide | 2Aib, 5S, 6αMePhe, 10V, 13αMePhe, 17K, 22αMePhe, 24E, 25Aib, 27E, 28A, 29G, 30G |
| Peptide 71 | H(Aib)QGS(αMePhe)TS DVSK(αMePhe)LDSK ((PEG)4-γE-γE-Stearoyl)17AAQD(αMePhe) VE(Aib)LEAGG- | 142 | Stearoyl | γE-γE-(PEG)4 | 17 | Amide | 2Aib, 5S, 6αMePhe, 10V, 13αMePhe, 17K, 18A, |

TABLE 1-continued

| | | | | | | |
|---|---|---|---|---|---|---|
| | | | | Linker (described | | Sequence modification |
| Peptide | Sequence | SEQ ID NO | Albumin binding moiety | N→C term.) | Acylation site | C-term. with respect to glucagon. |

| | | | | | | |
|---|---|---|---|---|---|---|
| | amide | | | | | 22αMePhe, 24E, 25Aib, 27E, 28A, 29G, 30G |
| Peptide 72 | H(Aib)QGS(αMePhe)TS DVSK(αMePhe)LDSK ((PEG)4-γE-γE-Palmitoyl)17AAQD (αMePhe)VE(Aib)LEAGG-amide | 143 | Palmitoyl | γE-γE-(PEG)4 | 17 | Amide2Aib, 5S, 6αMePhe, 10V, 13αMePhe, 17K, 18A, 22αMePhe, 24E, 25Aib 27E, 28A, 29G, 30G |
| Peptide 73 | H(Aib)QGS(αMePhe)TS DVSK(αMePhe)LDSK ((PEG)2-(PEG)2-γE-γE-Palmitoyl)17AAQD (αMePhe)VQ(Aib)IAN-amide | 144 | Palmitoyl | γE-γE-(PEG)2-(PEG)2 | 17 | Amide2Aib, 5S, 6αMePhe, 10V, 13αMePhe, 17K, 18A, 22αMePhe, 25Aib, 26I, 27A, des29T |
| Peptide 74 | H(Aib)QGS(αMePhe)TS DVSK(αMePhe)LDSK ((PEG)2-(PEG)2-γE-γE-Stearoyl)17(B-dimethylGln)AQD (αMePhe)VE(Aib)LEAGG-amide | 145 | Stearoyl | γE-γE-(PEG)2-(PEG)2 | 17 | Amide2Aib, 5S, 6αMePhe, 10V, 13αMePhe, 17K, 18β-dimethyl-R, 22αMePhe, 24E, 25Aib, 27E, 28Å, 29G, 30G |
| Peptide 75 | H(Aib)QGS(αMePhe)TS DVSK(αMePhe)LDSK ((PEG)2-(PEG)2-γE-γE-Palmitoyl)17AAQDIVQII AN-amide | 146 | Palmitoyl | γE-γE-(PEG)2-(PEG)2 | 17 | Amide2Aib, 5S, 6αMePhe, 10V, 13αMePhe, 17K, 18A, 22I, 25I, 26I, 27A, des29T |
| Peptide 76 | H(Aib)QGS(αMePhe)TS DVSK(αMePhe)LDSK ((PEG)2-(PEG)2-γE-γE-Stearoyl)17AAQD (αMePhe)VQ(Aib)VVEGG-amide | 147 | Stearoyl | γE-γE-(PEG)2-(PEG)2 | 17 | Amide2Aib, 5S, 6αMePhe, 10V, 13αMePhe, 17K, 18A, 22αMePhe, 25Aib, 26V, 27V, 28E, 29G, 30G |
| Peptide 77 | H(Aib)QGS(αMePhe)TS DVSK(αMePhe)LDSK ((PEG)2-(PEG)2-γE-γE-Stearoyl)17AAQD (αMePhe)VQ(Aib)LISG-amide | 148 | Stearoyl | γE-γE-(PEG)2-(PEG)2 | 17 | Amide2Aib, 5S, 6αMePhe, 10V, 13αMePhe, 17K, 18A, 22αMePhe, 25Aib, 27I, 28S, 29G |
| Peptide 78 | HSQGS(αMePhe)TSDVS K(αMePhe)LDSK((PEG)2-(PEG)2-γE-γE-Stearoyl)17AAQD (αMePhe)VQ(Aib)LEAGG-amide | 149 | Stearoyl | γE-γE-(PEG)2-(PEG)2 | 17 | Amide5S, 6αMePhe, 10V, 13αMePhe, 17K, 18A, 22αMePhe, 25Aib, 27E, 28A, 29G, 30G |

TABLE 1-continued

| | | | | Linker (described N→C term.) | | Sequence modification |
|---|---|---|---|---|---|---|
| Peptide | Sequence | SEQ ID NO | Albumin binding moiety | | Acylation site | C-term. | with respect to glucagon. |

Peptides Modified at Position 17

| Peptide | Sequence | SEQ ID NO | Albumin binding moiety | Linker (described N→C term.) | Acylation site | C-term. | Sequence modification with respect to glucagon. |
|---|---|---|---|---|---|---|---|
| Peptide 79 | HSQGS(αMePhe)TSDVS K(αMePhe)LDSK((PEG)2-(PEG)2-γE-γE-Palmitoyl)17AAQD (αMePhe)VQ(Aib)LEAGG-amide | 150 | Palmitoyl | γE-γE-(PEG)2-(PEG)2 | 17 | Amide | 5S, 6αMePhe, 10V, 13αMePhe, 17K, 18A, 22QMePhe, 25Aib, 27E, 28A, 29G, 30G |
| Peptide 80 | HSQGS(αMePhe)TSDVS K(αMePhe)LDSK(PEG)2-(PEG)2-γE-γE-Margaroyl)17AAQD (αMePhe)VQ(Aib)LEAGG-amide | 151 | Palmitoyl | γE-γE-(PEG)2-(PEG)2 | 17 | Amide | 5S, 6αMePhe, 10V, 13αMePhe, 17K, 18A, 22αMePhe, 25Aib, 27E, 28A, 29G, 30G |
| Peptide 81 | HSQGS(αMePhe)TSDVS K(αMePhe)LDSK((PEG)2-(PEG)2-γE-γE-Stearoyl)17AAQD (αMePhe)VE(Aib)LEAGG-amide | 152 | Stearoyl | γE-γE-(PEG)2-(PEG)2 | 17 | Amide | 5S, 6αMePhe, 10V, 13αMePhe, 17K, 18A, 22αMePhe, 25Aib, 27E, 28A, 29G, 30G |
| Peptide 82 | HSQGS(αMePhe)TSDVS K(αMePhe)LDSK((PEG)2-(PEG)2-γE-γE-Stearoyl)17AAQD (αMePhe)VQ(Aib)IANT-amide | 153 | Stearoyl | γE-γE-(PEG)2-(PEG)2 | 17 | Amide | 5S, 6αMePhe, 10V, 13αMePhe, 17K, 18A, 22αMePhe, 25Aib, 26I, 27A |
| Peptide 83 | HSQGS(αMePhe)TSDVS K(αMePhe)LDSK((PEG)2-(PEG)2-γE-γE-Stearoyl)17AAQD(αMePhe)VQ(Aib)IINT-amide | 154 | Stearoyl | γE-γE- F (PEG)2-(PEG)2 | 17 | Amide | 5S, 6αMePhe, 10V, 13αMePhe, 17K, 18A, 22αMePhe, 25Aib, 26I, 27I |
| Peptide 84 | HSQGS(αMePhe)TSDVS K(αMePhe)LDSK((PEG)2-(PEG)2-γE-γE-Stearoyl)17AAQD (αMePhe)VQ(Aib)LLNT-amide | 155 | Stearoyl | γE-γE-(PEG)2-(PEG)2 | 17 | Amide | 5S, 6αMePhe, 10V, 13αMePhe, 17K, 18A, 22αMePhe, 25Aib, 27L |
| Peptide 85 | HSQGS(αMePhe)TSDVS K(αMePhe)LDSK((PEG)2-(PEG)2-γE-γE-Stearoyl)17AAQD (αMePhe)VQ(Aib)VVEGG-amide | 156 | Stearoyl | γE-γE-(PEG)2-(PEG)2 | 17 | Amide | 5S, 6αMePhe, 10V, 13αMePhe, 17K, 18A, 22αMePhe, 25Aib, 26V, 27V, 28E, 29G, 30G |
| Peptide 86 | HSQGS(αMePhe)TSDVS K(αMePhe)LDSK((PEG)2-(PEG)2-γE-γE-Stearoyl)17AAQD(αMePhe)VQ(Aib)IAN-amide | 157 | Stearoyl | γE-γE-(PEG)2-(PEG)2 | 17 | Amide | 5S, 6αMePhe, 10V, 13αMePhe, 17K, 18A, 22αMePhe, |

TABLE 1-continued

| | | | | | | |
|---|---|---|---|---|---|---|
| | | | | Linker (described | | Sequence modification |
| | | | SEQ ID | Albumin binding | N→C | Acylation C- | with respect |
| Peptide | Sequence | NO | moiety | term.) | site term. | to glucagon. |

Peptides Modified at Position 17

| Peptide | Sequence | SEQ ID NO | Albumin binding moiety | Linker (described N→C term.) | Acylation site | C-term. | Sequence modification with respect to glucagon. |
|---|---|---|---|---|---|---|---|
| | | | | | | | 25Aib, 26I, 27A, des29T |
| Peptide 87 | HSQGS(αMePhe)TSDVS K(αMePhe)LDSK((PEG)2- (PEG)2-γE-γE- Palmitoyl)17AAQD (αMePhe)VQ(Aib)IAN- amide | 158 | Palmitoyl | γE-γE- (PEG)2- (PEG)2 | 17 | Amide | 5S, 6αMePhe, 10V, 13αMePhe, 17K, 18A, 22αMePhe, 25Aib, 26I, 27A, des29T |
| Peptide 88 | HSQGS(αMePhe)TSDVS K(αMePhe)LDSK((PEG)2- (PEG)2-γE-γE- Margaroyl)17AAQD (αMePhe)VQ(Aib)IAN- amide | 159 | Margaroyl | yE-yE- (PEG)2- (PEG)2 | 17 | Amide | 5S, 6αMePhe, 10V, 13αMePhe, 17K, 18A, 22αMePhe, 25Aib, 26I, 27A, des29T |
| Peptide 89 | HSQGS(αMePhe)TSDVS K(αMePhe)LDSK((PEG)2- (PEG)2-γE-γE- Palmitoyl)17AAQD (αMePhe)VQIIAN-amide | 160 | Palmitoyl | γE-γE- (PEG)2- (PEG)2 | 17 | Amide | 5S, 6αMePhe, 10V, 13αMePhe, 17K, 18A, 22αMePhe, 25Aib, 26I, 27A, des29T |
| Peptide 90 | HSQGS(αMePhe)TSDVS K(αMePhe)LDSK((PEG)2- (PEG)2-γE-γE- Palmitoyl)17AAQD (αMePhe)VE(Aib)IAN- amide | 161 | Palmitoyl | γE-yE- (PEG)2- (PEG)2 | 17 | Amide | 5S, 6αMePhe, 10V, 13αMePhe, 17K, 18A, 22αMePhe, 24E, 25Aib, 26I, 27A, des29T |
| Peptide 91 | HSQGS(αMePhe)TSDVS K(αMePhe)LDSK((PEG)2- (PEG)2-γE-γE- Palmitoyl)17AAQD (αMePhe)VQ(Aib)IAG- amide | 162 | Palmitoyl | γE-γE- (PEG)2- (PEG)2 | 17 | Amide | 5S, 6αMePhe, 10V, 13αMePhe, 17K, 18A, 22αMePhe, 25Aib, 26I, 27A, 28A, des29T |
| Peptide 92 | HSQGS(αMePhe)TSDVS K(AIb)LDSK((PEG)2- (PEG)2-γE-γE- Stearoyl)17AAQD(αMePhe) VQ(Aib)LEA-amide | 163 | Stearoyl | γE-γE- (PEG)2- (PEG)2 | 17 | Amide | 5S, 6αMePhe, 10V, 13Aib, 17K, 18A, 22αMePhe, 25Aib, 27E, 28A, des29T |
| Peptide 93 | HSQGS(αMePhe)TSDVS K(AIb)LDSK((PEG)2- (PEG)2-γE-γE- Stearoyl)17AAQD(αMePhe) VQ(Aib)LAN-amide | 164 | Stearoyl | γE-γE- (PEG)2- (PEG)2 | 17 | Amide | 5S, 6αMePhe, 10V, 13Aib, 17K, 18A, 22αMePhe, 25Aib, 27A, des29T |
| Peptide 94 | HSQGS(αMePhe)TSDVS K(Aib)LDSK((PEG)2- (PEG)2-γE-γE- Stearoyl)17AAQD(αMePhe) VQ(Aib)LSE-amide | 165 | Stearoyl | γE-γE- (PEG)2- (PEG)2 | 17 | Amide | 5S, 6αMePhe, 10V, 13Aib, 17K, 18A, 22αMePhe, 25Aib, 27S, 28E, des29T |

TABLE 1-continued

| | | | | Linker (described | | Sequence modification |
|---|---|---|---|---|---|---|
| Peptide | Sequence | SEQ ID NO | Albumin binding moiety | N→C term.) | Acylation site | C-term. | with respect to glucagon. |
| Peptide 95 | HSQGS(αMePhe)TSDVS K(AIb)LDSK((PEG)2-(PEG)2-γE-γE-Stearoyl)17AAQD Phe)VQ(Aib)LANT-(αMeamide | 166 | Stearoyl | γE-γE-(PEG)2-(PEG)2 | 17 | Amide | 5S, 6αMePhe, 10V, 13Aib, 17K, 18A, 22αMePhe, 25Aib, 27Å |
| Peptide 96 | HSQGS(αMePhe)TSDVS K(Aib)LDSK((PEG)2-(PEG)2-γE-γE-Stearoyl)17AAQD (αMePhe)VQ(Aib)LEAGG-amide | 167 | Stearoyl | γE-γE-(PEG)2-(PEG)2 | 17 | Amide | 5S, 6αMePhe, 10V, 13Aib, 17K, 18A, 22αMePhe, 25Aib, 27E, 28A, 29G, 30G |
| Peptide 97 | HSQGS(αMePhe)TSDVS K(AIb)LDSK((PEG)2-(PEG)2-γE-γE-Stearoyl)17AAQD(αMePhe) VQ(Aib)IAN-amide | 168 | Stearoyl | γE-γE-(PEG)2-(PEG)2 | 17 | Amide | 5S, 6αMePhe, 10V, 13Aib, 17K, 18A, 22αMePhe, 25Aib, 26I, 27A, des29T |
| Peptide 98 | HSQGS(αMePhe)TSDVS K(AIb)LDSK((PEG)2-(PEG)2-γE-γE-Stearoyl)17AAQD(αMePhe) VQ(Aib)IIE-amide | 169 | Stearoyl | γE-γE-(PEG)2-(PEG)2 | 17 | Amide | 5S, 6αMePhe, 10V, 13Aib, 17K, 18A, 22αMePhe, 25Aib, 26I, 27I, 28E, des29T |
| Peptide 99 | HSQGS(αMePhe)TSDVS K(Aib)LDSK((PEG)2-(PEG)2-γE-γE-Palmitoyl)17AAQD (αMePhe)VQ(Aib)IAN-amide | 170 | Palmitoyl | γE-γE-(PEG)2-(PEG)2 | 17 | Amide | 5S, 6αMePhe, 10V, 13Aib, 17K, 18A, 22αMePhe, 25Aib, 26I, 27A, des29T |
| Peptide 100 | H(Aib)QGS(αMePhe)TS DVSK(Aib)LDSK((PEG)2-(PEG)2-γE-γE-Stearyl)17AAQD(αMePhe) VQ(Aib)IAN-amide | 171 | Stearoyl | γE-γE-(PEG)2-(PEG)2 | 17 | Amide | 2Aib, 5S, 6αMePhe, 10V, 13Aib, 17K, 18A, 22αMePhe, 25Aib, 26I, 27A, des29T |
| Peptide 101 | H(Aib)QGS(αMePhe)TS DVSK(AIb)LDSK((PEG)2-(PEG)2-γE-γE-Stearyl)17AAQD(αMePhe) VQ(Aib)IAN-acid | 172 | Stearoyl | γE-γE-(PEG)2-(PEG)2 | 17 | Amide | 2Aib, 5S, 6αMePhe, 10V, 13Aib, 17K, 18A, 22αMePhe, 25Aib, 26I, 27A, des29T |
| Peptide 102 | H(Aib)QGS(αMePhe)TS DVSK(Aib)LDSK((PEG)2-(PEG)2-γE-γE-Stearyl)17RAQD(αMePhe) VQ(Aib)IAN-amide | 173 | Stearoyl | γE-γE-(PEG)2-(PEG)2 | 17 | Amide | 2Aib, 5S, 6αMePhe, 10V, 13Aib, 17K, 18R, 22αMePhe, 25Aib, 26I, 27A, des29T |
| Peptide 103 | H(Aib)QGS(αMePhe)TS DVSK(Aib)LDSK((PEG)2-(PEG)2-γE-γE-Stearyl)17AAQD(αMePhe) VQWIAN-amide | 174 | Stearoyl | γE-γE-(PEG)2-(PEG)2 | 17 | Amide | 2Aib, 5S, 6αMePhe, 10V, 13Aib, 17K, 18A, 22αMePhe, 26I, 27A, des29T |

TABLE 1-continued

| | | | | Linker (described | | Sequence modification |
|---|---|---|---|---|---|---|
| Peptide | Sequence | SEQ ID NO | Albumin binding moiety | N→C term.) | Acylation site | C-term. with respect to glucagon. |
| Peptide 104 | HTQGS(αMePhe)TSDVS K(Aib)LDSK((PEG)2-(PEG)2-γE-γE-Stearyl)17AAQD(αMePhe) VQ(Aib)IAN-amide | 175 | Stearoyl | γE-γE-(PEG)2-(PEG)2 | 17 | Amide2T,5S, 6αMePhe, 10V, 13Aib, 17K, 18A, 22αMePhe, 25Aib, 26I, 27A, des29T |
| Peptide 105 | HSQGS(αMePhe)TSDVS K(AIb)LDSK((PEG)2-(PEG)2-γE-γE-Palmitoyl)17QAQD(αMePhe) VQ(Aib)IAN-amide | 176 | Palmitoyl | γE-γE-(PEG)2-(PEG)2 | 17 | Amide5S, 6αMePhe, 10V, 13Aib, 17K, 18Q, 22αMePhe, 25Aib, 26I, 27A, des29T |
| Peptide 106 | HSQGS(αMePhe)TSDVS K(Aib)LDSK((PEG)2-(PEG)2-γE-γE-Palmitoyl)17AAQD(αMePhe) VQHIAN-amide | 177 | Palmitoyl | γE-γE-(PEG)2-(PEG)2 | 17 | Amide5S, 6αMePhe, 10V, 13Aib, 17K, 18A, 22αMePhe, 25H, 26I, 27A, des29T |
| Peptide 107 | HSQGS(αMePhe)TSDVS K(Aib)LDSK((PEG)2-(PEG)2-γE-γE-Palmitoyl)17QAQD(αMePhe) VQHIAN-amide | 178 | Palmitoyl | γE-γE-(PEG)2-(PEG)2 | 17 | Amide5S, 6αMePhe, 10V, 13Aib, 17K, 18Q, 22αMePhe 25H, 26I, 27A, des29T |
| Peptide 108 | HSQGS(αMePhe)TSDVS K(AIb)LDSK(O2Oc-O2Oc-γE-C18diacid)17AAQD(αMePhe) VQ(Aib)IAN-amide | 179 | C18diacid | γE-(O2Oc)-(O2Oc) | 17 | Amide5S, 6αMePhe, 10V, 13Aib, 17K, 18A, 22αMePhe, 25Aib, 26I, 27A, des29T |
| Peptide 109 | HSQGS(αMePhe)TSDVS (Ac-Lys)(Aib)LDSK(O2Oc-O2Oc-γE-C18diacid)17AAQD(αMePhe) VQ(Aib)IAN-amide | 180 | C18diacid | γE-(O2Oc)-(O2Oc) | 17 | Amide5S, 6αMePhe, 10V, 12Ac-Lys, 13Aib, 17K, 18A, 22αMePhe, 25Aib, 26I, 27A, des29T |
| Peptide 110 | HSQGS(αMePhe)TSDVS (Ac-Lys)(Aib)LDSK((PEG)2-(PEG)2-γE-γE-Stearyl)17AAQD(αMePhe) VQ(Aib)IAN-amide | 181 | Stearoyl | γE-γE-(PEG)2-(PEG)2 | 17 | Amide5S, 6αMePhe, 10V, 12Ac-Lys, 13Aib, 17K, 18A, 22αMePhe, 25Aib, 26I, 27A, des29T |
| Peptide 111 | HSQGS(αMePhe)TSDVS KILDSK((PEG)2-(PEG)2-γE-γE-Palmitoyl)17AAQD(αMePhe) VQ(Aib)IAN-amide | 182 | Palmitoyl | γE-γE-(PEG)2-(PEG)2 | 17 | Amide5S, 6αMePhe, 10V, 13I, 17K, 18A, 22αMePhe, 25Aib, 26I, 27A, des29T |
| Peptide 112 | HSQGS(αMePhe)TSDVS KILDSK((PEG)2-(PEG)2-γE-γE-Palmitoyl)17AAQD(αMePhe) | 183 | Palmitoyl | γE-γE-(PEG)2-(PEG)2 | 17 | Amide5S, 6αMePhe, 10V, 13I, 17K, 18A, |

TABLE 1-continued

| | | | | | | Sequence |
| | | | Albumin | Linker (described | Acylation | C- | modification with respect |
| Peptide | Sequence | SEQ ID NO | binding moiety | N→C term.) | site | term. | to glucagon. |
|---|---|---|---|---|---|---|---|
| | VQIIAN-amide | | | | | | 22αMePhe, 25I, 26I, 27A, des29T |
| Peptide 113 | HSQGS(αMePhe)TSDVS KILDSK((PEG)2-(PEG)2-γE-γE-Palmitoyl)17AAQD(αMePhe) VQIIAG-amide | 184 | Palmitoyl | γE-γE-(PEG)2-(PEG)2 | 17 | Amide | 5S, 6αMePhe, 10V, 13I, 17K, 18A, 22αMePhe, 25I, 26I, 27A, 28G, des29T |
| Peptide 114 | HSQGS(αMePhe)TSDVS KILDSK((PEG)2-(PEG)2-γE-γE-Palmitoyl)17AAQD(αMePhe) VEIIAN-amide | 185 | Palmitoyl | γE-γE-(PEG)2-(PEG)2 | 17 | Amide | 5S, 6αMePhe, 10V, 13I, 17K, 18A, 22αMePhe, 24E, 25I, 26I, 27A, des29T |
| Peptide 115 | HSQGS(αMePhe)TSDVS KILDSK((PEG)2-(PEG)2-γE-γE-Palmitoyl)17AAQD(αMePhe) VQ(αMePhe)IAN-amide | 186 | Palmitoyl | γE-γE-(PEG)2-(PEG)2 | 17 | Amide | 5S, 6αMePhe, 10V, 13I, 17K, 18A, 22αMePhe, 25αMePhe, 26I, 27A, des29T |
| Peptide 116 | HSQGS(αMePhe)TSDVS KILDSK((PEG)2-(PEG)2-γE-γE-Palmitoyl)17AAQD(αMePhe) VEWIINT-amide | 187 | Palmitoyl | γE-γE-(PEG)2-(PEG)2 | 17 | Amide | 5S, 6αMePhe, 10V, 13I, 17K, 18A, 22αMePhe, 24E, 26I, 27I |
| Peptide 117 | HSQGS(αMePhe)TSDVS KILDSK((PEG)2-(PEG)2-γE-γE-Stearoyl)17AAQD(αMePhe) VQ(Aib)IINT-amide | 188 | Stearoyl | γE-γE-(PEG)2-(PEG)2 | 17 | Amide | 5S, 6αMePhe, 10V, 13I, 17K, 18A, 22αMePhe, 25Aib, 26I, 27I |
| Peptide 118 | HSQGS(αMePhe)TSDVS KILDSK((PEG)2-(PEG)2-γE-γE-Palmitoyl)17AAQD(αMePhe) VQ(Aib)IINT-amide | 189 | Palmitoyl | γE-γE-(PEG)2-(PEG)2 | 17 | Amide | 5S, 6αMePhe, 10V, 13I, 17K, 18A, 22αMePhe, 25Aib, 26I, 27I |
| Peptide 119 | HSQGS(αMePhe)TSDVS KILDSK((PEG)2-(PEG)2-γE-γE-Myristoyl)17AAQD(αMePhe) VQ(Aib)IINT-amide | 190 | Myristovi | γE-γE-(PEG)2-(PEG)2 | 17 | Amide | 5S, 6αMePhe, 10V, 13I, 17K, 18A, 22αMePhe, 25Aib, 26I, 27I |
| Peptide 120 | HSQGS(αMePhe)TSDVS KILDSK((PEG)2-(PEG)2-γE-Stearoyl)17AAQD(αMePhe) VQ(Aib)IINT-amide | 191 | Stearoyl | γE-(PEG)2-(PEG)2 | 17 | Amide | 5S, 6OMePhe, 10V, 13I, 17K, 18A, 22αMePhe, 25Aib, 26I, 27I |
| Peptide 121 | HSQGS(αMePhe)TSDVS KILDSK((PEG)2-(PEG)2-γE-Palmitoyl)17AAQD(αMePhe) VQ(Aib)IINT- | 192 | Palmitoyl | γE-(PEG)2-(PEG)2 | 17 | Amide | 5S, 6αMePhe, 10V, 13I, 17K, 18A, 22αMePhe, |

TABLE 1-continued

| | | | | Linker (described | | Sequence modification |
| Peptide | Sequence | SEQ ID NO | Albumin binding moiety | N→C term.) | Acylation site | C- term. | with respect to glucagon. |
|---|---|---|---|---|---|---|---|
| | amide | | | | | | 25Aib, 26I, 27I |
| Peptide 122 | HSQGS(αMePhe)TSDVS KILDSK((PEG)2-(PEG)2-γE-Myristoyl)17AAQD(αMePhe) VQ(Aib)IINT-amide | 193 | Myristoyl | γE-(PEG)2-(PEG)2 | 17 | Amide | 5S, 6αMePhe, 10V, 13I, 17K, 18A, 22αMePhe, 25Aib, 26I, 27I |
| Peptide 123 | H(Aib)QGS(αMePhe)TS DVSKILDSK((PEG)2-(PEG)2-γE-γE-Palmitoyl)17AAQD(αMePhe) VQIIAN-amide | 194 | Palmitoyl | γE-γE-(PEG)2-(PEG)2 | 17 | Amide | 2Aib, 5S, 6αMePhe, 10V, 13I, 17K, 18A, 22αMePhe, 25I, 26I, 27A, des29T |
| Peptide 124 | H(Aib)QGS(αMePhe)TS DVSKILDSK((PEG)2-(PEG)2-γE-γE-Stearoyl)17AAQD(αMePhe) VQ(Aib)IINT-amide | 195 | Stearoyl | γE-γE-(PEG)2-(PEG)2 | 17 | Amide | 2Aib, 5S, 6αMePhe, 10V, 13I, 17K, 18A, 22αMePhe, 25Aib, 26I, 27I |
| Peptide 125 | H(Aib)QGS(αMePhe)TS DVSKILDSK((PEG)2-(PEG)2-γE-γE-Palmitoyl)17AAQD(αMePhe) VQ(Aib)IINT-amide | 196 | Palmitoyl | γE-γE-(PEG)2-(PEG)2 | 17 | Amide | 2Aib, 5S, 6αMePhe, 10V, 13I, 17K, 18A, 22αMePhe, 25Aib, 26I, 27I |
| Peptide 126 | H(Aib)QGS(αMePhe)TS DVSKILDSK((PEG)2-(PEG)2-γE-γE-Myristoyl)17AAQD(αMePhe) VQ(Aib)IINT-amide | 197 | Myristoyl | γE-γE-(PEG)2-(PEG)2 | 17 | Amide | 2Aib, 5S, 6αMePhe, 10V, 13I, 17K, 18A, 22αMePhe, 25Aib, 26I, 27I |
| Peptide 127 | H(Aib)QGS(αMePhe)TS DVSKILDSK((PEG)2-(PEG)2-yE-Stearoyl)17AAQD(αMePhe) VQ(Aib)IINT-amide | 198 | Stearoyl | γE-(PEG)2-(PEG)2 | 17 | Amide | 2Aib, 5S, 6oMePhe, 10V, 13I, 17K, 18A, 22αMePhe, 25Aib, 26I, 27I |
| Peptide 128 | H(Aib)QGS(αMePhe)TS DVSKILDSK((PEG)2-(PEG)2-γE-Palmitoyl)17AAQD(αMePhe) VQ(Aib)IINT-amide | 199 | Palmitoyl | γE-(PEG)2-(PEG)2 | 17 | Amide | 2Aib, 5S, 6αMePhe, 10V, 13I, 17K, 18A, 22αMePhe, 25Aib, 26I, 27I |
| Peptide 129 | H(Aib)QGS(αMePhe)TS DVSKILDSK((PEG)2-(PEG)2-γE-Myristoyl)17AAQD(αMePhe) VQ(Aib)IINT-amide | 200 | Myristoyl | γE-(PEG)2-(PEG)2 | 17 | Amide | 2Aib, 5S, 6αMePhe, 10V, 13I, 17K, 18A, 22αMePhe, 25Aib, 26I, 27I |
| Peptide 130 | H(αMeSer)QGS(αMePhe) TSDVSKILDSK((PEG)2-(PEG)2-γE-γE-Stearoyl)17AAQD(αMePhe) | 201 | Stearoyl | γE-γE-(PEG)2-(PEG)2 | 17 | Amide | 2αMeSer, 5S, 6αMePhe, 10V, 13I, |

TABLE 1-continued

| | | | | Linker (described | | Sequence modification |
| | | SEQ ID | Albumin binding | N→C | Acylation | C- | with respect |
| Peptide | Sequence | NO | moiety | term.) | site | term. | to glucagon. |
|---|---|---|---|---|---|---|---|
| | VQ(Aib)IINT-amide | | | | | | 17K, 18A, 22αMePhe, 25Aib, 26I, 27I |
| Peptide 131 | H(αMeSer)QGS(αMePhe) TSDVSKILDSK((PEG)2- (PEG)2-γE-γE- Palmitoyl)17AAQD(αMePhe) VQ(Aib)IINT- amide | 202 | Palmitoyl | γE-γE- (PEG)2- (PEG)2 | 17 | Amide | 2oMeSer, 5S, 6αMePhe, 10V, 13I, 17K, 18A, 22αMePhe, 25Aib, 26I, 27I |
| Peptide 132 | H(αMeSer)QGS(αMePhe) TSDVSKILDSK((PEG)2- (PEG)2-γE-yE- Myristoyl)17AAQD(αMePhe) VQ(Aib)IINT- amide | 203 | Myristoyl | γE-γE- (PEG)2- (PEG)2 | 17 | Amide | 2αMeSer, 5S, 6αMePhe 10V, 13I, 17K, 18A, 22αMePhe, 25Aib, 26I, 27I |
| Peptide 133 | H(αMeSer)QGS(αMePhe) TSDVSKILDSK((PEG)2- (PEG)2-γE- Stearoyl)17AAQD(αMePhe) VQ(Aib)IINT-amide | 204 | Stearoyl | γE- (PEG)2- (PEG)2 | 17 | Amide | 2αMeSer, 5S, 6αMePhe, 10V, 13I, 17K, 18A, 22αMePhe, 25Aib, 26I, 27I |
| Peptide 134 | H(αMeSer)QGS(αMePhe) TSDVSKILDSK((PEG)2- (PEG)2-γE- Palmitoyl)17AAQD(αMePhe) VQ(Aib)IINT- amide | 205 | Palmitoyl | γE- (PEG)2- (PEG)2 | 17 | Amide | 2αMeSer, 5S, 6αMePhe, 10V, 13I, 17K, 18A, 22αMePhe, 25Aib, 26I, 27I |
| Peptide 135 | H(αMeSer)QGS(αMePhe) TSDVSKILDSK((PEG)2- (PEG)2-γE- Myristoyl)17AAQD(αMePhe) VQ(Aib)IINT- amide | 206 | Myristoyl | γE- (PEG)2- (PEG)2 | 17 | Amide | 2αMeSer, 5S, 6αMePhe, 10V, 13I, 17K, 18A, 22αMePhe, 25Aib, 26I, 27I |
| Peptide 136 | H(Aib)QGTFTSDVSK (αMePhe)LDSK(yE-yE- O2Oc-O2Oc-γE-γE- C18diacid)17RARDFVR WLLE(Aib)G-acid | 48 | C18diacid | γE γE(O2Oc)- (O2Oc)- γE-γE | 17 | Acid | 2Aib, 10V, 13αMePhe, 17K, 20R, 24R, 27L, 28E, 29Aib, 30G |
| Peptide 137 | H(Aib)QGTFTSDVSK (αMePhe)LDSK(yE-yE- O2Oc-O2Oc-γE-γE- C18diacid)17RAQDFVR WLLEG(Aib)-acid | 49 | C18diacid | γE- γE(O2Oc)- (O2Oc)- γE-γE | 17 | Acid | 2Aib, 10V, 13αMePhe, 17K, 24R, 27L, 28E, 29G, 30Aib |
| Peptide 138 | H(Aib)QGTFTSDVSK (αMePhe)LDSK(yE-yE- O2Oc-O2Oc-γE-γE- C18diacid)17RAQDFVR WLLE(Alb)G-acid | 50 | C18diacid | γE- γE(O2Oc)- (O2Oc)- γE-γE | 17 | Acid | 2Aib, 10V, 13αMePhe, 17K, 24R, 27L, 28E, 29Aib, 30G |

TABLE 1-continued

| | | | | Linker (described | | | Sequence modification |
| Peptide | Sequence | SEQ ID NO | Albumin binding moiety | N→C term.) | Acylation site | C- term. | with respect to glucagon. |
| --- | --- | --- | --- | --- | --- | --- | --- |
| Peptide 139 | H(Aib)QGTFTSDVSK (αMePhe)LDSK(γE-γE-O2Oc-O2Oc-γE-γE-C20diacid)17RAQDFVR WLLE(Aib)G-acid | 51 | C20diacid | γE-γE(O2Oc)-(O2Oc)-γE-γE | 17 | Acid | 2Aib, 10V, 13αMePhe, 17K, 24R, 27L, 28E, 29Alb, 30G |
| Peptide 140 | H(Aib)QGTFTSDVSK (αMePhe)LDTK(O2Oc-O2Oc-γE-C18diacid)17RAQDFVR WLLE(Aib)G-acid | 52 | C18diacid | γE-(O2Oc)-(O2Oc) | 17 | Acid | 2Aib, 10V, 13αMePhe, 16T, 17K, 24R, 27L, 28E, 29Aib, 30G |
| Peptide 141 | H(Aib)QGTFTSDVSK (αMePhe)LDSK(O2Oc-O(αM2Oc-γE-C18diacid)17RAQDFVA WLLE(Aib)G-acid | 53 | C18diacid | γE-(O2Oc)-(O2Oc) | 17 | Acid | 2Aib, 10V, 13αMePhe, 17K, 24A, 27L, 28E, 29Aib, 30G |
| Peptide 142 | H(Aib)QGTFTSDVSK (αMePhe)LDSK(O2OC-O2Oc-γE-C18diacid)17RARDFVA WLLE(Aib)G-acid | 54 | C18diacid | γE-(O2Oc)-(O2Oc) | 17 | Acid | 2Aib, 10V, 13αMePhe, 17K, 20R, 24A, 27L, 28E, 29Aib, 30G |
| Peptide 143 | H(Aib)QGTFTSDVSK (αMePhe)LDSK(O2Oc-O2Oc-γE-C18diacid)17RARDFVQ WLLE(Aib)G-acid | 55 | C18diacid | γE-(O2Oc)-(O2Oc) | 17 | Acid | 2Aib, 10V, 13αMePhe, 17K, 20R, 27L, 28E, 29Aib, 30G |
| Peptide 144 | H(Aib)QGTFTSDVSK (αMePhe)LDSK(γE-γE-O2Oc-O2Oc-γE-γE-C18diacid)17RARDFVR WLLE(Aib)G-acid | 56 | C18diacid | γE-γE(O2Oc)-(O2Oc)-γE-γE | 17 | Acid | 2Aib, 10V, 13αMePhe, 17K, 20R, 24R, 27L, 28E, 29Aib, 30G |
| Peptide 145 | H(Aib)QGTFTSDVSK (αMePhe)LDSK(O2Oc-O2Oc-γE-C18diacid)17RAQDFVR WLASRGI-acid | 57 | C18diacid | γE-(O2Oc)-(O2Oc) | 17 | Acid | 2Aib, 10V, 13αMePhe, 17K, 24R, 27A, 28S, 29R, 30G, 31| |
| Peptide 146 | H(Aib)QGTFTSDVSK (αMePhe)LDSK(O2Oc-O2Oc-γE-C18diacid)17RAQDFVR WLASR-acid | 58 | C18diacid | γE-(O2Oc)-(O2Oc) | 17 | Acid | 2Aib, 10V, 13αMePhe, 17K, 24R, 27A, 28S, 29R |
| Peptide 147 | H(Aib)QGTFTSDVSK (αMePhe)LDSK(O2Oc-O2Oc-γE-C18diacid)17RAQDFVR WLEA(Aib)G-acid | 59 | C18diacid | γE-(O2Oc)-(O2Oc) | 17 | Acid | 2Aib, 10V, 13αMePhe, 17K, 24R, 27E, 28A, 29Aib, 30G |
| Peptide 148 | H(Aib)QGTFTSDVSK (αMePhe)LDSK(O2Oc-O2Oc-γE-C18diacid)17RAQDFVR WIAE(Aib)G-acid | 60 | C18diacid | γE-(O2Oc)-(O2Oc) | 17 | Acid | 2Aib, 10V, 13αMePhe, 17K, 24R, 26I, 27A, 28E, 29Aib, 30G |
| Peptide 149 | H(Aib)QGTFTSDVSK (αMePhe)LDSK(O2Oc-O2Oc-γE-C18diacid)17RAQDFVR WVVE(Aib)G-acid | 61 | C18diacid | γE-(O2Oc)-(O2Oc) | 17 | Acid | 2Aib, 10V, 13αMePhe, 17K, 24R, 26V, 27V, 28E, 29Aib, 30G |

TABLE 1-continued

| | | | | Linker (described | | | Sequence modification |
|---|---|---|---|---|---|---|---|
| Peptide | Sequence | SEQ ID NO | Albumin binding moiety | N→C term.) | Acylation site | C-term. | with respect to glucagon. |
| Peptide 150 | H(Aib)QGTFTSDVSK (αMePhe)LDSK(O2Oc-O2Oc-γE-C18diacid)17RAQDFVQ WLL(Aib)TE-acid | 62 | C18diacid | γE-(O2Oc)-(O2Oc) | 17 | Acid | 2Aib, 10V, 13αMePhe, 17K, 27L, 28Aib, 30E |
| Peptide 151 | H(Aib)OGTFTSDVSK (αMePhe)LDSK(O2Oc-O2Oc-γE-C20diacid)17RAQDFVR WLL(Aib)TE-acid | 63 | C20diacid | γE-(O2Oc)-(O2Oc) | 17 | Acid | 2Aib, 10V, 13αMePhe, 17K, 24R, 27L, 28Aib, 30E |
| Peptide 152 | H(Aib)QGTFTSDVSK (αMePhe)LDSK(O2Oc-O2Oc-γE-C18diacid)17RAQDFVR WLL(Ab)E-acid | 64 | C18diacid | γE-(O2Oc)-(O2Oc) | 17 | Acid | 2Aib, 10V, 13αMePhe, 17K, 24R, 27L, 28Aib, 29E |
| Peptide 153 | H(Aib)QGTFTSDVSK (αMePhe)LDSK(O2Oc-O2Oc-γE-C20diacid)17RAQDFVR WLL(Aib)E-acid | 65 | C20diacid | γE-(O2Oc)-(O2Oc) | 17 | Acid | 2Aib, 10V, 13αMePhe, 17K, 24R, 27L, 28Aib, 29E |
| Peptide 154 | H(Aib)QGTFTSDVSK (αMePhe)LDSK(γE-C18diacid)17RAQDFVQ WLL(Aib)T-acid | 65 | C18diacid | γE | 17 | Acid | 2Aib, 10V, 13αMePhe, 17K, 27L, 28Aib |
| Peptide 155 | H(Aib)QGTFTSDVSK (αMePhe)LDSK(γE-C18diacid)17RAQDFVR WLLE(Aib)G-acid | 66 | C18diacid | γE | 17 | Acid | 2Aib, 10V, 13αMePhe, 17K, 24R, 27L, 28E, 29Aib, 30G |
| Peptide 156 | H(Aib)QGTFTSDVSK (αMePhe)LDSK(O2Oc-O2Oc-γE-C18diacid)17RAQDFVR WLLEG(Aib)-acid | 67 | C18diacid | γE-(O2Oc)-(O2Oc) | 17 | Acid | 2Aib, 10V, 13αMePhe, 17K, 24R, 27L, 28E, 29G, 30Aib |
| Peptide 157 | H(Aib)QGTFTSDVSK (αMePhe)LDSK(γE-C18diacid)17RAQDFVR WLLEG(Aib)-acid | 68 | C18diacid | γE | 17 | Acid | 2Aib, 10V, 13αMePhe, 17K, 24R, 27L, 28E, 29G, 30Aib |
| Peptide 158 | H(Aib)QGTFTSDVSK (αMePhe)LDSK(O2OC-O2Oc-γE-C20diacid)17RAQDFVR WLLE(Aib)G-acid | 69 | C20diacid | γE-(O2Oc)-(O2Oc) | 17 | Acid | 2Aib, 10V, 13αMePhe, 17K, 24R, 27L, 28E, 29Aib, 30G |
| Peptide 159 | H(Aib)QGTFTSDVSK (αMePhe)LDTK(O2Oc-O2Oc-γE-C20diacid)17RAQDFVR WLLE(Aib)G-acid | 70 | C20diacid | γE-(O2Oc)-(O2Oc) | 17 | Acid | 2Aib, 10V, 13αMePhe, 16T, 17K, 24R, 27L, 28E, 29Aib, 30G |
| Peptide 160 | H(Aib)QGTFTSDVSK (αMePhe)LESK(O2Oc-O2Oc-γE-C18diacid)17RAQDFVR WLLE(Aib)G-acid | 71 | C18diacid | γE-(O2Oc)-(O2Oc) | 17 | Acid | 2Aib, 10V, 13αMePhe, 15E, 17K, 24R, 27L, 28E, 29Aib, 30G |
| Peptide 161 | H(Aib)QGTFTSDVSK (αMePhe)LEAK(O2Oc-O2Oc-γE-C18diacid)17RARDFVA WLLE(Aib)G-acid | 72 | C18diacid | γE-(O2Oc)-(O2Oc) | 17 | Acid | 2Aib, 10V, 13αMePhe, 15E, 16A, 17K, 20R, 24A, 27L, |

TABLE 1-continued

| | | | | Linker (described N→C term.) | | Sequence modification |
|---------|----------|--------|------------------------|-------------------------------|-----------------|------------------------|
| Peptide | Sequence | SEQ ID NO | Albumin binding moiety | Linker (described N→C term.) | Acylation site | C-term. | Sequence modification with respect to glucagon. |

| Peptide | Sequence | SEQ ID NO | Albumin binding moiety | Linker (described N→C term.) | Acylation site | C-term. | Sequence modification with respect to glucagon. |
|---------|----------|-----------|------------------------|------------------------------|----------------|---------|------------------------------------------------|
| | | | | | | | 28E, 29Aib, 30G |
| Peptide 162 | H(Aib)QGTFTSDVSK (αMePhe)LDSK(O2Oc-O2Oc-γE-C18diacid)17RAQDFVR WIA(Aib)TE-acid | 73 | C18diacid | γE-(O2Oc)-(O2Oc) | 17 | Acid | 2Aib, 10V, 13αMePhe, 17K, 24R, 26I, 27A, 28Aib, 30E |
| Peptide 163 | H(Aib)QGTFTSDVSK (αMePhe)LDSK(O2Oc-O2Oc-γE-C18diacid)17RAQDFVR WLLE(Aib)A-acid | 74 | C18diacid | γE-(O2Oc)-(O2Oc) | 17 | Acid | 2Aib, 10V, 13αMePhe, 17K, 24R, 27L, 28E, 29Aib, 30A |
| Peptide 164 | H(Aib)QGTFTSDVSK (αMePhe)LDSK(O2Oc-O2Oc-γE-C18diacid)17RAQDFVR WLLEA(Aib)-acid | 75 | C18diacid | γE-(O2Oc)-(O2Oc) | 17 | Acid | 2Aib, 10V, 13αMePhe, 17K, 24R, 27L, 28E, 29A, 30Aib |
| Peptide 165 | H(Aib)QGTFTSDVSK (αMePhe)LDSK(O2Oc-O2Oc-γE-C18diacid)17RAQDFVR WLV(Aib)TE-acid | 76 | C18diacid | γE-(O2Oc)-(O2Oc) | 17 | Acid | 2Aib, 10V, 13αMePhe, 17K, 24R, 27V, 28Aib, 30E |
| Peptide 166 | H(Aib)QGTFTSDVSK (αMePhe)LDSK(O2Oc-O2Oc-γE-C18diacid)17RARDFVR WLL(Aib)TE-acid | 77 | C18diacid | γE-(O2Oc)-(O2Oc) | 17 | Acid | 2Aib, 10V, 13αMePhe, 17K, 20R, 24R, 27L, 28Aib, 30E |
| Peptide 167 | H(Aib)QGTFTSDVSK (αMePhe)LDSK(O2Oc-O2Oc-γE-C18diacid)17RARDFVA WLL(Aib)TE-acid | 78 | C18diacid | γE-(O2Oc)-(O2Oc) | 17 | Acid | 2Aib, 10V, 13αMePhe, 17K, 20R, 24A, 27L, 28Aib, 30E |
| Peptide 168 | H(Aib)QGTFTSDVSK (αMePhe)LDSK(O2Oc-O2Oc-γE-C18diacid)17RALDFVR WLL(Aib)TE-acid | 79 | C18diacid | γE-(O2Oc)-(O2Oc) | 17 | Acid | 2Aib, 10V, 13αMePhe, 17K, 20L, 24A, 27L, 28Aib, 30E |
| Peptide 169 | H(Aib)QGTFTSDVSK (αMePhe)LELK(O2Oc-O2Oc-γE-C18diacid)17RAQDFVR WLL(Aib)TE-acid | 80 | C18diacid | γE-(O2Oc)-(O2Oc) | 17 | Acid | 2Aib, 10V, 13αMePhe, 15E, 16L, 17K, 24R, 27L, 28Aib, 30E |
| Peptide 170 | H(Aib)QGTFTSDVSK (αMePhe)LDEK(O2Oc-O2Oc-γE-C18diacid)17RAQDFVR WLL(Aib)TE-acid | 81 | C18diacid | γE-(O2Oc)-(O2Oc) | 17 | Acid | 2Aib, 10V, 13αMePhe, 16E, 17K, 24R, 27L, 28Aib, 30E |
| Peptide 171 | H(Ab)QGTFTSDVSK (αMePhe)LDSK(O2Oc-O2Oc-γE-C18diacid)17RAQDFVR WLE(Aib)TE-acid | 82 | C18diacid | γE-(O2Oc)-(O2Oc) | 17 | Acid | 2Aib, 10V, 13αMePhe, 17K, 24R, 27E, 28Aib, 30E |
| Peptide 172 | H(Aib)QGTFTSDVSK (αMePhe)LESK(O2Oc-O2Oc-γE-C18diacid)17RAQDFVR WLL(Aib)TE-acid | 83 | C18diacid | γE-(O2Oc)-(O2Oc) | 17 | Acid | 2Aib, 10V, 13αMePhe, 15E, 17K, 24R, 27L, 28Aib, 30E |
| Peptide 173 | H(Aib)QGTFTSDVSK (αMePhe)LESK(O2Oc-O2Oc-γE- | 84 | C18diacid | γE-(O2Oc)-(O2Oc) | 17 | Acid | 2Aib, 10V, 13αMePhe, 15E, 17K, |

TABLE 1-continued

| | | | | Linker (described N→C term.) | | Sequence modification |
|---|---|---|---|---|---|---|
| Peptide | Sequence | SEQ ID NO | Albumin binding moiety | | Acylation site | C-term. | with respect to glucagon. |

| Peptide | Sequence | SEQ ID NO | Albumin binding moiety | Linker | Acylation site | C-term. | Sequence modification with respect to glucagon. |
|---|---|---|---|---|---|---|---|
| | C18diacid)17RAQDFVR WLL(Aib)E-acid | | | | | | 24R, 27L, 28Alb, 29E |
| Peptide 174 | H(Aib)QGTFTSDVSK (αMePhe)LDTK(O2Oc-O2Oc-γE-C18diacid)17RAQDFVR WLL(Aib)TE-acid | 85 | C18diacid | γE-(O2Oc)-(O2Oc) | 17 | Acid | 2Aib, 10V, 13αMePhe, 16T, 17K, 24R, 27L, 28Aib, 30E |
| Peptide 175 | H(Ab)QGTFTSDVSK (αMePhe)LDSK(O2Oc-O2Oc-γE-C18diacid)17RAQDFVR WLA(Aib)TE-acid | 86 | C18diacid | γE-(O2Oc)-(O2Oc) | 17 | Acid | 2Aib, 10V, 13αMePhe, 17K, 24R, 27A, 28Aib, 30E |
| Peptide 176 | H(Aib)QGTFTSDVSK (αMePhe)LDSK(O2Oc-O2Oc-yE-C18diacid)17RAQDFVR WLL(Aib)TA-acid | 87 | C18diacid | γE-(O2Oc)-(O2Oc) | 17 | Acid | 2Aib, 10V, 13αMePhe, 17K, 24R, 27A, 28Aib, 30A |
| Peptide 177 | H(Aib)QGTFTSDVSK (αMePhe)LDSK(O2Oc-O2Oc-γE-C18diacid)17RAQDFVR WLL(Aib)TK-acid | 88 | C18diacid | γE-(O2Oc)-(O2Oc) | 17 | Acid | 2Aib, 10V, 13αMePhe, 17K, 24R, 27A, 28Aib, 30K |
| Peptide 178 | H(Aib)QGTFTSDVSK (αMePhe)LDKK(O2Oc-O2Oc-γE-C18diacid)17RAQDFVR WLL(Aib)TE-acid | 89 | C18diacid | γE-(O2Oc)-(O2Oc) | 17 | Acid | 2Aib, 10V, 13αMePhe, 16K, 17K, 24R, 27L, 28Aib, 30E |
| Peptide 179 | H(Aib)QGTFTSDVSK (αMePhe)LDSK(O2OC-O2Oc-γE-C18diacid)17RAQDFVR WLLEAG-acid | 90 | C18diacid | γE-(O2Oc)-(O2Oc) | 17 | Acid | 2Aib, 10V, 13αMePhe, 17K, 24R, 27L, 28E, 29A, 30G |
| Peptide 180 | H(Aib)QGTFTSDVSK (αMePhe)LDSK(O2Oc-O2Oc-yE-C18diacid)17RAQDFVR WLLA(Aib)G-acid | 91 | C18diacid | γE-(O2Oc)-(O2Oc) | 17 | Acid | 2Aib, 10V, 13αMePhe, 17K, 24R, 27L, 28A, 29Aib, 30G |
| Peptide 181 | H(Aib)QGTFTSDVSK (αMePhe)LDSK(O2Oc-O2Oc-C18diacid)17RAQDFVR WLLE(Aib)G-acid | 92 | C18diacid | (O2Oc)-(O2Oc) | 17 | Acid | 2Aib, 10V, 13αMePhe, 17K, 24R, 27L, 28E, 29Aib, 30G |
| Peptide 182 | H(Aib)QGTFTSDVSK (αMePhe)LDKK(O2Oc-O2Oc-γE-C18diacid)17RAQDFVR WLLE(Aib)G-acid | 93 | C18diacid | γE-(O2Oc)-(O2Oc) | 17 | Acid | 2Aib, 10V, 13αMePhe, 16K, 17K, 24R, 27L, 28E, 29Alb, 30G |
| Peptide 183 | H(Aib)QGTFTSDVSK (αMePhe)LDSK(O2Oc-O2Oc-γE-C18diacid)17RAQDFVR WLLE(Aib)K-acid | 94 | C18diacid | γE-(O2Oc)-(O2Oc) | 17 | Acid | 2Aib, 10V, 13αMePhe, 17K, 24R, 27L, 28E, 29Aib, 30K |
| Peptide 184 | H(Aib)QGTFTSDVSK (αMePhe)LDKK(O2Oc-O2Oc-C18diacid)17RAQDFVR WLLA(Aib)K-acid | 95 | C18diacid | (O2Oc)-(O2Oc) | 17 | Acid | 2Aib, 10V, 13αMePhe, 16K, 17K, 24R, 27L, 28A, 29Aib, 30K |
| Peptide 185 | H(Aib)QGTFTSDVSK (αMePhe)LDTK(O2Oc- | 96 | C18diacid | γE-(O2Oc)- | 17 | Amide | 2Aib, 10V, 13αMePhe, |

TABLE 1-continued

| | | | | Linker | | | Sequence |
| | | | | (described | | | modification |
| | | SEQ ID | Albumin binding | N→C | Acylation | C- | with respect |
| Peptide | Sequence | NO | moiety | term.) | site | term. | to glucagon. |
|---|---|---|---|---|---|---|---|
| | O2Oc-γE-<br>C18diacid)17RAQDFVR<br>WLLE(Aib)G-amide | | | (O2Oc) | | | 16T, 17K,<br>24R, 27L,<br>28E, 29Aib,<br>30G |
| Peptide<br>186 | H(Aib)QGTFTSDVSK<br>(αMePhe)LDTK(O2Oc-<br>O2Oc-γE-<br>C18diacid)17RAQDFVR<br>WLLEAG-acid | 97 | C18diacid | γE-<br>(O2Oc)-<br>(O2Oc) | 17 | Acid | 2Aib, 10V,<br>13αMePhe,<br>16T, 17K,<br>24R, 27L,<br>28E, 29A,<br>30G |
| Peptide<br>187 | H(Aib)QGTFTSDVSK<br>(αMePhe)LDTK(O2Oc-<br>O2Oc-γE-<br>C18diacid)17RARDFVR<br>WLVE(Aib)G-acid | 98 | C18diacid | γE-<br>(O2Oc)-<br>(O2Oc) | 17 | Acid | 2Aib, 10V,<br>13αMePhe,<br>16T, 17K,<br>20R, 24R,<br>27V, 28E,<br>29Aib, 30G |
| Peptide<br>188 | H(Aib)QGTFTSDVSK<br>(αMePhe)LDTK(O2Oc-<br>O2Oc-γE-<br>C18diacid)17RARDFVQ<br>WLLE(Aib)G-acid | 99 | C18diacid | γE-<br>(O2Oc)-<br>(O2Oc) | 17 | Acid | 2Aib, 10V,<br>13αMePhe,<br>16T, 17K,<br>20R, 27L,<br>28E, 29Aib,<br>30G |
| Peptide<br>189 | H(Aib)QGTFTSDVSK<br>(αMePhe)LDTK(O2Oc-<br>O2Oc-γE-<br>C18diacid)17RARDFVR<br>WLLE(Aib)G-acid | 100 | C18diacid | γE-<br>(O2Oc)-<br>(O2Oc) | 17 | Acid | 2Aib, 10V,<br>13αMePhe,<br>16T, 17K,<br>20R, 24R,<br>27L, 28E,<br>29Aib, 30G |
| Peptide<br>190 | H(Aib)QGTFTSDVSK<br>(αMePhe)LDTK(O2Oc-<br>O2Oc-γE-<br>C20diacid)17RAQDFVR<br>WLVE(Aib)G-acid | 101 | C20diacid | γE-<br>(O2Oc)-<br>(O2Oc) | 17 | Acid | 2Aib, 10V,<br>13αMePhe,<br>16T, 17K,<br>24R, 27V,<br>28E, 29Aib,<br>30G |
| Peptide<br>191 | H(Aib)QGTFTSDVSK<br>(αMePhe)LDTK(O2Oc-<br>O2Oc-γE-<br>C18diacid)17RAQDFVR<br>WLVE(Aib)G-acid | 102 | C18diacid | γE-<br>(O2Oc)-<br>(O2Oc) | 17 | Acid | 2Aib, 10V,<br>13αMePhe,<br>16T, 17K,<br>24R, 27V,<br>28E, 29Aib,<br>30G |
| Peptide<br>192 | H(Aib)QGTFTSDVSK<br>(αMePhe)LDTK(O2Oc-<br>O2Oc-γE-<br>C18diacid)17RAQDFVR<br>WLL(Aib)E-acid | 103 | C18diacid | γE-<br>(O2Oc)-<br>(O2Oc) | 17 | Acid | 2Aib, 10V,<br>13αMePhe,<br>16T, 17K,<br>24R, 27L,<br>28Aib, 29E |
| Peptide<br>193 | H(Aib)QGTFTSDVSK<br>(αMePhe)LDTK(O2Oc-<br>O2Oc-γE-<br>C20diacid)17RAQDFVR<br>WLL(Aib)E-acid | 104 | C20diacid | γE-<br>(O2Oc)-<br>(O2Oc) | 17 | Acid | 2Aib, 10V,<br>13αMePhe,<br>16T, 17K,<br>24R, 27L,<br>28Aib, 29E |
| Peptide<br>194 | H(Aib)QGTFTSDVSK<br>(αMePhe)LDTK(O2Oc-<br>O2Oc-yE-γE-<br>C20diacid)17RAQDFVR<br>WLL(Aib)E-acid | 105 | C20diacid | γE-<br>(O2Oc)-<br>(O2Oc) | 17 | Acid | 2Aib, 10V,<br>13αMePhe,<br>16T, 17K,<br>24R, 27L,<br>28Aib, 29E |
| Peptide<br>195 | H(Aib)QGTFTSDVSK<br>(αMePhe)LDTK(O2Oc-<br>O2Oc-γE-<br>C20diacid)17RARDFVQ<br>WLLE(Aib)G-acid | 106 | C20diacid | γE-<br>(O2Oc)-<br>(O2Oc) | 17 | Acid | 2Aib, 10V,<br>13αMePhe,<br>16T, 17K,<br>20R, 27L,<br>28E, 29Aib,<br>30G |

TABLE 1-continued

| | | | | Linker (described | | | Sequence modification |
|---|---|---|---|---|---|---|---|
| Peptide | Sequence | SEQ ID NO | Albumin binding moiety | N→C term.) | Acylation site | C-term. | with respect to glucagon. |
| Peptide 196 | H(Aib)QGTFTSDVSK (αMePhe)LDSK(O2Oc-O2Oc-γE-C18diacid)17RAQDFVR WLI(Aib)E-acid | 107 | C18diacid | γE-(O2Oc)-(O2Oc) | 17 | Acid | 2Aib, 10V, 13αMePhe, 17K, 24R, 27I, 28Aib, 29E |
| Peptide 197 | H(Aib)QGTFTSDVSK (αMePhe)LDTK(O2Oc-O2Oc-γE-C18diacid)17RARDFVR WLL(Aib)E-acid | 108 | C18diacid | γE-(O2Oc)-(O2Oc) | 17 | Acid | 2Aib, 10V, 13αMePhe, 16T, 17K, 20R, 24R, 27L, 28Aib, 29E |
| Peptide 198 | H(Aib)QGTFTSDVSK (αMePhe)LDTK(O2Oc-O2Oc-γE-C18diacid)17RARDFIA WLL(Aib)E-acid | 109 | C18diacid | γE-(O2Oc)-(O2Oc) | 17 | Acid | 2Aib, 10V, 13αMePhe, 16T, 17K, 20R, 23I, 24A, 27L, 28Aib, 29E |
| Peptide 199 | H(Aib)QGTFTSDVSK (αMePhe)LDTK(O2Oc-O2Oc-yE-C18diacid)17RARDFIA WLLE(Aib)G-acid | 110 | C18diacid | γE-(O2Oc)-(O2Oc) | 17 | Acid | 2Aib, 10V, 13αMePhe, 16T, 17K, 20R, 23I, 24A, 27L, 28E, 29Aib, 30G |
| Peptide 200 | H(Aib)QGTFTSDVSK (αMePhe)LDTK(O2Oc-O2Oc-γE-C18diacid)17RARDFVA WLLE(Aib)G-acid | 111 | C18diacid | γE-(O2Oc)-(O2Oc) | 17 | Acid | 2Aib, 10V, 13αMePhe, 16T, 17K, 20R, 24A, 27L, 28E, 29Aib, 30G |
| Peptide 201 | H(Aib)QGTFTSDVSK (αMePhe)LDTK(O2Oc-O2Oc-γE-C18diacid)17RARDFVA WLEA(Aib)G-acid | 112 | C18diacid | γE-(O2Oc)-(O2Oc) | 17 | Acid | 2Aib, 10V, 13αMePhe, 16T, 17K, 20R, 24A, 27E, 28A, 29Aib, 30G |
| Peptide 202 | H(Aib)QGTFTSDVSK (αMePhe)LDTK(O2Oc-O2Oc-γE-C18diacid)17RARDFVQ WLEA(Aib)G-acid | 113 | C18diacid | γE-(O2Oc)-(O2Oc) | 17 | Acid | 2Aib, 10V, 13αMePhe, 16T, 17K, 20R, 27E, 28A, 29Aib, 30G |
| Peptide 407 | H(Aib)QGTFTSDVSK (αMePhe)LDTK(O2Oc-O2Oc-yE-C20diacid)17RAQDFVR WLEA(Aib)G-acid | 418 | C20diacid | γE-(O2Oc)-(O2Oc) | 17 | Acid | 2(Aib), 10V, 13(αMePhe), 16T, 17K, 24R, 27E, 28A, 29(Aib), 30G |
| Peptide 408 | H(Aib)QGTFTSDVSK (αMePhe)LDTK(O2Oc-O2Oc-γE-yE-C20diacid)17RAQDFVR WLEA(Aib)G-acid | 419 | C20diacid | γE-γE-(O2Oc)-(O2Oc) | 17 | Acid | 2(Aib), 10V, 13(αMePhe), 16T, 17K, 24R, 27E, 28A, 29(Aib), 30G |
| Peptide 409 | H(Aib)OGTFTSDVSK (αMePhe)LDTK(O2Oc-O2Oc-γE-C18diacid)17RARDFVA WLL(Aib)TE-acid | 420 | C18diacid | γE-(O2Oc)-(O2Oc) | 17 | Acid | 2(Aib), 10V, 13(αMePhe), 16T, 17K, 20R, 24A, 27L, 28(Aib), 30E |
| Peptide 410 | H(Aib)QGTFTSDVSK (αMePhe)LDTK(O2Oc- | 421 | C20diacid | γE-(O2Oc)- | 17 | Acid | 2(Aib), 10V, 13(αMePhe), |

TABLE 1-continued

Peptides Modified at Position 17

| Peptide | Sequence | SEQ ID NO | Albumin binding moiety | Linker (described N→C term.) | Acylation site | C-term. | Sequence modification with respect to glucagon. |
|---------|----------|-----------|------------------------|------------------------------|----------------|---------|--------------------------------------------------|
| | O2Oc-γE-C20diacid)17RARDFVA WLL(Aib)TE-acid | | | (O2Oc) | | | 16T, 17K, 20R, 24A, 27L, 28(Aib), 30E |
| Peptide 411 | H(Aib)QGTFTSDVSK (αMePhe)LDTK(O2Oc-O2Oc-γE-C18diacid)17RAQDFVA WLEAGG-acid | 422 | C18diacid | γE-(O2Oc)-(O2Oc) | 17 | Acid | 2(Aib), 10V, 13(αMePhe), 16T, 17K, 24A, 27E, 28A, 29G, 30G |
| Peptide 412 | H(Aib)QGTFTSDVSK (αMePhe)LDTK(O2Oc-O2Oc-γE-C20diacid)17RAQDFVA WLEAGG-acid | 423 | C20diacid | γE-(O2Oc)-(O2Oc) | 17 | Acid | 2(Aib), 10V, 13(αMePhe), 16T, 17K, 24A, 27E, 28A, 29G, 30G |
| Peptide 413 | H(Aib)QGTFTSDVSK (αMePhe)LDTK(O2Oc-O2Oc-yE-γE-C20diacid)17RAQDFVA WLEAGG-acid | 424 | C20diacid | γE-γE-(O2Oc)-(O2Oc) | 17 | Acid | 2(Aib), 10V, 13(αMePhe), 16T, 17K, 24A, 27E, 28A, 29G, 30G |
| Peptide 414 | H(Ab)QGTFTSDVSK (αMePhe)LDKK(O2Oc-O2Oc-γE-C18diacid)17RARDFVR WLL(Aib)E-acid | 425 | C18diacid | γE-(O2Oc)-(O2Oc) | 17 | Acid | 2(Aib), 10V, 13(αMePhe), 16K, 17K, 20R, 24R, 27L, 28(Aib), 29E |
| Peptide 415 | H(Aib)QGTFTSDVSK (αMePhe)LESK(O2Oc-O2Oc-γE-C18diacid)17RAQDFVR WLEA(Aib)G-acid | 426 | C18diacid | γE-(O2Oc)-(O2Oc) | 17 | Acid | 2(Aib), 10V, 13(αMePhe), 15€, 17K, 24R, 27E, 28A, 29(Aib), 30G |
| Peptide 416 | H(Aib)QGTFTSDVSK (αMePhe)LESK(O2Oc-O2Oc-γE-C20diacid)17RAQDFVR WLEA(Aib)G-acid | 427 | C20diacid | γE-(O2Oc)-(O2Oc) | 17 | Acid | 2(Aib), 10V, 13(αMePhe), 15E, 17K, 24R, 27E, 28A, 29(Aib), 30G |
| Peptide 417 | H(Aib)OGTFTSDVSK (αMePhe)LDTK(O2Oc-O2Oc-γE-γE-C18diacid)17RAQDFVA WLEA(Aib)G-acid | 428 | C18diacid | γE-γE-(O2Oc)-(O2Oc) | 17 | Acid | 2(Aib), 10V, 13(αMePhe), 16T, 17K, 24A, 27E, 28A, 29(Aib), 30G |
| Peptide 418 | H(Aib)QGTFTSDVSK (αMePhe)LDTK(O2Oc-O2Oc-γE-γE-C20diacid)17RAODFVA WLEA(Aib)G-acid | 429 | C20diacid | γE-γE-(O2Oc)-(O2Oc) | 17 | Acid | 2(Aib), 10V, 13(αMePhe), 16T, 17K, 24A, 27E, 28A, 29(Aib), 30G |
| Peptide 419 | H(Ab)QGTFTSDVSK (αMePhe)LDTK(O2Oc-O2Oc-γE-C18diacid)17RAQDFVR WLE(Aib)E-acid | 430 | C18diacid | γE-(O2Oc)-(O2Oc) | 17 | Acid | 2(Aib), 10V, 13(αMePhe), 16T, 17K, 24R, 27E, 28(Aib), 29E |
| Peptide 420 | H(Aib)QGTFTSDVSK (αMePhe)LDKK(O2Oc-O2Oc-γE-C18diacid)17RAQDFVR WLL(Aib)E-amide | 431 | C18diacid | γE-(O2Oc)-(O2Oc) | 17 | Amide | 2(Aib), 10V, 13(αMePhe), 16K, 17K, 24R, 27L, 28(Aib), 29E |

TABLE 1-continued

Peptides Modified at Position 17

| Peptide | Sequence | SEQ ID NO | Albumin binding moiety | Linker (described N→C term.) | Acylation site | C-term. | Sequence modification with respect to glucagon. |
|---|---|---|---|---|---|---|---|
| Peptide 421 | H(Aib)QGTFTSDVSK(αMePhe)LDRK(O2Oc-O2Oc-γE-C18diacid)17RAQDFVRWLL(Aib)TE-acid | 432 | C18diacid | γE-(O2Oc)-(O2Oc) | 17 | Acid | 2(Aib), 10V, 13(αMePhe), 16R, 17K, 24R, 27L, 28(Aib), 30E |
| Peptide 422 | H(Aib)QGTFTSDVSK(αMePhe)LDRK(O2Oc-O2Oc-γE-C18diacid)17RAQDFVRWLL(Aib)TE-amide | 433 | C18diacid | γE-(O2Oc)-(O2Oc) | 17 | Amide | 2(Aib), 10V, 13(αMePhe), 16R, 17K, 24R, 27L, 28(Aib), 30E |
| Peptide 423 | H(Aib)QGTFTSDVSK(αMePhe)LDKK(O2Oc-O2Oc-γE-C18diacid)17RAQDFVRWLK(Aib)TE-acid | 434 | C18diacid | γE-(O2Oc)-(O2Oc) | 17 | Acid | 2(Aib), 10V, 13(αMePhe), 16K, 17K, 24R, 27K, 28(Aib), 30E |
| Peptide 424 | H(Aib)QGTFTSDVSK(αMePhe)LDKK(O2Oc-O2Oc-γE-C18diacid)17RAQDFVRWLL(Aib)TK-acid | 435 | C18diacid | γE-(O2Oc)-(O2Oc) | 17 | Acid | 2(Aib), 10V, 13(αMePhe), 16K, 17K, 24R, 27L, 28(Aib), 30K |
| Peptide 425 | H(Aib)QGTFTSDVSK(αMePhe)LDKK(O2Oc-O2Oc-γE-C18diacid)17RAQDFVRWLKA(Aib)G-acid | 436 | C18diacid | γE-(O2Oc)-(O2Oc) | 17 | Acid | 2(Aib), 10V, 13(αMePhe), 16K, 17K, 24R, 27K, 28A, 29(Aib), 30G |
| Peptide 426 | H(Aib)QGTFTSDVSK(αMePhe)LDKK(O2Oc-O2Oc-γE-C18diacid)17RAQDFVRWLLR(Aib)K-acid | 437 | C18diacid | γE-(O2Oc)-(O2Oc) | 17 | Acid | 2(Aib), 10V, 13(αMePhe), 16K, 17K, 24R, 27L, 28R, 29(Aib), 30K |
| Peptide 427 | H(Aib)QGTFTSDVSK(αMePhe)LDTK(O2Oc-O2Oc-γE-C18diacid)17RARDFVQWLLE(Aib)G-amide | 438 | C18diacid | γE-(O2Oc)-(O2Oc) | 17 | Amide | 2(Aib), 10V, 13(αMePhe), 16T, 17K, 20R, 27L, 28E, 29(Aib), 30G |
| Peptide 428 | H(Aib)QGTFTSDVSK(αMePhe)LDTK(O2Oc-O2Oc-γE-γE-C18diacid)17RARDFVQWLLE(Aib)G-amide | 439 | C18diacid | γE-γE-(O2Oc)-(O2Oc) | 17 | Amide | 2(Aib), 10V, 13(αMePhe), 16T, 17K, 20R, 27L, 28E, 29(Aib), 30G |
| Peptide 429 | H(Alb)QGTFTSDVSK(αMePhe)LDSK(O2Oc-O2Oc-γE-C18diacid)17RAQDFVRWLEA(Alb)G-amide | 440 | C18diacid | γE-(O2Oc)-(O2Oc) | 17 | Amide | 2(Aib), 10V, 13(αMePhe), 17K, 24R, 27E, 28A, 29(Aib), 30G |
| Peptide 430 | H(Aib)QGTFTSDVSK(αMePhe)LDSK(O2Oc-O2Oc-γE-γE-C18diacid)17RAQDFVRWLEA(Aib)G-amide | 441 | C18diacid | γE-γE-(O2Oc)-(O2Oc) | 17 | Amide | 2(Aib), 10V, 13(αMePhe), 17K, 24R, 27E, 28A, 29(Aib), 30G |
| Peptide 431 | H(Aib)QGTFTSDVSK(αMePhe)LDTK(O2Oc-O2Oc-γE-γE-C18diacid)17RAQDFVAWLEA(Aib)G-amide | 442 | C18diacid | γE-γE-(O2Oc)-(O2Oc) | 17 | Amide | 2(Aib), 10V, 13(αMePhe), 16T, 17K, 24A, 27E, 28A, 29(Aib), 30G |
| Peptide 432 | H(Aib)QGTFTSDVSK(αMePhe)LDSK(O2Oc- | 443 | C18diacid | γE-(O2Oc)- | 17 | Acid | 2(Aib), 10V, 13(αMePhe), |

TABLE 1-continued

Peptides Modified at Position 17

| Peptide | Sequence | SEQ ID NO | Albumin binding moiety | Linker (described N→C term.) | Acylation site | C-term. | Sequence modification with respect to glucagon. |
|---|---|---|---|---|---|---|---|
| | O2Oc-γE-C18diacid)17RAQDFVR (Bip)LL(Aib)E-acid | | | (O2Oc) | | | 17K, 24R, 25(Bip), 27L, 28(Aib), 29E |
| Peptide 433 | H(Aib)QGTFTSDVSK (αMePhe)LDSK(O2Oc-O2Oc-γE-C18diacid)17RAQDFVR (1-Methyl-Trp)LL(Aib)E-acid | 444 | C18diacid | γE-(O2Oc)-(O2Oc) | 17 | Acid | 2(Aib), 10V, 13(αMePhe), 17K, 24R, 25(1-Methyl-Trp), 27L, 28(Aib), 29E |
| Peptide 434 | H(Aib)OGTFTSDVSK (αMePhe)LDSK(O2Oc-O2Oc-γE-C18diacid)17RAQDFVR (5-BrTrp)LL(Aib)E-acid | 445 | C18diacid | γE-(O2Oc)-(O2Oc) | 17 | Acid | 2(Aib), 10V, 13(αMePhe), 17K, 24R, 25(5-BrTrp), 27L, 28(Aib), 29E |
| Peptide 435 | H(Aib)OGTFTSDVSK (αMePhe)LDTK(O2Oc-O2Oc-γE-C18diacid)17RARDFVQ (Aib)LLE(Aib)G-acid | 446 | C18diacid | γE-(O2Oc)-(O2Oc) | 17 | Acid | 2(Aib), 10V, 13(αMePhe), 16T, 17K, 20R, 25(Aib), 27L, 28E, 29(Aib), 30G |
| Peptide 436 | H(Aib)QGTFTSDVSK (αMePhe)LDRK(O2Oc-O2Oc-γE-C18diacid)17RAQDFVR WLV(Aib)E-amide | 447 | C18diacid | γE-(O2Oc)-(O2Oc) | 17 | Amide | 2(Aib), 10V, 13(αMePhe), 16R, 17K, 24R, 27V, 28(Aib), 29E |
| Peptide 437 | H(Aib)QGTFTSDVSK (αMePhe)LDRK(O2Oc-O2Oc-γE-C20diacid)17RAQDFVR WLV(Aib)E-amide | 448 | C20diacid | γE-(O2Oc)-(O2Oc) | 17 | Amide | 2(Aib), 10V, 13(αMePhe), 16R, 17K, 24R, 27V, 28(Aib), 29E |
| Peptide 438 | H(Aib)QGTFTSDVSK (αMePhe)LDKK(O2Oc-O2Oc-γE-C18diacid)17RAQDFVR WLEA(Aib)G-amide | 449 | C18diacid | γE-(O2Oc)-(O2Oc) | 17 | Amide | 2(Aib), 10V, 13(αMePhe), 16K, 17K, 24R, 27E, 28A, 29(Aib), 30G |
| Peptide 439 | H(Aib)QGTFTSDVSK (αMePhe)LDRK(O2Oc-O2Oc-γE-C18diacid)17RAQDFVR WLL(Aib)E-amide | 450 | C18diacid | γE-(O2Oc)-(O2Oc) | 17 | Amide | 2(Aib), 10V, 13(αMePhe), 16R, 17K, 24R, 27L, 28(Aib), 29E |
| Peptide 440 | H(Aib)QGTFTSDVSK (αMePhe)LDKK(O2Oc-O2Oc-γE-C20diacid)17RARDFVR WLL(Aib)E-acid | 451 | C20diacid | γE-(O2Oc)-(O2Oc) | 17 | Acid | 2(Aib), 10V, 13(αMePhe), 16K, 17K, 20R, 24R, 27L, 28(Aib), 29E |
| Peptide 441 | H(Aib)QGTFTSDVSK (αMePhe)LDKK(O2Oc-O2Oc-γE-C20diacid)17RAQDFVR WLL(Aib)E-amide | 452 | C20diacid | γE-(O2Oc)-(O2Oc) | 17 | Amide | 2(Aib), 10V, 13(αMePhe), 16K, 17K, 24R, 27L, 28(Aib), 29E |
| Peptide 442 | H(Aib)OGTFTSDVSK (αMePhe)LDKK(O2Oc-O2Oc-γE-C18diacid)17RAQDFVR WLLE(Aib)G-amide | 453 | C18diacid | γE-(O2Oc)-(O2Oc) | 17 | Amide | 2(Aib), 10V, 13(αMePhe), 16K, 17K, 24R, 27L, 28E, 29(Aib), 30G |
| Peptide 443 | H(Aib)QGTFTSDVSK (αMePhe)LDKK(O2Oc-O2Oc-γE- | 454 | C18diacid | γE-(O2Oc)-(O2Oc) | 17 | Amide | 2(Aib), 10V, 13(αMePhe), 16K, 17K, |

TABLE 1-continued

| | | | | | | |
|---|---|---|---|---|---|---|
| | | | | Peptides Modified at Position 17 | | |
| Peptide | Sequence | SEQ ID NO | Albumin binding moiety | Linker (described N→C term.) | Acylation site | C- term. | Sequence modification with respect to glucagon. |

| Peptide | Sequence | SEQ ID NO | Albumin binding moiety | Linker (described N→C term.) | Acylation site | C-term. | Sequence modification with respect to glucagon. |
|---|---|---|---|---|---|---|---|
| | C18diacid)17RARDFVR WLL(Aib)E-amide | | | | | | 20R, 24R, 27L, 28(Aib), 29E |
| Peptide 444 | H(Aib)QGTFTSDVSK (αMePhe)LETK(O2Oc- O2Oc-γE- C20diacid)17RARDFVQ WLLE(Aib)G-acid | 455 | C18diacid | γE- (O2Oc)- (O2Oc) | 17 | Acid | 2(Aib), 10V, 13(αMePhe), 15E, 16T, 17K, 20R, 27L, 28E, 29(Aib), 30G |
| Peptide 445 | H(Aib)QGTFTSDVSK (αMePhe)LETK(O2Oc- O2Oc-yE- C18diacid)17RARDFVQ WLLE(Aib)G-acid | 456 | C18diacid | γE- (O2Oc)- (O2Oc) | 17 | Acid | 2(Aib), 10V, 13(αMePhe), 15E, 16T, 17K, 20R, 27L, 28E, 29(Aib), 30G |
| Peptide 446 | H(Aib)QGTFTSDVSK (αMePhe)LDRK(O2Oc- O2Oc-γE-γE- C18diacid)17RAQDFVR WLV(Aib)E-amide | 457 | C18diacid | γE-γE- (O2Oc)- (O2Oc) | 17 | Amide | 2(Aib), 10V, 13(αMePhe), 16R, 17K, 24R, 27V, 28(Aib), 29E |
| Peptide 447 | H(Aib)QGTFTSDVSK (αMePhe)LDRK(O2Oc- O2Oc-vE-yE- C20diacid)17RAQDFVR WLV(Aib)E-amide | 458 | C20diacid | γE-γE- (O2Oc)- (O2Oc) | 17 | Amide | 2(Aib), 10V, 13(αMePhe), 16R, 17K, 24R, 27V, 28(Aib), 29E |
| Peptide 448 | H(Aib)QGTFTSDVSK (αMePhe)LDKK(O2Oc- O2Oc-γE-γE- C18diacid)17RARDFVR WILL(Aib)E-acid | 459 | C18diacid | γE-γE- (O2Oc)- (O2Oc) | 17 | Acid | 2(Aib), 10V, 13(αMePhe), 16K, 17K, 20R, 24R, 27L, 28(Aib), 29E |
| Peptide 449 | H(Aib)QGTFTSDVSK (αMePhe)LDTK(O2Oc- O2Oc-γE-γE- C20diacid)17RARDFVQ WLLE(Aib)G-acid | 460 | C20diacid | γE-γE- (O2Oc)- (O2Oc) | 17 | Acid | 2(Aib), 10V, 13(αMePhe), 16T, 17K, 20R, 27L, 28E, 29(Aib), 30G |
| Peptide 450 | H(Aib)OGTFTSDVSK (αMePhe)LDKK(O2Oc- O2Oc-γE-γE- C18diacid)17RAQDFVR WLLE(Aib)G-acid | 461 | C18diacid | γE-γE- (O2Oc)- (O2Oc) | 17 | Acid | 2(Aib), 10V, 13(αMePhe), 16K, 17K, 24R, 27L, 28E, 29(Aib), 30G |
| Peptide 451 | H(Ab)QGTFTSDVSK (αMePhe)LDKK(O2Oc- O2Oc-γE- C20diacid)17RARDFVL WLL(Aib)E-amide | 462 | C20diacid | γE- (O2Oc)- (O2Oc) | 17 | Amide | 2(Aib), 10V, 13(αMePhe), 16K, 17K, 20R, 24L, 27L, 28(Aib), 29E |
| Peptide 452 | H(Aib)QGTFTSDVSK (αMePhe)LDKK(O2Oc- O2Oc-γE- C20diacid)17RALDFVR WLL(Aib)E-amide | 463 | C20diacid | γE- (O2Oc)- (O2Oc) | 17 | Amide | 2(Aib), 10V, 13(αMePhe), 16K, 17K, 20L, 24R, 27L, 28(Aib), 29E |
| Peptide 453 | H(Aib)QGTFTSDVSK (αMePhe)LDKK(O2Oc- O2Oc-γE- C20diacid)17RAQDFVR WLLE(Aib)G-amide | 464 | C20diacid | γE- (O2Oc)- (O2Oc) | 17 | Amide | 2(Aib), 10V, 13(αMePhe), 16K, 17K, 24R, 27L, 28E, 29(Aib), 30G |

TABLE 1-continued

| | | | | Linker (described N→C | | C- | Sequence modification |
|---|---|---|---|---|---|---|---|
| Peptide | Sequence | SEQ ID NO | Albumin binding moiety | term.) | Acylation site | term. | with respect to glucagon. |
| Peptide 454 | H(Ab)QGTFTSDVSK (αMePhe)LDKK(O2Oc- O2Oc-γE- C20diacid)17RAQDFVR WLEA(Aib)G-amide | 465 | C20diacid | γE- (O2Oc)- (O2Oc) | 17 | Amide | 2(Aib), 10V, 13(αMePhe), 16K, 17K, 24R, 27E, 28A, 29(Aib), 30G |
| Peptide 455 | H(Aib)QGTFTSDVSK (αMePhe)LDKK(O2Oc- O2Oc-γE-yE- C20diacid)17RAQDFVR WLL(Aib)E-amide | 466 | C20diacid | γE-γE- (O2Oc)- (O2Oc) | 17 | Amide | 2(Aib), 10V, 13(αMePhe), 16K, 17K, 24R, 27L, 28(Aib), 29E |
| Peptide 456 | H(Aib)OGTFTSDVSK (αMePhe)LDRK(O2Oc- O2Oc-γE- C20diacid)17RAQDFVR WLL(Aib)E-amide | 467 | C20diacid | γE- (O2Oc)- (O2Oc) | 17 | Amide | 2(Aib), 10V, 13(αMePhe), 16R, 17K, 24R, 27L, 28(Aib), 29E |
| Peptide 457 | H(Aib)QGTFTSDVSK (αMePhe)LDTK(O2Oc- O2Oc-γE- C20diacid)17RARDFVQ WLLE(Aib)G-amide | 468 | C20diacid | γE- (O2Oc)- (O2Oc) | 17 | Amide | 2(Aib), 10V, 13(αMePhe), 16T, 17K, 20R, 27L, 28E, 29(Aib), 30G |
| Peptide 458 | H(Aib)QGTFTSDVSK (αMePhe)LDTK(O2Oc- O2Oc-γE-γE- C20diacid)17RARDFVQ WLLE(Aib)G-amide | 469 | C20diacid | γE-γE- (O2Oc)- (O2Oc) | 17 | Amide | 2(Aib), 10V, 13(αMePhe), 16T, 17K, 20R, 27L, 28E, 29(Aib), 30G |
| Peptide 459 | H(Aib)QGTFTSDVSK (αMePhe)LDKK(O2Oc- O2Oc-yE- C18diacid)17RAQDFVR WLLAE-amide | 470 | C18diacid | γE- (O2Oc)- (O2Oc) | 17 | Amide | 2(Aib), 10V, 13(αMePhe), 16K, 17K, 24R, 27L, 28A, 29E |
| Peptide 460 | H(Aib)OGTFTSDVSK (αMePhe)LDKK(O2Oc- O2Oc-γE- C20diacid)17RAQDFVR WLLAE-amide | 471 | C20diacid | γE- (O2Oc)- (O2Oc) | 17 | Amide | 2(Aib), 10V, 13(αMePhe), 16K, 17K, 24R, 27L, 28A, 29E |
| Peptide 461 | H(Aib)QGTFTSDVSK (αMePhe)LDRK(O2Oc- O2Oc-yE- C18diacid)17RAQDFVR WLLAE-amide | 472 | C18diacid | γE- (O2Oc)- (O2Oc) | 17 | Amide | 2(Aib), 10V, 13(αMePhe), 16R, 17K, 24R, 27L, 28A, 29E |
| Peptide 462 | H(AIb)QGTFTSDVSK (αMePhe)LDTK(O2Oc- O2Oc-yE- C18diacid)17RARDFVQ WLLEAG-acid | 473 | C18diacid | γE- (O2Oc)- (O2Oc) | 17 | Acid | 2(Aib), 10V, 13(αMePhe), 16T, 17K, 20R, 27L, 28E, 29A, 30G |
| Peptide 463 | H(Aib)QGTFTSDVSK (αMePhe)LDSK(O2Oc- O2Oc-γE-γE- C18diacid)17RAQDFVQ WLL(Aib)T-amide | 474 | C18diacid | γE-γE- (O2Oc)- (O2Oc) | 17 | Amide | 2(Aib), 10V, 13(αMePhe), 17K, 27L, 28(Aib) |
| Peptide 464 | H(Aib)QGTFTSDVSK (αMePhe)LDTK(O2Oc- O2Oc-yE- C18diacid)17RAQDFVQ WLLE(Aib)G-acid | 475 | C18diacid | γE- (O2Oc)- (O2Oc) | 17 | Acid | 2(Aib), 10V, 13(αMePhe), 16T, 17K, 27L, 28E, 29(Aib), 30G |
| Peptide 465 | H(Aib)OGTFTSDVSK (αMePhe)LDLK(O2Oc- O2Oc-γE-γE- | 476 | C18diacid | γE-γE- (O2Oc)- (O2Oc) | 17 | Acid | 2(Aib), 10V, 13(αMePhe), 16L, 17K, |

TABLE 1-continued

| | | | | Linker (described | | Sequence modification |
| Peptide | Sequence | SEQ ID NO | Albumin binding moiety | N→C term.) | Acylation site | with respect to glucagon. |
|---|---|---|---|---|---|---|
| | C18diacid)17RAQDFVQ WLL(Aib)T-acid | | | | | 27L, 28(Aib) |
| Peptide 466 | H(Aib)QGTFTSDVSK (αMePhe)LDTK(O2Oc- O2Oc-γE- C18diacid)17RAQDFVQ WLLE(Aib)G-amide | 477 | C18diacid | γE- (O2Oc)- (O2Oc) | 17 | Amide2(Aib), 10V, 13(αMePhe), 16T, 17K, 27L, 28E, 29(Aib), 30G |
| Peptide 467 | H(Aib)QGTFTSDVSK (αMePhe)LDTK(O2Oc- O2Oc-γE- C20diacid)17RAQDFVQ WLLE(Aib)G-amide | 478 | C20diacid | γE- (O2Oc)- (O2Oc) | 17 | Amide2(Aib), 10V, 13(αMePhe), 16T, 17K, 27L, 28E, 29(Aib), 30G |
| Peptide 468 | H(Aib)QGTFTSDVSK (αMePhe)LDTK(O2Oc- O2Oc-γE-γE- C18diacid)17RAQDFVQ WLLE(Aib)G-amide | 479 | C18diacid | γE-γE- (O2Oc)- (O2Oc) | 17 | Amide2(Aib), 10V, 13(αMePhe), 16T, 17K, 27L, 28E, 29(Aib), 30G |
| Peptide 469 | H(Aib)OGTFTSDVSK (αMePhe)LDTK(O2Oc- O2Oc-γE-γE- C20diacid)17RAQDFVQ WLLE(Alb)G-amide | 480 | C20diacid | γE-γE- (O2Oc)- (O2Oc) | 17 | Amide2(Aib), 10V, 13(αMePhe), 16T, 17K, 27L, 28E, 29(Aib), 30G |
| Peptide 470 | H(Aib)QGTFTSDVSK (αMePhe)LDKK(O2Oc- O2Oc-γE- C20diacid)17RARDFVQ WLL(Aib)E-amide | 481 | C20diacid | γE- (O2Oc)- (O2Oc) | 17 | Amide2(Aib), 10V, 13(αMePhe), 16K, 17K, 20R, 27L, 28(Aib), 29E |
| Peptide 471 | H(Aib)QGTFTSDVSK (αMePhe)LDRK(O2Oc- O2Oc-γE- C20diacid)17RARDFVQ WLL(Aib)E-amide | 482 | C20diacid | γE- (O2Oc)- (O2Oc) | 17 | Amide2(Aib), 10V, 13(αMePhe), 16R, 17K, 20R, 27L, 28(Aib), 29E |
| Peptide 472 | H(Aib)QGTFTSDVSK (αMePhe)LDKK(O2Oc- O2Oc-γE- C18diacid)17RARDFVQ WLL(Aib)E-amide | 483 | C18diacid | γE- (O2Oc)- (O2Oc) | 17 | Amide2(Aib), 10V, 13(αMePhe), 16K, 17K, 20R, 27L, 28(Aib), 29E |
| Peptide 473 | H(Aib)QGTFTSDVSK (αMePhe)LDRK(O2Oc- O2Oc-γE- C18diacid)17RARDFVQ WLL(Aib)E-amide | 484 | C18diacid | γE- (O2Oc)- (O2Oc) | 17 | Amide2(Aib), 10V, 13(αMePhe), 16R, 17K, 20R, 27L, 28(Aib), 29E |
| Peptide 474 | H(Aib)QGTFTSDVSK (αMePhe)LDTK(O2Oc- O2Oc-γE- C18diacid)17RARDFVQ WLLA(Aib)G-amide | 485 | C18diacid | γE- (O2Oc)- (O2Oc) | 17 | Amide2(Aib), 10V, 13(αMePhe), 16T, 17K, 20R, 27L, 28A, 29(Aib), 30G |
| Peptide 475 | H(Aib)QGTFTSDVSK (αMePhe)LDTK(O2Oc- O2Oc-γE- C20diacid)17RARDFVQ WLLA(Aib)G-amide | 486 | C20diacid | γE- (O2Oc)- (O2Oc) | 17 | Amide2(Aib), 10V, 13(αMePhe), 16T, 17K, 20R, 27L, 28A, 29(Aib), 30G |
| Peptide 476 | H(Aib)OGTFTSDVSK (αMePhe)LDTK(O2Oc- O2Oc-γE- C18diacid)17RAQDFVR WILLA(Aib)G-amide | 487 | C18diacid | γE- (O2Oc)- (O2Oc) | 17 | Amide2(Aib), 10V, 13(αMePhe), 16T, 17K, 24R, 27L, 28A, 29(Aib), 30G |

TABLE 1-continued

| | | | | Linker (described N→C term.) | | Sequence modification |
|---|---|---|---|---|---|---|
| Peptide | Sequence | SEQ ID NO | Albumin binding moiety | | Acylation site | C-term. | with respect to glucagon. |

| Peptide | Sequence | SEQ ID NO | Albumin binding moiety | Linker (described N→C term.) | Acylation site | C-term. | Sequence modification with respect to glucagon. |
|---|---|---|---|---|---|---|---|
| Peptide 477 | H(Aib)QGTFTSDVSK (αMePhe)LDTK(O2Oc-O2Oc-γE-C20diacid)17RAQDFVR WLLA(Aib)G-amide | 488 | C20diacid | γE-(O2Oc)-(O2Oc) | 17 | Amide | 2(Aib), 10V, 13(αMePhe), 16T, 17K, 24R, 27L, 28A, 29(Aib), 30G |
| Peptide 478 | H(Aib)QGTFTSDVSK (αMePhe)LDTK(O2Oc-O2Oc-γE-C18diacid)17RAQDFVR WLLE(Aib)K-amide | 489 | C18diacid | γE-(O2Oc)-(O2Oc) | 17 | Amide | 2(Aib), 10V, 13(αMePhe), 16T, 17K, 24R, 27L, 28E, 29(Aib), 30K |
| Peptide 479 | H(Aib)QGTFTSDVSK (αMePhe)LDTK(O2Oc-O2Oc-yE-C20diacid)17RAQDFVR WLLE(Aib)K-amide | 490 | C20diacid | γE-(O2Oc)-(O2Oc) | 17 | Amide | 2(Aib), 10V, 13(αMePhe), 16T, 17K, 24R, 27L, 28E, 29(Aib), 30K |
| Peptide 480 | H(Aib)OGTFTSDVSK (αMePhe)LDTK(O2Oc-O2Oc-yE-C18diacid)17RARDFVQ WLLE(Aib)K-amide | 491 | C18diacid | γE-(O2Oc)-(O2Oc) | 17 | Amide | 2(Aib), 10V, 13(αMePhe), 16T, 17K, 20R, 27L, 28E, 29(Aib), 30K |
| Peptide 481 | H(Ab)QGTFTSDVSK (αMePhe)LDTK(O2Oc-O2Oc-yE-C20diacid)17RARDFVQ WLLE(Aib)K-amide | 492 | C20diacid | γE-(O2Oc)-(O2Oc) | 17 | Amide | 2(Aib), 10V, 13(αMePhe), 16T, 17K, 20R, 27L, 28E, 29(Aib), 30K |
| Peptide 482 | H(Aib)OGTFTSDVSK (αMePhe)LESK(O2Oc-O2Oc-γE-C18diacid)17RAQDFVQ WLL(Aib)E-acid | 493 | C18diacid | γE-(O2Oc)-(O2Oc) | 17 | Acid | 2(Aib), 10V, 13(αMePhe), 15E, 17K, 27L, 28(Aib), 29E |
| Peptide 483 | H(Aib)QGTFTSDVSK (αMePhe)LDTK(O2Oc-O2Oc-γE-C18diacid)17RAQDFVQ WLL(Aib)E-acid | 494 | C18diacid | γE-(O2Oc)-(O2Oc) | 17 | Acid | 2(Aib), 10V, 13(αMePhe), 16T, 17K, 27L, 28(Aib), 29E |
| Peptide 484 | H(Ab)QGTFTSDVSK (αMePhe)LDTK(O2Oc-O2Oc-γE-C20diacid)17RAQDFVQ WLL(Aib)E-acid | 495 | C20diacid | γE-(O2Oc)-(O2Oc) | 17 | Acid | 2(Aib), 10V, 13(αMePhe), 16T, 17K 27L, 28(Aib), 29E |
| Peptide 485 | H(Aib)QGTFTSDVSK (αMePhe)LDTK(O2Oc-O2Oc-yE-C20diacid)17RAQDFVQ WLL(Aib)E-amide | 496 | C20diacid | γE-(O2Oc)-(O2Oc) | 17 | Amide | 2(Aib), 10V, 13(αMePhe), 16T, 17K, 27L, 28(Aib), 29E |
| Peptide 486 | H(Aib)QGTFTSDVSK (αMePhe)LDLK(O2Oc-O2Oc-γE-C20diacid)17RAQDFVR WLL(Aib)E-acid | 497 | C20diacid | γE-(O2Oc)-(O2Oc) | 17 | Acid | 2(Aib), 10V, 13(αMePhe), 16L, 17K, 24R, 27L, 28(Aib), 29E |
| Peptide 487 | H(Aib)QGTFTSDVSK (αMePhe)LDTK(O2Oc-O2Oc-γE-C18diacid)17RARDFVQ WLL(Aib)TE-acid | 498 | C18diacid | γE-(O2Oc)-(O2Oc) | 17 | Acid | 2(Aib), 10V, 13(αMePhe), 16T, 17K, 20R, 27L, 28(Aib), 30E |

TABLE 1-continued

| | | | | Linker (described | | | Sequence modification |
|---|---|---|---|---|---|---|---|
| Peptide | Sequence | SEQ ID NO | Albumin binding moiety | N→C term.) | Acylation site | C-term. | with respect to glucagon. |

Peptides Modified at Position 17

| Peptide | Sequence | SEQ ID NO | Albumin binding moiety | Linker (described N→C term.) | Acylation site | C-term. | Sequence modification with respect to glucagon. |
|---|---|---|---|---|---|---|---|
| Peptide 488 | H(Aib)QGTFTSDVSK (αMePhe)LDTK(O2Oc-O2Oc-γE-C20diacid)17RARDEVQ WLL(Aib)TE-acid | 499 | C20diacid | γE-(O2Oc)-(O2Oc) | 17 | Acid | 2(Aib), 10V, 13(αMePhe), 16T, 17K, 20R, 27L, 28(Aib), 30E |
| Peptide 489 | H(Aib)QGTFTSDVSK (αMePhe)LDTK(O2Oc-O2Oc-γE-C18diacid)17RARDFVQ WLL(Aib)TE-amide | 500 | C18diacid | γE-(O2Oc)-(O2Oc) | 17 | Amide | 2(Aib), 10V, 13(αMePhe), 16T, 17K, 20R, 27L, 28(Aib), 30E |
| Peptide 490 | H(Aib)QGTFTSDVSK (αMePhe)LDTK(O2Oc-O2Oc-γE-C20diacid)17RARDFVQ WLL(Aib)TE-amide | 501 | C20diacid | γE-(O2Oc)-(O2Oc) | 17 | Amide | 2(Aib), 10V, 13(αMePhe), 16T, 17K, 20R, 27L, 28(Aib), 30E |
| Peptide 491 | H(Aib)QGTFTSDVSK (αMePhe)LDTK(O2Oc-O2Oc-yE-C18diacid)17RARDFVR WLL(Aib)TE-acid | 502 | C18diacid | γE-(O2Oc)-(O2Oc) | 17 | Acid | 2(Aib), 10V, 13(αMePhe), 16T, 17K, 20R, 24R, 27L, 28(Aib), 30E |
| Peptide 492 | H(Aib)QGTFTSDVSK (αMePhe)LDTK(O2Oc-O2Oc-γE-C20diacid)17RARDFVR WLL(Aib)TE-acid | 503 | C20diacid | γE-(O2Oc)-(O2Oc) | 17 | Acid | 2(Aib), 10V, 13(αMePhe), 16T, 17K, 20R, 24R, 27L, 28(Aib), 30E |
| Peptide 493 | H(Ab)QGTFTSDVSK (αMePhe)LDTK(O2Oc-O2Oc-γE-C18diacid)17RAQDFVR WLLR(Aib)K-acid | 504 | C18diacid | γE-(O2Oc)-(O2Oc) | 17 | Acid | 2(Aib), 10V, 13(αMePhe), 16T, 17K, 24R, 27L, 28R, 29(Aib), 30K |
| Peptide 494 | H(Aib)QGTFTSDVSK (αMePhe)LDTK(O2Oc-O2Oc-γE-C20diacid)17RAQDFVR WLLR(Aib)K-acid | 505 | C20diacid | γE-(O2Oc)-(O2Oc) | 17 | Acid | 2(Aib), 10V, 13(αMePhe), 16T, 17K, 24R, 27L, 28R, 29(Aib), 30K |
| Peptide 495 | H(Aib)QGTFTSDVSK (αMePhe)LDTK(O2Oc-O2Oc-γE-C18diacid)17RAQDFVR WLLR(Aib)K-amide | 506 | C18diacid | γE-(O2Oc)-(O2Oc) | 17 | Amide | 2(Aib), 10V, 13(αMePhe), 16T, 17K, 24R, 27L, 28R, 29(Aib), 30K |
| Peptide 496 | H(Aib)QGTFTSDVSK (αMePhe)LDTK(O2Oc-O2Oc-γE-C20diacid)17RAQDFVR WLLR(Aib)K-amide | 507 | C20diacid | γE-(O2Oc)-(O2Oc) | 17 | Amide | 2(Aib), 10V, 13(αMePhe), 16T, 17K, 24R, 27L, 28R, 29(Aib), 30K |
| Peptide 497 | H(Aib)QGTFTSDVSK (αMePhe)LDTK(O2Oc-O2Oc-γE-C18diacid)17RAQDFVR WLLR(Aib)A-acid | 508 | C18diacid | γE-(O2Oc)-(O2Oc) | 17 | Acid | 2(Aib), 10V, 13(αMePhe), 16T, 17K, 24R, 27L, 28R, 29(Aib), 30A |
| Peptide 498 | H(Aib)QGTFTSDVSK (αMePhe)LDTK(O2Oc-O2Oc-γE- | 509 | C20diacid | γE-(O2Oc)-(O2Oc) | 17 | Acid | 2(Aib), 10V, 13(αMePhe), 16T, 17K, |

TABLE 1-continued

| | | | | Linker (described | | Sequence modification |
| | | SEQ ID | Albumin binding | N→C | Acylation | C- | with respect |
| Peptide | Sequence | NO | moiety | term.) | site | term. | to glucagon. |
|---|---|---|---|---|---|---|---|
| | C20diacid)17RAQDFVR WLLR(Aib)A-acid | | | | | | 24R, 27L, 28R, 29(Aib), 30A |
| Peptide 499 | H(Aib)QGTFTSDVSK (αMePhe)LDTK(O2Oc-O2Oc-γE-C18diacid)17RAQDFVQ WLLR(Aib)A-acid | 510 | C18diacid | γE-(O2Oc)-(O2Oc) | 17 | Acid | 2(Aib), 10V, 13(αMePhe), 16T, 17K, 27L, 28R, 29(Aib), 30A |
| Peptide 500 | H(Aib)QGTFTSDVSK (αMePhe)LDTK(O2Oc-O2Oc-γE-C20diacid)17RAQDFVQ WLLR(Aib)A-acid | 511 | C20diacid | γE-(O2Oc)-(O2Oc) | 17 | Acid | 2(Aib), 10V, 13(αMePhe), 16T, 17K, 27L, 28R, 29(Aib), 30A |
| Peptide 501 | H(Aib)OGTFTSDVSK (αMePhe)LDTK(O2Oc-O2Oc-γE-C18diacid)17RARDFVQ WLLR(Aib)A-acid | 512 | C18diacid | γE-(O2Oc)-(O2Oc) | 17 | Acid | 2(Aib), 10V, 13(αMePhe), 16T, 17K, 20R, 27L, 28R, 29(Aib), 30A |
| Peptide 502 | H(Aib)QGTFTSDVSK (αMePhe)LDTK(O2Oc-O2Oc-γE-C20diacid)17RARDFVQ WLLR(Aib)A-acid | 513 | C20diacid | γE-(O2Oc)-(O2Oc) | 17 | Acid | 2(Aib), 10V, 13(αMePhe), 16T, 17K, 20R, 27L, 28R, 29(Aib), 30A |
| Peptide 503 | H(Aib)QGTFTSDVSK (αMePhe)LDTK(O2Oc-O2Oc-γE-C20diacid)17RAQDFVR WLLE(Aib)K-acid | 514 | C20diacid | γE-(O2Oc)-(O2Oc) | 17 | Acid | 2(Aib), 10V, 13(αMePhe), 16T, 17K, 24R, 27L, 28E, 29(Aib), 30K |
| Peptide 504 | H(Aib)QGTFTSDVSK (αMePhe)LESK(O2Oc-O2Oc-γE-C20diacid)17RAQDFVR WLLE(Aib)K-acid | 515 | C20diacid | γE-(O2Oc)-(O2Oc) | 17 | Acid | 2(Aib), 10V, 13(αMePhe), 15E, 17K, 24R, 27L, 28E, 29(Aib), 30K |
| Peptide 505 | H(Aib)QGTFTSDVSK (αMePhe)LDTK(O2Oc-O2Oc-γE-C20diacid)17RAQDFVQ WLLE(Aib)K-amide | 516 | C20diacid | γE-(O2Oc)-(O2Oc) | 17 | Amide | 2(Aib), 10V, 13(αMePhe), 16T, 17K, 27L, 28E, 29(Aib), 30K |
| Peptide 506 | H(Aib)QGTFTSDVSK (αMePhe)LDTK(O2Oc-O2Oc-γE-C20diacid)17RARDFVA WLLE(Aib)G-acid | 517 | C20diacid | γE-(O2Oc)-(O2Oc) | 17 | Acid | 2(Aib), 10V, 13(αMePhe), 16T, 17K, 20R, 24A, 27L, 28E, 29(Aib), 30G |
| Peptide 507 | H(Aib)QGTFTSDVSK (αMePhe)LDTK(O2Oc-O2Oc-γE-C20diacid)17RARDFVA WLLE(Aib)G-amide | 518 | C20diacid | γE-(O2Oc)-(O2Oc) | 17 | Amide | 2(Aib), 10V, 13(αMePhe), 16T, 17K, 20R, 24A, 27L, 28E, 29(Aib), 30G |
| Peptide 508 | H(Aib)QGTFTSDVSK (αMePhe)LESK(O2Oc-O2Oc-γE-C20diacid)17RAQDFVR WLVE(Aib)G-amide | 519 | C20diacid | γE-(O2Oc)-(O2Oc) | 17 | Amide | 2(Aib), 10V, 13(αMePhe), 15E, 17K, 24R, 27V, 28E, 29(Aib), 30G |
| Peptide 509 | H(Ab)QGTFTSDVSK (αMePhe)LESK(O2Oc-O2Oc- | 520 | C20diacid | γE-(O2Oc)- | 17 | Acid | 2(Aib), 10V, 13(αMePhe), |

TABLE 1-continued

| | | | | | | |
|---|---|---|---|---|---|---|
| Peptides Modified at Position 17 | | | | | | |
| Peptide | Sequence | SEQ ID NO | Albumin binding moiety | Linker (described N→C term.) | Acylation site | C-term. | Sequence modification with respect to glucagon. |
| | γE-C20diacid)17RAQDFVR WILL(Aib)TE-acid | | | (O2Oc) | | | 15E, 17K, 24R, 27L, 28(Aib), 30E |
| Peptide 510 | H(Aib)QGTFTSDVSK (αMePhe)LDTK(O2Oc-O2Oc-γE-C20diacid)17RARDFVR WLL(Aib)E-acid | 521 | C20diacid | γE-(O2Oc)-(O2Oc) | 17 | Acid | 2(Aib), 10V, 13(αMePhe), 16T, 17K, 20R, 24R, 27L, 28(Aib), 29E |
| Peptide 511 | H(AIb)QGTFTSDVSK (αMePhe)LDTK(O2Oc-O2Oc-γE-C20diacid)17RARDFVR WLL(Aib)E-amide | 522 | C20diacid | γE-(O2Oc)-(O2Oc) | 17 | Amide | 2(Aib), 10V, 13(αMePhe), 16T, 17K, 20R, 24R, 27L, 28(Aib), 29E |
| Peptide 512 | H(Aib)QGT(αMePhe)TS DVSK(αMePhe)LDTK (O2Oc-O2Oc-γE-C18diacid)17RAQD (αMePhe)VRWLLA(Aib)G-amide | 523 | C18diacid | γE-(O2Oc)-(O2Oc) | 17 | Amide | 2(Aib), 6(αMePhe), 10V, 13(αMePhe), 16T, 17K, 22(αMePhe), 24R, 27L, 28A, 29(Aib), 30G |
| Peptide 513 | H(Aib)QGT(αMePhe)TS DVSK(αMePhe)LDTK (O2Oc-O2Oc-γE-C18diacid)17RARD (αMePhe)VQWLLA(Aib)G-amide | 524 | C18diacid | γE-(O2Oc)-(O2Oc) | 17 | Amide | 2(Aib), 6(αMePhe) 10V, 13(αMePhe), 16T, 17K, 20R 22(αMePhe), 27L, 28A, 29(Aib), 30G |
| Peptide 514 | H(Aib)QGTFTSDVSK (αMePhe)LDTK(O2Oc-O2Oc-γE-C18diacid)17AARDFVQ WLLE(Aib)G-amide | 525 | C18diacid | γE-(O2Oc)-(O2Oc) | 17 | Amide | 2(Aib), 10V, 13(αMePhe), 16T, 17K, 18A, 20R, 27L, 28E, 29(Aib), 30G |
| Peptide 515 | H(Aib)QGTFTSDVSK (αMePhe)LDTK(O2Oc-O2Oc-γE-C20diacid)17AARDFVQ WLLE(Aib)G-amide | 526 | C20diacid | γE-(O2Oc)-(O2Oc) | 17 | Amide | 2(Aib), 10V, 13(αMePhe), 16T, 17K, 18A, 20R, 27L, 28E, 29(Aib), 30G |
| Peptide 516 | H(Aib)QGTFTSDVSK (αMePhe)LESK(O2Oc-O2Oc-γE-C20diacid)17RAQDFVR WLLA(Aib)G-amide | 527 | C20diacid | γE-(O2Oc)-(O2Oc) | 17 | Amide | 2(Aib), 10V, 13(αMePhe), 15E, 17K, 24R, 27L, 28A, 29(Aib), 30G |
| Peptide 517 | H(Aib)QGTFTSDVSK (αMePhe)LEAK(O2Oc-O2Oc-γE-γE-C18diacid)17AAREFIAW LLET-amide | 528 | C18diacid | γE-γE-(O2Oc)-(O2Oc) | 17 | Amide | 2(Aib), 10V, 13(αMePhe), 15E, 16A, 17K, 18A, 20R, 21E, 23I, 24A, 27L, 28E |
| Peptide 518 | H(Aib)QGTFTSDVSK (αMePhe)LDTK(O2Oc-O2Oc-γE-γE-C18diacid)17RARDFVQ WLLE(Aib)G-acid | 529 | C18diacid | γE-γE-(O2Oc)-(O2Oc) | 17 | Acid | 2(Aib), 10V, 13(αMePhe), 16T, 17K, 20R, 27L 28E, 29(Aib), 30G |

TABLE 1-continued

| | | | | Linker (described | | Sequence modification |
| | | SEQ ID | Albumin binding | N→C | Acylation C- | with respect |
| Peptide | Sequence | NO | moiety | term.) | site term. | to glucagon. |
| --- | --- | --- | --- | --- | --- | --- |
| Peptide 519 | H(Aib)QGTFTSDVSK (αMePhe)LDTK(γE-γE-O2Oc-O2Oc-γE-γE-C18diacid)17RARDFVQ WLLE(Aib)G-acid | 530 | C18diacid | γE-γE-(O2Oc)-(O2Oc)-γE-γE | 17 Acid | 2(Aib), 10V, 13(αMePhe), 16T, 17K, 20R, 27L, 28E, 29(Aib), 30G |
| Peptide 520 | H(Ab)QGTFTSDVSK (αMePhe)LDTK(γE-γE-O2Oc-O2Oc-γE-γE-C20diacid)17RARDFVQ WLLE(Aib)G-acid | 531 | C20diacid | γE-γE-(O2Oc)-(O2Oc)-γE-γE | 17 Acid | 2(Aib), 10V, 13(αMePhe), 16T, 17K, 20R, 27L, 28E, 29(Aib), 30G |

In some aspects, the peptide comprises the sequence: H-X2-X3-G-X5-X6-T-S-D-X10-S-X12-X13-L-X15-X16-X17-X18-X19-X20-X21-X22-X23-X24-X25-X26-X27-X28-X29-X30-X31-Z, wherein X2 is S, Aminoisobutyric acid (Aib), αMethyl-Serine (αMeS), D-serine (dSer), 1-aminocyclopropane-1-carboxylic acid (Acpr), or S, 1-aminocyclobutane-1-carboxylic acid (Acbu), X3 is Q, H, αMethyl-Glutamine (αMeGln), N-Methyl-Glutamine (N-MeGln), D-glutamine (dGln) or β-dimethylglutamine (β-dimethyl-Gln), X5 is T or S, X6 is F or αMethyl-Phenylalanine (αMePhe), X10 is Y or V, X12 is K, E, or R, X13 is Y, αMePhe, or Aib, X15 is D or E, X16 is S, T, E, or Aib, X17 is R, Q, or E, X18 is R, A, Aib, or S, X19 is A or V, X20 is Q or K, wherein the K can comprise an acyl moiety and/or can be lipidated, X21 is D or L, X22 is F or αMethyl-Phenylalanine (αMePhe), X23 is V or I, X24 is Q, E, A, or R, X25 is W, Aib, or S, X26 is L or I, X27 is M, A, L, E, I, or V, X28 is N, E, (PEG)4, Aib, S, or A, X29 is T, not present, E, or G, X30 is not present, E, T, or G, X31 is not present or G, and Z is amide or acid (SEQ ID NO: 413), wherein the peptide does not comprise SEQ ID NO: 1.

In some aspects, the residue at position 20 is acylated. In some aspects, the residue at position 20 is lipidated. In some aspects, the lipid is selected from the group consisting of a palmitoyl group, stearoyl group, lauryl group, myristoyl group, margaroyl group, octadecanedioic acid (C18diacid), and icosanedioic acid (C20diacid). In some aspects, the lipid is selected from the group consisting of a stearoyl group, octadecanedioic acid (C18diacid), and icosanedioic acid (C20diacid).

In some aspects, the lipid attached to the residue at position 20 is attached via a linker. In some aspects, the linker is selected from the group consisting of (O2Oc), (O2Oc)-(O2Oc), (O2Oc)-γE-(O2Oc), (PEG)2-(PEG)2-γE-γE, (PEG)2-γE-(PEG)2-γE, γE, γE-(O2Oc), γE-(O2Oc)-(O2Oc), γE-(O2Oc)-γE-(O2Oc), γE-(PEG)2-(PEG)2, γE-(PEG)2-γE-(PEG)2, γE-(PEG)4, γE-γE, γE-γE-(O2Oc), γE-γE-(O2Oc)-(O2Oc), γE-γE-(PEG)12, γE-γE-(PEG)2-(PEG)2, γE-γE-(PEG)2-γE-γE, γE-γE-(PEG)4, and γE-γE-(PEG)8. In some aspects, the linker is selected from the group consisting of γE, γE-γE, γE-γE-(O2Oc), γE-(O2Oc)-

(O2Oc), γE-γE-(O2Oc)-(O2Oc), γE-(O2Oc), γE-γE-(PEG)2-(PEG)2, γE-(O2Oc)-γE-(O2Oc), γE-(PEG)4, γE-γE-(PEG)4, (O2Oc)-γE-(O2Oc), (O2Oc)-(O2Oc), and (O2Oc).

In some aspects, the peptide comprises the sequence: H-Aminoisobutyric acid (Aib)-Q-G-T-F-T-S-D-X10-S-X12-αMethyl-Phenylalanine (αMePhe)-L-D-X16-X17-X18-A-K-D-F-V-X24-W-X26-X27-X28-X29-X30-Z, wherein X10 is V or Y, X12 is K or E, X16 is S or Aib, X17 is R or E, X18 is R or A, X24 is A, R, or Q, X26 is L or I, X27 is E, L, A, or I, X28 is A, E, Aib, S, or N, X29 is G, Aib, T, or E, X30 is G, E, T, or not present, and Z is amide or acid (SEQ ID NO: 414).

In some aspects, the lysine at position 20 is acylated. In some aspects, the lysine at position 20 is lipidated. In some aspects, the lipid is selected from the group consisting of a palmitoyl group, stearoyl group, lauryl group, myristoyl group, margaroyl group, octadecanedioic acid (C18diacid), and icosanedioic acid (C20diacid). In some aspects, the lipid is octadecanedioic acid (C18diacid).

In some aspects, the lipid is linked to the lysine at position 20 via a linker. In some aspects, the linker is selected from the group consisting of (O2Oc), (O2Oc)-(O2Oc), (O2Oc)-γE-(O2Oc), (PEG)2-(PEG)2-γE-γE, (PEG)2-γE-(PEG)2-γE, γE, γE-(O2Oc), γE-(O2Oc)-(O2Oc), γE-(O2Oc)-γE-(O2Oc), γE-(PEG)2-(PEG)2, γE-(PEG)2-γE-(PEG)2, γE-(PEG)4, γE-γE, γE-γE-(O2Oc), γE-γE-(O2Oc)-(O2Oc), γE-γE-(PEG) 12, γE-γE-(PEG)2-(PEG)2, γE-γE-(PEG)2-γE-γE, γE-γE-(PEG)4, and γE-γE-(PEG)8. In some aspects, the linker is selected from the group consisting of γE, γE-(O2Oc)-(O2Oc), and γE-γE(O2Oc)-(O2Oc)-γE-γE.

In some aspects, the peptide comprises any one of SEQ ID NOs: 207-347 and 532-537. In some aspects, the peptide comprises SEQ ID NO: 228. In some aspects, the peptide comprises SEQ ID NO: 233.

In some aspects, the peptide has the structure of any one of the structures depicted in FIGS. 4A-4B. In some aspects, the peptide has the structure of FIG. 4A. In some aspects, the peptide has the structure of FIG. 4B.

In some aspects, the peptide is any one of the peptides in Table 2.

TABLE 2

Peptides Modified at Position 20

| Peptide | Sequence | SEQ ID NO | Aibumin binding moiety | Linker (described N→C term) | Acyl- ation site | C- term. | Sequence modification with respect to glucagon |
|---|---|---|---|---|---|---|---|
| Peptide 203 | H(Aib)HGS(αMePhe)TS DVSK(αMePhe)LDSQAA K(O2Oc-O2Oc-γE- C18diacid)20DFVQWIA NT-amide | 207 | C18diacid | γE- (O2Oc)- (O2Oc) | 20 | Amide | 2Aib, 3H, 5S, 6αMePhe, 10V, 13αMePhe, 17Q, 18A, 20K, 26I, 27A |
| Peptide 204 | H(Aib)QGT(αMePhe)TS DVSK(αMePhe)LDSRAA K(O2Oc-O2Oc-γE- C18diacid)20DFVQWIA NT-amide | 208 | C18diacid | γE- (O2Oc)- (O2Oc) | 20 | Amide | 2Aib, 5S, 6αMePhe, 10V, 13αMePhe, 18A, 20K, 26I, 27A |
| Peptide 205 | H(Aib)HGS(αMePhe)TS DVSK(αMePhe)LDSRAA K(O2Oc-O2Oc-γE- C18diacid)20DFVQWIA NT-amide | 209 | C18diacid | γE- (O2Oc)- (O2OC) | 20 | Amide | 2Aib, 3H, 5S, 6αMePhe, 10V, 13αMePhe, 18A, 20K, 26I ,27A |
| Peptide 206 | H(Aib)HGS(αMePhe)TS DVSK(αMePhe)LDSR (Aib)AK(O2Oc-O2Oc-γE- C18diacid)20DFVQWIA NT-amide | 210 | C18diacid | γE- (O2Oc)- (O2Oc) | 20 | Amide | 2Aib, 3H, 5S, 6αMePhe, 10V, 13αMePhe, 18Aib, 20K, 26I, 27A |
| Peptide 207 | H(Aib)HGS(αMePhe)TS DVSK(αMePhe)LDSQAA K(O2Oc-O2Oc-γE- C18diacid)20DFVQ(Aib) IANT-amide | 211 | C18diacid | γE- (O2Oc)- (O2Oc) | 20 | Amide | 2Aib, 3H, 5S, 6αMePhe, 10V, 13αMePhe, 17Q, 18A, 20K, 25Aib, 26I, 27A |
| Peptide 208 | H(Aib)QGTFTSDVSK (αMePhe)LDSRAAK(γE- C18diacid)20DFVQWIA NT-amide | 212 | C18diacid | γE | 20 | Amide | 2Aib, 10V, 13αMePhe, 18A, 20K, 26I, 27A |
| Peptide 209 | H(Aib)HGS(αMePhe)TS DVSK(αMePhe)LDSQAA K(O2Oc-O2Oc-γE- C18diacid)20DFVEWIA NT-amide | 213 | C18diacid | γE- (O2Oc)- (O2Oc) | 20 | Amide | 2Aib, 3H, 5S, 6αMePhe, 10V 13αMePhe, 17Q, 18A, 20K, 24E, 26I, 27A |
| Peptide 210 | H(Aib)HGS(αMePhe)TS DVSK(αMePhe)LDSQAA K(O2Oc-O2Oc-γE-γE- C18diacid)20DFVEWIA NT-amide | 214 | C18diacid | γE-γE- (O2Oc)- (O2Oc) | 20 | Amide | 2Aib, 3H, 5S, 6αMePhe, 10V, 13αMePhe, 17Q,18A, 20K, 24E, 26I, 27A |
| Peptide 211 | H(Aib)HGS(αMePhe)TS DVSK(αMePhe)LDSRAA K(O2Oc-O2Oc-γE-γE- C20diacid)20DFVQWIA NT-amide | 215 | C20diacid | γE-γE- (O2Oc)- (O2Oc) | 20 | Amide | 2Aib, 3H, 5S, 6αMePhe, 10V, 13αMePhe, 18A, 20K, 26I, 27A |
| Peptide 212 | H(Aib)HGS(αMePhe)TS DVSK(αMePhe)LDSRAA K(O2Oc-O2Oc-γE- C20diacid)20DFVEWIA NT-amide | 216 | C20diacid | γE- (O2Oc)- (O2Oc) | 20 | Amide | 2Aib, 3H, 5S, 6αMePhe, 10V, 13αMePhe, 18A, 20K, 24E, 26I, 27A |
| Peptide 213 | H(Aib)HGS(αMePhe)TS DVSK(αMePhe)LDSRAA | 217 | C20diacid | γE-γE- (O2Oc)- | 20 | Amide | 2Aib, 3H, 5S, 6αMePhe, |

TABLE 2-continued

| | | | | Linker (described N→C term) | Acyl- ation site | C- term. | Sequence modification with respect to glucagon |
|---|---|---|---|---|---|---|---|
| Peptide | Sequence | SEQ ID NO | Albumin binding moiety | | | | |
| | K(O2Oc-O2Oc-γE-γE-C20diacid)20DFVEWIA NT-amide | | | (O2Oc) | | | 10V, 13αMePhe, 18A, 20K, 24E, 26I, 27A |
| Peptide 214 | H(Aib)HGS(αMePhe)TS DVSK(αMePhe)LDSRAA K(O2Oc-O2Oc-γE-C20diacid)20DFVQWIA NT-amide | 218 | C20diacid | γE-(O2Oc)-(O2Oc) | 20 | Amide | 2Aib, 3H, 5S, 6αMePhe, 10V, 13αMePhe, 18A, 20K, 26I, 27A |
| Peptide 215 | H(Aib)HGS(αMePhe)TS DVSK(αMePhe)LDSRAA K(O2Oc-O2Oc-γE-C20diacid)20D (αMePhe)VQWIANT-amide | 219 | C20diacid | γE-(O2Oc)-(O2Oc) | 20 | Amide | 2Aib, 3H, 5S, 6αMePhe, 10V, 13αMePhe, 18A, 20K, 22αMePhe, 26I, 27A |
| Peptide 216 | H(Aib)HGS(αMePhe)TS DVSK(αMePhe)LDSRAA K(O2Oc-O2Oc-γE-C20diacid)20D (αMePhe)VEWIANT-amide | 220 | C20diacid | γE-(O2Oc)-(O2Oc) | 20 | Amide | 2Aib, 3H, 5S, 6αMePhe, 10V, 13αMePhe, 18A, 20K, 22αMePhe, 24E, 26I, 27A |
| Peptide 217 | H(Aib)HGS(αMePhe)TS DVSK(αMePhe)LDSR (Aib)AK(O2Oc-O2Oc-γE-γE-C20diacid)20DFVQWIA NT-amide | 221 | C20diacid | γE-γE-(O2Oc)-(O2Oc) | 20 | Amide | 2Aib, 3H, 5S, 6αMePhe, 10V, 13αMePhe, 18Aib, 20K, 26I, 27A |
| Peptide 218 | H(Aib)HGS(αMePhe)TS DVSK(αMePhe)LDSRAA K(O2Oc-O2Oc-γE-γE-C20diacid)20DFVQWIA NTG-amide | 222 | C20diacid | γE-γE-(O2Oc)-(O2Oc) | 20 | Amide | 2Aib, 3H, 5S, 6αMePhe, 10V, 13αMePhe, 18A, 20K, 26I, 27A, 30G |
| Peptide 219 | H(Aib)HGS(αMePhe)TS DVSK(αMePhe)LDSRAA K(O2Oc-O2Oc-γE-γE-C20diacid)20DFVQWIA NTGG-amide | 223 | C20diacid | γE-γE-(O2Oc)-(O2Oc) | 20 | Amide | 2Aib, 3H, 5S, 6αMePhe, 10V, 13αMePhe, 18A, 20K, 26I, 27A, 30G, 31G |
| Peptide 220 | H(Aib)HGS(αMePhe)TS DVSK(αMePhe)LDSR (Aib)AK(O2Oc-O2Oc-γE-γE-C20diacid)20DFVQ(Aib) IANT-amide | 224 | C20diacid | γE-γE-(O2Oc)-(O2Oc) | 20 | Amide | 2Aib, 3H, 5S, 6αMePhe, 10V, 13αMePhe, 18Aib, 20K, 25Aib, 26I, 27A |
| Peptide 221 | H(Aib)HGS(αMePhe)TS DVSK(αMePhe)LDSRAA K(O2Oc-O2Oc-γE-γE-C20diacid)20DFVQ(Aib) IANT-amide | 225 | C20diacid | γE-γE-(O2Oc)-(O2Oc) | 20 | Amide | 2Aib, 3H, 5S, 6αMePhe, 10V, 13αMePhe, 18A, 20K, 25Aib, 26I, 27A |
| Peptide 222 | H(Aib)HGS(αMePhe)TS DVSK(αMePhe)LDSQAA K(O2Oc-O2Oc-γE-C18diacid)20DFVQSIAN | 226 | C18diacid | γE-(O2Oc)-(O2Oc) | 20 | Amide | 2Aib, 3H, 5S, 6αMePhe, 10V, 13αMePhe, |

TABLE 2-continued

| | | | | Linker | | | Sequence |
| | | SEQ | Albumin | (described | Acyl- | | modification |
| | | ID | binding | N→C | ation | C- | with respect |
| Peptide | Sequence | NO | moiety | term) | site | term. | to glucagon |
|---|---|---|---|---|---|---|---|
| | T-amide | | | | | | 17Q, 18A, 20K, 25S, 26I, 27A |
| Peptide 223 | H(Aib)HGS(αMePhe)TS DVSK(αMePhe)LDSR (Aib)AK(O2Oc-O2Oc-γE-C18diacid)20DFVQSIAN T-amide | 227 | C18diacid | γE-(O2Oc)-(O2Oc) | 20 | Amide | 2Aib, 3H, 5S, 6αMePhe, 10V, 13αMePhe, 18Aib, 20K, 25S, 26I, 27A |
| Peptide 224 | H(Aib)HGS(αMePhe)TS DVSK(αMePhe)LDSRAA K(O2Oc-O2Oc-γE-C18diacid)20D(αMePhe) VQ(Aib)IANT-amide | 228 | C18diacid | γE-(O2Oc)-(O2Oc) | 20 | Amide | 2Aib, 3H, 5S, 6αMePhe, 10V, 13αMePhe, 18A, 20K, 22αMePhe, 25Aib, 26I, 27A |
| Peptide 225 | H(Aib)HGS(αMePhe)TS DVSK(αMePhe)LDSRAA K(O2Oc-O2Oc-γE-C18diacid)20D(αMePhe) VQ(Aib)IANTGG-amide | 229 | C18diacid | γE-(O2Oc)-(O2Oc) | 20 | Amide | 2Aib, 3H, 5S, 6αMePhe, 10V, 13αMePhe, 18A, 20K, 22αMePhe, 25Aib, 26I, 27A, 30G, 31G |
| Peptide 226 | H(Aib)HGS(αMePhe)TS DVSK(αMePhe)LDSRAA K(O2Oc-O2Oc-γE-C18diacid)20D(αMePhe) VE(Aib)IANT-amide | 230 | C18diacid | γE-(O2Oc)-(O2Oc) | 20 | Amide | 2Aib, 3H, 5S, 6αMePhe, 10V, 13αMePhe, 18A, 20K, 22αMePhe, 24E, 25Aib, 26I, 27A |
| Peptide 227 | H(Aib)HGS(αMePhe)TS DVSK(αMePhe)LDSRAA K(O2Oc-O2Oc-γE-C18diacid)20D(αMePhe) IA(Aib)IANT-amide | 231 | C18diacid | γE-(O2Oc)-(O2Oc) | 20 | Amide | 2Aib, 3H, 5S, 6αMePhe, 10V, 13αMePhe, 18A, 20K, 22αMePhe, 23I, 24A, 25Aib, 26I, 27A |
| Peptide 228 | H(Aib)HGS(αMePhe)TS DVSK(αMePhe)LDSRAA K(O2Oc-O2Oc-γE-γE-C20diacid)20D(αMePhe) VQWIANT-amide | 232 | C20diacid | γE-γE-(O2Oc)-(O2Oc) | 20 | Amide | 2Aib, 3H, 5S, 6αMePhe, 10V, 13αMePhe, 18A, 20K, 22αMePhe, 26I, 27A |
| Peptide 229 | H(Aib)HGS(αMePhe)TS DVSK(αMePhe)LDSRAA K(O2Oc-O2Oc-γE-γE-C20diacid)20D(αMePhe) VQ(Aib)IANT-amide | 233 | C20diacid | γE-γE-(O2Oc)-(O2Oc) | 20 | Amide | 2Aib, 3H, 5S, 6αMePhe, 10V, 13αMePhe, 18A, 20K, 22αMePhe, 25Aib, 26I, 27A |
| Peptide 230 | H(Aib)HGS(αMePhe)TS DVSK(αMePhe)LDSRAA K(O2Oc-O2Oc-γE-C18diacid)20D(αMePhe) IAWIANT-amide | 234 | C18diacid | γE-(O2Oc)-(O2Oc) | 20 | Amide | 2Aib, 3H, 5S, 6αMePhe, 10V, 13αMePhe, 18A, 20K, 22αMePhe, 26I, 27A |

TABLE 2-continued

| | | | | Linker | | | Sequence |
| | | SEQ | Aibumin | (described | Acyl- | | modification |
| | | ID | binding | N→C | ation | C- | with respect |
| Peptide | Sequence | NO | moiety | term) | site | term. | to glucagon |
| --- | --- | --- | --- | --- | --- | --- | --- |
| Peptide 231 | H(Aib)HGS(αMePhe)TS DVSK(αMePhe)LDSRAA K(O2Oc-O2Oc-γE-γE- C18diacid)20D(αMePhe) VQ(Aib)IANT-amide | 235 | C18diacid | γE-γE- (O2Oc)- (O2Oc) | 20 | Amide | 2Aib, 3H, 5S, 6αMePhe, 10V, 13αMePhe, 18A, 20K, 22αMePhe, 25Aib, 26I, 27A |
| Peptide 232 | H(Aib)HGS(αMePhe)TS DVSK(αMePhe)LDSRAA K(O2Oc-O2Oc-γE-γE- C20diacid)20D(αMePhe) VQ(Aib)IANTGG- amide | 236 | C20diacid | γE-γE- (O2Oc)- (O2Oc) | 20 | Amide | 2Aib, 3H, 5S, 6αMePhe, 10V, 13αMePhe, 18A, 20K, 22αMePhe, 25Aib, 26I, 27A, 30G, 31G |
| Peptide 233 | H(Aib)HGS(αMePhe)TS DVSK(αMePhe)LDSRAA K(O2Oc-O2Oc-γE-γE- C20diacid)20D(αMePhe) VE(Aib)IANT-amide | 237 | C20diacid | γE-γE- (O2Oc) (O2Oc) | 20 | Amide | 2Aib, 3H, 5S, 6αMePhe, 10V, 13αMePhe, 18A, 20K, 22αMePhe, 24E, 25Aib, 26I, 27A |
| Peptide 234 | H(Aib)HGS(αMePhe)TS DVSK(αMePhe)LDSRAA K(O2Oc-O2Oc-γE-γE- C20diacid)20DFVQ(Aib) IANTG-amide | 238 | C20diacid | γE-γE- (O2Oc)- (O2Oc) | 20 | Amide | 2Aib, 3H, 5S, 6αMePhe, 10V, 13αMePhe, 18A, 20K, 25Aib, 26I, 27A, 30G |
| Peptide 235 | H(Aib)HGS(αMePhe)TS DVSK(αMePhe)LDSRAA K(O2Oc-O2Oc-γE-γE- C20diacid)20DFVQ(Aib) IANTGG-amide | 239 | C20diacid | γE-γE- (O2Oc)- (O2Oc) | 20 | Amide | 2Aib, 3H, 5S, 6αMePhe, 10V, 13αMePhe, 18A, 20K, 22αMePhe, 25Aib, 26I, 27A, 30G, 31G |
| Peptide 236 | H(Aib)HGS(αMePhe)TS DVSK(αMePhe)LDSRAA K(O2Oc-O2Oc-γE-γE- C18diacid)20DFVQ(Aib) IANTG-amide | 240 | C18diacid | γE-γE- (O2Oc)- (O2Oc) | 20 | Amide | 2Aib, 3H, 5S, 6αMePhe, 10V, 13αMePhe, 18A, 20K, 25Aib, 26I, 27A, 30G |
| Peptide 237 | H(Aib)HGS(αMePhe)TS DVSK(αMePhe)LDSRAA K(O2Oc-O2Oc-γE-γE- C18diacid)20DFVQ(Aib) IANTGG-amide | 241 | C18diacid | γE-γE- (O2Oc)- (O2Oc) | 20 | Amide | 2Aib, 3H, 5S, 6αMePhe, 10V, 13αMePhe, 18A, 20K, 22αMePhe, 25Aib, 26I, 27A, 30G, 31G |
| Peptide 238 | H(Aib)HGS(αMePhe)TS DVSK(αMePhe)LDSRAA K(O2Oc-O2Oc-γE-γE- C20diacid)20D(αMePhe) VQWIANTG-amide | 242 | C20diacid | γE-γE- (O2Oc)- (O2Oc) | 20 | Amide | 2Aib, 3H, 5S, 6αMePhe, 10V 13αMePhe, 18A, 20K, 22αMePhe, 26I, 27A, 30G |

TABLE 2-continued

Peptides Modified at Position 20

| Peptide | Sequence | SEQ ID NO | Aibumin binding moiety | Linker (described N→C term) | Acyl-ation site | C-term. | Sequence modification with respect to glucagon |
|---|---|---|---|---|---|---|---|
| Peptide 239 | H(Aib)HGS(αMePhe)TS DVSK(αMePhe)LDSRAA K(O2Oc-O2Oc-γE-γE-C20diacid)20D(αMePhe) VQWIANTGG-amide | 243 | C20diacid | γE-γE-(O2Oc)-(O2Oc) | 20 | Amide | 2Aib, 3H, 5S, 6αMePhe, 10V, 13αMePhe, 18A, 20K, 22αMePhe, 26I, 27A, 30G, 31G |
| Peptide 240 | H(Aib)HGS(αMePhe)TS DVSK(αMePhe)LDSRAA K(O2Oc-O2Oc-γE-γE-C18diacid)20D(αMePhe) VQWIANTG-amide | 244 | C18diacid | γE-γE-(O2Oc)-(O2Oc) | 20 | Amide | 2Aib, 3H, 5S, 6αMePhe, 10V, 13αMePhe, 18A, 20K, 22αMePhe, 26I, 27A, 30G |
| Peptide 241 | H(Aib)HGS(αMePhe)TS DVSK(αMePhe)LDSRAA K(O2Oc-O2Oc-γE-γE-C18diacid)20D(αMePhe) VQWIANTGG-amide | 245 | C18diacid | γE-γE-(O2Oc)-(O2Oc) | 20 | Amide | 2Aib, 3H, 5S, 6αMePhe, 10V, 13αMePhe, 18A, 20K, 22αMePhe, 26I, 27A, 30G, 31G |
| Peptide 242 | H(Aib)HGS(αMePhe)TS DVSK(αMePhe)LDSR (Aib)AK(O2Oc-O2Oc-γE-γE-C20diacid)20DFVQSIAN T-amide | 246 | C20diacid | γE-γE-(O2Oc)-(O2Oc) | 20 | Amide | 2Aib, 3H, 5S, 6αMePhe, 10V, 13αMePhe, 18Aib, 20K, 25S, 26I, 27A |
| Peptide 243 | H(Aib)HGS(αMePhe)TS DVSK(αMePhe)LDSRAA K(O2Oc-O2Oc-γE-C18diacid)20D(αMePhe) VQSIANT-amide | 247 | C18diacid | γE-(O2Oc)-(O2Oc) | 20 | Amide | 2Aib, 3H, 5S, 6αMePhe, 10V, 13αMePhe, 18A, 20K, 22αMePhe, 25S, 26I, 27A |
| Peptide 244 | H(Aib)HGS(αMePhe)TS DVSK(αMePhe)LDSRAA K(O2Oc-O2Oc-γE-γE-C20diacid)20D(αMePh e)VQSIANT-amide | 248 | C20diacid | γE-γE-(O2Oc)-(O2Oc) | 20 | Amide | 2Aib, 3H, 5S, 6αMePhe, 10V, 13αMePhe, 18A, 20K, 22αMePhe, 25S, 26I, 27A |
| Peptide 245 | H(Aib)HGS(αMePhe)TS DVSK(αMePhe)LDSRAA K(O2Oc-O2Oc-γE-C18diacid)20D(αMePhe) VESIANT-amide | 249 | C18diacid | γE-(O2Oc)-(O2Oc) | 20 | Amide | 2Aib, 3H, 5S, 6αMePhe, 10V, 13αMePhe, 18A, 20K, 22αMePhe, 24E, 25S, 26I, 27A |
| Peptide 246 | H(Aib)HGS(αMePhe)TS DVSK(αMePhe)LDSRAA K(O2Oc-O2Oc-γE-γE-C20diacid)20D(αMePhe) VESIANT-amide | 250 | C20diacid | γE-γE-(O2Oc)-(O2Oc) | 20 | Amide | 2Aib, 3H, 5S, 6αMePhe, 10V, 13αMePhe, 18A, 20K, 22αMePhe, 24E, 25S, 26I, 27A |
| Peptide 247 | H(Aib)HGS(αMePhe)TS DVSK(αMePhe)LDSRAA K(O2Oc-O2Oc-γE-γE-C18diacid)20D(αMePhe) | 251 | C18diacid | γE-γE-(O2Oc)-(O2Oc) | 20 | Amide | 2Aib, 3H, 5S, 6αMePhe, 10V, 13αMePhe, |

TABLE 2-continued

Peptides Modified at Position 20

| Peptide | Sequence | SEQ ID NO | Aibumin binding moiety | Linker (described N→C term) | Acyl- ation site | C- term. | Sequence modification with respect to glucagon |
|---|---|---|---|---|---|---|---|
| | VQWIANT-amide | | | | | | 18A, 20K, 22αMePhe, 26I, 27A |
| Peptide 248 | (NHis)SHGS(αMePhe)T SDVSK(αMePhe)LDSRA AK(O2Oc-O2Oc-γE-γE- C20diacid)20D(αMePhe) VQWIANT-amide | 252 | C20diacid | γE-γE- (O2Oc)- (O2Oc) | 20 | Amide | 2Aib, 3H, 5S, 6αMePhe, 10V, 13αMePhe, 18A, 20K, 22αMePhe, 26I, 27A |
| Peptide 249 | H(Aib)HGS(αMePhe)TS DVSK(αMePhe)LDSR (Aib)AK(O2Oc-O2Oc-γE- γE- C20diacid)20D(αMePhe) VESIANT-amide | 253 | C20diacid | γE-γE- (O2Oc)- (O2Oc) | 20 | Amide | 2Aib, 3H, 5S, 6αMePhe, 10V, 13αMePhe, 18Aib, 20K, 22αMePhe, 24E, 25S, 26I, 27A |
| Peptide 250 | H(Aib)HGS(αMePhe)TS DVSK(αMePhe)LDSR (Aib)AK(O2Oc-O2Oc-γE- γE- C18diacid)20D(αMePhe) VESIANT-amide | 254 | C18diacid | γE-γE- (O2Oc)- (O2Oc) | 20 | Amide | 2Aib, 3H, 5S, 6αMePhe, 10V, 13αMePhe, 18Aib, 20K, 22αMePhe, 24E, 25S, 26I, 27A |
| Peptide 251 | H(Aib)HGS(αMePhe)TS DVSK(αMePhe)LDSR (Aib)AK(O2Oc-O2Oc-γE- C18diacid)20DFVESIAN T-amide | 255 | C18diacid | γE- (O2Oc)- (O2Oc) | 20 | Amide | 2Aib, 3H, 5S, 6αMePhe, 10V, 13αMePhe, 18Aib, 20K, 24E, 25S, 26I, 27A |
| Peptide 252 | H(Aib)HGS(αMePhe)TS DVSK(αMePhe)LDSR (Aib)AK(O2Oc-O2Oc-γE- C20diacid)20DFVESIAN T-amide | 256 | C20diacid | γE- (O2Oc)- (O2Oc) | 20 | Amide | 2Aib, 3H, 5S, 6αMePhe, 10V, 13αMePhe, 18Aib, 20K, 24E, 25S, 26I, 27A |
| Peptide 253 | H(Aib)HGS(αMePhe)TS DVSK(αMePhe)LDSR (Aib)AK(O2Oc-γE- C18diacid)20DFVESIAN T-amide | 257 | C18diacid | γE- (O2Oc) | 20 | Amide | 2Aib, 3H, 5S, 6αMePhe, 10V, 13αMePhe, 18Aib, 20K, 24E, 25S, 26I, 27A |
| Peptide 254 | H(Aib)HGS(αMePhe)TS DVSK(αMePhe)LDSR (Aib)AK(γE- C18diacid)20DFVESIAN T-amide | 258 | C18diacid | YE | 20 | Amide | 2Aib, 3H, 5S, 6αMePhe, 10V, 13αMePhe, 18Aib, 20K, 24E, 25S, 26I, 27A |
| Peptide 255 | H(Aib)HGS(αMePhe)TS DVSK(αMePhe)LDSQAA K(O2Oc-O2Oc-γE- C18diacid)20D(αMePhe) VQ(Aib)IANT-amide | 259 | C18diacid | γE- (O2Oc)- (O2Oc) | 20 | Amide | 2Aib, 3H, 5S, 6αMePhe, 10V, 13αMePhe, 17Q, 18A, 20K 22αMePhe, 25Aib, 26I, 27A |

TABLE 2-continued

Peptides Modified at Position 20

| Peptide | Sequence | SEQ ID NO | Aibumin binding moiety | Linker (described N→C term) | Acyl-ation site | C-term. | Sequence modification with respect to glucagon |
|---|---|---|---|---|---|---|---|
| Peptide 256 | H(Aib)HGS(αMePhe)TS DVSK(αMePhe)LDSQAA K(O2Oc-O2Oc-γE-γE-C20diacid)20D(αMePhe) VQ(Aib)IANT-amide | 260 | C20diacid | γE-γE-(O2Oc)-(O2Oc) | 20 | Amide | 2Aib, 3H, 5S, 6αMePhe, 10V 13αMePhe, 17Q,18A, 20K 22αMePhe, 25Aib, 26I, 27A |
| Peptide 257 | H(Aib)HGS(αMePhe)TS DVSK(αMePhe)LDSRAA K(O2Oc-O2Oc-γE-γE-Stearoyl)20D(αMePhe) VQ(Aib)IANT-amide | 261 | Stearoyl | γE-γE-(O2Oc)-(O2Oc) | 20 | Amide | 2Aib, 3H, 5S, 6αMePhe, 10V, 13αMePhe, 18A, 20K, 22αMePhe, 25Aib, 26I, 27A |
| Peptide 258 | H(Aib)HGS(αMePhe)TS DVSK(αMePhe)LDSRAA K((PEG)2-(PEG)2-γE-γE-C18diacid)20D(αMePhe) VQ(Aib)IANT-amide | 262 | C18diacid | γE-γE-(PEG)2-(PEG)2 | 20 | Amide | 2Aib, 3H, 5S, 6αMePhe, 10V, 13αMePhe, 18A, 20K, 22αMePhe, 25Aib, 26I, 27A |
| Peptide 259 | H(Aib)HGS(αMePhe)TS DVSK(αMePhe)LDSRAA K(O2Oc-γE-O2Oc-C18diacid)20D(αMePhe) VQ(Aib)IANT-amide | 263 | C18diacid | (O2Oc)-γE-(O2Oc) | 20 | Amide | 2Aib, 3H, 5S, 6αMePhe, 10V, 13αMePhe, 18A, 20K, 22αMePhe, 25Aib, 26I, 27A |
| Peptide 260 | H(Aib)HGS(αMePhe)TS DVSK(αMePhe)LDSRAA K(O2Oc-γE-O2Oc-γE-C18diacid)20D(αMePhe) VQ(Aib)IANT-amide | 264 | C18diacid | γE-(O2Oc)-γE-(O2Oc) | 20 | Amide | 2Aib, 3H, 5S, 6αMePhe, 10V, 13αMePhe, 18A, 20K, 22αMePhe, 25Aib, 26I, 27A |
| Peptide 261 | H(Aib)HGS(αMePhe)TS DVSK(αMePhe)LDSRAA K((PEG)4-γE-C18diacid)20D(αMePhe) VQ(Aib)IANT-amide | 265 | C18diacid | γE-(PEG)4 | 20 | Amide | 2Aib, 3H, 5S, 6αMePhe, 10V, 13αMePhe, 18A, 20K, 22αMePhe, 25Aib, 26I, 27A |
| Peptide 262 | H(Aib)HGS(αMePhe)TS DVSK(αMePhe)LDSRAA K(O2Oc-γE-C18diacid)20D(αMePhe) VQ(Aib)IANT-amide | 266 | C18diacid | γE-(O2Oc) | 20 | Amide | 2Aib, 3H, 5S, 6αMePhe, 10V, 13αMePhe, 18A, 20K, 22αMePhe, 25Aib, 26I, 27A |
| Peptide 263 | H(Aib)HGS(αMePhe)TS DVSK(αMePhe)LDSRAA K((PEG)4-γE-γE-C18diacid)20D(αMePhe) VQ(Aib)IANT-amide | 267 | C18diacid | γE-γE-(PEG)4 | 20 | Amide | 2Aib, 3H, 5S, 6αMePhe, 10V, 13αMePhe, 18A, 20K, 22αMePhe, 25Aib, 26I, 27A |

TABLE 2-continued

| | | | | Peptides Modified at Position 20 | | | |
|---|---|---|---|---|---|---|---|
| Peptide | Sequence | SEQ ID NO | Aibumin binding moiety | Linker (described N→C term) | Acyl- ation site | C- term. | Sequence modification with respect to glucagon |
| Peptide 264 | H(Aib)HGS(αMePhe)TS DVSK(αMePhe)LDSRAA K((PEG)2-(PEG)2-γE-γE- C20diacid)20D(αMePhe) VQ(Aib)IANT-amide | 268 | C20diacid | γE-γE- (PEG)2- (PEG)2 | 20 | Amide | 2Aib, 3H, 5S, 6αMePhe, 10V, 13αMePhe, 18A, 20K, 22αMePhe, 25Aib, 26I, 27A |
| Peptide 265 | H(Aib)HGS(αMePhe)TS DVSK(αMePhe)LDSRAA K(O2Oc-γE-O2Oc- C20diacid)20D(αMePhe) VQ(Aib)IANT-amide | 269 | C20diacid | (O2Oc)- γE- (O2Oc) | 20 | Amide | 2Aib, 3H, 5S, 6αMePhe, 10V, 13αMePhe, 18A, 20K, 22αMePhe, 25Aib, 26I, 27A |
| Peptide 266 | H(Aib)HGS(αMePhe)TS DVSK(αMePhe)LDSRAA K(O2Oc-γE-O2Oc-γE- C20diacid)20D(αMePhe) VQ(Aib)IANT-amide | 270 | C20diacid | γE- (O2Oc)- γE- (O2Oc) | 20 | Amide | 2Aib, 3H, 5S, 6αMePhe, 10V, 13αMePhe, 18A, 20K, 22αMePhe, 25Aib, 26I, 27A |
| Peptide 267 | H(Aib)HGS(αMePhe)TS DVSK(αMePhe)LDSRAA K(PEG)4-γE- C20diacid)20D(αMePhe) VQ(Aib)IANT-amide | 271 | C20diacid | γE- (PEG)4 | 20 | Amide | 2Aib, 3H, 5S, 6αMePhe, 10V, 13αMePhe, 18A, 20K, 22αMePhe, 25Aib, 26I, 27A |
| Peptide 268 | H(Aib)HGS(αMePhe)TS DVSK(αMePhe)LDSRAA K(O2Oc-γE- C20diacid)20D(αMePhe) VQ(Aib)IANT-amide | 272 | C20diacid | γE- (O2Oc) | 20 | Amide | 2Aib, 3H, 5S, 6αMePhe, 10V, 13αMePhe, 18A, 20K, 22αMePhe, 25Aib, 26I, 27A |
| Peptide 269 | H(Aib)HGS(αMePhe)TS DVSK(αMePhe)LDSRAA K((PEG)4-γE-γE- C20diacid)20D(αMePhe) VQ(Aib)IANT-amide | 273 | C20diacid | γE-γE- (PEG)4 | 20 | Amide | 2Aib, 3H, 5S, 6αMePhe, 10V, 13αMePhe, 18A, 20K, 22αMePhe, 25Aib, 26I, 27A |
| Peptide 270 | H(Aib)HGS(αMePhe)TS DVSK(αMePhe)LDSRAA K(γE-γE- C18diacid)20D(αMePhe) VQ(Aib)IANT-amide | 274 | C18diacid | γE-γE | 20 | Amide | 2Aib, 3H, 5S, 6αMePhe, 10V, 13αMePhe, 18A, 20K, 22αMePhe, 25Aib, 26I, 27A |
| Peptide 271 | H(Aib)HGS(αMePhe)TS DVSK(αMePhe)LDSRAA K(γE- C18diacid)20D(αMePhe) VQ(Aib)IANT-amide | 275 | C18diacid | γE | 20 | Amide | 2Aib, 3H, 5S, 6αMePhe, 10V, 13αMePhe, 18A, 20K, 22αMePhe, 25Aib, 26I, 27A |

TABLE 2-continued

| | | | | Linker (described N→C term) | Acyl-ation site | C-term. | Sequence modification with respect to glucagon |
|---|---|---|---|---|---|---|---|
| Peptide | Sequence | SEQ ID NO | Albumin binding moiety | | | | |
| Peptide 272 | H(Aib)HGS(αMePhe)TS DVSK(αMePhe)LDSRAA K(O2Oc-O2Oc- C18diacid)20D(αMePhe) VQ(Aib)IANT-amide | 276 | C18diacid | (O2Oc)- (O2Oc) | 20 | Amide | 2Aib, 3H, 5S, 6αMePhe, 10V, 13αMePhe, 18A, 20K, 22αMePhe, 25Aib, 26I, 27A |
| Peptide 273 | H(Aib)HGS(αMePhe)TS DVSK(αMePhe)LDSRAA K(O2Oc- C18diacid)20D(αMePhe) VQ(Aib)IANT-amide | 277 | C18diacid | (O2Oc) | 20 | Amide | 2Aib, 3H, 5S, 6αMePhe, 10V, 13αMePhe, 18A, 20K, 22αMePhe, 25Aib, 26I, 27A |
| Peptide 274 | H(Aib)HGS(αMePhe)TS DVSK(αMePhe)LDSRAA K(O2Oc-γE-γE- C18diacid)20D(αMePhe) VQ(Aib)IANT-amide | 278 | C18diacid | γE-γE- (O2Oc) | 20 | Amide | 2Aib, 3H, 5S, 6αMePhe, 10V, 13αMePhe, 18A, 20K, 22αMePhe, 25Aib, 26I, 27A |
| Peptide 275 | H(Aib)HGS(αMePhe)TS DVSK(αMePhe)LDSRAA K(γE-γE- C20diacid)20D(αMePhe) VQ(Aib)IANT-amide | 279 | C20diacid | γE-γE | 20 | Amide | 2Aib, 3H, 5S, 6αMePhe, 10V, 13αMePhe, 18A, 20K, 22αMePhe, 25Aib, 26I, 27A |
| Peptide 276 | H(Aib)HGS(αMePhe)TS DVSK(αMePhe)LDSRAA K(γE- C20diacid)20D(αMePhe) VQ(Aib)IANT-amide | 280 | C20diacid | γE | 20 | Amide | 2Aib, 3H, 5S, 6αMePhe, 10V, 13αMePhe, 18A, 20K, 22αMePhe, 25Aib, 26I, 27A |
| Peptide 277 | H(Aib)HGS(αMePhe)TS DVSK(αMePhe)LDSRAA K(O2Oc-O2Oc- C20diacid)20D(αMePhe) VQ(Aib)IANT-amide | 281 | C20diacid | (O2Oc)- (O2Oc) | 20 | Amide | 2Aib, 3H, 5S, 6αMePhe, 10V, 13αMePhe, 18A, 20K, 22αMePhe, 25Aib, 26I, 27A |
| Peptide 278 | H(Aib)HGS(αMePhe)TS DVSK(αMePhe)LDSRAA K(O2Oc- C20diacid)20D(αMePhe) VQ(Aib)IANT-amide | 282 | C20diacid | (O2Oc) | 20 | Amide | 2Aib, 3H, 5S, 6αMePhe, 10V, 13αMePhe, 18A, 20K, 22αMePhe, 25Aib, 26I, 27A |
| Peptide 279 | H(Aib)HGS(αMePhe)TS DVSK(αMePhe)LDSRAA K(O2Oc-γE-γE- C20diacid)20D(αMePhe) VQ(Aib)IANT-amide | 283 | C20diacid | γE-γE- (O2Oc) | 20 | Amide | 2Aib, 3H, 5S, 6αMePhe, 10V, 13αMePhe, 18A, 20K, 22αMePhe, 25Aib, 26I, 27A |

TABLE 2-continued

| | | | | | | | |
|---|---|---|---|---|---|---|---|
| | | | | Linker | | | Sequence |
| | | | | (described | Acyl- | | modification |
| | | SEQ | Albumin | N→C | ation | C- | with respect |
| Peptide | Sequence | ID NO | binding moiety | term) | site | term. | to glucagon |
| Peptide 280 | H(Aib)HGS(αMePhe)TS DVSK(αMePhe)LDSRAA K(O2Oc-O2Oc-γE-C20diacid)20D(αMePhe) VQ(Aib)IANT-amide | 284 | C20diacid | γE-(O2Oc)-(O2Oc) | 20 | Amide | 2Aib, 3H, 5S, 6αMePhe, 10V, 13αMePhe, 18A, 20K, 22αMePhe, 25Aib, 26I, 27A |
| Peptide 281 | HSHGS(αMePhe)TSDVS K(αMePhe)LDSRAAK (O2Oc-O2Oc-γE-γE-C20diacid)20D(αMePhe) VQ(Aib)IANT-amide | 285 | C20diacid | γE-γE-(O2Oc)-(O2Oc) | 20 | Amide | 3H, 5S, 6αMePhe, 10V, 13αMePhe, 18A, 20K, 22αMePhe, 25Aib, 26I, 27A |
| Peptide 282 | H(Aib)HGSFTSDVSK (αMePhe)LDSRAAK(O2Oc-O2Oc-γE-γE-C20diacid)20D(αMePhe) VQ(Aib)IANT-amide | 286 | C20diacid | γE-γE-(O2Oc)-(O2Oc) | 20 | Amide | 2Aib, 3H, 5S, 10V, 13αMePhe, 18A, 20K, 22αMePhe, 25Aib, 26I, 27A |
| Peptide 283 | H(Aib)HGS(αMePhe)TS DVSKYLDSRAAK(O2Oc-O2Oc-γE-γE-C20diacid)20D(αMePhe) VQ(Aib)IANT-amide | 287 | C20diacid | γE-γE-(O2Oc)-(O2Oc) | 20 | Amide | 2Aib, 3H, 5S, 6αMePhe, 10V, 18A, 20K, 22αMePhe, 25Aib, 26I, 27A |
| Peptide 284 | HSHGS(αMePhe)TSDVS K(αMePhe)LDSRAAK (O2Oc-O2Oc-γE-C18diacid)20D(αMePhe) VQ(Aib)IANT-amide | 288 | C18diacid | γE-(O2Oc)-(O2Oc) | 20 | Amide | 3H, 5S, 6αMePhe, 10V, 13αMePhe, 18A, 20K, 22αMePhe, 25Aib, 26I, 27A |
| Peptide 285 | H(Aib)HGSFTSDVSK(QM ePhe)LDSRAAK(O2Oc-O2Oc-γE-C18diacid)20D(αMePhe) VQ(Aib)IANT-amide | 289 | C18diacid | γE-(O2Oc)-(O2Oc) | 20 | Amide | 2Aib, 3H, 5S, 10V, 13αMePhe, 18A, 20K, 22αMePhe, 25Aib, 26I, 27A |
| Peptide 286 | H(Aib)HGS(αMePhe)TS DVSKYLDSRAAK(O2Oc-O2Oc-γE-C18diacid)20D(αMePhe) VQ(Aib)IANT-amide | 290 | C18diacid | γE-(O2Oc)-(O2Oc) | 20 | Amide | 2Aib, 3H, 5S, 6αMePhe, 10V, 18A, 20K, 22αMePhe, 25Aib, 26I, 27A |
| Peptide 287 | H(Aib)HGS(αMePhe)TS DVSK(αMePhe)LDSRAA K(O2Oc-O2Oc-γE-C18diacid)20DFVQ(Aib) IANT-amide | 291 | C18diacid | γE-(O2Oc)-(O2Oc) | 20 | Amide | 2Aib, 3H, 5S, 6αMePhe, 10V, 13αMePhe, 18A, 20K, 25Aib, 26I, 27A |
| Peptide 288 | H(Aib)HGS(αMePhe)TS DVSK(αMePhe)LDSRAA K(O2Oc-O2Oc-γE-C18diacid)20D(αMePhe) VQWIANT-amide | 292 | C18diacid | γE-(O2Oc)-(O2Oc) | 20 | Amide | 2Aib, 3H, 5S, 6αMePhe, 10V, 13αMePhe, 18A, 20K, |

TABLE 2-continued

| | | | | Linker | | | Sequence |
| | | SEQ | Albumin | (described | Acyl- | | modification |
| | | ID | binding | N→C | ation | C- | with respect |
| Peptide | Sequence | NO | moiety | term) | site | term. | to glucagon |
|---|---|---|---|---|---|---|---|
| | | | | | | | 22αMePhe, 26I, 27A |
| Peptide 289 | H(Aib)HGS(αMePhe)TS DVSKYLDSRAAK(O2Oc- O2Oc-γE-γE- C20diacid)20DFVQWIA NT-amide | 293 | C20diacid | γE-γE- (O2Oc)- (O2Oc) | 20 | Amide | 2Aib, 3H, 5S, 6αMePhe, 10V, 18A, 20K, 26I, 27A |
| Peptide 290 | H(Aib)HGSFTSDVSK (αMePhe)LDSRAAK(O2Oc- O2Oc-γE-γE- C20diacid)20DFVQWIA NT-amide | 294 | C20diacid | γE-γE- (O2Oc)- (O2Oc) | 20 | Amide | 2Aib, 3H, 5S, 10V, 13αMePhe, 18A, 20K, 26I, 27A |
| Peptide 291 | H(Aib)HGSFTSDVSKYLD SRAAK(O2Oc-O2Oc-γE- γE- C20diacid)20D(αMePhe) VQWIANT-amide | 295 | C20diacid | γE-γE- (O2Oc)- (O2Oc) | 20 | Amide | 2Aib, 3H, 5S, 10V, 18A, 20K, 22αMePhe, 26I, 27A |
| Peptide 292 | H(Aib)HGS(αMePhe)TS DVSKYLDSRAAK(O2Oc- O2Oc-γE- C18diacid)20DFVQWIA NT-amide | 296 | C18diacid | γE- (O2Oc)- (O2Oc) | 20 | Amide | 2Aib, 3H, 5S, 6αMePhe, 10V, 18A, 20K, 26I, 27A |
| Peptide 293 | H(Aib)HGSFTSDVSK (αMePhe)LDSRAAK(O2Oc- O2Oc-γE- C18diacid)20DFVQWIA NT-amide | 297 | C18diacid | γE- (O2Oc)- (O2Oc) | 20 | Amide | 2Aib, 3H, 5S, 10V, 13αMePhe, 18A, 20K, 26I, 27A |
| Peptide 294 | H(Aib)HGSFTSDVSKYLD SRAAK(O2Oc-O2Oc-γE- C18diacid)20D(αMePhe) VQWIANT-amide | 298 | C18diacid | γE- (O2Oc)- (O2Oc) | 20 | Amide | 2Aib, 3H, 5S, 10V, 18A, 20K, 22αMePhe, 26I, 27A |
| Peptide 295 | H(Aib)HGS(αMePhe)TS DVSK(AIb)LDSRAAK (O2Oc-O2Oc-γE-γE- C20diacid)20D(αMePhe) VQ(Aib)IANT-amide | 299 | C20diacid | γE-γE- (O2Oc)- (O2Oc) | 20 | Amide | 2Aib, 3H, 5S, 6αMePhe, 10V, 13Aib, 18A, 20K, 22αMePhe, 25Aib, 26I, 27A |
| Peptide 296 | H(Aib)HGS(αMePhe)TS DVSK(Aib)LDSRAAK (O2Oc-O2Oc-γE- C18diacid)20D(αMePhe) VQ(Aib)IANT-amide | 300 | C18diacid | γE- (O2Oc)- (O2Oc) | 20 | Amide | 2Aib, 3H, 5S, 6αMePhe, 10V, 13Aib, 18A, 20K, 22αMePhe, 25Aib, 26I, 27A |
| Peptide 297 | H(Aib)HGS(αMePhe)TS DVSR(αMePhe)LDSRAA K(O2Oc-O2Oc-γE- C18diacid)20D(αMePhe) VQ(Aib)IANT-amide | 301 | C18diacid | γE- (O2Oc)- (O2Oc) | 20 | Amide | 2Aib, 3H, 5S, 6αMePhe, 10V, 12R, 13αMePhe, 18A, 20K, 22αMePhe, 25Aib, 26I, 27A |
| Peptide 298 | H(Aib)HGS(αMePhe)TS DVSR(αMePhe)LDSRAA K(O2Oc-O2Oc-γE-γE- C20diacid)20D(αMePhe) VQ(Aib)IANT-amide | 302 | C20diacid | γE-γE- (O2Oc)- (O2Oc) | 20 | Amide | 2Aib, 3H, 5S, 6αMePhe, 10V, 12R, 13αMePhe, 18A, 20K, 22αMePhe, 25Aib, 26I, 27A |

TABLE 2-continued

| | | | | Linker | | | Sequence |
|---|---|---|---|---|---|---|---|
| | | | | (described | Acyl- | | modification |
| | | SEQ | Albumin | N→C | ation | C- | with respect |
| Peptide | Sequence | ID NO | binding moiety | term) | site | term. | to glucagon |
| Peptide 299 | H(Aib)HGS(αMePhe)TS DVSK(αMePhe)LDSRAA K(O2Oc-O2Oc-γE-γE- C20diacid)20D(αMePhe) VQ(Aib)IAET-amide | 303 | C20diacid | γE-γE- (O2Oc)- (O2Oc) | 20 | Amide | 2Aib, 3H, 5S, 6αMePhe, 10V, 13αMePhe, 18A, 20K, 22αMePhe, 25Aib, 26I, 27A, 28E |
| Peptide 300 | H(Aib)HGS(αMePhe)TS DVSK(αMePhe)LDSRAA K(O2Oc-O2Oc-γE- C18diacid)20D(αMePhe) VQ(Aib)IAET-amide | 304 | C18diacid | γE- (O2Oc)- (O2Oc) | 20 | Amide | 2Aib, 3H, 5S, 6αMePhe, 10V, 13αMePhe, 18A, 20K, 22αMePhe, 25Aib, 26I, 27A, 28E |
| Peptide 301 | H(Aib)HGS(αMePhe)TS DVSK(αMePhe)LDSRAA K(O2Oc-O2Oc-γE- C18diacid)20D(αMePhe) IA(Aib)IAET-amide | 305 | C18diacid | γE- (O2Oc)- (O2Oc) | 20 | Amide | 2Aib, 3H, 5S, 6αMePhe, 10V, 13αMePhe, 18A, 20K, 22αMePhe, 23I, 24A, 25Aib, 26I, 27A, 28E |
| Peptide 302 | H(Aib)HGS(αMePhe)TS DVSK(αMePhe)LDSRAA K(O2Oc-O2Oc-γE-γE- C20diacid)20D(αMePhe) IA(Aib)IAET-amide | 306 | C20diacid | γE-γE- (O2Oc)- (O2Oc) | 20 | Amide | 2Aib, 3H, 5S, 6αMePhe, 10V, 13αMePhe, 18A, 20K, 22αMePhe, 23I, 24A, 25Aib, 26I, 27A, 28E |
| Peptide 303 | H(Aib)HGS(αMePhe)TS DVSK(αMePhe)LDSRAA K(O2Oc-O2Oc-γE- C18diacid)20D(αMePhe) VQ(Aib)IANT-acid | 307 | C18diacid | γE- (O2Oc)- (O2Oc) | 20 | Acid | 2Aib, 3H, 5S, 6αMePhe, 10V, 13αMePhe, 18A, 20K, 22αMePhe, 25Aib, 26I, 27A |
| Peptide 304 | H(Aib)HGS(αMePhe)TS DVSK(αMePhe)LDSRAA K(O2Oc-O2Oc-γE-γE- C20diacid)20D(αMePhe) VQ(Aib)IANT-acid | 308 | C20diacid | γE-γE- (O2Oc)- (O2Oc) | 20 | Acid | 2Aib, 3H, 5S, 6αMePhe, 10V, 13αMePhe, 18A, 20K, 22αMePhe, 25Aib, 26I, 27A |
| Peptide 305 | H(Aib)HGTFTSDVSK (αMePhe)LDSRAAK(O2Oc- O2Oc-γE-γE- C20diacid)20DFVQWIA NT-amide | 309 | C20diacid | γE-γE- (O2Oc)- (O2Oc) | 20 | Amide | 2Aib, 3H, 10V, 13αMePhe, 18A, 20K, 26I, 27A |
| Peptide 306 | H(Aib)QGTFTSDVSK (αMePhe)LDSRAAK(O2Oc- O2Oc-γE- C18diacid)20DFVEWIA NT-amide | 310 | C18diacid | γE- (O2Oc)- (O2Oc) | 20 | Amide | 2Aib, 10V, 13αMePhe, 18A, 20K, 24E, 26I, 27A |
| Peptide 307 | H(Aib)QGTFTSDVSK (αMePhe)LDSRAAK(O2Oc- O2Oc-γE- C18diacid)20DFVRWIA NT-amide | 311 | C18diacid | γE- (O2Oc)- (O2Oc) | 20 | Amide | 2Aib, 10V, 13αMePhe, 18A, 20K, 24R, 26I, 27A |

TABLE 2-continued

| | | | | | Linker | | | Sequence |
| | | | | SEQ | (described | Acyl- | | modification |
| | | | Albumin | ID | N→C | ation | C- | with respect |
| Peptide | Sequence | | NO | binding moiety | term) | site | term. | to glucagon |
|---|---|---|---|---|---|---|---|---|
| Peptide 308 | H(Aib)QGTFTSDVSK (αMePhe)LDTRAAK(O2Oc-O2Oc-γE-C18diacid)20DFVQWIA NT-amide | | 312 | C18diacid | γE-(O2Oc)-(O2Oc) | 20 | Amide | 2Aib, 10V, 13αMePhe, 16T, 18A, 20K, 26I, 27A |
| Peptide 309 | H(Ab)QGTFTSDVSK (αMePhe)LDERAAK(O2Oc-O2Oc-γE-C18diacid)20DFVQWIA NT-amide | | 313 | C18diacid | γE-(O2Oc)-(O2Oc) | 20 | Amide | 2Aib, 10V, 13αMePhe, 16E, 18A, 20K, 26I, 27A |
| Peptide 310 | H(Aib)QGTFTSDVSK (αMePhe)LDSRAAK(O2Oc-O2Oc-γE-C18diacid)20DFVQWLE AGG-amide | | 314 | C18diacid | γE-(O2Oc)-(O2Oc) | 20 | Amide | 2Aib, 10V, 13αMePhe, 18A, 20K, 27E, 28A, 29G, 30G |
| Peptide 311 | H(Aib)QGTFTSDVSK (αMePhe)LDSRAAK(O2Oc-O2Oc-γE-C18diacid)20DFVQWLV ET-amide | | 315 | C18diacid | γE-(O2Oc)-(O2Oc) | 20 | Amide | 2Aib, 10V, 13αMePhe, 18A, 20K, 27V, 28E |
| Peptide 312 | H(Aib)QGTFTSDYSK (αMePhe)LDSRRAK(O2Oc-O2Oc-γE-C18diacid)20DFVQWLV ((PEG)4)-amide | | 316 | C18diacid | γE-(O2Oc)-(O2Oc) | 20 | Amide | 2Aib, 10V, 13αMePhe, 18A, 20K, 27V, 28(PEG)4, des29 |
| Peptide 313 | H(Aib)QGTFTSDVSK (αMePhe)LDSR(Aib)AK (O2Oc-O2Oc-γE-C18diacid)20DFVQWLL NT-acid | | 317 | C18diacid | γE-(O2Oc)-(O2Oc) | 20 | Acid | 2Aib, 10V, 13αMePhe, 18Aib, 20K, 27L |
| Peptide 314 | H(Aib)QGTFTSDVSK (αMePhe)LDSR(Aib)AK (O2Oc-O2Oc-γE-C18diacid)20DFVQ(Aib) LVAT-amide | | 318 | C18diacid | γE-(O2Oc)-(O2Oc) | 20 | Amide | 2Aib, 10V, 13αMePhe, 18Aib, 20K, 25Aib, 27V, 28A |
| Peptide 315 | H(Aib)QGTFTSDVSK (αMePhe)LDSRAAK(O2Oc-O2Oc-γE-C18diacid)20DFVQ(Aib) LVAT-amide | | 319 | C18diacid | γE-(O2Oc)-(O2Oc) | 20 | Amide | 2Aib, 10V, 13αMePhe, 18A, 20K, 25Aib, 27V, 28A |
| Peptide 316 | HSQGTFTSDYSK(αMePhe) LEEEAVK(O2Oc-O2Oc-γE-stearOOH)20LFIRWLM NT-amide | | 320 | C18diacid | γE-(O2Oc)-(O2Oc) | 20 | Amide | 13αMeF, 15E, 16E, 17E, 18A, 19V, 20K, 21L, 23I, 24R |
| Peptide 317 | H(Aib)QGTFTSDVSK (αMePhe)LD(Aib)RAAK (O2Oc-O2Oc-γE-C18diacid)20DFVQWIA NT-amide | | 321 | C18diacid | γE-(O2Oc)-(O2Oc) | 20 | Amide | 2Aib, 10V, 13αMePhe, 16Aib, 18A, 20K, 25Aib, 26I, 27A |
| Peptide 318 | H(αMeSer)QGTFTSDVS K(αMePhe)LDSRAAK (O2Oc-O2Oc-γE-C18diacid)20DFVQWIA NT-amide | | 322 | C18diacid | γE-(O2Oc)-(O2Oc) | 20 | Amide | 2αMeSer, 10V, 13αMePhe, 18A, 20K, 26I, 27A |
| Peptide 319 | HS(αMeGln)GTFTSDVS K(αMePhe)LDSRAAK (O2Oc-O2Oc-γE-C18diacid)20DFVQWIA NT-amide | | 323 | C18diacid | γE-(O2Oc)-(O2Oc) | 20 | Amide | 3αMeGln, 10V 13αMePhe, 18A, 20K, 26I, 27A |

TABLE 2-continued

Peptides Modified at Position 20

| Peptide | Sequence | SEQ ID NO | Aibumin binding moiety | Linker (described N→C term) | Acyl-ation site | C-term. | Sequence modification with respect to glucagon |
|---------|----------|-----------|------------------------|------------------------------|------------------|---------|-----------------------------------------------|
| Peptide 320 | H(DSer)QGTFTSDVSK (αMePhe)LDSRAAK(O2Oc-O2Oc-γE-C18diacid)20DFVQWIA NT-amide | 324 | C18diacid | γE-(O2Oc)-(O2Oc) | 20 | Amide | 2ds, 10V, 13αMePhe, 18A, 20K, 26I, 27A |
| Peptide 321 | H(Aib)QGS(αMePhe)TS DVSK(αMePhe)LDSRAA K(O2Oc-O2Oc-γE-C18diacid)20D(αMePhe) VQ(Aib)IANT-amide | 325 | C18diacid | γE-(O2Oc)-(O2Oc) | 20 | Amide | 2Aib, 5S, 6αMePhe, 10V, 13αMePhe, 18A, 20K, 22αMePhe, 25Aib, 26I, 27A |
| Peptide 322 | H(Aib)QGS(αMePhe)TS DVSK(αMePhe)LDSRAA K(O2Oc-O2Oc-γE-γE-C20diacid)20D(αMePhe) VQ(Aib)IANT-amide | 326 | C20diacid | γE-(O2Oc)-(O2Oc) | 20 | Amide | 2Aib, 5S, 6αMePhe, 10V, 13αMePhe, 18A, 20K, 22αMePhe, 25Aib, 26I, 27A |
| Peptide 323 | HS(αMeGln)GS(αMePhe) TSDVSK(αMePhe)LDS RAAK(O2Oc-O2Oc-γE-C18diacid)20D(αMePhe) VQ(Aib)IANT-amide | 327 | C18diacid | γE-(O2Oc)-(O2Oc) | 20 | Amide | 3αMeGln, 5S, 6αMePhe, 10V, 13αMePhe, 18A, 20K, 22αMePhe, 25Aib, 26I, 27A |
| Peptide 324 | HS(ß-dimethylGln)GS(αMePhe) TSDVSK(αMePhe)LD SRAAK(O2Oc-O2Oc-γE-C18diacid)20D(αMePhe) VQ(Aib)IANT-amide | 328 | C18diacid | γE-(O2Oc)-(O2Oc) | 20 | Amide | 3ß-dimethylGln, 5S, 6αMePhe, 10V, 13αMePhe, 18A, 20K, 22αMePhe, 25Aib, 26I, 27A |
| Peptide 325 | HS(N-MeGln)GS(αMePhe)TS DVSK(αMePhe)LDSRAA K(O2Oc-O2Oc-γE-C18diacid)20D(αMePhe) VQ(Aib)IANT-amide | 329 | C18diacid | γE-(O2Oc)-(O2Oc) | 20 | Amide | 3N-MeGln, 5S, 6αMePhe, 10V, 13αMePhe, 18A, 20K, 22αMePhe, 25Aib, 26I, 27A |
| Peptide 326 | HS(dGln)GS(αMePhe)T SDVSK(αMePhe)LDSRA AK(O2Oc-O2Oc-γE-C18diacid)20D(αMePhe) VQ(Aib)IANT-amide | 330 | C18diacid | γE-(O2Oc)-(O2Oc) | 20 | Amide | 3dGln, 5S, 6αMePhe, 10V, 13αMePhe, 18A, 20K, 22αMePhe, 25Aib, 26I, 27A |
| Peptide 327 | H(Acpr)QGS(αMePhe)T SDVSK(αMePhe)LDSRA AK(O2Oc-O2Oc-γE-C18diacid)20D(αMePhe) VQ(Aib)IANT-amide | 331 | C18diacid | γE-(O2Oc)-(O2Oc) | 20 | Amide | 2Acpr, 5S, 6αMePhe, 10V, 13αMePhe, 18A, 20K, 22αMePhe, 25Aib, 26I, 27A |

TABLE 2-continued

Peptides Modified at Position 20

| Peptide | Sequence | SEQ ID NO | Aibumin binding moiety | Linker (described N→C term) | Acyl- ation site | C- term. | Sequence modification with respect to glucagon |
|---|---|---|---|---|---|---|---|
| Peptide 328 | H(Acbu)QGS(αMePhe) TSDVSK(αMePhe)LDSR AAK(O2Oc-O2Oc-γE- C18diacid)20D(αMePhe) VQ(Aib)IANT-amide | 332 | C18diacid | γE- (O2Oc)- (O2Oc) | 20 | Amide | 2Acbu, 5S, 6αMePhe, 10V, 13αMePhe, 18A, 20K, 22αMePhe, 25Aib, 26I, 27A |
| Peptide 329 | H(αMeSer)QGS(αMePhe) TSDVSK(αMePhe)LDS RAAK(O2Oc-O2Oc-γE- C18diacid)20D(αMePhe) VQ(Aib)IANT-amide | 333 | C18diacid | γE- (O2Oc)- (O2Oc) | 20 | Amide | 2αMeSer, 5S, 6αMePhe, 10V, 13αMePhe, 18A, 20K, 22αMePhe, 25Aib, 26I, 27A |
| Peptide 330 | H(dSer)QGS(αMePhe)T SDVSK(αMePhe)LDSRA AK(O2Oc-O2Oc-γE- C18diacid)20D(αMePhe) VQ(Aib)IANT-amide | 334 | C18diacid | γE- (O2Oc)- (O2Oc) | 20 | Amide | 2dSer, 5S, 6αMePhe, 10V, 13αMePhe, 18A, 20K, 22αMePhe, 25Aib, 26I, 27A |
| Peptide 331 | H(Aib)QGTFTSDVSK (αMePhe)LDSRRAK(O2Oc- O2Oc-γE- C18diacid)20DFVRWLL E(Aib)G-acid | 335 | C18diacid | γE- (O2Oc)- (O2Oc) | 20 | Acid | 2Aib, 10V, 13αMePhe, 20K, 24R, 27L, 28E, 29Aib, 30G |
| Peptide 332 | H(Aib)QGTFTSDVSK (αMePhe)LDSRRAK(O2Oc- O2Oc-γE- C18diacid)20DFVQWLL E(Aib)G-acid | 336 | C18diacid | γE- (O2Oc)- (O2Oc) | 20 | Acid | 2Aib, 10V, 13αMePhe, 20K, 27L, 28E, 29Aib, 30G |
| Peptide 333 | H(Aib)QGTFTSDVSK (αMePhe)LDSRRAK(O2Oc- O2Oc-γE- C18diacid)20DFVQWLL (Aib)TE-acid | 337 | C18diacid | γE- (O2Oc)- (O2Oc) | 20 | Acid | 2Aib, 10V, 13αMePhe, 20K, 27L, 28Aib, 30E |
| Peptide 334 | H(Aib)QGTFTSDYSK (αMePhe)LDSRRAK(γE- C18diacid)20DFVQWLA (Aib)E-acid | 338 | C18diacid | γE | 20 | Acid | 2Aib, 13αMePhe, 20K, 27A, 28Aib, 30E |
| Peptide 335 | H(Ab)QGTFTSDYSK (αMePhe)LDSRRAK(γE- C18diacid)20DFVQWLL E(Aib)G-acid | 339 | C18diacid | γE | 20 | Acid | 2Aib, 13αMePhe, 20K, 27L, 28E, 29Aib, 30G |
| Peptide 336 | H(Ab)QGTFTSDYSK (αMePhe)LDSRRAK(γE- C18diacid)20DFVQWLIS E-acid | 340 | C18diacid | γE | 20 | Acid | 2Aib, 13αMePhe, 20K, 27I, 28S, 29E |
| Peptide 337 | H(Aib)QGTFTSDYSK (αMePhe)LDSRRAK(γE- C18diacid)20DFVQWLL (Aib)T-acid | 341 | C18diacid | γE | 20 | Acid | 2Aib, 13αMePhe, 20K, 27L, 28Aib |
| Peptide 338 | H(Aib)QGTFTSDYSK (αMePhe)LD(Aib)RRAK (γE-C18diacid)20DFVQW LL(Aib)T-acid | 342 | C18diacid | γE | 20 | Acid | 2Aib, 13αMePhe, 16Aib, 20K, 27L, 28Aib |

TABLE 2-continued

| | | | | Linker (described N→C term) | Acyl-ation site | C-term. | Sequence modification with respect to glucagon |
|---|---|---|---|---|---|---|---|
| Peptide | Sequence | SEQ ID NO | Albumin binding moiety | | | | |
| Peptide 339 | H(Aib)QGTFTSDYSK(αMePhe)LDSRRAK(γE-C18diacid)20DFVQWLL(Aib)E-acid | 343 | C18diacid | γE | 20 | Acid | 2Aib, 13αMePhe, 20K, 27L, 28Aib, 29E |
| Peptide 340 | H(Aib)QGTFTSDYSK(αMePhe)LDSRRAK(γE-C18diacid)20DFVQWLL(Aib)TE-acid | 344 | C18diacid | γE | 20 | Acid | 2Aib, 13αMePhe, 20K, 27L, 28Aib, 30E |
| Peptide 341 | H(Aib)QGTFTSDYSK(αMePhe)LDSRRAK(γE-C18diacid)20DFVQWLLE(Aib)T-acid | 345 | C18diacid | γE | 20 | Acid | 2Aib, 13αMePhe, 20K, 27L 28E, 29Aib, 30T |
| Peptide 342 | H(Aib)QGTFTSDVSK(αMePhe)LDSRAAK(γE-C18diacid)20DFVQWIANT-acid | 346 | C18diacid | γE | 20 | Acid | 2Aib, 10V, 13αMePhe, 18A, 20K, 26I, 27A |
| Peptide 343 | H(Aib)QGTFTSDVSK(αMePhe)LDSRAAK(γE-γE-O2Oc-O2Oc-γE-γE-C18diacid)20DFVQWIANT-amide | 347 | C18diacid | γE-γE(O2Oc 1-(O2Oc)-γE-γE | 20 | Amide | 2Aib, 10V, 13αMePhe, 18A, 20K, 26I, 27A |
| Peptide 521 | H(Aib)QGTFTSDVSK(αMePhe)LDSERAK(O2Oc-O2Oc-γE-C18diacid)20DFVQWLEAGG-acid | 532 | C18diacid | γE-(O2Oc)-(O2Oc) | 20 | Acid | 2Aib, 10V, 13αMePhe, 17E, 20K, 27E, 28A, 29G, 30G |
| Peptide 522 | H(Aib)QGTFTSDVSK(αMePhe)LDSERAK(O2Oc-O2Oc-γE-C18diacid)20DFVAWLEAGG-acid | 533 | C18diacid | γE-(O2Oc)-(O2Oc) | 20 | Acid | 2Aib, 10V, 13αMePhe, 17E, 20K, 24A, 27E, 28A, 29G, 30G |
| Peptide 523 | H(Ab)QGTFTSDVSK(αMePhe)LDSERAK(O2Oc-O2Oc-γE-C20diacid)20DFVAWLEAGG-acid | 534 | C20diacid | γE-(O2Oc)-(O2Oc) | 20 | Acid | 2Aib, 10V, 13αMePhe, 17E, 20K, 24A, 27E, 28A, 29G, 30G |
| Peptide 524 | H(Aib)QGTFTSDVSE(αMePhe)LDSERAK(O2Oc-O2Oc-γE-C18diacid)20DFVRWLEAGG-acid | 535 | C18diacid | γE-(O2Oc)-(O2Oc) | 20 | Acio | 2Aib, 10V, 12E 13αMePhe, 17E, 20K, 24R, 27E, 28A, 29G, 30G |
| Peptide 525 | H(Aib)QGTFTSDVSK(αMePhe)LDSERAK(O2Oc-O2Oc-γE-C18diacid)20DFVQWLEA(Aib)G-acid | 536 | C18diacid | γE-(O2Oc)-(O2Oc) | 20 | Acid | 2Aib, 10V, 13αMePhe, 17E, 20K, 27E, 28A, 29Aib, 30G |
| Peptide 526 | H(Aib)QGTFTSDVSK(αMePhe)LDSERAK(O2Oc-O2Oc-γE-C18diacid)20DFVAWLEA(Aib)G-acid | 537 | C18diacid | γE-(O2Oc)-(O2Oc) | 20 | Acid | 2Aib, 10V, 13αMePhe, 17E, 20K, 24A, 27E, 28A, 29Aib, 30G |

In some aspects, the peptide comprises the sequence: X1-X2-X3-G-X5-X6-T-S-D-X10-S-K-X13-L-X15-X16-X17-X18-X19-X20-X21-X22-X23-X24-X25-X26-X27-X28-X29-X30-X31-Z, wherein X1 is H or ((1H-imidazol-4-yl)methyl)glycine (NHis), X2 is S or Aminoisobutyric acid (Aib), X3 is Q, H, or I, X5 is T or S, X6 is F or αMethyl-Phenylalanine (αMePhe), X10 is Y or V, X13 is Y, αMePhe, Aib, or Diphenylalanine (Dip), X15 is D or E, X16 is S, E, or L, X17 is R, Q, or E, X18 is R, A, or Aib, X19 is A or V, X20 is Q or R, X21 is D or L, X22 is F or αMePhe, X23 is V or I, X24 is Q or K, wherein the K can comprise an acyl moiety and/or can be lipidated, X25 is W, Aib, or S, X26 is L or I, X27 is M, V, L, or A, X28 is N, E, or Aib, X29 is T, Aib, G, or not present, X30 is not present, Aib, or G, X31 is not present or G, and Z is amide or acid (SEQ ID NO: 415), wherein the peptide does not comprise SEQ ID NO: 1.

In some aspects, the residue at position 24 is acylated. In some aspects, the residue at position 24 is lipidated. In some aspects, the lipid is selected from the group consisting of a palmitoyl group, stearoyl group, lauryl group, myristoyl group, margaroyl group, octadecanedioic acid (C18diacid), and icosanedioic acid (C20diacid). In some aspects, the lipid is selected from the group consisting of an octadecanedioic acid (C18diacid), and icosanedioic acid (C20diacid).

In some aspects, the lipid attached to the residue at position 24 is attached via a linker. In some aspects, the linker is selected from the group consisting of (O2Oc), (O2Oc)-(O2Oc), (O2Oc)-γE-(O2Oc), (PEG)2-(PEG)2-γE-γE, (PEG)2-γE-(PEG)2-γE, γE, γE-(O2Oc), γE-(O2Oc)-(O2Oc), γE-(O2Oc)-γE-(O2Oc), γE-(PEG)2-(PEG)2, γE-(PEG)2-γE-(PEG)2, γE-(PEG)4, γE-γE, γE-γE-(O2Oc), γE-γE-(O2Oc)-(O2Oc), γE-γE-(PEG)12, γE-γE-(PEG)2-(PEG)2, γE-γE-(PEG)2-γE-γE, γE-γE-(PEG)4, and γE-γE-

(PEG)8. In some aspects, linker is selected from the group consisting of γE, γE-(O2Oc)-(O2Oc), γE-γE-(PEG)2-(PEG)2, γE-γE-(PEG)2-γE-γE, and γE-γE-(O2Oc)-(O2Oc).

In some aspects, the peptide comprises the sequence: H-Aminoisobutyric acid (Aib)-Q-G-T-F-T-S-D-V-S-K-αMethyl-Phenylalanine (αMePhe)-L-X15-X16-R-R-A-Q-D-F-V-K-W-L-X27-X28-X29-X30-Z, wherein X15 is D or E, X16 is S or L, X27 is V or L, X28 is E or Aib, X29 is T, Aib or G, X30 is G or Aib or not present, Z is amide or acid (SEQ ID NO: 416).

In some aspects, the lysine at position 24 is acylated. In some aspects, the lipid is selected from the group consisting of a palmitoyl group, stearoyl group, lauryl group, myristoyl group, margaroyl group, octadecanedioic acid (C18diacid), and icosanedioic acid (C20diacid). In some aspects, the lysine at position 24 is lipidated. In some aspects, the lipid is octadecanedioic acid (C18diacid).

In some aspects, the lipid is linked to the lysine at position 24 via a linker. In some aspects, the linker is selected from the group consisting of (O2Oc), (O2Oc)-(O2Oc), (O2Oc)-γE-(O2Oc), (PEG)2-(PEG)2-γE-γE, (PEG)2-γE-(PEG)2-γE, γE, γE-(O2Oc), γE-(O2Oc)-(O2Oc), γE-(O2Oc)-γE-(O2Oc), γE-(PEG)2-(PEG)2, γE-(PEG)21γE-(PEG)2, γE-(PEG)4, γE-γE, γE-γE-(O2Oc), γE-γE-(O2Oc)-(O2Oc), γE-γE-(PEG)12, γE-γE-(PEG)2-(PEG)2, γE-γE-(PEG)2-γE-γE, γE-γE-(PEG)4, and γE-γE-(PEG)8. In some aspects, the linker is γE-(O2Oc)-(O2Oc).

In certain aspects, GLP-1/glucagon agonist peptides as disclosed have desirable potencies at the glucagon and GLP-1 receptors.

In some aspects, the peptide comprises any one of SEQ ID NOs: 348-395.

In some aspects, the peptide is any one any of the peptides in Table 3.

TABLE 3

Peptides Modified at Position 24

| Peptide | Sequence | Albumin binding moiety | Linker (described N→C term) | Acyl-ation site | C-term. | Sequence modification with respect to glucagon |
|---------|----------|------------------------|----------------------------|-----------------|---------|-----------------------------------------------|
| Peptide 343 | H(Aib)QGSFTSDVSK(Dip)LDSRAAQDFVK(γE-C18diacid)24WIANT-amide | 348 | C18diacid | γE | 24 | Amide | 2Aib, 5S, 10V, 13Dip, 18A, 24K, 26I, 27A |
| Peptide 344 | HSQGS(αMePhe)TSDVSK(Aib)LDSRAAQD(αMePhe)VK(O2OC-O2OC-γE-C18diacid)24(Aib)IAN-amide | 349 | C18diacid | γE-(O2Oc)-(O2Oc) | 24 | Amide | 5S, 6αMePhe, 10V, 13Aib, 18A, 22αMePhe, 24K, 25Aib, 26I, 27A, des29T |
| Peptide 345 | H(Aib)HGTFTSDVSK(αMePhe)LDSQAAQDFVK(O2Oc-O2Oc-γE-C18diacid)24WIANT-amide | 350 | C18diacid | γE-(O2Oc)-(O2Oc) | 2.4 | Amide | 2Aib, 3H, 10V, 13αMePhe, 17Q, 18A, 24K, 26I, 27A |
| Peptide 346 | H(Aib)HGTFTSDVSK(αMePhe)LDSQAAQDFVK(γE-C18diacid)24WIANT-amide | 351 | C18diacid | γE | 24 | Amide | 2Aib, 3H, 10V, 13αMePhe, 17Q, 18A, 24K, 26I, 27A |

TABLE 3-continued

| | | | Linker (described N→C term) | | | Sequence |
|---|---|---|---|---|---|---|
| | | Albumin binding moiety | | Acylation site | C-term. | modification with respect to glucagon |
| Peptide | Sequence | | | | | |
| Peptide 347 | H(Aib)HGTFTSDVSK (αMePhe)LDSQAAQDFVK (γE-C20diacid)24WIANT-amide | 352 | C20diacid | γE | 24 | Amide | 2Aib, 3H, 10V, 13αMePhe, 17O, 18A, 24K, 26I, 27A |
| Peptide 348 | H(Aib)QGS(αMePhe)TS DVSK(αMePhe)LDSQAA QDFVK(O2Oc-O2Oc-γE-C18diacid)24WIANT-amide | 353 | C18diacid | γE-(O2Oc)-(O2Oc) | 24 | Amide | 2Aib, 5S, 6αMePhe, 10V, 13αMePhe, 17Q, 18A, 24K, 26I, 27A |
| Peptide 349 | H(Aib)HGS(αMePhe)TS DVSK(αMePhe)LDSQAA QDFVK(O2Oc-O2Oc-γE-C18diacid)24WIANT-amide | 354 | C18diacid | γE-(O2Oc)-(O2Oc) | 24 | Amide | 2Aib, 3H, 5S, 6αMePhe, 10V, 13αMePhe, 17Q, 18A, 24K, 26I, 27A |
| Peptide 350 | H(Aib)HGS(αMePhe)TS DVSK(αMePhe)LDSQAA QDFVK(O2Oc-O2Oc-γE-C18diacid)24WIANTGG-amide | 355 | C18diacid | γE-(O2Oc)-(O2Oc) | 24 | Amide | 2Aib, 3H, 5S, 6αMePhe, 10V, 13αMePhe, 17Q,18A, 24K, 26I, 27A, 30G, 31G |
| Peptide 351 | H(Aib)HGS(αMePhe)TS DVSK(αMePhe)LDSQAA QDFVK(γE-C18diacid)24WIANT-amide | 356 | C18diacid | γE | 24 | Amide | 2Aib, 3H, 5S, 6αMePhe, 10V, 13αMePhe, 17O,18A, 24K, 26I, 27A |
| Peptide 352 | H(Aib)HGS(αMePhe)TS DVSK(αMePhe)LDSQAA QDFVK((PEG)2-(PEG)2-γE-γE-C18diacid)24WIANT-amide | 357 | C18diacid | γE-γE-(PEG)2-(PEG)2 | 24 | Amide | 2Aib, 3H, 5S, 6αMePhe, 10V, 13αMePhe, 17O, 18A, 24K, 26I, 27A |
| Peptide 353 | H(Aib)HGS(αMePhe)TS DVSK(αMePhe)LDSQAA QDFVK(YE-YE-(PEG)2-γE-γE-C18diacid)24WIANT-amide | 358 | C18diacid | γE-γE-(PEG)2-γE-γE | 24 | Amide | 2Aib, 3H, 5S, 6αMePhe, 10V, 13αMePhe, 17Q, 18A, 24K, 26I, 27A |
| Peptide 354 | H(Aib)HGS(αMePhe)TS DVSK(αMePhe)LDSQAA QDFVK(γE-C20diacid)24WIANT-amide | 359 | C20diacid | γE | 24 | Amide | 2Aib, 3H, 5S, 6αMePhe, 10V, 13αMePhe, 17O,18A, 24K, 26I, 27A |
| Peptide 355 | H(Aib)HGS(αMePhe)TS DVSK(αMePhe)LDSQAA QDFVK((PEG)2-(PEG)2-γE-γE-C20diacid)24WIANT-amide | 360 | C20diacid | γE-γE-(PEG)2-(PEG)2 | 24 | Amide | 2Aib, 3H, 5S, 6αMePhe, 10V, 13αMePhe, 17O, 18A, 24K, 26I, 27A |
| Peptide 356 | H(Aib)HGS(αMePhe)TS DVSK(αMePhe)LDSQAA QDFVK(O2OC-O2OC-γE-C20diacid)24WIANT-amide | 361 | C20diacid | γE-(O2Oc)-(O2Oc) | 24 | Amide | 2Aib, 3H, 5S, 6αMePhe, 10V, 13αMePhe, 17O, 18A, 24K, 26I, 27A |
| Peptide 357 | H(Aib)HGS(αMePhe)TS DVSK(αMePhe)LDSQAA | 362 | C20diacid | γE-γE-(PEG)2- | 24 | Amide | 2Aib, 3H, 5S, 6αMePhe, |

TABLE 3-continued

Peptides Modified at Position 24

| Peptide | Sequence | Albumin binding moiety | Linker (described N→C term) | Acyl-ation site | C-term. | Sequence modification with respect to glucagon |
|---|---|---|---|---|---|---|
| | QDFVK(γE-γE-(PEG)2-γE-γE-C20diacid)24WIANT-amide | | γE-γE | | | 10V, 13αMePhe, 17Q, 18A, 24K, 26I, 27A |
| Peptide 358 | H(Aib)IGS(αMePhe)TSD VSK(αMePhe)LDSQAA QDFVK(O2Oc-O2Oc-γE-C18diacid)24WIANT-amide | 363 | C18diacid | γE-(O2Oc)-(O2Oc) | 24 | Amide | 2Aib, 3I, 5S, 6αMePhe, 10V, 13αMePhe, 17Q,18A, 24K, 26I, 27A |
| Peptide 359 | H(Aib)IGS(αMePhe)TSD VSK(αMePhe)LDSRAAQ DFVK(O2Oc-O2Oc-γE-C18diacid)24WIANT-amide | 364 | C18diacid | γE-(O2Oc)-(O2Oc) | 24 | Amide | 2Aib, 3I, 5S, 6αMePhe, 10V, 13αMePhe, 18A, 24K, 26I, 27A |
| Peptide 360 | H(Aib)IGS(αMePhe)TSD VSK(αMePhe)LDSRAAQ DFVK(O2OC-O2OC-γE-C20diacid)24WIANT-amide | 365 | C20diacid | γE-(O2Oc)-(O2Oc) | 24 | Amide | 2Aib, 3I, 5S, 6αMePhe, 10V, 13αMePhe, 18A, 24K, 26I, 27A |
| Peptide 361 | H(Aib)HGS(αMePhe)TS DVSK(αMePhe)LDSRAA QDFVK(O2Oc-O2Oc-γE-C18diacid)24WIANT-amide | 366 | C18diacid | γE-(O2Oc)-(O2Oc) | 24 | Amide | 2Aib, 3H, 5S, 6αMePhe, 10V 13αMePhe, 18A, 24K, 26I, 27A |
| Peptide 362 | H(Aib)HGS(αMePhe)TS DVSK(αMePhe)LDSRAA QDFVK(O2OC-O2OC-γE-γE-C18diacid)24WIANT-amide | 367 | C18diacid | γE-γE-(O2Oc)-(O2Oc) | 24 | Amide | 2Aib, 3H, 5S, 6αMePhe, 10V, 13αMePhe, 18A, 24K, 26I, 27A |
| Peptide 363 | H(Aib)HGS(αMePhe)TS DVSK(αMePhe)LDSRAA QDFVK(O2OC-O2OC-γE-γE-C18diacid)24WIANTG-amide | 368 | C18diacid | γE-γE-(O2Oc)-(O2Oc) | 24 | Amide | 2Aib, 3H, 5S, 6αMePhe, 10V, 13αMePhe, 18A, 24K, 26I, 27A, 30G |
| Peptide 364 | H(Aib)HGS(αMePhe)TS DVSK(αMePhe)LDSRAA QDFVK(O2OC-O2OC-γE-γE-C18diacid)24WIANTGG-amide | 369 | C18diacid | γE-γE-(O2Oc)-(O2Oc) | 24 | Amide | 2Aib, 3H, 5S, 6αMePhe, 10V, 13αMePhe, 18A, 24K, 26I, 27A, 31G |
| Peptide 365 | H(Aib)HGS(αMePhe)TS DVSK(αMePhe)LDSR(Aib) AQDFVK(O2Oc-O2Oc-γE-C18diacid)24WIANT-amide | 370 | C18diacid | γE-(O2Oc)-(O2Oc) | 24 | Amide | 2Aib, 3H, 5S, 6αMePhe, 10V, 13αMePhe, 18Aib, 24K, 26I, 27A |
| Peptide 366 | H(Aib)HGS(αMePhe)TS DVSK(αMePhe)LDSRAA QDFVK(O2Oc-O2Oc-γE-C18diacid)24(Aib)IANT-amide | 371 | C18diacid | γE-(O2Oc)-(O2Oc) | 24 | Amide | 2Aib, 3H, 5S, 6αMePhe, 10V, 13αMePhe, 18A, 24K, 25Aib, 26I, 27A |
| Peptide 367 | H(Aib)HGS(αMePhe)TS DVSK(αMePhe)LDSRAA QDFVK(O2OC-O2OC-γE- | 372 | C20diacid | γE-(O2Oc)-(O2Oc) | 24 | Amide | 2Aib, 3H, 5S, 6αMePhe, 10V, 13αMePhe, |

TABLE 3-continued

| | | | | | | |
|---|---|---|---|---|---|---|
| | | | Peptides Modified at Position 24 | | | |
| Peptide | Sequence | Albumin binding moiety | Linker (described N→C term) | Acyl-ation site | C-term. | Sequence modification with respect to glucagon |
| | C20diacid)24WIANT-amide | | | | | 18A, 24K, 26I, 27A |
| Peptide 368 | H(Aib)HGS(αMePhe)TS DVSK(αMePhe)LDSR(Aib) AQDFVK(O2OC-O2OC-γE-C20diacid)24WIANT-amide | 373 | C20diacid | γE-(O2Oc)-(O2Oc) | 24 | Amide | 2Aib, 3H, 5S, 6αMePhe, 10V, 13αMePhe, 18Aib, 24K, 26I, 27A |
| Peptide 369 | H(Aib)HGS(αMePhe)TS DVSK(αMePhe)LDSRAA QDFVK(O2OC-O2OC-γE-C20diacid)24(Aib)IANT-amide | 374 | C20diacid | γE-(O2Oc)-(O2Oc) | 24 | Amide | 2Aib, 3H, 5S, 6αMePhe, 10V, 13αMePhe, 18A, 24K, 25Aib, 26I, 27A |
| Peptide 370 | H(Aib)HGS(αMePhe)TS DVSK(αMePhe)LDSQAA QD(αMePhe)VK(O2Oc-O2Oc-γE-C18diacid)24WIANT-amide | 375 | C18diacid | γE-(O2Oc)-(O2Oc) | 24 | Amide | 2Aib, 3H, 5S, 6αMePhe, 10V, 13αMePhe, 17O,18A, 22αMePhe, 24K, 26I, 27A |
| Peptide 371 | H(Aib)HGS(αMePhe)TS DVSK(αMePhe)LDSRAA QD(αMePhe)VK(O2OC₂-γE-γE-C18diacid)24WIANT-amide | 376 | C18diacid | γE-γE-(O2Oc)-(O2Oc) | 24 | Amide | 2Aib, 3H, 5S, 6αMePhe, 10V, 13αMePhe, 18A, 22αMePhe, 24K, 26I, 27A |
| Peptide 372 | H(Ab)HGS(αMePhe)TS DVSK(αMePhe)LDSRAA QD(αMePhe)VK(O2OC₂-γE-γE-C18diacid)24(Aib)IANT-amide | 377 | C18diacid | γE-γE-(O2Oc)-(O2Oc) | 24 | Amide | 2Aib, 3H, 5S, 6αMePhe, 10V, 13QMePhe, 18A, 22αMePhe, 24K, 25Aib, 26I, 27A |
| Peptide 373 | H(Aib)HGS(αMePhe)TS DVSK(αMePhe)LDSRAA QD(αMePhe)VK(O2OC₂-γE-γE-C18diacid)24(Aib)IANT GG-amide | 378 | C18diacid | γE-γE-(O2Oc)-(O2Oc) | 24 | Amide | 2Aib, 3H, 5S, 6αMePhe, 10V, 13αMePhe, 18A, 22αMePhe, 24K, 25Aib, 26I, 27A, 30G, 31G |
| Peptide 374 | H(Aib)HGS(αMePhe)TS DVSK(αMePhe)LDSRAA QD(αMePhe)VK(O2OC₂-γE-γE-C20diacid)24WIANT-amide | 379 | C20diacid | γE-γE-(O2Oc)-(O2Oc) | 24 | Amide | 2Aib, 3H, 5S, 6αMePhe, 10V, 13αMePhe, 18A, 22αMePhe, 24K, 26I, 27A |
| Peptide 375 | H(Aib)HGS(αMePhe)TS DVSK(αMePhe)LDSRAA QD(αMePhe)VK(O2OC₂-γE-γE-C20diacid)24(Aib)IANT-amide | 380 | C20diacid | γE-γE-(O2Oc)-(O2Oc) | 24 | Amide | 2Aib, 3H, 5S, 6OMePhe, 10V, 13αMePhe, 18A, 22αMePhe, 24K, 25Aib, 26I ,27A |
| Peptide 376 | H(Aib)HGS(αMePhe)TS DVSK(αMePhe)LDSRAA QD(αMePhe)VK(O2OC₂- | 381 | C20diacid | γE-γE-(O2Oc)-(020° C.) | 24 | Amide | 2Aib, 3H, 5S, 6αMePhe, 10V, |

TABLE 3-continued

| | | | | | | |
|---|---|---|---|---|---|---|
| | | | Linker | | | Sequence |
| | | Albumin | (described | Acyl- | | modification |
| | | binding | N→C | ation | C- | with respect |
| Peptide | Sequence | moiety | term) | site | term. | to glucagon |
| | γE-γE-C20diacid)24(Aib)IANT GG-amide | | | | | 13αMePhe, 18A, 22oMePhe, 24K, 25Aib, 26I,27A, 30G, 31G |
| Peptide 377 | H(Aib)HGS(αMePhe)TS DVSK(αMePhe)LDSRAA QDFVK(O2OC₂-γE-γE-C20diacid)24WIANT-amide | 382 | C20diacid | γE-γE-(O2Oc)-(O2Oc) | 24 | Amide | 2Aib, 3H, 5S, 6αMePhe, 10V, 13αMePhe, 18A, 24K, 26I, 27A |
| Peptide 378 | H(Aib)HGS(αMePhe)TS DVSK(αMePhe)LDSRAA QD(αMePhe)VK(O2OC₂-γE-γE-C18diacid)24SIANT-amide | 383 | C18diacid | γE-γE-(O2Oc)-(O2Oc) | 24 | Amide | 2Aib, 3H, 5S, 6αMePhe, 10V, 13QMePhe, 18A, 22QMePhe, 24K, 25S, 26I, 27A |
| Peptide 379 | H(Aib)HGS(αMePhe)TS DVSK(αMePhe)LDSRAA QD(αMePhe)VK(O2OC₂-γE-C18diacid)24SIANT-amide | 384 | C18diacid | γE-γE-(O2Oc)-(O2Oc) | 24 | Amide | 2Aib, 3H, 5S, 6αMePhe, 10V, 13αMePhe, 18A, 22αMePhe, 24K, 25S, 26I, 27A |
| Peptide 380 | (NHis)SHGS(αMePhe)T SDVSK(αMePhe)LDSRA AQDFVK(O2OC₂-γE-γE-C20diacid)24WIANT-amide | 385 | C20diacid | γE-γE-(O2Oc)-(O2Oc) | 24 | Amide | 1NHis, 3H, 5S, 6αMePhe, 10V, 13αMePhe, 18A, 24K, 26I, 27A |
| Peptide 381 | H(Aib)HGS(αMePhe)TS DVSK(αMePhe)LDSRAA QDFVK(O2OC-O2OC-γE-γE-C18diacid)24SIANTGG-amide | 386 | C18diacid | γE-γE-(O2Oc)-(O2Oc) | 24 | Amide | 2Aib, 3H, 5S, 6αMePhe, 10V, 13αMePhe, 18A, 24K, 25S, 26I, 27A, 30G, 31G |
| Peptide 382 | H(Aib)HGS(αMePhe)TS DVSK(αMePhe)LDSR (Aib)AQDFVK(O2OC-O2OC-γE-γE-C18diacid)24SIANTGG-amide | 387 | C18diacid | γE-γE-(O2Oc)-(O2Oc) | 24 | Amide | 2Aib, 3H, 5S, 6αMePhe, 10V, 13αMePhe, 18Aib, 24K, 25S, 26I, 27A, 30G, 31G |
| Peptide 383 | H(Aib)HGS(αMePhe)TS DVSK(αMePhe)LDSQAA QD(αMePhe)VK(O2Oc-O2Oc-γE-γE-C18diacid)24(Aib)IANT-amide | 388 | C18diacid | γE-(O2Oc)-(O2Oc) | 24 | Amide | 2Aib, 3H, 5S, 6αMePhe, 10V, 13αMePhe, 17Q, 18A, 22αMePhe, 24K, 25Aib, 26I, 27A |
| Peptide 384 | H(Aib)HGS(αMePhe)TS DVSK(αMePhe)LDSQAA QD(αMePhe)VK(O2OC-O2OC-γE-γE-C20diacid)24(Aib)IANT-amide | 389 | C20diacid | γE-γE-(O2Oc)-(O2Oc) | 24 | Amide | 2Aib, 3H, 5S, 6αMePhe, 10V, 13QMePhe, 17Q, 18A, 22αMePhe, 24K, 25Aib, 26I, 27A |

TABLE 3-continued

| | | | Linker | | | Sequence |
| | | Albumin | (described | Acyl- | | modification |
| | | binding | N→C | ation | C- | with respect |
| Peptide | Sequence | moiety | term) | site | term. | to glucagon |
| --- | --- | --- | --- | --- | --- | --- |
| Peptide 385 | HSQGTFTSDYSK(αMePhe) LEEEAVRLFIK(O2OC- O2OC-γE- stearOOH)24WLMNT- amide | 390 | C18diacid | γE- (O2Oc)- (O2Oc) | 24 | Amide | 13αMePhe, 15E, 16E, 17E, 18A, 19V, 20R, 21L, 23I, 24K, |
| Peptide 386 | H(Aib)QGTFTSDVSK (αMePhe)LDSRRAQDFVK (O2OC-O2OC-γE- C18diacid)24WLVE(Aib) G-acid | 391 | C18diacid | γE- (O2Oc)- (O2Oc) | 24 | Acid | 2Aib, 10V, 13αMePhe, 24K, 25Aib, 27V, 28E, 29Aib, 30G |
| Peptide 387 | H(Aib)QGTFTSDVSK (αMePhe)LESRRAQDFVK (O2OC-O2OC-γE- C18diacid)24WLVE(Aib) G-acid | 392 | C18diacid | γE- (O2Oc)- (O2Oc) | 24 | Acid | 2Aib, 10V, 13αMePhe, 15E, 24K, 25Aib, 27V, 28E, 29Aib, 30G |
| Peptide 388 | H(Aib)QGTFTSDVSK (αMePhe)LDLRRAQDFVK (O2OC-O2OC-γE- C18diacid)24WLVE(Aib) G-acid | 393 | C18diacid | γE- (O2Oc)- (O2Oc) | 24 | Acid | 2Aib, 10V, 13αMePhe, 16L, 24K, 25Aib, 27V, 28E, 29Aib, 30G |
| Peptide 389 | H(Aib)QGTFTSDVSK (αMePhe)LDSRRAQDFVK (O2OC-O2OC-γE- C18diacid)24WLL(Aib)T- acid | 394 | C18diacid | γE- (O2Oc)- (O2Oc) | 24 | Acid | 2Aib, 10V, 13αMePhe, 24K, 25Aib, 27L, 28Aib |
| Peptide 390 | H(Aib)QGTFTSDVSK (αMePhe)LDSRRAQDFVK (O2OC-O2OC-γE- C18diacid)24WLVEG (Aib)-acid | 395 | C18diacid | γE- (O2Oc)- (O2Oc) | 24 | Acid | 2Aib, 10V, 13αMePhe, 24K, 25Aib, 27V, 28E, 29G, 30Aib |

In some aspects, the peptide comprises the sequence: H-X2-X3-G-X5-X6-T-S-D-X10-S-K-X13-L-D-S-X17-X18-A-Q-D-X22-V-X24-X25-X26-X27-N-T-X(30)-X(31)-Z, wherein X2 is S or Aminoisobutyric acid (Aib), X3 is Q or H, X5 is T or S, X6 is F or α-methylphenylalanine (αMePhe), X10 is Y, V, or K, wherein the K can comprise an acyl moiety and/or can be lipidated, X13 is Y, αMePhe, I, or Diphenylalanine (Dip), or K wherein the K can comprise an acyl moiety and/or can be lipidated, X17 is R, Q, or β-dimethylarganine (β-diMeArg), X18 is R or A, X22 is F or αMePhe, X24 is Q or E, X25 is W, Aib, or H, X26 is L or I, X27 is M or A, X(30) is not present, X(31) is not present, and Z is amide or acid (SEQ ID NO: 417), wherein the peptide does not comprise SEQ ID NO: 1.

In some aspects, the residue at position 10 or 13 is acylated. In some aspects, the residue at position 10 or 13 is lipidated. In some aspects, the lipid is selected from the group consisting of a palmitoyl group, stearoyl group, lauryl group, myristoyl group, margaroyl group, octadecanedioic acid (C18diacid), and icosanedioic acid (C20diacid). In some aspects, the lipid is selected from the group consisting of an octadecanedioic acid (C18diacid), and icosanedioic acid (C20diacid), stearoyl group, and palmitoyl group.

In some aspects, the lipid attached to the residue at position 10 or 13 is attached via a linker. In some aspects, the linker is selected from the group consisting of (O2Oc), (O2Oc)-(O2Oc), (O2Oc)-γE-(O2Oc), (PEG)2-(PEG)2-γE-γE, (PEG)2-γE-(PEG)2-γE, γE, γE-(O2Oc), γE-(O2Oc)-(O2Oc), γE-(O2Oc)-γE-(O2Oc), γE-(PEG)2-(PEG)2, γE-(PEG)2-γE-(PEG)2, γE-(PEG)4, γE-γE, γE-γE-(O2Oc), γE-γE-(O2Oc)-(O2Oc), γE-γE-(PEG)12, γE-γE-(PEG)2-(PEG)2, γE-γE-(PEG)2-γE-γE, γE-γE-(PEG)4, and γE-γE-(PEG)8. In some aspects, the linker is selected from the group consisting of γE-γE-(O2Oc)-(O2Oc), γE-(O2Oc)-(O2Oc), γE-γE-(PEG)2-(PEG)2, and γE-(PEG)2-(PEG)2.

In some aspects, the peptide comprises any one of SEQ ID NOs: 396-411.

In some aspects, the peptide is any one of the peptides in Table 4 or Table 5.

TABLE 4

| | | | Albumin | Linker | Acyl- | | Sequence modification |
| | | SEQ ID | binding | (described | ation | C- | with respect |
| Peptide | Sequence | NO | moiety | N→C) | site | term. | to glucagon |
|---|---|---|---|---|---|---|---|
| Peptide 390 | H(Aib)HGS(αMePhe)TS DK(O2OC-O2OC-γE-γE-C20diacid)10SK(αMePhe) LDSRAAQD(αMePhe) VQ(Aib)IANT-amide | 396 | C20diacid | γE-γE-(O2Oc)-(O2Oc) | 10 | Amide | 2Aib, 3H, 5S, 6αMePhe, 10K, 13αMePhe, 18A, 22αMePhe, 25Aib, 26I, 27A |
| Peptide 391 | H(Aib)HGS(αMePhe)TS DK(O2OC-O2OC-γE-C18diacid)10SK(αMePhe) LDSRAAQD(αMePhe) VQ(Aib)IANT-amide | 397 | C18diacid | γE-(O2Oc)-(O2Oc) | 10 | Amide | 2Aib, 3H, 5S, 6αMePhe, 10K, 13αMePhe, 18A, 22αMePhe, 25Aib, 26I, 27A |
| Peptide 392 | HSQGS(αMePhe)TSDK ((PEG)2-(PEG)2-γE-γE-Stearoyl)10SK(Dip)LDS (ß-dimethylArg)AAQD (αMePhe)VE(Aib)LANT-amide | 398 | Stearoyl | γE-γE-(PEG)2-(PEG)2 | 10 | Amide | 5S, 6αMePhe, 10K, 13Dip, 17ß-dimethylR, 18A, 22αMePhe, 24E, 25Aib, 27A |
| Peptide 393 | HSQGS(αMePhe)TSDK ((PEG)2-(PEG)2-γE-γE-Palmitoyl)10SK(Dip)LDS (ß-dimethylArg)AAQD (αMePhe)VE(Aib)LANT-amide | 399 | Palmitoyl | γE-γE-(PEG)2-(PEG)2 | 10 | Amide | 5S, 6αMePhe, 10K, 13Dip, 17ß-dimethylR, 18A, 22αMePhe, 24E, 25Aib, 27A |
| Peptide 394 | H(Aib)QGSFTSDK(PEG) 2-(PEG)2-γE-Palmitoyl)10SKILDSRAA QDEVEWIANT-amide | 400 | Palmitoyl | γE-(PEG)2-(PEG)2 | 10 | Amide | 2Aib, 5S, 10K, 13I, 18A, 24E, 26I, 27A |
| Peptide 395 | H(Aib)QGS(αMePhe)TS DK((PEG)2-(PEG)2-γE-Palmitoyl)10SKILDSRAA QD(αMePhe)VEWIANT-amide | 401 | Palmitoyl | γE-(PEG)2-(PEG)2 | 10 | Amide | 2Aib, 5S, 6αMePhe, 10K, 13I, 18A, 22αMePhe, 24E, 26I, 27A |
| Peptide 396 | HSQGS(αMePhe)TSDK ((PEG)2-(PEG)2-γE-γE-Stearoyl)10SK(Dip)LDS QAAQD(αMePhe)VE (Aib)LANT-amide | 402 | Stearoyl | γE-γE-(PEG)2-(PEG)2 | 10 | Amide | 5S, 6αMePhe, 10K, 13Dip, 17Q, 18A, 22αMePhe, 24E, 25Aib, 27A |
| Peptide 397 | HSQGS(αMePhe)TSDK ((PEG)2-(PEG)2-γE-γE-Stearoyl)10SK(Dip)LDS (ß-dimethylArg)AAQD (αMePhe)VEHLANT-amide | 403 | Stearoyl | γE-γE-(PEG)2-(PEG)2 | 10 | Amide | 5S, 6αMePhe, 10K, 13Dip, 17ß-dimethylR, 18A, 22αMePhe, 24E, 25H, 27A |

129 130

TABLE 5

Peptides Modified at Position 13

| Peptide | Sequence | SEQ ID NO | Albumin binding moiety | Linker (described N→C term.) | Acyl- ation site | C- term. | Sequence modification with respect to glucagon |
|---------|----------|-----------|-----------------------|------------------------------|------------------|----------|--------------------------------------------------|
| Peptide 398 | HSQGS(αMePhe)TSDVS KK((PEG)2-(PEG)2-γE- γE-Stearoyl)13LDS(ß- dimethylArg)AAQD (αMePhe)VE(Aib)LANT- amide | 404 | Stearoyl | γE-γE- (PEG)2- (PEG)2 | 13 | Amide | 5S 6αMePhe, 10V, 13K, 17ß- dimethylR, 18A, 22αMePhe, 24E, 25Aib, 27A |
| Peptide 399 | HSQGS(αMePhe)TSDVS KK((PEG)2-(PEG)2-γE- VE-Palmitoyl)13LDS(B- dimethylArg)AAQD(aM ePhe)VE(Aib)LANT- amide | 405 | Palmitoyl | γE-γE- (PEG)2- (PEG)2 | 13 | Amide | 5S, 6αMePhe, 10V, 13K, 17ß- dimethylR, 18A, 22αMePhe, 24E, 27A |
| Peptide 340 | H(Aib)QGS(αMePhe)TS DVSKK((PEG)2-(PEG)2- γE- Palmitoyl)13LDSRAAQ D(αMePhe)VEWIANT- amide | 406 | Palmitoyl | γE- (PEG)2- (PEG)2 | 13 | Amide | 2Aib, 5S, 6αMePhe, 10V, 13K, 18A, 22αMePhe, 24E, 26I, 27A |
| Peptide 341 | H(Aib)QGSFTSDVSKK ((PEG)2-(PEG)2-γE- Palmitoyl)13LDSRAAQ DEVEWIANT-amide | 407 | Palmitoyl | γE- (PEG)2- (PEG)2 | 13 | Amide | 2Aib, 5S, 10V, 13K, 18A, 24E, 26I, 27A |
| Peptide 342 | HSQGS(αMePhe)TSDVS KK((PEG)2-(PEG)2-γE- γE- Stearoyl)13LDSQAAQD (αMePhe)VE(Aib)LANT- amide | 408 | Stearoyl | γE-γE- (PEG)2- (PEG)2 | 13 | Amide | 5S, 6αMePhe, 10V, 13K, 17Q, 18A, 22αMePhe, 24E, 25Aib, 27A |
| Peptide 343 | HSQGS(αMePhe)TSDVS KK((PEG)2-(PEG)2-γE- γE-Stearoyl)13LDS(ß- dimethylArg)AAQD (αMePhe)VEHLANT-amide | 409 | Stearoyl | γE-γE- (PEG)2- (PEG)2 | 13 | Amide | 5S, 6αMePhe, 10V, 13K, 17ß- dimethylR, 18A, 22αMePhe, 24E, 25H, 27A |
| Peptide 344 | H(Aib)HGS(αMePhe)TS DVSKK(O2OC-O2OC-γE- γE- C20diacid)13LDSRAAQ D(αMePhe)VQ(Aib)IAN T-amide | 410 | C20diacid | γE-γE- (O2Oc)- (O2Oc) | 13 | Amide | 2Aib, 3H, 5S, 6αMePhe, 10V, 13K, 18A, 22αMePhe, 25Aib, 26I, 27A |
| Peptide 345 | H(Aib)HGS(αMePhe)TS DVSKK(O2OC-O2OC-γE- C18diacid)13LDSRAAQ D(αMePhe)VQ(Aib)IAN T-amide | 411 | C18diacid | γE- (O2Oc)- (O2Oc) | 13 | Amide | 2Aib, 3H, 5S, 6αMePhe, 10V, 13K, 18A, 22αMePhe, 25Aib, 26I, 27A |

In some aspects, the peptide comprises the sequence: H-X2-X3-G-X5-X6-T-S-D-X10-S-X12-αMethyl-Phenyl- alanine (αMePhe)-L-X15-X16-X17-X18-A-X20-X21-X22- X23-X24-X25-X26-X27-X28-X29-X30-X31-Z, wherein X2 is Aminoisobutyric acid (Aib), S, or A, X3 is Q, H, or E, X5 is T or S, X6 is F or αMePhe, X10 is V, K or Y, X11 is S, X12 is K, E, or S, X15 is D or E, X16 is T, S, or G, X17 is K, R, E, or Q, X18 is R or A, X20 is R, K, or Q, X21 is D or E, X22 is αMePhe or F, X23 is V or I, X24 is Q or A, X25 is Aib or W, X26 is L or I, X27 is L, A, E, V, or M, X28 is E, N, A, R, or K, X29 is Aib, T, or G, X30 is G, R, or not present, X31 is G or not present, and Z is amide or acid (SEQ ID NO: 540).

In some aspects, X2 is Aib. In some aspects, X3 is Q. In some aspects, X3 is H. In some aspects, X5 is T. In some aspects, X5 is S. In some aspects, X6 is F. In some aspects, X6 is αMePhe. In some aspects, X10 is V. In some aspects, X12 is K. In some aspects, X15 is D. In some aspects, X16 is T. In some aspects, X16 is S. In some aspects, X17 is K. In some aspects, X17 is R. In some aspects, X18 is R. In some aspects, X18 is A. In some aspects, X20 is R. In some aspects, X20 is K. In some aspects, X21 is D. In some aspects, X22 is F. In some aspects, X22 is αMePhe. In some aspects, X23 is V. In some aspects, X24 is Q. In some aspects, X25 is W. In some aspects, X25 is Aib. In some aspects, X26 is L. In some aspects, X26 is I. In some aspects, X27 is L. In some aspects, X27 is A. In some aspects, X28 is E. In some aspects, X28 is N. In some aspects, X29 is Aib. In some aspects, X29 is T. In some aspects, X30 is G. In some aspects, X30 is not present. In some aspects, X31 is not present. In some aspects, Z is amide. In some aspects, Z is acid.

In some aspects, X2 is Aib, X12 is K, and X24 is Q. In some aspects, X16 is T, X17 is K, X27 is L, X28, is E, and X29 is Aib.

In some aspects, X3 is Q, X5 is T, X6 is F, X10 is V, X12 is K, X15 is D, X16 is T, X17 is K, X18 is R, X20 is R, X21 is D, X22 is F, X23 is V, X24 is Q, X25 is W, X26 is L, X27 is L, X28 is E, X29 is Aib, X30 is G, and X31 is not present.

In some aspects, X3 is H, X5 is S, X6 is αMePhe, X10 is V, X12 is K, X15 is D, X16 is S, X17 is R, X18 is A, X20 is K, X21 is D, X22 is αMePhe, X23 is V, X24 is Q, X25 is Aib, X26 is I, X27 is A, X28 is N, X29 is T, X30 is not present, and X31 is not present.

In some aspects, one or more lysine residues are acylated. In some aspects, the lysine at position 17 is acylated. In some aspects, the lysine at position 20 is acylated.

In some aspects, one or more lysine resides are lipidated. In some aspects, the lysine at position 17 is lipidated. In some aspects, the lysine at position 20 is lipidated.

In some aspects, the lipid is selected from the group consisting of octadecanedioic acid (C18diacid) and icosanedioic acid (C20diacid). In some aspects, the lipid is octadecanedioic acid (C18diacid). In some aspects, the lipid is icosanedioic acid (C20diacid).

In some aspects, the lipid is linked to the residue at position 17 or 20 via a linker. In some aspects, the linker is γE-(O2Oc)-(O2Oc) or γE-γE-(O2Oc)-(O2Oc). In some aspects, the linker is γE-(O2Oc)-(O2Oc). In some aspects, the linker is γE-γE-(O2Oc)-(O2Oc). In some aspects, the linker is linked to the epsilon amino group of the residue at position 17 or 20.

Certain aspects of the disclosure are directed to a peptide comprising the sequence of H-Aib-Q-G-T-F-T-S-D-V-S-K-αMePhe-L-D-T-K-R-A-R-D-F-V-Q-W-LL-E-Aib-G-acid (SEQ ID NO: 541).

In some aspects, the lysine at position 17 is acylated and lipidated, the lipid is linked to the acylated lysine via a (E-(O2Oc)-(O2Oc)-γE-C18diacid).

In some aspects, the lysine at position 17 is acylated and lipidated, the lipid is linked to the acylated lysine at position 17 via a (ε-(O2Oc)-(O2Oc)-γE-C20diacid).

Certain aspects of the disclosure are directed to a peptide comprising the sequence H-Aib-H-G-S-αMePhe-T-S-D-V-S-K-αMePhe-L-D-S-R-A-A-K(ε-(O2Oc)-(O2Oc)-γE-C18diacid)20-D-αMePhe-V-Q-Aib-I-A-N-T-amide (SEQ ID NO: 228).

Certain aspects of the disclosure are directed to a peptide comprising the sequence H-Aib-H-G-S-αMePhe-T-S-D-V-S-K-αMePhe-L-D-S-R-A-A-K(E-(O2Oc)-(O2Oc)-γE-γE-C20diacid)20-D-αMePhe-V-Q-Aib-I-A-N-T-amide (SEQ ID NO: 233).

In some aspects, the peptide binds to the GLP-1 receptor (GLP-1R), binds to the glucagon receptor (GCGR), or binds to both a GLP-1 receptor and a glucagon receptor. In some aspects, the GLP-1R is a human GLP-1R. In some aspects, the GCGR is a human GCGR. In some aspects, the peptide is an agonist of GLP-1 activity, an agonist of glucagon activity, or an agonist of both GLP-1 and glucagon activity.

In some aspects, the peptide has increased proteolytic-resistance relative to the natural ligand of the GLP-1R and/or GCGR.

In some aspects, the peptide is isolated.

In some aspects, the peptide has at least 50%, at least 60%, at least 70%, at least 75%, at least 80%, at least 85%, at least 90%, at least 95, or 100% of intact peptide remaining after incubation with a protease at 37° C. for 5 min, 10 min, 15 min, 30 min, 2 hr, 4 hr or 24 hr. In some aspects, the protease is selected from the group consisting of neprilysin, pepsin, pancreatin, simulated gastric fluid with pepsin, and simulated intestinal fluid with pancreatin.

In some aspects, the peptide has a half-life in cynomolgus monkeys after intravenous administration of at least 45 hours, at least 50 hours, at least 60 hours, at least 70 hours, at least 80 hours, at least 90 hours, at least 100 hours, at least 110 hours, at least 120 hours, or about 130 hours.

In some aspects, the peptide has an s.c. bioavailability in cynomolgus monkeys of at least 75%, at least 80%, at least 90%, or about 95%.

III. Methods of Making GLP-1/Glucagon Agonist Peptides

GLP-1/glucagon agonist peptides for uses provided herein can be made by any suitable method. For example, in some aspects provided herein, the GLP-1/glucagon agonist peptides for uses provided herein are chemically synthesized by methods well known to those of ordinary skill in the art, e.g., by solid phase synthesis as described by Merrifield (1963, *J. Am. Chem. Soc.* 85:2149-2154). Solid phase peptide synthesis can be accomplished, e.g., by using automated synthesizers, using standard reagents, e.g., as explained in Example 1 of WO 2014/091316, which is herein incorporated by reference in its entirety.

Alternatively, GLP-1/glucagon agonist peptides for uses provided herein can be produced recombinantly using a convenient vector/host cell combination as would be well known to the person of ordinary skill in the art. A variety of methods are available for recombinantly producing GLP-1/glucagon agonist peptides. Generally, a polynucleotide sequence encoding the GLP-1/glucagon agonist peptide is inserted into an appropriate expression vehicle, e.g., a vector which contains the necessary elements for the transcription and translation of the inserted coding sequence. The nucleic acid encoding the GLP-1/glucagon agonist peptide is inserted into the vector in proper reading frame. The expression vector is then transfected into a suitable host cell which will express the GLP-1/glucagon agonist peptide. Suitable host cells include without limitation bacteria, yeast, or mammalian cells. A variety of commercially-available host-expression vector systems can be utilized to express the GLP-1/glucagon agonist peptides described herein.

Pharmaceutical Compositions

Further provided are compositions, e.g., pharmaceutical compositions, that contain an effective amount of a GLP-1/glucagon agonist peptide as provided herein, formulated for the treatment of metabolic diseases, e.g., obesity, type 2 diabetes, and/or NASH.

Compositions of the disclosure can be formulated according to known methods. Suitable preparation methods are described, for example, in *Remington's Pharmaceutical Sciences,* 19th Edition, A. R. Gennaro, ed., Mack Publishing Co., Easton, PA (1995), which is incorporated herein by reference in its entirety. Composition can be in a variety of forms, including, but not limited to an aqueous solution, an emulsion, a gel, a suspension, lyophilized form, or any other form known in the art. In addition, the composition can contain pharmaceutically acceptable additives including, for example, diluents, binders, stabilizers, and preservatives. Once formulated, compositions of the invention can be administered directly to the subject.

In some aspects, the pharmaceutical composition is a solid composition. In some aspects, the pharmaceutical composition is a liquid composition.

IV. Methods of Using GLP-1/Glucagon Agonist Peptides

As provided herein, GLP-1/glucagon agonist peptides can be used to improve glycemic control, reduce weight, type 2 diabetes mellitus (T2DM), and/or treat or prevent non-alcoholic steatohepatitis (NASH).

In some aspects, administration of the GLP-1/glucagon agonist peptides decreases body weight of the subject, increases insulin secretion in the subject, delays gastric emptying in the subject, decreases food intake in the subject, increases mitochondria function in the subject, inhibits de novo lipogenesis in the subject, decreases HbA1c in the subject, enhances fatty oxidation in the subject, decreases hepatic mitochondrial oxidative stress in the subject, decreases steatosis in the subject, decreases fibrosis in the subject, decreases glycogen synthesis in the subject, increases gluconeogenesis in the subject, halts disease progression in the subject, reverses fibrosis in the subject, and/or reduces risk of death due to cirrhosis, hepatocellular carcinoma, and/or cardiorenal disease in the subject.

As provided herein a method of improving glycemic control or reduce weight in a human subject with T2DM and/or NASH can comprise administering to the subject a GLP-1/glucagon agonist peptide.

This disclosure also provides a GLP-1/glucagon agonist peptide for use in the manufacture of a medicament for improving glycemic control or reduce weight in a human subject with T2DM and/or NASH.

In some aspects, the peptide is administered about once a week.

In some aspects, the GLP-1/glucagon agonist peptide is administered to treat or prevent a disease or condition cause or characterized by excess body weight. In some aspects, the disease or condition is obesity. In some aspects, the disease or condition is type 2 diabetes.

In some aspects, the GLP-1/glucagon agonist peptide is administered to treat or non-alcoholic steatohepatitis (NASH). In some aspects, the GLP-1/glucagon agonist peptide is administered by injection. In some aspects, the GLP-1/glucagon agonist peptide is administered orally. In some aspects, administration of the GLP-1/glucagon agonist peptide decreases body weight of the subject, increases insulin secretion in the subject, delays gastric emptying in the subject, decreases food intake in the subject, increases mitochondria function in the subject, inhibits de novo lipogenesis in the subject, decreases HbA1c in the subject, enhances fatty oxidation in the subject, decreases hepatic mitochondrial oxidative stress in the subject, decreases steatosis in the subject, decreases fibrosis in the subject, decreases glycogen synthesis in the subject, increases gluconeogenesis in the subject, halts disease progression in the subject, reverses fibrosis in the subject, and/or reduces risk of death due to cirrhosis, hepatocellular carcinoma, and/or cardiorenal disease in the subject. In some aspects, the subject is a human. In some aspects, the peptide is administered about once a week.

EXAMPLES

Example 1: Lipidated-GLP-1/Glucagon Dual Agonist Peptide Analogue Preparation Lipidated-GLP-1R/GCGR dual agonist peptides were synthesized as C-terminal carboxamides or carboxylic acids using rink amide MBHA resin (100-200 mesh) or Wang resin (100-200 mesh). All peptides were prepared by automated synthesis using a PTI Prelude solid phase peptide synthesizer using the 9-fluorenylmethoxycarbonyl (Fmoc)/tert-butyl ($^t$Bu) protocol. Manufacturer-supplied protocols were applied for coupling of amino acids in N,N-dimethylformamide (DMF) and deprotection of Fmoc protecting group using piperidine in DMF (20% v/v). Asparagine (Asn), glutamine (Gln) and histidine (His) were incorporated as their sidechain triphenylmethyl, trityl (Trt) derivatives. Lysine (Lys) was incorporated as the sidechain tert-butyloxycarbonyl (Boc) derivative. Serine (Ser), threonine (Thr) and tyrosine (Tyr) were incorporated as sidechain tBu ethers, and aspartate (Asp) and glutamate (Glu) as their sidechain O$^t$Bu esters. Arginine (Arg) was incorporated as the sidechain 2,2,4,6,7-pentamethyldihydrobenzofuran-5-sulfonyl (Pbf) derivative. Other amino acids were incorporated with an appropriate sidechain protection.

Lys(Mmt) was incorporated when a subsequent chemical modification of the lysine side chain was required. Upon completion of the peptide chain elongation, Mmt side chain protection was removed by treatment of the resin with selective deprotection cocktail (1% trifluoroacetic acid (TFA), 5% TIPS in dichloromethane (DCM)) at 100 mL/mmol for 1 min, and repeated at least 10 times until Mmt group deprotection was completed. The reaction was quenched with 10% N,N-diisopropylethylamine (DIPEA)/NMP. Subsequent coupling of a albumin binding moiety, such as a lipid and linker, was performed manually using 1-[Bis(dimethylamino)methylene]-1H-1,2,3-triazolo[4,5-b]pyridinium 3-oxide hexafluorophosphate (HATU) as a coupling reagent in the presence of DIPEA.

Peptides were cleaved from the solid support by treatment with a mixture of TFA: triisopropylsilane (TIS):water (92.5.5:2.5 v/v) for 4 h with agitation at room temperature. Thereafter, the cleavage mixtures were filtered, concentrated in vacuo, precipitated and washed with diethyl ether and solids were isolated by centrifugation. The crude peptides were dried under a flow of nitrogen and dissolved in 20% acetonitrile (MeCN)/water (v/v) and filtered. The crude peptides were purified using a preparative reversed-phase high-performance liquid chromatography (RP-HPLC) on a Varian SD-1 Prep Star binary pump system, monitoring by ultraviolet (UV) absorption at 210 nm using an Xbridge C18-A stationary phase (19.0×250 mm, 5 micron) column eluting a linear solvent gradient of 25-70% MeCN (0.1% TFA v/v) in water (0.1% TFA v/v) over 25 min. The purified fractions were pooled, frozen and lyophilised.

Liquid chromatography/mass spectrometry (LC/MS) characterization of purified peptides were performed on a Waters MassLynx 3100 platform using a XBridge C18 stationary phase (4.6×100 mm, 3 micron) eluting a linear binary gradient of 10-90% MeCN (0.1% TFA v/v) in water (0.1% TFA v/v) over 10 minutes at 1.5 mL/min at ambient temperature. Analytes were detected by both UV absorption at 210 nm and ionization using a Waters 3100 mass detector (electrospray ionisation (ESI)+ mode). Analytical RP-HPLC characterization was performed on an Agilent 1260 Infinity system using an Agilent Polaris CS-A stationary phase (4.6×100 mm, 3 micron) eluting a linear binary gradient of 10-90% MeCN (0.1% TFA v/v) in water (0.1% TFA v/v) at 1.5 mL/min over 15 minutes at 40° C.

Example 2: GLP-1 Receptor and Glucagon Receptor In Vitro Functional Assay

The functional activities of lipidated-GLP-1R/GCGR peptides, such as cAMP production, were tested in CHO cell line with stable recombinant expression of human GLP-1 receptor (hGLP-1R) or human glucagon receptor (hGCGR).

Cryopreserved cell stocks were thawed rapidly in a water-bath, suspended in assay buffer (0.1% BSA (Sigma #A3059) in HBSS (Sigma #H8264) with 25 mM HEPES, pH 7.4 and containing 0.5 mM IBMX (Sigma #17018)) and centrifuged at 240×g for 5 minutes. Cells were re-suspended in assay buffer at a batch-dependent optimized concentration (typically hGLP-1R cells at $1 \times 10^5$ cells/mL, hGCGR cells at $2 \times 10^5$ cells/mL).

The test peptide stock was prepared in DMSO and serially diluted in assay buffer to prepare 11-point concentration response curves, in duplicate, in 384-well low volume microtiter assay plates (Corning #4514) using a non-contact liquid dispenser (ECHO™, LabCyte). Cells were added to the assay plate using a multidrop dispenser and incubated at room temperature for 30 minutes before measuring the cAMP level using a cAMP dynamic 2 homogeneous time resolved Fluorescence (HTRF) kit (Cisbio Bioassays #62AM4PEJ) following the two-step protocol as per manufacturer's recommendations. In brief, anti-cAMP cryptate (donor fluorophore) and cAMP-d2 (acceptor fluorophore) were made up separately by diluting each 1 in 20 in conjugate and lysis buffer provided in the kit. Anti-cAMP cryptate was added to all wells of the assay plate, followed by cAMP-d2 added to all wells except non-specific binding (NSB) wells (to which conjugate and lysis buffer was added). Plates were incubated at room temperature for one hour and then read on an Envision (Perkin Elmer) using an excitation wavelength of 320 nm and emission wavelengths of 620 nm & 665 nm.

Data was transformed to % Delta F as described in the manufacturer's guidelines and analyzed by 4-parameter logistic fit to determine $EC_{50}$ values. The selectivity ratio of a peptide to hGLP-1R vs hGCGR is defined as: % Relative Potency Ratio=% GLP-1R activity relative to GLP-1/% GlucR activity relative to glucagon. Data is shown as the geometric mean $EC_{50}$ (pM) from >n=2 independent experiments.

The relative potency ratios of peptides is listed in Tables 6-10.

136

TABLE 6

| | | | |
|---|---|---|---|
| Potency of Peptides with Modification on Amino Acid at Position 17 | | | |
| Peptide | hGLP-1R $EC_{50}$ (pM) | hGluc-R $EC_{50}$ (pM) | % Relative Potency Ratio |
| GLP-1(7-36) amide | 2.196 | — | — |
| Glucagon | — | 1.110 | — |
| 1 | 3197.264 | >27100 | — |
| 2 | 1281.484 | 4192.851 | 6.5 |
| 3 | 69.013 | 149.198 | 4.3 |
| 4 | 240.004 | 1167.129 | 9.6 |
| 5 | 282.756 | 7137.899 | 49.9 |
| 6 | 567.937 | 516.038 | 1.8 |
| 7 | 84.551 | 30.666 | 0.7 |
| 8 | 87.845 | 53.635 | 1.2 |
| 9 | 241.876 | 278.726 | 2.3 |
| 10 | 657.981 | 376.720 | 1.1 |
| 11 | 156.625 | 117.572 | 1.5 |
| 12 | 14.531 | 47.666 | 6.5 |
| 13 | 15.895 | 44.043 | 5.5 |
| 14 | 93.788 | 462.195 | 9.7 |
| 15 | 33.122 | 61.419 | 3.7 |
| 16 | 32.959 | 104.788 | 6.3 |
| 17 | 44.976 | 134.979 | 5.9 |
| 18 | 20.493 | 121.569 | 11.7 |
| 19 | 38.345 | 133.477 | 6.9 |
| 20 | 152.448 | 135.633 | 1.8 |
| 21 | 377.683 | 68.754 | 0.4 |
| 22 | 1226.703 | 2724.463 | 4.4 |
| 23 | 266.349 | 321.178 | 2.4 |
| 24 | 82.803 | 101.130 | 2.4 |
| 25 | 725.678 | 1311.347 | 3.6 |
| 26 | 80.600 | 8904.381 | 218.5 |
| 27 | 18.189 | 1438.437 | 156.4 |
| 28 | 129.321 | 259.647 | 4.0 |
| 29 | 106.638 | 629.359 | 11.7 |
| 30 | 52.683 | 234.982 | 8.8 |
| 31 | 41.292 | 56.793 | 2.7 |
| 40 | 29.909 | 123.325 | 8.2 |
| 41 | 662.690 | 5737.086 | 17.1 |
| 42 | 665.048 | 8189.848 | 24.4 |
| 136 | 45.196 | 509.273 | 22.3 |
| 137 | 143.435 | 267.783 | 3.7 |
| 138 | 104.274 | 183.767 | 3.5 |
| 139 | 630.031 | 983.762 | 3.1 |
| 140 | 22.725 | 46.408 | 4.0 |
| 141 | 263.906 | 392.259 | 2.9 |
| 142 | 59.361 | 107.506 | 3.6 |
| 143 | 19.134 | 32.638 | 3.4 |
| 144 | 45.230 | 702.417 | 30.7 |
| 145 | 22.618 | 4587.203 | 401.2 |
| 146 | 24.628 | 1634.605 | 131.3 |
| 147 | 15.328 | 43.496 | 5.6 |
| 148 | 40.233 | 567.838 | 27.9 |
| 149 | 8.707 | 2653.203 | 602.8 |
| 150 | 166.473 | 355.432 | 4.2 |
| 151 | 111.202 | 178.430 | 3.2 |
| 152 | 11.912 | 20.350 | 3.4 |
| 153 | 41.161 | 99.002 | 4.8 |
| 158 | 303.611 | 332.670 | 2.2 |
| 159 | 145.208 | 144.564 | 2.0 |
| 160 | 55.178 | 416.851 | 14.9 |
| 162 | 59.567 | 1027.507 | 34.1 |
| 161 | 50.942 | 1030.580 | 40.0 |
| 166 | 48.005 | 269.638 | 11.1 |
| 167 | 76.814 | 310.656 | 8.0 |
| 43 | 1.894 | 5.520 | 5.8 |
| 44 | 2.117 | 18.235 | 17.0 |
| 45 | 2.028 | 14.943 | 14.6 |
| 46 | 3.395 | 5.914 | 3.4 |
| 47 | 1.715 | 2.381 | 2.7 |
| 48 | 19.862 | 43.244 | 4.3 |
| 49 | 1.738 | 1.728 | 2.0 |
| 50 | 4.903 | 8.738 | 3.5 |
| 51 | 18.101 | 41.930 | 4.6 |
| 52 | 22.733 | 6.646 | 0.6 |
| 53 | 3.025 | 18.850 | 12.3 |
| 54 | 2.810 | 2.588 | 1.8 |
| 55 | 18.800 | 19.085 | 2.0 |

TABLE 6-continued

Potency of Peptides with Modification
on Amino Acid at Position 17

| Peptide | hGLP-1R EC$_{50}$ (pM) | hGluc-R EC$_{50}$ (pM) | % Relative Potency Ratio |
|---|---|---|---|
| 56 | 4.860 | 10.909 | 4.4 |
| 57 | 9.093 | 16.912 | 3.7 |
| 58 | 3.900 | 11.329 | 5.7 |
| 59 | 6.181 | 28.350 | 9.1 |
| 60 | 5.161 | 21.118 | 8.1 |
| 61 | 4.125 | 9.554 | 4.6 |
| 62 | 10.098 | 15.204 | 3.0 |
| 63 | 3.139 | 2.488 | 1.6 |
| 64 | 2.574 | 3.065 | 2.4 |
| 65 | 1230.000 | 2060.580 | 3.3 |
| 66 | 1.524 | 6.426 | 8.3 |
| 67 | 2.432 | 9.488 | 7.7 |
| 68 | 1.095 | 4.670 | 8.4 |
| 69 | 1.145 | 6.442 | 11.1 |
| 70 | 1.550 | 30.865 | 39.4 |
| 71 | 2.174 | 53.722 | 48.9 |
| 72 | 3.418 | 73.660 | 42.6 |
| 73 | 0.275 | 21.956 | 157.9 |
| 74 | 1.831 | 10.893 | 11.8 |
| 75 | 18.897 | 2803.488 | 293.5 |
| 76 | 1.776 | 339.882 | 378.6 |
| 77 | 8.682 | 243.406 | 55.5 |
| 78 | 1.135 | 8.972 | 15.6 |
| 79 | 1.733 | 10.679 | 12.2 |
| 80 | 1.033 | 9.179 | 17.6 |
| 81 | 1.188 | 13.543 | 22.6 |
| 82 | 0.839 | 7.774 | 18.3 |
| 83 | 1.043 | 15.604 | 29.6 |
| 84 | 2.798 | 44.887 | 31.7 |
| 85 | 1.038 | 47.687 | 90.9 |
| 86 | 0.772 | 6.459 | 16.6 |
| 87 | 1.289 | 8.465 | 13.0 |
| 88 | 1.040 | 6.467 | 12.3 |
| 89 | 3.769 | 15.282 | 8.0 |
| 90 | 1.866 | 6.606 | 7.0 |
| 91 | 1.570 | 7.797 | 9.8 |
| 92 | 0.895 | 10.899 | 24.1 |
| 93 | 0.472 | 8.920 | 37.4 |
| 94 | 0.515 | 5.397 | 20.7 |
| 95 | 0.608 | 12.464 | 40.6 |
| 96 | 0.851 | 30.053 | 69.9 |
| 97 | 1.055 | 12.962 | 24.3 |
| 98 | 2.442 | 54.125 | 43.8 |
| 99 | 2.212 | 33.196 | 29.7 |
| 100 | 0.258 | 40.473 | 310.3 |
| 101 | 0.713 | 119.000 | 330.1 |
| 102 | 0.231 | 26.508 | 227.0 |
| 103 | 0.532 | 59.381 | 220.8 |
| 104 | 246.670 | 45.636 | 0.4 |
| 105 | 64.817 | 121.121 | 3.7 |
| 106 | 6.819 | 36.794 | 10.7 |
| 107 | 65.867 | 99.074 | 3.0 |
| 108 | 3197.264 | >27100.000 | — |
| 109 | 697.596 | >26800.000 | — |
| 110 | 0.627 | 48.465 | 152.9 |
| 111 | 1.918 | 2.090 | 2.2 |
| 112 | 3.364 | 2.689 | 1.6 |
| 113 | 1.613 | 4.603 | 5.6 |
| 114 | 3.647 | 2.648 | 1.4 |
| 117 | 15.615 | 2.990 | 0.4 |
| 116 | 24.329 | 10.308 | 0.8 |
| 117 | 1.398 | 1.848 | 2.6 |
| 118 | 1.068 | 1.201 | 2.2 |
| 119 | 1.392 | 1.700 | 2.4 |
| 120 | 1.810 | 2.616 | 2.9 |
| 121 | 1.502 | 1.200 | 1.6 |
| 122 | 1.417 | 0.857 | 1.2 |
| 123 | 0.496 | 12.883 | 51.4 |
| 124 | 1.274 | 9.790 | 15.2 |
| 125 | 0.575 | 6.676 | 23.0 |
| 128 | 0.594 | 10.997 | 36.6 |
| 127 | 0.998 | 12.649 | 25.1 |
| 128 | 0.788 | 4.695 | 11.8 |
| 129 | 0.462 | 4.100 | 17.6 |

TABLE 6-continued

Potency of Peptides with Modification
on Amino Acid at Position 17

| Peptide | hGLP-1R EC$_{50}$ (pM) | hGluc-R EC$_{50}$ (pM) | % Relative Potency Ratio |
|---|---|---|---|
| 130 | 1.087 | 32.889 | 59.9 |
| 131 | 0.511 | 17.811 | 68.9 |
| 132 | 0.949 | 34.315 | 71.5 |
| 133 | 1.060 | 29.964 | 55.9 |
| 134 | 0.592 | 15.008 | 50.1 |
| 135 | 0.407 | 14.984 | 72.8 |
| 407 | 208.719 | 462.060 | 4.4 |
| 408 | 370.323 | 828.459 | 4.4 |
| 409 | 22.673 | 203.000 | 17.7 |
| 410 | 78.013 | 455.043 | 11.5 |
| 411 | 98.122 | 377.956 | 7.6 |
| 412 | 185.707 | 397.402 | 4.2 |
| 413 | 406.086 | 1023.554 | 5.0 |
| 414 | 32.273 | 26.904 | 1.6 |
| 415 | 14.693 | 301.237 | 40.6 |
| 416 | 67.741 | 581.428 | 17.0 |
| 417 | 33.876 | 16.440 | 1.0 |
| 418 | 88.091 | 221.794 | 5.0 |
| 419 | 96.888 | 264.191 | 5.4 |
| 420 | 23.104 | 36.906 | 3.2 |
| 421 | 87.299 | 179.876 | 4.1 |
| 422 | 27.559 | 123.460 | 8.9 |
| 423 | 26.123 | 2219.743 | 168.1 |
| 424 | 15.540 | 129.497 | 16.5 |
| 425 | 11.490 | 826.662 | 142.3 |
| 426 | 7.303 | 61.169 | 16.6 |
| 427 | 12.433 | 47.225 | 7.5 |
| 428 | 33.081 | 10.501 | 0.6 |
| 429 | 15.013 | 144.446 | 19.0 |
| 430 | 24.421 | 160.262 | 13.0 |
| 431 | 44.587 | 193.903 | 8.6 |
| 432 | 1377.330 | 1164.734 | 1.7 |
| 433 | 4464.399 | 10463.230 | 4.6 |
| 434 | 152.763 | 293.928 | 3.8 |
| 435 | 22.659 | 240.076 | 21.0 |
| 436 | 7.427 | 68.750 | 18.3 |
| 437 | 26.892 | 96.876 | 7.1 |
| 438 | 17.923 | 68.908 | 7.6 |
| 439 | 30.650 | 57.730 | 3.7 |
| 440 | 153.518 | 81.008 | 1.0 |
| 441 | 62.730 | 72.810 | 2.3 |
| 442 | 19.052 | 35.819 | 3.7 |
| 443 | 20.559 | 22.434 | 2.2 |
| 444 | 247.415 | 1758.388 | 14.1 |
| 445 | 33.016 | 683.673 | 41.0 |
| 446 | 32.889 | 365.880 | 22.0 |
| 447 | 169.598 | 666.503 | 7.8 |
| 448 | 53.134 | 28.953 | 1.1 |
| 449 | 207.17 | 241.70 | 2.3 |
| 450 | 57.318 | 57.789 | 2.0 |
| 451 | 894.881 | 503.273 | 1.1 |
| 452 | 495.050 | 150.934 | 0.6 |
| 453 | 169.523 | 161.692 | 1.9 |
| 454 | 173.343 | 273.630 | 3.1 |
| 455 | 127.140 | 114.432 | 1.8 |
| 456 | 132.866 | 80.328 | 1.2 |
| 457 | 109.278 | 202.834 | 3.7 |
| 458 | 114.344 | 384.540 | 6.7 |
| 459 | 32.674 | 36.947 | 2.2 |
| 460 | 116.724 | 66.478 | 1.1 |
| 461 | 167.051 | Not tested | — |
| 462 | 39.497 | 89.240 | 4.5 |
| 463 | 273.563 | Not tested | — |
| 464 | Not tested | Not tested | — |
| 465 | 485.020 | 436.382 | 1.8 |
| 466 | 35.571 | 131.195 | 7.3 |
| 467 | Not tested | Not tested | — |
| 468 | 67.532 | 292.374 | 8.6 |
| 469 | 254.776 | 538.155 | 4.2 |
| 470 | 55.908 | 30.269 | 1.1 |
| 471 | 101.756 | 63.584 | 1.2 |
| 472 | 7.627 | 11.060 | 2.9 |
| 473 | 11.463 | 14.135 | 2.4 |
| 474 | 8.043 | 56.901 | 14.0 |

TABLE 6-continued

| | Potency of Peptides with Modification on Amino Acid at Position 17 | | |
|---|---|---|---|
| Peptide | hGLP-1R EC$_{50}$ (pM) | hGluc-R EC$_{50}$ (pM) | % Relative Potency Ratio |
| 475 | 6.748 | 61.516 | 18.0 |
| 476 | 57.309 | 103.924 | 3.6 |
| 477 | 54.091 | 117.426 | 4.3 |
| 478 | 9.178 | 189.932 | 40.9 |
| 479 | 34.154 | 206.779 | 12.0 |
| 480 | 12.573 | 136.201 | 21.4 |
| 481 | 52.209 | 349.837 | 13.3 |
| 482 | 190.311 | 691.097 | 7.2 |
| 483 | 177.661 | 168.551 | 1.9 |
| 484 | 338.595 | 168.884 | 1.0 |
| 485 | 219.193 | 90.425 | 0.8 |
| 486 | 420.381 | 166.466 | 0.8 |
| 487 | 65.455 | 164.468 | 5.0 |
| 488 | 201.998 | 300.737 | 2.9 |
| 489 | 22.787 | 167.608 | 14.5 |
| 490 | 69.046 | 396.488 | 11.4 |
| 491 | 73.584 | 231.822 | 6.2 |
| 492 | 212.412 | 374.486 | 3.5 |
| 493 | 23.450 | 165.822 | 14.0 |
| 494 | 98.727 | 212.207 | 4.3 |
| 495 | 23.165 | 379.702 | 32.4 |
| 496 | 64.887 | 482.010 | 14.7 |
| 497 | 37.397 | 118.244 | 6.3 |
| 498 | 156.406 | 169.974 | 2.1 |
| 499 | 40.647 | 78.787 | 3.8 |
| 500 | 101.880 | 101.482 | 2.0 |
| 501 | 26.516 | 75.630 | 5.6 |
| 502 | 82.090 | 174.964 | 4.2 |
| 503 | 81.209 | 84.902 | 2.1 |
| 504 | 123.927 | 551.274 | 8.8 |
| 505 | 42.121 | 190.780 | 9.0 |
| 506 | 162.104 | 148.973 | 1.8 |
| 507 | 52.850 | 86.602 | 3.2 |
| 508 | 67.930 | 2802.216 | 81.6 |
| 509 | 594.123 | 3020.408 | 10.1 |
| 510 | 176.244 | 117.832 | 1.3 |
| 511 | 117.715 | 139.920 | 2.4 |
| 512 | 159.226 | 2308.999 | 28.7 |
| 513 | 93.821 | 1340.613 | 28.3 |
| 514 | 76.660 | 1373.731 | 35.4 |
| 515 | 296.991 | 2659.628 | 17.7 |
| 516 | 137.100 | 784.568 | 11.3 |
| 517 | 145.751 | 737.919 | 10.0 |
| 136 | 45.196 | 509.273 | 22.3 |
| 137 | 143.435 | 267.783 | 3.7 |
| 138 | 104.274 | 183.767 | 3.5 |
| 139 | 630.031 | 983.762 | 3.1 |
| 140 | 22.725 | 46.408 | 4.0 |
| 141 | 263.906 | 392.259 | 2.9 |
| 142 | 59.361 | 107.506 | 3.6 |
| 143 | 19.134 | 32.638 | 3.4 |
| 144 | 45.230 | 702.417 | 30.7 |
| 145 | 22.618 | 4587.203 | 401.2 |
| 146 | 24.628 | 1634.605 | 131.3 |
| 147 | 15.328 | 43.496 | 5.6 |
| 148 | 40.233 | 567.838 | 27.9 |
| 149 | 8.707 | 2653.203 | 602.8 |
| 150 | 166.473 | 355.432 | 4.2 |
| 151 | 111.202 | 178.430 | 3.2 |
| 152 | 11.912 | 20.350 | 3.4 |
| 153 | 41.161 | 99.002 | 4.8 |
| 158 | 303.611 | 332.670 | 2.2 |
| 159 | 145.208 | 144.564 | 2.0 |
| 160 | 55.178 | 416.851 | 14.9 |
| 162 | 59.567 | 1027.507 | 34.1 |
| 165 | 50.942 | 1030.580 | 40.0 |
| 166 | 48.005 | 269.638 | 11.1 |
| 167 | 76.814 | 310.656 | 8.0 |
| 518 | 31.000 | 77.320 | 4.9 |
| 519 | 172.230 | 385.880 | 4.4 |
| 520 | 542.600 | 1616.230 | 5.9 |
| 32 | 12.953 | 240.474 | 36.7 |
| 33 | 213.123 | 548.248 | 5.1 |
| 34 | 82.377 | 160.622 | 3.9 |

TABLE 6-continued

| | Potency of Peptides with Modification on Amino Acid at Position 17 | | |
|---|---|---|---|
| Peptide | hGLP-1R EC$_{50}$ (pM) | hGluc-R EC$_{50}$ (pM) | % Relative Potency Ratio |
| 35 | 83.697 | 334.904 | 7.9 |
| 36 | 43.060 | 277.733 | 12.8 |
| 37 | 68.620 | 2748.412 | 79.2 |
| 38 | 75.589 | 441.481 | 11.6 |
| 39 | 76.068 | 193.860 | 5.0 |
| 161 | 17.234 | 188.040 | 21.6 |
| 163 | 90.154 | 143.715 | 3.2 |
| 168 | 447.505 | 886.110 | 3.9 |
| 169 | 210.397 | 1404.311 | 13.2 |
| 170 | 147.744 | 835.556 | 11.2 |
| 171 | 106.863 | 376.304 | 7.0 |
| 172 | 213.354 | 1273.732 | 11.8 |
| 173 | 134.317 | 874.131 | 12.9 |
| 174 | 127.027 | 420.420 | 6.5 |
| 175 | 68.376 | 2018.944 | 58.4 |
| 176 | 59.942 | 480.338 | 15.9 |
| 177 | 23.777 | 306.464 | 25.5 |
| 178 | 51.770 | 104.397 | 4.0 |
| 179 | 130.928 | 203.431 | 3.1 |
| 180 | 24.377 | 71.735 | 5.8 |
| 181 | 56.000 | 33.440 | 1.2 |
| 182 | 29.060 | 22.580 | 1.5 |
| 183 | 23.730 | 81.430 | 6.8 |
| 184 | 22.040 | 29.620 | 2.7 |
| 185 | 44.113 | 229.651 | 10.3 |
| 186 | 44.923 | 100.835 | 4.4 |
| 188 | 20.847 | 34.713 | 3.3 |
| 189 | 11.315 | 44.301 | 7.7 |
| 192 | 107.568 | 227.117 | 4.2 |
| 193 | 282.849 | 476.105 | 3.3 |
| 194 | 424.799 | 592.863 | 2.8 |
| 195 | 86.016 | 94.577 | 2.2 |
| 196 | 26.953 | 240.329 | 17.6 |
| 197 | 64.040 | 111.890 | 3.5 |
| 198 | 211.810 | 302.200 | 2.8 |
| 199 | 31.604 | 180.232 | 11.3 |
| 200 | 22.687 | 97.711 | 8.5 |
| 201 | 22.724 | 182.560 | 15.9 |
| 202 | 17.824 | 242.436 | 26.9 |

TABLE 7

| | Potency of Peptides with Modification on Amino Acid at Position 20 | | |
|---|---|---|---|
| Peptide | hGLP-1R EC$_{50}$ (pM) | hGluc-R EC$_{50}$ (pM) | % Relative Potency Ratio |
| 203 | 77.466 | 34.112 | 0.9 |
| 204 | 43.306 | 595.006 | 27.2 |
| 205 | 29.901 | 8.136 | 0.5 |
| 206 | 70.949 | 18.170 | 0.5 |
| 207 | 177.618 | 96.175 | 1.1 |
| 208 | 64.412 | 658.298 | 20.2 |
| 209 | 126.544 | 42.591 | 0.7 |
| 210 | 156.403 | 93.732 | 1.2 |
| 211 | 166.600 | 60.904 | 0.7 |
| 212 | 531.595 | 97.476 | 0.4 |
| 213 | 534.307 | 140.535 | 0.5 |
| 214 | 2339.231 | 809.862 | 0.7 |
| 215 | 7623.287 | 2609.521 | 0.7 |
| 216 | 18055.470 | 5672.548 | 0.6 |
| 217 | 263.939 | 126.681 | 0.9 |
| 218 | 138.770 | 422.882 | 6.0 |
| 219 | 94.472 | 297.862 | 6.2 |
| 220 | 240.450 | 405.230 | 3.3 |
| 221 | 122.449 | 122.801 | 2.0 |
| 222 | 151.493 | 243.967 | 3.2 |
| 223 | 48.761 | 103.522 | 4.2 |
| 224 | 32.095 | 28.693 | 1.8 |
| 225 | 34.873 | 144.655 | 8.2 |

TABLE 7-continued

Potency of Peptides with Modification
on Amino Acid at Position 20

| Peptide | hGLP-1R EC$_{50}$ (pM) | hGluc-R EC$_{50}$ (pM) | % Relative Potency Ratio |
|---|---|---|---|
| 226 | 82.675 | 27.435 | 0.7 |
| 227 | 70.467 | 27.208 | 0.8 |
| 228 | 200.219 | 176.842 | 1.7 |
| 229 | 68.511 | 198.144 | 5.7 |
| 230 | 170.050 | 37.108 | 0.4 |
| 231 | 49.851 | 58.542 | 2.3 |
| 232 | 110.306 | 1023.865 | 18.4 |
| 233 | 440.364 | 407.411 | 1.8 |
| 234 | 68.020 | 1285.410 | 37.4 |
| 235 | 94.790 | 1262.350 | 26.3 |
| 236 | 22.063 | 214.558 | 19.2 |
| 237 | 26.745 | 298.747 | 22.1 |
| 238 | 154.658 | 990.172 | 12.7 |
| 239 | 105.489 | 704.613 | 13.2 |
| 240 | 57.099 | 332.464 | 11.5 |
| 241 | 35.843 | 175.226 | 9.7 |
| 242 | 248.687 | 1234.326 | 9.8 |
| 243 | 59.292 | 50.633 | 1.7 |
| 244 | 143.475 | 420.232 | 5.8 |
| 245 | 110.173 | 62.682 | 1.1 |
| 246 | 320.437 | 556.602 | 3.4 |
| 247 | 84.851 | 51.143 | 1.2 |
| 248 | 1089.266 | 13553.228 | 24.6 |
| 249 | 558.256 | 545.142 | 1.9 |
| 250 | 601.166 | 1566.333 | 5.2 |
| 251 | 79.751 | 248.071 | 6.2 |
| 252 | 119.246 | 1309.962 | 21.7 |
| 253 | 75.451 | 53.089 | 1.4 |
| 254 | 101.863 | 125.276 | 2.4 |
| 255 | 147.550 | 145.739 | 2.0 |
| 256 | 345.977 | 1306.254 | 7.5 |
| 257 | 7.348 | 1.659 | 0.4 |
| 258 | 34.046 | 93.123 | 5.4 |
| 259 | 19.118 | 34.833 | 3.6 |
| 260 | 33.080 | 76.881 | 4.6 |
| 261 | 16.152 | 29.390 | 3.6 |
| 262 | 13.017 | 11.700 | 1.8 |
| 263 | 25.386 | 64.646 | 5.0 |
| 264 | 69.537 | 297.466 | 8.5 |
| 265 | 71.223 | 130.903 | 3.6 |
| 266 | 66.478 | 293.480 | 8.7 |
| 267 | 65.581 | 127.683 | 3.9 |
| 268 | 39.521 | 29.251 | 1.5 |
| 269 | 51.951 | 271.143 | 10.3 |
| 270 | 24.445 | 31.318 | 2.5 |
| 271 | 54.604 | 27.999 | 1.0 |
| 272 | 15.650 | 14.309 | 1.8 |
| 273 | 22.118 | 23.336 | 2.1 |
| 274 | 27.112 | 31.277 | 2.3 |
| 275 | 110.638 | 175.236 | 3.1 |
| 276 | 143.383 | 91.395 | 1.3 |
| 277 | 49.494 | 57.270 | 2.3 |
| 278 | 78.855 | 83.493 | 2.1 |
| 279 | 86.544 | 150.224 | 3.4 |
| 280 | 78.346 | 154.623 | 3.9 |
| 281 | 155.104 | 1042.071 | 13.3 |
| 282 | 1230.958 | 1135.696 | 1.8 |
| 283 | 129.487 | 552.440 | 8.4 |
| 284 | 43.422 | 118.686 | 5.4 |
| 285 | 300.590 | 87.044 | 0.6 |
| 286 | 31.616 | 52.951 | 3.3 |
| 287 | 27.519 | 26.538 | 1.9 |
| 288 | 42.719 | 26.875 | 1.2 |
| 289 | 118.366 | 148.058 | 2.5 |
| 290 | 346.546 | 260.062 | 1.5 |
| 291 | 1509.011 | 847.167 | 1.1 |
| 292 | 28.705 | 20.397 | 1.4 |
| 293 | 91.968 | 33.473 | 0.7 |
| 294 | 510.108 | 102.417 | 0.4 |
| 295 | 312.053 | 17071.588 | 108.2 |
| 296 | 64.149 | 3253.412 | 100.3 |
| 297 | 30.440 | 103.940 | 6.8 |
| 298 | 75.450 | 572.856 | 15.0 |
| 299 | 75.820 | 193.220 | 5.0 |

TABLE 7-continued

Potency of Peptides with Modification
on Amino Acid at Position 20

| Peptide | hGLP-1R EC$_{50}$ (pM) | hGluc-R EC$_{50}$ (pM) | % Relative Potency Ratio |
|---|---|---|---|
| 300 | 19.742 | 18.360 | 1.8 |
| 301 | 55.339 | 31.826 | 1.1 |
| 302 | 151.070 | 270.815 | 3.5 |
| 303 | 99.136 | 99.581 | 2.0 |
| 304 | 238.821 | 687.098 | 5.7 |
| 305 | 211.193 | 154.945 | 1.5 |
| 306 | 47.214 | 775.451 | 32.5 |
| 307 | 22.180 | 1126.909 | 100.5 |
| 308 | 27.499 | 1716.004 | 123.4 |
| 309 | 70.607 | 17377.186 | 486.8 |
| 310 | 56.382 | 1836.826 | 64.4 |
| 311 | 35.100 | 468.731 | 26.4 |
| 312 | 152.183 | 2775.255 | 36.1 |
| 313 | 138.271 | 1227.004 | 17.6 |
| 314 | 30.764 | 6832.600 | 439.3 |
| 315 | 18.118 | 5853.796 | 639.1 |
| 318 | 55.250 | 12001.370 | 429.7 |
| 321 | 22.635 | 4402.316 | 384.7 |
| 322 | 68.302 | >24663.650 | — |
| 323 | 11406.357 | >25553.360 | — |
| 324 | 1329.728 | 1927.309 | 2.9 |
| 325 | 928.583 | >25546.770 | — |
| 326 | 6741.438 | >25645.230 | — |
| 327 | 30.097 | >25671.500 | — |
| 328 | 15.357 | 1698.302 | 218.8 |
| 330 | 487.667 | >25645.230 | — |
| 331 | 62.577 | 66.606 | 2.1 |
| 332 | 77.474 | 58.853 | 1.5 |
| 333 | 134.727 | 212.627 | 3.1 |
| 334 | 249.757 | 461.777 | 3.7 |
| 335 | 1060.440 | 311.556 | 0.6 |
| 336 | 631.959 | 304.533 | 1.0 |
| 337 | 400.475 | 89.638 | 0.4 |
| 338 | 307.997 | 25.677 | 0.2 |
| 339 | 311.774 | 70.289 | 0.4 |
| 340 | 312.126 | 94.738 | 0.6 |
| 341 | 362.926 | 72.771 | 0.4 |
| 342 | 220.158 | 4832.731 | 43.4 |
| 343 | 198.013 | 19629.289 | 196.1 |
| 521 | 677.458 | 10099.850 | 29.5 |
| 522 | 508.426 | 6363.603 | 24.8 |
| 523 | 615.272 | >24743.230 | — |
| 524 | 365.830 | >24393.160 | — |
| 525 | 177.315 | 2454.700 | 27.4 |
| 526 | 194.459 | 689.991 | 7.0 |

TABLE 8

Potency of Peptides with Modification
on Amino Acid at Position 24

| Peptide | hGLP-1R EC$_{50}$ (pM) | hGluc-R EC$_{50}$ (pM) | % Relative Potency Ratio |
|---|---|---|---|
| 343 | 58.553 | 125.666 | 4.2 |
| 344 | 134.933 | >26900.000 | — |
| 345 | 2860.629 | 167.753 | 0.1 |
| 346 | 7318.019 | 202.791 | 0.1 |
| 347 | 4971.036 | 596.962 | 0.2 |
| 348 | 70.074 | 4107.919 | 116.0 |
| 349 | 121.061 | 83.684 | 1.4 |
| 350 | 88.617 | 383.622 | 8.6 |
| 351 | 605.282 | 216.444 | 0.7 |
| 352 | 192.562 | 139.241 | 1.4 |
| 353 | 311.480 | 162.628 | 1.0 |
| 354 | 1106.278 | 901.878 | 1.6 |
| 355 | 424.009 | 478.456 | 2.2 |
| 356 | 304.243 | 315.728 | 2.1 |
| 357 | 916.728 | 550.189 | 1.2 |
| 358 | 74.855 | 16049.922 | 424.1 |
| 359 | 46.101 | 5048.643 | 216.6 |

TABLE 8-continued

| | Potency of Peptides with Modification on Amino Acid at Position 24 | | |
|---|---|---|---|
| Peptide | hGLP-1R EC$_{50}$ (pM) | hGluc-R EC$_{50}$ (pM) | % Relative Potency Ratio |
| 360 | 107.773 | 5640.213 | 103.5 |
| 361 | 35.698 | 23.565 | 1.3 |
| 362 | 54.824 | 42.799 | 1.5 |
| 363 | 18.268 | 47.517 | 5.1 |
| 364 | 23.354 | 30.435 | 2.6 |
| 365 | 51.340 | 8.774 | 0.3 |
| 366 | 31.038 | 27.411 | 1.7 |
| 367 | 139.499 | 72.449 | 1.0 |
| 368 | 186.325 | 290.003 | 3.1 |
| 369 | 103.653 | 201.633 | 3.8 |
| 370 | 323.469 | 182.253 | 1.1 |
| 371 | 190.869 | 87.178 | 0.9 |
| 372 | 71.789 | 35.094 | 1.0 |
| 373 | 66.677 | 242.458 | 7.2 |
| 374 | 434.390 | 260.160 | 1.2 |
| 375 | 225.465 | 154.858 | 1.4 |
| 376 | 155.910 | 853.499 | 10.8 |
| 377 | 149.787 | 189.515 | 2.5 |
| 378 | 158.745 | 157.793 | 2.0 |
| 379 | 71.766 | 85.739 | 2.4 |
| 380 | 871.183 | 14947.910 | 33.9 |
| 381 | 174.069 | 1308.052 | 14.9 |
| 382 | 56.012 | 329.333 | 11.6 |
| 383 | 197.271 | 231.689 | 2.3 |
| 384 | 796.819 | 1244.347 | 3.1 |
| 386 | 31.186 | 140.185 | 8.9 |
| 387 | 82.603 | 1573.075 | 37.7 |
| 388 | 52.732 | 71.929 | 2.7 |
| 389 | 224.224 | 135.698 | 1.2 |

TABLE 9

| | Potency of Peptides with Modification on Amino Acid at Position 10 | | |
|---|---|---|---|
| Peptide | hGLP-1R EC$_{50}$ (pM) | hGluc-R EC$_{50}$ (pM) | % Relative Potency Ratio |
| 391 | 892.536 | 22172.801 | 49.1 |
| 392 | 312.355 | 6922.306 | 43.8 |
| 393 | 0.458 | 2.158 | 9.3 |
| 394 | 0.652 | 2.408 | 7.3 |
| 395 | 0.774 | 9.554 | 24.4 |
| 396 | 0.583 | 11.835 | 40.2 |
| 397 | 5.360 | 10.003 | 3.7 |
| 398 | 3.280 | 2.449 | 1.5 |

TABLE 10

| | Potency of Peptides with Modification on Amino Acid at Position 13 | | |
|---|---|---|---|
| Peptide | hGLP-1R EC$_{50}$ (pM) | hGluc-R EC$_{50}$ (pM) | % Relative Potency Ratio |
| 399 | 0.672 | 5.567 | 16.4 |
| 400 | 1.268 | 10.714 | 16.7 |
| 401 | 0.585 | 9.542 | 32.3 |
| 402 | 1.044 | 18.081 | 34.3 |
| 404 | 5.652 | 21.821 | 7.6 |
| 405 | 1041.139 | 8585.500 | 16.3 |
| 406 | 457.645 | 7308.311 | 31.6 |

Example 3: Mouse Acute Food Intake Study

Male C57Bl/6 mice obtained from Jackson Laboratories or Charles River at 8-9 weeks of age and were housed one per cage in BioDaq (Research Diets) cages. Mice were placed on Alpha Dri bedding, standard chow diet (Envigo, 2018) and given water pouches. Mice were allowed to acclimate for 1-2 weeks. Body weight was measured to ensure appropriate acclimation. After acclimation, mice were sham dosed a minimum of 2 times prior to initiation of food intake study. On study day, mice were placed in clean cage bottoms, weighed, and fasted for 6-8 hours. Mice were sorted into groups based on average 24-hour food intake data and body weight. 1-2 hours prior to lights out, mice were dosed subcutaneously with one vehicle or test peptide dissolved in an appropriate vehicle at 5 mL/kg. Mice were left undisturbed and allowed access to food and water for 48 hours. Automated food intake was monitored in the BioDaq system was monitored during this time. Discrete food intake data was exported into MS Excel from which cumulative food intake data was generated and analyzed. Food intake at 24 hours compared to vehicle food intake (percent) is provided in Table 11.

TABLE 11

| | Food Intake of Mice Administered Lipidated Peptides | | |
|---|---|---|---|
| Peptide | Dose | 24 hr % Vehicle Food Intake | Standard Error of the Mean (SEM) |
| 43 | 10 nmol/kg | 53.2 | 4.9 |
| 46 | 10 nmol/kg | 72.1 | 4.3 |
| 47 | 10 nmol/kg | 51.4 | 4.9 |
| 49 | 10 nmol/kg | 69.2 | 9.0 |
| 50 | 10 nmol/kg | 78.5 | 4.1 |
| 69 | 10 nmol/kg | 74.3 | 4.6 |
| 68 | 10 nmol/kg | 74.2 | 4.2 |
| 96 | 10 nmol/kg | 51.9 | 5.5 |
| 62 | 10 nmol/kg | 52.7 | 3.1 |
| 63 | 10 nmol/kg | 37.9 | 7.0 |
| 71 | 10 nmol/kg | 80.6 | 11.5 |
| 45 | 10 nmol/kg | 76.2 | 4.7 |
| 399 | 10 nmol/kg | 72.3 | 9.6 |
| 102 | 10 nmol/kg | 81.9 | 14.6 |
| 73 | 10 nmol/kg | 63.4 | 4.2 |
| 7 | 10 nmol/kg | 55.0 | 4.0 |
| 349 | 10 nmol/kg | 79.9 | 4.2 |
| 203 | 10 nmol/kg | 81.4 | 7.3 |
| 361 | 10 nmol/kg | 78.8 | 5.3 |
| 364 | 10 nmol/kg | 63.7 | 5.5 |
| 366 | 10 nmol/kg | 83.5 | 9.4 |
| 223 | 10 nmol/kg | 63.6 | 6.3 |
| 229 | 10 nmol/kg | 54.8 | 5.6 |
| 224 | 10 nmol/kg | 66.5 | 7.8 |
| 375 | 10 nmol/kg | 66.0 | 7.7 |
| 247 | 10 nmol/kg | 66.9 | 5.5 |
| 257 | 3 nmol/kg | 94.7 | 6.6 |
| 257 | 10 nmol/kg | 96.5 | 3.7 |
| 224 | 1 nmol/kg | 91.3 | 10.9 |
| 224 | 3 nmol/kg | 76.6 | 3.3 |
| 224 | 10 nmol/kg | 72.5 | 8.3 |
| 229 | 1 nmol/kg | 86.0 | 4.7 |
| 229 | 3 nmol/kg | 72.5 | 3.6 |
| 229 | 10 nmol/kg | 50.5 | 3.7 |
| 289 | 3 nmol/kg | 76.1 | 6.9 |
| 289 | 10 nmol/kg | 49.6 | 6.7 |
| 299 | 30 nmol/kg | 43.7 | 7.3 |
| 301 | 10 nmol/kg | 54.9 | 7.6 |
| 300 | 10 nmol/kg | 45.2 | 6.5 |
| 302 | 30 nmol/kg | 46.4 | 9.5 |
| 140 | 10 nmol/kg | 65.4 | 5.5 |
| 195 | 10 nmol/kg | 58.2 | 8.7 |
| 188 | 10 nmol/kg | 60.7 | 6.3 |
| 188 | 1 nmol/kg | 99.9 | 6.3 |
| 188 | 3 nmol/kg | 80.6 | 5.6 |
| 188 | 10 nmol/kg | 49.8 | 5.1 |
| 195 | 1 nmol/kg | 102.1 | 16.9 |
| 195 | 3 nmol/kg | 84.0 | 13.3 |
| 195 | 10 nmol/kg | 49.9 | 4.4 |

Example 4: Evaluating Proteolytic-Resistance of Lipidated Peptides to Fasted State Stimulated Gastric Fluid (FasSSGF) Containing Porcine Pancreatic Pepsin Lyophilized porcine pancreatic pepsin (Sigma: P7012) was reconstituted to 0.5 mg/mL (~2500 units/mL) in freshly prepared FasSSGF (Biorelevant media) to give the enzyme stock solution. Peptide stock solution was prepared to a concentration of 250 μM (~1.0 mg/mL) in FasSSGF. 200 μL (10 μg, ~250 units) of pepsin stock solution was added to 200 μL of peptide solution (1.0 mg/mL, ~100 μg of peptide, ~25 nmoles) and the mixture was co-incubated in a temperature-regulated incubator at 37° C. for the duration of the experiment. 30 μL aliquot of the peptide-enzyme mixture was periodically withdrawn (t=0, 5, 10, 15, and 30 min) and quenched immediately by addition of 80 μL of 0.1 M ammonium bicarbonate solution in water/acetonitrile (4:1, pH 8) to arrest proteolytic activity. 30 μL aliquot was analyzed by analytical RP-HPLC. Analytical RP-HPLC method: Agilent Polaris C8-A column (4.6×100 mm, 3 micron) eluted with a linear binary gradient of 10-90°/ MeCN (0.1% TFA v/v) in water (0.1% TFA v/v) over either 10 or 15 mins at 1.5 mL min-1 at 40° C. with detection by UV absorption at 210 nm. Manual integration (AUC) allowed estimation of remaining intact peptide over the time course of the experiment. Peptide stability data is provided in Table 12.

TABLE 12

Stability of Lipidated Peptides Incubated with FasSSGF

| Peptide | % intact peptide over time (min) | | | | |
|---|---|---|---|---|---|
| | 0 | 5 | 10 | 15 | 30 |
| Semaglutide | 100 | 15 | 13 | 12 | 14 |
| 7 | 100 | 81 | 60 | 35 | 18 |
| 229 | 100 | 100 | 97 | 91 | 79 |
| 15 | 100 | ND | ND | 91 | 77 |
| 78 | 100 | ND | ND | 100 | 100 |
| 290 | 100 | ND | ND | 0 | 0 |
| 282 | 100 | ND | ND | 83 | 76 |
| 283 | 100 | ND | ND | 68 | 48 |
| 287 | 100 | ND | ND | 0 | 0 |
| 367 | 100 | ND | ND | 0 | 0 |

Example 5: Evaluating Proteolytic Resistance of Peptides to Neprilysin 10.0 μg (~10 units) recombinant Neprilysin (R&D Systems: 1182-ZNC-010) was reconstituted to 100 μL (100 μg/mL, ~100 units/mL) in assay buffer (50 mM Tris, 50 mM NaCl, 50 mM NaHCO$_3$, adjusted to pH 8.3) to give the enzyme stock solution. Peptide stock solutions were prepared to a concentration of ~250 μM (~1.0 mg/mL of 4 kDa peptide) in assay buffer. 100 μL (10 μg, ~10 units) of neprilysin stock solution was added to 100 μL of peptide stock solution (1.0 mg/mL, ~100 μg of peptide) and the mixture was co-incubated in a temperature regulated incubator at 37° C. for the duration of the experiment. 25 μL aliquots (~12.5 μg initial peptide) of the peptide-enzyme mixture were periodically withdrawn (t=0, 30 mins, 1 h, 2 h, 4 h and 24 h) and quenched immediately by addition to an equal volume (75 μL) of 10% TFA (v/v) in 1:1 water/ acetonitrile to arrest proteolytic activity. The quenched aliquot centrifuged at 7800 rpm, and 30 μL of the supernatant was analyzed by analytical RP-HPLC as follows: Analytical RP-HPLC method: Agilent Polaris C8-A column (4.6×100 mm, 3 micron) eluted with a linear binary gradient of 10-90% MeCN (0.1% TFA v/v) in water (0.1% TFA v/v) over either 10 or 15 mins at 1.5 mL min$^{-1}$ at 40° C. with detection by UV absorption at 210 nm. Manual integration (AUC) allowed estimation of remaining intact peptide over the time course of the experiment. Peptide stability data is provided in Table 13.

TABLE 13

Stability of Lipidated Peptides Incubated with Neprilysin

| Peptide | % intact peptide over time | | | | |
|---|---|---|---|---|---|
| | 0 | 30 min | 2 hr | 4 hr | 24 hr |
| Semaglutide | 100 | 100 | 100 | 83 | 48 |
| 7 | 100 | 100 | 100 | 97 | 84 |
| 229 | 100 | 100 | 100 | 100 | 100 |
| 15 | 100 | ND | ND | 100 | 83 |
| 78 | 100 | ND | ND | 100 | 100 |
| 290 | 100 | ND | ND | 89 | 82 |
| 282 | 100 | ND | ND | 100 | 97 |
| 283 | 100 | ND | ND | 81 | 63 |
| 287 | 100 | ND | ND | 77 | 59 |

Example 6: Evaluating Proteolytic-Resistance of Mono-Lipidated Peptides to Fasted-State Simulated Intestinal Fluid (FasSSIF/Pancreatin)

A fresh suspension of FasSSIF/P (Fasted-State Simulated Intestinal Fluid+USP Pancreatin®) was prepared according to that described by Galia, Nicolaides, Hörter, Löbenberg, Reppas and Dressman: Pharm. Res. 15 (1998) 698-70.5, and USP XL requirements. The preparation of FasSSIF/P is provided in Table 14. The resulting preparation was used immediately without storage.

TABLE 14

Preparation of FasSSIF/Pancreatin

| Composition | Conc. mM | Mol. Weight | Mass L–1 | Supplier data |
|---|---|---|---|---|
| Sodium Taurocholate hydrate | 3 | 537.68 | 1.61 g | Sigma: 86339 |
| L-α-phosphatidylcholine (soybean) | 0.5 | av. 768 | 0.38 g | Sigma: 44924 |
| Dibasic sodium phosphate | 30 | 141.96 | 4.26 g | Sigma: S7907 |
| Sodium hydroxide | 10 | 40.00 | 0.40 g | Sigma: S8045 |
| Sodium Chloride | 100 | 58.44 | 5.84 g | Sigma: S7653 |
| Pancreatin (8 × USP) | — | — | 1.25 g | Sigma: P7545 |

Peptide for evaluation (1.0 mg) was dissolved in pre-warmed FasSSIF without Pancreatin® (200 μL). To this fresh FasSSIF/Pancreatin® (100 μL) was added to initiate potential proteolysis. Following momentary vortexing of the reaction tube the mixture was incubated at 37° C. in a thermostatic water bath for the duration of the experiment. 25 μL aliquot of the co-incubated peptide-enzyme mixture was periodically withdrawn (t=0, 5, 10 15 and 30 min) and quenched immediately by addition to a solution of 10% TFA in 1:1 water/acetonitrile (75 μL) to arrest proteolytic activity. Quenched samples were centrifuged (7800 RPM, 3 mins) to pellet solids and 10 μL aliquots of the supernatant solution were analyzed using analytical RP-HPLC as follows: Analytical RP-HPLC method: Agilent Polaris C8-A column (4.6×100 mm, 3 micron) eluted with a linear binary gradient of 10-90% MeCN (0.1% TFA v/v) in water (0.1% TFA v/v)

over either 10 or 15 mins at 1.5 mL min⁻¹ at 40° C. with detection by UV absorption at 210 nm. Manual integration (AUC) allowed estimation of remaining intact peptide over the time course of the experiment. Peptide stability data is provided in Table 15.

TABLE 15

Stability of Lipidated Peptides Incubated with FasSSIF.

| | % intact peptide over time (min) | | | | |
|---|---|---|---|---|---|
| Peptide | 0 | 5 | 10 | 15 | 30 |
| Semaglutide | 100 | 22 | 0 | 0 | 0 |
| 7 | 100 | 96 | 98 | 96 | 94 |
| 229 | 100 | 60 | 46 | 33 | 26 |
| 78 | 100 | 83 | 76 | 69 | 58 |
| 47 | 100 | 90 | 88 | 83 | 75 |
| 49 | 100 | 97 | 96 | 95 | 90 |
| 117 | 100 | 54 | 35 | 22 | 8 |
| 43 | 100 | 83 | 33 | 29 | 19 |
| 48 | 100 | ND | ND | ND | 94 |
| 50 | 100 | ND | ND | ND | 98 |
| 51 | 100 | ND | ND | ND | 91 |
| 52 | 100 | ND | ND | ND | 90 |
| 53 | 100 | ND | ND | ND | 92 |

Example 7: Glucose Levels in GLP-1R Knockout Mice Treated with GLP-1/Glucagon Peptides GLP-JR knockout (KG) and wildtype (WT) mice at 8-14 weeks of age were singly housed on standard chow diet (Envigo, 2918) and automatic water. They acclimated for a minimum of ~1-2 weeks, and mice were sorted into groups (n=4-8/group) based on body weight. On day of study, mice were fasted briefly for 2 hrs prior to study start. In some studies, mice were pre-treated with octreotide (BaChem, 10 mg/kg) at 30 minutes prior to peptide injection. Mice were dosed by subcutaneous injection, with peptide administration at doses listed in the Tables 16 and 17. Glucose was measured via glucometer at various timepoints including −30 min (prior to octreotide when used in studies), 0 min (before peptide dose), 30, 60, 120, 180, 240, and 360 minutes. Since these studies are acute in nature, mice were re-used for multiple studies (no more than 3) and always allowed at least a minimum wash-out period of 1 week. Glucose changes represented as percent glucose change (at 60 or 120 min) from time 0 min are provided in Tables 16 and 17.

TABLE 16

Glucose Change in GLP-1R KO and WT Mice
Treated with GLP-1/Glucagon Peptides

| Peptide | Dose | WT % glucose change 120 min | WT SEM | GLP-1R KO % glucose change 120 min | KO % glucose change SEM | Somatostatin pretreatment? |
|---|---|---|---|---|---|---|
| Vehicle | 5 mL/kg | 0.9 | 6.3 | −0.7 | 7.6 | No |
| 78 | 3 nmol/kg | −42.0 | 2.1 | 51.3 | 15.4 | No |
| Vehicle | 5 mL/kg | −19.2 | 6.7 | −9.1 | 9.5 | No |
| 69 | 3 nmol/kg | −27.2 | 7.7 | 17.6 | 4.8 | No |
| 43 | 3 nmol/kg | −56.0 | 4.7 | 63.9 | 39.2 | No |
| Vehicle | 5 mL/kg | 43.3 | 12.6 | 72.4 | 24.9 | yes 30 min prior to cpd |
| 49 | 10 nmol/kg | −1.2 | 7.2 | 193.3 | 16.2 | yes 30 min prior to cpd |
| 49 | 30 nmol/kg | 16.8 | 25.9 | 154.3 | 17.0 | yes 30 min prior to cpd |
| Vehicle | 5 mL/kg | 28.6 | 6.2 | 23.4 | 8.7 | yes 30 min prior to cpd |
| 97 | 10 nmol/kg | −41.9 | 3.0 | 91.1 | 25.5 | yes 30 min prior to cpd |
| 97 | 30 nmol/kg | −14.7 | 7.8 | 150.8 | 17.3 | yes 30 min prior to cpd |
| Vehicle | 5 mL/kg | 25.8 | 12.9 | 14.1 | 6.9 | yes 30 min prior to cpd |
| 63 | 10 nmol/kg | −26.4 | 5.2 | 68.2 | 10.2 | yes 30 min prior to cpd |
| 63 | 30 nmol/kg | −23.8 | 12.1 | 113.0 | 40.1 | yes 30 min prior to cpd |
| Vehicle | 5 mL/kg | 30.0 | 17.4 | 29.2 | 14 | yes 30 min prior to cpd |
| 126 | 10 nmol/kg | −26.6 | 6.1 | 76.1 | 16.6 | yes 30 min prior to cpd |
| 126 | 30 nmol/kg | −46.2 | 3.9 | 92.4 | 30.2 | yes 30 min prior to cpd |
| Vehicle | 5 mL/kg | 2.2 | 5.2 | 20.5 | 7 | yes 30 min prior to cpd |
| 399 | 10 nmol/kg | −35.4 | 3.6 | 151.0 | 52.7 | yes 30 min prior to cpd |
| 399 | 30 nmol/kg | −45.0 | 2.9 | 121.3 | 15.6 | yes 30 min prior to cpd |
| Vehicle | 5 mL/kg | 11.2 | 6.5 | 12.0 | 8.7 | yes 30 min prior to cpd |
| 203 | 10 nmol/kg | −29.5 | 4.9 | 54.6 | 17.3 | yes 30 min prior to cpd |
| 203 | 30 nmol/kg | −36.5 | 5.1 | 106.9 | 19.5 | yes 30 min prior to cpd |
| Vehicle | 5 mL/kg | 14.4 | 7.0 | 49.9 | 17.7 | yes 30 min prior to cpd |
| 361 | 10 nmol/kg | −23.0 | 10.6 | 91.5 | 14.5 | yes 30 min prior to cpd |
| 361 | 30 nmol/kg | −38.1 | 4.7 | 93.8 | 21.1 | yes 30 min prior to cpd |
| Vehicle | 5 mL/kg | 10.7 | 8.9 | 31.4 | 16.6 | yes 30 min prior to cpd |
| 7 | 1.5 nmol/kg | 5.4 | 8.3 | 80.8 | 14.3 | yes 30 min prior to cpd |
| 7 | 5 nmol/kg | −21.2 | 9.8 | 152.9 | 43.0 | yes 30 min prior to cpd |
| Vehicle | 5 mL/kg | 51.6 | 16.5 | 15.5 | 13.8 | yes 30 min prior to cpd |
| 349 | 10 nmol/kg | 4.9 | 14.3 | 27.8 | 13.5 | yes 30 min prior to cpd |
| 349 | 30 nmol/kg | −17.3 | 7.3 | 100.2 | 21.8 | yes 30 min prior to cpd |
| Vehicle | 5 mL/kg | 19.9 | 9.0 | 39.1 | 10.6 | yes 30 min prior to cpd |
| 224 | 3 nmol/kg | −46.3 | 4.8 | 100.3 | 34 | yes 30 min prior to cpd |
| 224 | 10 nmol/kg | −40.0 | 5.0 | 132.3 | 32.6 | yes 30 min prior to cpd |
| Vehicle | 5 mL/kg | 2.5 | 4.4 | 10.2 | 4.9 | No |
| 229 | 10 nmol/kg | −36.7 | 5.2 | 14.2 | 9.0 | No |
| 229 | 30 nmol/kg | −40.6 | 2.3 | 44.5 | 5.3 | No |

TABLE 16-continued

Glucose Change in GLP-1R KO and WT Mice
Treated with GLP-1/Glucagon Peptides

| Peptide | Dose | WT % glucose change 120 min | WT SEM | GLP-1R KO % glucose change 120 min | KO % glucose change SEM | Somatostatin pretreatment? |
|---|---|---|---|---|---|---|
| Vehicle | 5 mL/kg | 7.3 | 9.2 | 19.2 | 4.1 | No |
| 289 | 10 nmol/kg | −8.5 | 7.7 | 8.9 | 4.6 | No |
| 289 | 30 nmol/kg | −16.1 | 5.9 | 7.7 | 5.6 | No |

TABLE 17

Glucose Change in GLP-1R KO and WT Mice
Treated with GLP-1/Glucagon Peptides

| Peptide | Dose | WT % glucose change 60 min | WT SEM | GLP-1R KO % glucose change −60 min | KO % glucose change SEM | Somatostatin pretreatment? |
|---|---|---|---|---|---|---|
| Vehicle | 5 mL/kg | −4.1 | 4.4 | 16.2 | 7.4 | No |
| 301 | 10 nmol/kg | −43 | 3.2 | 29.1 | 16.1 | No |
| 301 | 30 nmol/kg | −35.7 | 4.3 | 17.9 | 7.7 | No |
| Vehicle | 5 mL/kg | 3.7 | 3.7 | 6.3 | 2.1 | No |
| 140 | 10 nmol/kg | −32.1 | 2.8 | 46.2 | 6.8 | No |
| 140 | 30 nmol/kg | −29.0 | 3.0 | 59.8 | 11.4 | No |
| Vehicle | 5 mL/kg | 9.9 | 6.9 | 2.8 | 3.4 | No |
| 188 | 10 nmol/kg | −23.2 | 3.9 | 64 | 15.6 | No |
| 188 | 30 nmol/kg | −31.3 | 2.5 | 44.6 | 11.0 | No |
| Vehicle | 5 mL/kg | 10.5 | 5.4 | 7.8 | 4.0 | No |
| 195 | 10 nmol/kg | 1.4 | 3.4 | 35.3 | 5.4 | No |
| 195 | 30 nmol/kg | −17.0 | 4.9 | 48.0 | 15.1 | No |

Example 8: Pharmacokinetic Profiling in Pre-Clinical Species

Selected test peptides (n=8) were profiled for pharmacokinetic (PK) properties in the mouse after single intravenous (i.v.) or subcutaneous (s.c.) dose. A subset (n=4) meeting the acceptance criteria was subsequently profiled in the dog (single i.v. dose) and non-human primate (single i.v. and s.c. dose). After administration, blood was sampled up to 48 hrs in the mouse, 120 hrs in the dog and 168 hrs in the non-human primate, at time points selected to accurately determine the full pharmacokinetic profile in each species. Low-binding plasticware containers were used during preparation and sample handling to avoid non-specific binding.

Mouse: PK was studied in lean male C57BL/6 (Peptide 140, Peptide 188, Peptide 195, Peptide 420, Peptide 477 and Peptide 472) or male C57BL/6 DIG pre-conditioned mice on high-fat diet (Peptide 224, Peptide 229). After dosing, PK samples were collected from the dorsal metatarsal vein. Blood of each sample was transferred into plastic micro centrifuge tubes containing EDTA-K2, inverted several times for proper mixing of contents and then placed on wet ice. The blood samples were centrifuged at 4° C. to obtain plasma and stored at −75° C. prior to analysis.

Dog: PK was studied in non-naïve male Beagle dogs. After dosing, PK samples were collected from the jugular vein. Blood of each sample was transferred into plastic micro centrifuge tubes containing EDTA-K2, inverted several times for proper mixing of contents and then placed on wet ice. Plasma was separated by centrifugation and stored frozen in matrix tubes at a temperature set to maintain −20° C. until analysis.

Non-human primate: PK was studied in non-naïve male cynomolgus monkeys. After dosing, PK samples were collected from the femoral vein. Blood of each sample was transferred into plastic micro centrifuge tubes containing EDTA-K2, inverted several times for proper mixing of contents and then placed on wet ice. The blood samples were centrifuged under refrigerated (2° C. to 8° C.) conditions within 30 minutes following sample collection to obtain plasma and stored at −60° C. to −90° C. ° C. prior to analysis.

Formulation: Test articles were formulated in 20 mM Sodium Phosphate, 220 mM Sorbitol pH 7.5 (Peptide 224, Peptide 229, Peptide 140, Peptide 188, Peptide 195) or 20 mM sodium acetate 220 mM mannitol pH 4.5 (Peptide 420, Peptide 477, Peptide 472).

Samples analysis: Samples were analyzed by LC-MS/MS. Calibration standards were injected at the beginning and end of each batch and the determined concentration for each prepared standard was used to construct a calibration curve. Plasma and dose aliquot sample concentrations were determined from the plasma calibration curve.

Data analysis: Plasma concentration data was analyzed by non-compartmental analysis (NCA) using Phoenix Winnonlin v. 8.3.3.33. Linear trapezoidal rule was used for increasing values and log trapezoidal rule was used for decreasing values, applying uniform weighting for lambda_z calculations. Subcutaneous bioavailability was calculated as the ratio $AUC(s.c.)_{0\text{-}inf}/AUC(i.v.)_{0\text{-}inf}$. Reported values (Table 18) represent the mean of the individual estimates.

Results: Test peptide half-life after intravenous administration and absolute bioavailability after subcutaneous administration calculated by NCA are reported in Table 18. Generally, test peptides displayed pro-longed circulation half-lives in all studied pre-clinical species, and additionally a significant extension in higher order species as compared to rodent. In the mouse, estimated half-lives spanned 2.9-19 hrs, in the dog 86-71 hrs and in non-human primates 49-130 hrs. The bioavailability after subcutaneous administration was generally ≥50%, with comparable levels in the mice and non-human primates. Test peptides evaluated in non-human primates all displayed high bioavailability ≥75%.

TABLE 18

Pre-clinical PK. Half-life after intravenous administration and absolute subcutaneous bioavailability of profiled test peptides in mouse, dog and non-human primate at specified doses.

| Species | Strain | Alias | Dose nmol/kg | Half-life i.v. administration h | S.c. bioavailability % |
|---------|--------|-------|--------------|--------------------------------|------------------------|
| Mouse | C57bl/6 | Peptide 140 | 10 | 6.4 | 102 |
| | | Peptide 188 | 10 | 7.9 | 98 |
| | | Peptide 195 | 10 | 11 | 66 |
| | | Peptide 420 | 10 | 5.7 | 49 |

TABLE 18-continued

Pre-clinical PK. Half-life after intravenous administration and absolute subcutaneous bioavailability of profiled test peptides in mouse, dog and non-human primate at specified doses.

| Species | Strain | Alias | Dose nmol/kg | Half-life i.v. administration h | S.c. bioavailability % |
|---------|--------|-------|--------------|--------------------------------|------------------------|
| | | Peptide 472 | 10 | 2.9 | 83 |
| | | Peptide 477 | 10 | 8.9 | 50 |
| | C57bl/6 (DIO) | Peptide 224 | 10 | 9.5 | 109 |
| | | Peptide 229 | 10 | 19 | 86 |
| Dog | Beagle | Peptide 224 | 10 | 75 | n.d. |
| | | Peptide 229 | 10 | 86 | n.d. |
| | | Peptide 188 | 10 | 71 | n.d. |
| | | Peptide 195 | 10 | 78 | n.d. |
| NHP | Cynomolgus | Peptide 224 | 10 | 100 | 95 |
| | | Peptide 229 | 20 | 130 | 75 |
| | | Peptide 188 | 10 | 67 | 79 |
| | | Peptide 195 | 10 | 49 | 77 | n.d.: not determined.

What is claimed is:

1. A peptide comprising the amino acid sequence selected from the group consisting of:
   (i) H-Aib-Q-G-T-F-T-S-D-V-S-K-αMePhe-L-D-T-X17-R-A-R-D-F-V-Q-W-L-L-E-Aib-G-acid (SEQ ID NO: 100);
   wherein X17 is K(O2Oc)-(O2Oc)-γE-C18diacid);
   (ii) H-Aib-Q-G-T-F-T-S-D-V-S-K-αMePhe-L-D-T-X17-R-A-R-D-F-V-Q-W-L-L-E-Aib-G-acid (SEQ ID NO: 107);
   wherein X17 is K(O2Oc)-(O2Oc)-γE-C20diacid);
   (iii) H-Aib-H-G-S-αMePhe-T-S-D-V-S-K-αMePhe-L-D-S-R-A-A-X20-D-αMePhe-V-Q-Aib-I-A-N-T-amide (SEQ ID NO: 228);
   wherein X20 is K(ε-(O2Oc)-(O2Oc)-γE-C18diacid); and
   (iv) H-Aib-H-G-S-αMePhe-T-S-D-V-S-K-αMePhe-L-D-S-R-A-A-X20-D-αMePhe-V-Q-Aib-I-A-N-T-amide (SEQ ID NO: 233);
   wherein X20 is K(ε-(O2Oc)-(O2Oc)-γE-γE-C20diacid).

2. The peptide of claim 1, wherein the peptide binds to the GLP-1 receptor (GLP-1R), binds to the glucagon receptor (GCGR), or binds to both a GLP-1 receptor and a glucagon receptor.

3. The peptide of claim 2, wherein the GLP-1R is a human GLP-1R.

4. The peptide of claim 2, wherein the GCGR is a human GCGR.

5. The peptide of claim 1, wherein the peptide is an agonist of GLP-1 activity, an agonist of glucagon activity, or an agonist of both GLP-1 and glucagon activity.

6. The peptide of claim 1, wherein the peptide has increased proteolytic-resistance relative to the natural ligand of the GLP-1R and/or GCGR.

7. The peptide of claim 1, wherein the peptide is isolated.

8. The peptide of claim 1, wherein the peptide has at least 50%, at least 60%, at least 70%, at least 75%, at least 80%, at least 85%, at least 90%, at least 95, or 100% of intact peptide remaining after incubation with a protease at 37° C. for 5 min, 10 min, 15 min, 30 min, 2 hr, 4 hr or 24 hr.

9. The peptide of claim 8, wherein the protease is selected from the group consisting of neprilysin, pepsin, pancreatin, simulated gastric fluid with pepsin, and simulated intestinal fluid with pancreatin.

10. The peptide of claim 1, wherein the peptide has a half-life in cynomolgus monkeys after intravenous administration of at least 45 hours, at least 50 hours, at least 60 hours, at least 70 hours, at least 80 hours, at least 90 hours, at least 100 hours, at least 110 hours, at least 120 hours, or about 130 hours.

11. The peptide of claim 1, wherein the peptide has an s.c. bioavailability in cynomolgus monkeys of at least 75%, at least 80%, at least 90%, or about 95%.

12. A pharmaceutical composition comprising the peptide of claim 1.

13. The composition of claim 12, wherein the composition is a solid composition.

14. The composition of claim 12, wherein the composition is a liquid composition.

15. The peptide of claim 1, wherein the peptide comprises the amino acid sequence H-Aib-Q-G-T-F-T-S-D-V-S-K-αMePhe-L-D-T    X17-R-A-R-D-F-V-Q-W-L-L-E-Aib-G-acid (SEQ ID NO: 100);
   wherein X17 is K(O2Oc)-(O2Oc)-γE-C18diacid).

16. The peptide of claim 1, wherein the peptide comprises the amino acid sequence H-Aib-Q-G-T-F-T-S-D-V-S-K-αMePhe-L-D-T-X17-R-A-R-D-F-V-Q-W-L-L-E-Aib-G-acid (SEQ ID NO: 107);
   wherein X17 is K(O2Oc)-(O2Oc)-γE-C20diacid).

17. The peptide of claim 1, wherein the peptide comprises the amino acid sequence H-Aib-H-G-S-αMePhe-T-S-D-V-S-K-αMePhe-L-D-S-R-A-A-X20-D-αMePhe-V-Q-Aib-I-A-N-T-amide (SEQ ID NO: 228);
   wherein X20 is K(ε-(O2Oc)-(O2Oc)-γE-C18diacid).

18. The peptide of claim 1, wherein the peptide comprises the amino acid sequence H-Aib-H-G-S-αMePhe-T-S-D-V-S-K-αMePhe-L-D-S-R-A-A-X20-D-αMePhe-V-Q-Aib-I-A-N-T-amide (SEQ ID NO: 233);

wherein X20 is K(ε-(O2Oc)-(O2Oc)-γE-γE-C20diacid).    5

* * * * *